US012630865B2

(12) United States Patent
Honisch et al.

(10) Patent No.: US 12,630,865 B2
(45) Date of Patent: **\*May 19, 2026**

(54) PRODUCTS AND PROCESSES FOR MULTIPLEX NUCLEIC ACID IDENTIFICATION

(71) Applicant: Agena Bioscience, Inc., San Diego, CA (US)

(72) Inventors: Christiane Honisch, La Jolla, CA (US); Dirk Van Den Boom, Encinitas, CA (US); Michael Mosko, Poway, CA (US); Anders Nygren, San Diego, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,303

(22) Filed: Apr. 25, 2023

(65) Prior Publication Data

US 2023/0407375 A1     Dec. 21, 2023

Related U.S. Application Data

(63) Continuation of application No. 16/793,732, filed on Feb. 18, 2020, now Pat. No. 11,667,958, which is a continuation of application No. 13/551,486, filed on Jul. 17, 2012, now Pat. No. 10,604,791, which is a continuation of application No. PCT/US2012/038710, filed on May 18, 2012.

(60) Provisional application No. 61/488,082, filed on May 19, 2011.

(51) Int. Cl.
*C12Q 1/6823* (2018.01)
*C12Q 1/6809* (2018.01)
*C12Q 1/6853* (2018.01)
*C12Q 1/6858* (2018.01)

(52) U.S. Cl.
CPC ......... *C12Q 1/6823* (2013.01); *C12Q 1/6809* (2013.01); *C12Q 1/6853* (2013.01); *C12Q 1/6858* (2013.01)

(58) Field of Classification Search
CPC .. C12Q 1/6809; C12Q 1/6853; C12Q 1/6858; C12Q 2537/143; C12Q 2563/167; C12Q 2565/518
See application file for complete search history.

(56) References Cited

U.S. PATENT DOCUMENTS

| | | |
|---|---|---|
| 4,515,781 A | 5/1985 | Torrence et al. |
| 4,582,789 A | 4/1986 | Sheldon et al. |
| 4,683,195 A | 7/1987 | Mullis et al. |
| 4,689,405 A | 8/1987 | Frank et al. |
| 4,711,955 A | 12/1987 | Ward et al. |
| 5,003,059 A | 3/1991 | Brennan |
| 5,013,830 A | 5/1991 | Ohtsuka et al. |
| 5,037,882 A | 8/1991 | Steel |
| 5,059,654 A | 10/1991 | Hou et al. |
| 5,064,754 A | 11/1991 | Mills |
| 5,118,605 A | 6/1992 | Urdea |
| 5,237,016 A | 8/1993 | Ghosh et al. |
| 5,242,974 A | 9/1993 | Holmes |
| 5,364,760 A | 11/1994 | Chu et al. |
| 5,380,833 A | 1/1995 | Urdea |
| 5,399,857 A | 3/1995 | Doroshenko et al. |
| 5,412,083 A | 5/1995 | Giese et al. |
| 5,480,784 A | 1/1996 | Kacian et al. |
| 5,489,507 A | 2/1996 | Chehab |
| 5,510,270 A | 4/1996 | Fodor et al. |
| 5,512,439 A | 4/1996 | Hornes et al. |
| 5,547,835 A | 8/1996 | Koester |
| 5,605,798 A | 2/1997 | Koester |
| 5,622,824 A | 4/1997 | Koester |
| 5,650,489 A | 7/1997 | Lam |
| 5,691,141 A | 11/1997 | Koester |
| 5,700,642 A | 12/1997 | Monforte et al. |
| 5,710,028 A | 1/1998 | Eyal et al. |
| 5,770,272 A | 6/1998 | Biemann et al. |
| 5,800,984 A | 9/1998 | Vary |

(Continued)

FOREIGN PATENT DOCUMENTS

| | | |
|---|---|---|
| CN | 1670222 A | 9/2005 |
| CN | 101194023 A | 6/2008 |

(Continued)

OTHER PUBLICATIONS

Singer-Sam et al., "A Sensitive, Quantitative Assay for Measurement of Allele-specific Transcripts Differing by a Single Nucleotide," PCR Methods and Applications, February, vol. 1, pp. 160-163. (Year: 1992).*

(Continued)

*Primary Examiner* — Young J Kim

(74) *Attorney, Agent, or Firm* — LOZA & LOZA, LLP

(57) ABSTRACT

Provided herein are products and processes for detecting the presence or absence of multiple target nucleic acids. Certain methods include amplifying the target nucleic acids, or portion thereof; extending oligonucleotides that specifically hybridize to the amplicons, where the extended oligonucleotides include a capture agent; capturing the extended oligonucleotides to a solid phase via the capture agent; releasing the extended oligonucleotide by competition with a competitor; detecting the extended oligonucleotide, and thereby determining the presence or absence of each target nucleic acid by the presence or absence of the extended oligonucleotide.

15 Claims, 53 Drawing Sheets

Specification includes a Sequence Listing.

(56) References Cited

U.S. PATENT DOCUMENTS

| | | |
|---|---|---|
| 5,851,765 A | 12/1998 | Koester |
| 5,869,242 A | 2/1999 | Kamb |
| 5,872,003 A | 2/1999 | Koester |
| 5,885,775 A | 3/1999 | Haff et al. |
| 5,888,819 A | 3/1999 | Goelet et al. |
| 5,925,520 A | 7/1999 | Tully et al. |
| 5,965,363 A | 10/1999 | Monforte et al. |
| 5,976,798 A | 11/1999 | Parker et al. |
| 5,989,871 A | 11/1999 | Grossman et al. |
| 6,004,744 A | 12/1999 | Goelet et al. |
| 6,043,031 A | 3/2000 | Koester et al. |
| 6,074,823 A | 6/2000 | Koester |
| 6,194,144 B1 | 2/2001 | Koester |
| 6,197,498 B1 | 3/2001 | Koester |
| 6,221,601 B1 | 4/2001 | Koester et al. |
| 6,221,605 B1 | 4/2001 | Koester |
| 6,225,450 B1 | 5/2001 | Koester |
| 6,235,478 B1 | 5/2001 | Koester |
| 6,238,871 B1 | 5/2001 | Koester |
| 6,258,538 B1 | 7/2001 | Koester et al. |
| 6,268,144 B1 | 7/2001 | Koester |
| 6,277,573 B1 | 8/2001 | Koester |
| 6,300,076 B1 | 10/2001 | Koester |
| 6,428,955 B1 | 8/2002 | Koester |
| 6,500,621 B2 | 12/2002 | Koester |
| 6,602,662 B1 | 8/2003 | Koester et al. |
| 6,613,509 B1 | 9/2003 | Chen |
| 7,074,563 B2 | 7/2006 | Koester |
| 7,108,974 B2 | 9/2006 | Ecker et al. |
| 7,198,893 B1 | 4/2007 | Koester et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,419,787 B2 | 9/2008 | Koester |
| 7,759,065 B2 | 7/2010 | Koester |
| 8,003,317 B2 | 8/2011 | Beaulieu et al. |
| 8,153,377 B2 | 4/2012 | Cantor et al. |
| 8,349,566 B2 | 1/2013 | Beaulieu et al. |
| 8,586,708 B2 | 11/2013 | Ting et al. |
| 9,068,223 B2 | 6/2015 | Beaulieu et al. |
| 9,896,724 B2 | 2/2018 | Beaulieu et al. |
| 10,233,489 B2 | 3/2019 | Nygren |
| 10,513,728 B2 | 12/2019 | Nygren |
| 10,604,791 B2* | 3/2020 | Honisch ............... C12Q 1/6809 |
| 10,640,817 B2 | 5/2020 | Nygren |
| 10,865,439 B2 | 12/2020 | Nygren |
| 11,111,530 B2 | 9/2021 | Beaulieu et al. |
| 11,667,958 B2* | 6/2023 | Honisch ............... C12Q 1/6858 |
| | | 435/6.12 |
| 11,680,289 B2 | 6/2023 | Nygren |
| 2003/0022225 A1 | 1/2003 | Monforte et al. |
| 2003/0027169 A1 | 2/2003 | Zhang et al. |
| 2003/0119004 A1 | 6/2003 | Wenz et al. |
| 2003/0203381 A1* | 10/2003 | Kambara ............. C12Q 1/6876 |
| | | 435/91.2 |
| 2004/0259105 A1 | 12/2004 | Fan et al. |
| 2005/0079521 A1 | 4/2005 | Beaulieu et al. |
| 2005/0233381 A1 | 10/2005 | Liu et al. |
| 2005/0287533 A1 | 12/2005 | Ehrich et al. |
| 2005/0287592 A1 | 12/2005 | Kless |
| 2006/0003352 A1 | 1/2006 | Lipkin et al. |
| 2006/0166201 A1 | 7/2006 | Schatz et al. |
| 2007/0202514 A1 | 8/2007 | Koester et al. |
| 2007/0292861 A1 | 12/2007 | Thompson |
| 2008/0167197 A1 | 7/2008 | Schmidt et al. |
| 2008/0305479 A1 | 12/2008 | Van Den et al. |
| 2011/0165133 A1 | 7/2011 | Rabinovich et al. |
| 2012/0015826 A1 | 1/2012 | Beaulieu et al. |
| 2012/0046178 A1 | 2/2012 | Den et al. |
| 2012/0156685 A1 | 6/2012 | Cantor et al. |
| 2013/0017960 A1 | 1/2013 | Honisch et al. |
| 2013/0237428 A1 | 9/2013 | Beaulieu et al. |
| 2014/0011195 A1 | 1/2014 | Honisch et al. |
| 2016/0102347 A1 | 4/2016 | Beaulieu et al. |
| 2016/0312278 A1 | 10/2016 | Nygren |
| 2018/0298433 A1 | 10/2018 | Nygren |
| 2019/0153526 A1 | 5/2019 | Nygren |
| 2020/0123601 A1 | 4/2020 | Nygren |
| 2020/0318169 A1 | 10/2020 | Honisch et al. |
| 2021/0062254 A1 | 3/2021 | Nygren |
| 2022/0106637 A1 | 4/2022 | Beaulieu et al. |
| 2023/0383340 A1 | 11/2023 | Nygren |

FOREIGN PATENT DOCUMENTS

| | | |
|---|---|---|
| CN | 103333952 A | 10/2013 |
| CN | 103602740 A | 4/2014 |
| CN | 103717751 A | 4/2014 |
| CN | 103131787 B | 5/2014 |
| CN | 104685064 A | 6/2015 |
| EP | 0269520 A2 | 6/1988 |
| EP | 0655501 A1 | 5/1995 |
| EP | 1176212 A1 | 1/2002 |
| JP | H07-159404 A | 6/1995 |
| JP | H08-256764 A | 10/1996 |
| JP | 2011-501008 A | 1/1999 |
| JP | 2004-527732 A | 9/2004 |
| JP | 2005-336107 A | 12/2005 |
| JP | 2006-320271 A | 11/2006 |
| JP | 2008-531052 A | 8/2008 |
| JP | 2014-515264 A | 6/2014 |
| WO | 89/10977 A1 | 11/1989 |
| WO | 91/11533 A1 | 8/1991 |
| WO | 92/13969 A1 | 8/1992 |
| WO | 94/00562 A1 | 1/1994 |
| WO | 94/16101 A2 | 7/1994 |
| WO | 96/30545 A1 | 10/1996 |
| WO | 96/32504 A2 | 10/1996 |
| WO | 97/37041 A2 | 10/1997 |
| WO | 03/104420 A2 | 12/2003 |
| WO | 2004/007773 A1 | 1/2004 |
| WO | 2005/012578 A1 | 2/2005 |
| WO | 2006/133840 A1 | 12/2006 |
| WO | 2010/054110 A2 | 5/2010 |
| WO | 2010/056513 A2 | 5/2010 |
| WO | 2011/034115 A1 | 3/2011 |
| WO | 2012/159089 A1 | 11/2012 |
| WO | 2014/018080 A1 | 1/2014 |
| WO | 2016/172571 A1 | 10/2016 |
| WO | 2016/172579 | 10/2016 |

OTHER PUBLICATIONS

Hammond et al., Rapid mass spectrometric identification of human genomic polymorphisms using multiplexed photocleavable mass-tagged probes and solid phase capture, Org. Biomol. Chem., vol. 5, pp. 1878-1885. (Year: 2007).*

Mengel-Jorgensen et al., "MALDI-TOF Mass Spectrometric Detection of Multiplex Single Base Extended Primers. A Study of 17 Y-Chromosome Single-Nucleotide Polymorphisms," Anal. Chem., vol. 76, pp. 6039-6045. (Year: 2004).*

Chinese Search Report issued in Chinese Patent Application No. 201680013462.4, mailed on Sep. 7, 2020, 2 pages of English Translation.

Ex Parte Quayle Action mailed on Apr. 20, 1999, in U.S. Appl. No. 08/617,256, filed Mar. 18, 1996.

Extended European Search Report mailed on Oct. 15, 2012, in European Patent Application No. 09826542.4, filed on Oct. 27, 2009, 8 pages.

Final Office Action mailed on Apr. 15, 1996, in U.S. Appl. No. 08/406,199, filed Mar. 17, 1995.

Final Office Action mailed on Apr. 19, 2005, in U.S. Appl. No. 09/686,148, filed Oct. 10, 2000, 6 pages.

Final Office Action mailed on Apr. 5, 1994, in U.S. Appl. No. 08/001,323, filed Jan. 7, 1993.

Final Office Action mailed on Aug. 3, 2018, in U.S. Appl. No. 13/551,486, filed Jul. 17, 2012, 24 pages.

Final Office Action mailed on Aug. 22, 1995, in U.S. Appl. No. 08/178,216, filed Jan. 6, 1994.

Final Office Action mailed on Aug. 27, 2003, in U.S. Appl. No. 09/686,148, filed Oct. 10, 2000, 8 pages.

(56)        References Cited

OTHER PUBLICATIONS

Final Office Action mailed on Dec. 26, 2001, in U.S. Appl. No. 09/179,536, filed Oct. 26, 1998.
Final Office Action mailed on Dec. 30, 2015, in U.S. Appl. No. 13/551,486, filed Jul. 17, 2012, 23 pages.
Final Office Action mailed on Feb. 26, 2014, in U.S. Appl. No. 13/551,486, filed Jul. 17, 2012, 30 pages.
Final Office Action mailed on Jan. 20, 2017, in U.S. Appl. No. 13/551,486, filed Jul. 17, 2012, 21 pages.
Final Office Action mailed on Jun. 15, 2017, in U.S. Appl. No. 13/551,486, filed Jul. 17, 2012, 19 pages.
Final Office Action mailed on Nov. 16, 2009, in U.S. Appl. No. 12/163,923, filed Jun. 27, 2008, 6 pages.
Final Office Action mailed on Sep. 7, 2021, in U.S. Appl. No. 16/793,732, filed Feb. 18, 2020, 31 pages.
Final Office Action mailed on Nov. 6, 1997, in U.S. Appl. No. 08/617,256, filed Mar. 18, 1996.
Non-Final Office Action mailed on Jun. 29, 1993, in U.S. Appl. No. 08/001,323, filed Jan. 7, 1993.
Non-Final Office Action mailed on Sep. 8, 2000, in U.S. Appl. No. 09/495,444, filed Jan. 31, 2000.
Non-Final Office Action mailed on May 27, 2022, in U.S. Appl. No. 16/793,732, filed Feb. 18, 2020, 31 pages.
Non-Final Office Action mailed on Apr. 10, 2014, in U.S. Appl. No. 13/126,684, filed Oct. 12, 2011, 18 pages.
Non-Final Office Action mailed on Apr. 10, 2002, in U.S. Appl. No. 09/879,341, filed Jun. 11, 2001.
Non-Final Office Action mailed on Apr. 28, 2020, in U.S. Appl. No. 16/669,311, filed Oct. 30, 2019, 5 pages.
Non-Final Office Action mailed on Aug. 8, 2001, in U.S. Appl. No. 09/297,576, filed Jun. 28, 1999.
Non-Final Office Action mailed on Aug. 17, 1998, in U.S. Appl. No. 08/744,481, filed Nov. 6, 1996.
Non-Final Office Action mailed on Aug. 21, 2000, in U.S. Appl. No. 09/431,613, filed Nov. 2, 1999.
Non-Final Office Action mailed on Aug. 26, 2022, in U.S. Appl. No. 17/098,993, filed Nov. 16, 2020, 5 pages.
Non-Final Office Action mailed on Aug. 5, 2005, in U.S. Appl. No. 10/375,714, filed Feb. 24, 2003, 8 pages.
Non-Final Office Action mailed on Dec. 19, 2001, in U.S. Appl. No. 09/796,416, filed Feb. 28, 2001.
Non-Final Office Action mailed on Feb. 6, 2009, in U.S. Appl. No. 12/163,923, filed Jun. 27, 2008, 6 pages.
Non-Final Office Action mailed on Feb. 16, 2000, in U.S. Appl. No. 09/287,682, filed Apr. 6, 1999.
Non-Final Office Action mailed on Feb. 20, 2008, in U.S. Appl. No. 11/541,871, filed Oct. 2, 2006, 9 pages.
Non-Final Office Action mailed on Feb. 23, 1995, in U.S. Appl. No. 08/178,216, filed Jan. 6, 1994.
Non-Final Office Action mailed on Feb. 28, 2013, in U.S. Appl. No. 13/551,486, filed Jul. 17, 2012, 27 pages.
Non-Final Office Action mailed on Jan. 9, 2018, in U.S. Appl. No. 13/551,486, filed Jul. 17, 2012, 19 pages.
Non-Final Office Action mailed on Jan. 27, 2021, in U.S. Appl. No. 16/793,732, filed Feb. 18, 2020, 24 pages.
Non-Final Office Action mailed on Jul. 6, 2000, in U.S. Appl. No. 09/179,536, filed Oct. 26, 1998.
Non-Final Office Action mailed on Jul. 8, 2015, in U.S. Appl. No. 13/551,486, filed Jul. 17, 2012, 23 pages.
Non-Final Office Action mailed on Jul. 25, 2002, in U.S. Appl. No. 09/179,536, filed Oct. 26, 1998.
Non-Final Office Action mailed on Jul. 3, 2007, in U.S. Appl. No. 11/432,171, filed May 11, 2006, 11 pages.
Non-Final Office Action mailed on Jun. 6, 2019, in U.S. Appl. No. 15/568,701, filed Oct. 23, 2017, 6 pages.
Non-Final Office Action mailed on Jun. 28, 2000, in U.S. Appl. No. 09/287,681, filed Apr. 6, 1999.
Non-Final Office Action mailed on Jun. 28, 2002, in U.S. Appl. No. 09/724,877, filed Nov. 28, 2000.
Non-Final Office Action mailed on Mar. 8, 2019, in U.S. Appl. No. 13/551,486, filed Jul. 17, 2012, 25 pages.
Non-Final Office Action mailed on Mar. 28, 2001, in U.S. Appl. No. 09/179,536, filed Oct. 26, 1998.
Non-Final Office Action mailed on May 5, 2000, in U.S. Appl. No. 09/287,679, filed Apr. 6, 1999.
Non-Final Office Action mailed on May 8, 2002, in U.S. Appl. No. 09/297,576, filed Jun. 28, 1999.
Non-Final Office Action mailed on May 11, 2009, in U.S. Appl. No. 12/125,857, filed May 22, 2008, 11 pages.
Non-Final Office Action mailed on May 13, 2019, in U.S. Appl. No. 16/255,718, filed Jan. 23, 2019, 5 pages.
Non-Final Office Action mailed on May 20, 2009, in U.S. Appl. No. 12/163,915, filed Jun. 27, 2008, 12 pages.
Non-Final Office Action mailed on May 29, 2018, in U.S. Appl. No. 15/136,024, filed Apr. 22, 2016, 6 pages.
Non-Final Office Action mailed on Nov. 3, 2010, in U.S. Appl. No. 12/795,155, filed Jun. 7, 2010, 11 pages.
Non-Final Office Action mailed on Nov. 20, 2002, in U.S. Appl. No. 09/686,148, filed Oct. 10, 2000, 9 pages.
Non-Final Office Action mailed on Oct. 4, 2016, in U.S. Appl. No. 13/551,486, filed Jul. 17, 2012, 16 pages.
Non-Final Office Action mailed on Sep. 5, 2013, in U.S. Appl. No. 13/551,486, filed Jul. 17, 2012, 26 pages.
Non-Final Office Action mailed on Sep. 8, 2000, in U.S. Appl. No. 09/504,245, filed Feb. 15, 2000.
Non-Final Office Action mailed on Sep. 14, 1995, in U.S. Appl. No. 08/406,199, filed Mar. 17, 1995.
Non-Final Office Action mailed on Sep. 22, 2000, in U.S. Appl. No. 09/287,679, filed Apr. 6, 1999.
Non-Final Office Action mailed on Feb. 16, 2000, in U.S. Appl. No. 09/287,141, filed Apr. 6, 1999.
Non-Final Office Action mailed on May 5, 1997, in U.S. Appl. No. 08/617,256, filed Mar. 18, 1996.
Notice of Allowance mailed on Apr. 1, 1999, in U.S. Appl. No. 08/744,481, filed Nov. 6, 1996.
Notice of Allowance mailed on Apr. 28, 2006, in U.S. Appl. No. 09/686,148, filed Oct. 10, 2000, 7 pages.
Notice of Allowance mailed on Aug. 2, 2019, in U.S. Appl. No. 16/255,718, filed Jan. 23, 2019, 6 pages.
Notice of Allowance mailed on Aug. 18, 2020, in U.S. Appl. No. 16/669,311, filed Oct. 30, 2019, 6 pages.
Notice of Allowance mailed on Dec. 9, 2019, in U.S. Appl. No. 13/551,486, filed Jul. 17, 2012, 10 pages.
Notice of Allowance mailed on Feb. 23, 2010, in U.S. Appl. No. 12/125,857, filed May 22, 2008, 10 pages.
Notice of Allowance mailed on Feb. 25, 2000, in U.S. Appl. No. 09/287,681, filed Apr. 6, 1999.
Notice of Allowance mailed on Feb. 25, 2008, in U.S. Appl. No. 11/432,171, filed May 11, 2006, 7 pages.
Notice of Allowance mailed on Feb. 3, 2023, in U.S. Appl. No. 17/098,993, filed Nov. 16, 2020, 6 pages.
Notice of Allowance mailed on Jan. 2, 2001, in U.S. Appl. No. 08/744,481, filed Nov. 6, 1996.
Notice of Allowance mailed on Jan. 3, 2020, in U.S. Appl. No. 15/568,701, filed Oct. 23, 2017, 7 pages.
Notice of Allowance mailed on Jan. 10, 2006, in U.S. Appl. No. 10/375,714, filed Feb. 24, 2003, 7 pages.
Notice of Allowance mailed on Jan. 26, 2023, in U.S. Appl. No. 16/793,732, filed Feb. 18, 2020, 11 pages.
Notice of Allowance mailed on Jun. 14, 2000, in U.S. Appl. No. 09/287,682, filed Apr. 6, 1999.
Notice of Allowance mailed on May 17, 2002, in U.S. Appl. No. 09/796,416, filed Feb. 28, 2001.
Notice of Allowance mailed on Nov. 3, 2000, in U.S. Appl. No. 09/495,444, filed Jan. 31, 2000.
Notice of Allowance mailed on Nov. 16, 2000, in U.S. Appl. No. 09/287,679, filed Apr. 6, 1999.
Notice of Allowance mailed on Nov. 27, 2002, in U.S. Appl. No. 09/879,341, filed Jun. 11, 2001.
Notice of Allowance mailed on Oct. 8, 2008, in U.S. Appl. No. 11/541,871, filed Oct. 2, 2006, 5 pages.

(56) References Cited

OTHER PUBLICATIONS

Notice of Allowance mailed on Oct. 10, 2000, in U.S. Appl. No. 09/431,613, filed Nov. 2, 1999.

Notice of Allowance mailed on Oct. 20, 2000, in U.S. Appl. No. 09/504,245, filed Feb. 15, 2000.

Notice of Allowance mailed on Oct. 21, 1998, in U.S. Appl. No. 08/617,256, filed Mar. 18, 1996.

Notice of Allowance mailed on Oct. 22, 2018, in U.S. Appl. No. 15/136,024, filed Apr. 22, 2016, 5 pages.

Notice of Allowance mailed on Sep. 8, 2000, in U.S. Appl. No. 09/397,766, filed Sep. 15, 1999.

Notice of Allowance mailed on Sep. 10, 1999, in U.S. Appl. No. 08/617,256, filed Mar. 18, 1996.

Notice of Allowance mailed on Sep. 19, 2002, in U.S. Appl. No. 09/724,877, filed Nov. 28, 2000.

Notice of Allowance mailed on Feb. 3, 1998, in U.S. Appl. No. 08/617,256, filed Mar. 18, 1996.

Notice of Allowance mailed on May 30, 2000, in U.S. Appl. No. 09/287,141, filed Apr. 6, 1999.

Office Action mailed on Apr. 22, 2016, in U.S. Appl. No. 13/790,996, filed Mar. 8, 2013.

Office Action mailed on Aug. 1, 2003, in U.S. Appl. No. 08/467,208, filed Jun. 6, 1995.

Office Action mailed on Aug. 19, 1998, in U.S. Appl. No. 08/467,208, filed Jun. 6, 1995.

Office Action mailed on Aug. 22, 2019, in U.S. Appl. No. 13/126,684, filed Oct. 12, 2011, 23 pages.

Office Action mailed on Aug. 27, 2002, in U.S. Appl. No. 09/783,881, filed Feb. 13, 2001.

Office Action mailed on Dec. 16, 2016, in U.S. Appl. No. 13/790,996, filed Mar. 8, 2013.

Office Action mailed on Dec. 26, 2014, in U.S. Appl. No. 13/126,684, filed Oct. 12, 2011.

Office Action mailed on Feb. 7, 2019, in U.S. Appl. No. 13/790,996, filed Mar. 8, 2013.

Office Action mailed on Jan. 12, 1999, in U.S. Appl. No. 08/467,208, filed Jun. 6, 1995.

Office Action mailed on Jan. 17, 2017, in U.S. Appl. No. 13/126,684, filed Oct. 12, 2011.

Office Action mailed on Jan. 17, 2018, in U.S. Appl. No. 13/790,996, filed Mar. 8, 2013.

Office Action mailed on Jan. 29, 2016, in U.S. Appl. No. 13/126,684, filed Oct. 12, 2011.

Office Action mailed on Jan. 6, 2016, in U.S. Appl. No. 13/790,996, filed Mar. 8, 2013.

Office Action mailed on Jul. 16, 2001, in U.S. Appl. No. 08/467,208, filed Jun. 6, 1995.

Office Action mailed on Jul. 18, 2017, in U.S. Appl. No. 13/126,684, filed Oct. 12, 2011.

Office Action mailed on Jul. 29, 2002, in U.S. Appl. No. 08/467,208, filed Jun. 6, 1995.

Office Action mailed on Jul. 31, 2000, in U.S. Appl. No. 08/467,208, filed Jun. 6, 1995.

Office Action mailed on Jun. 19, 2015, in U.S. Appl. No. 13/790,996, filed Mar. 8, 2013.

Office Action mailed on Jun. 27, 2017, in U.S. Appl. No. 13/790,996, filed Mar. 8, 2013.

Office Action mailed on Jun. 28, 2018, in U.S. Appl. No. 13/126,684, filed Oct. 12, 2011.

Office Action mailed on Mar. 20, 1997, in U.S. Appl. No. 08/467,208, filed Jun. 6, 1995.

Office Action mailed on Mar. 26, 2001, in U.S. Appl. No. 08/467,208, filed Jun. 6, 1995.

Office Action mailed on Nov. 15, 2017, in U.S. Appl. No. 13/126,684, filed Oct. 12, 2011.

Office Action mailed on Nov. 16, 2018, in U.S. Appl. No. 13/126,684, filed Oct. 12, 2011.

Office Action mailed on Oct. 13, 1999, in U.S. Appl. No. 08/467,208, filed Jun. 6, 1995.

Office Action mailed on Oct. 28, 1997, in U.S. Appl. No. 08/467,208, filed Jun. 6, 1995.

Office Action mailed on Oct. 3, 2014, in U.S. Appl. No. 13/790,996, filed Mar. 8, 2013, 19 pages.

Office Action mailed on Oct. 3, 2016, in U.S. Appl. No. 13/126,684, filed Oct. 12, 2011.

Office Action mailed on Oct. 4, 2016, in U.S. Appl. No. 13/551,486, filed Jul. 17, 2012.

Office Action mailed on Sep. 8, 2005, in U.S. Appl. No. 08/467,208, filed Jun. 6, 1995.

Office Action mailed on Sep. 9, 2004, in U.S. Appl. No. 08/467,208, filed Jun. 6, 1995.

Office Action mailed on Sep. 8, 2014, in U.S. Appl. No. 13/099,236, filed May 2, 2011.

International Preliminary Report on Patentability mailed on May 12, 2011, in International Patent Application No. PCT/US2009/062239, filed on Oct. 27, 2009, 8 pages.

International Preliminary Report on Patentability mailed on Nov. 2, 2017, in International Patent Application No. PCT/US2016/028971, filed on Apr. 22, 2016, 10 pages.

International Preliminary Report on Patentability mailed on Nov. 2, 2017, in International Patent Application No. PCT/US2016/028980, filed on Apr. 22, 2016, 8 pages.

International Preliminary Report on Patentability mailed on Nov. 28, 2013, in International Patent Application No. PCT/US2012/038710, filed on May 18, 2012, 7 pages.

International Search Report and Written Opinion mailed on Jul. 9, 2010, in International Patent Application No. PCT/US2009/062239, filed on Oct. 27, 2009, 10 pages.

International Search Report and Written Opinion mailed on Jul. 15, 2016, in International Patent Application No. PCT/US2016/028971, filed on Apr. 22, 2016, 12 pages.

International Search Report and Written Opinion mailed on Jun. 22, 2016, in International Patent Application No. PCT/US2016/028980, filed on Apr. 22, 2016, 10 pages.

International Search Report and Written Opinion mailed on Sep. 5, 2012, in International Patent Application No. PCT/US2012/038710, filed on May 18, 2012, 10 pages.

Adler, et al., "Cell Membrane Coating with Glutaraldehyde: Application to a versatile Solid-Phase Assay for Thyroid Membrane Proteins and Molecules Interacting with Thyroid Membranes", Analytical Biochemistry, 1985, 148:320-327.

Anker, et al. "Tetranucleotide Repeat Polymorphism at the Human Thyroid Peroxidase (hTPO) Locus", Human Molecular Genetics, 1992, 1:137.

Banerjee, et al., "inhA, a Gene Encoding a Target for Isoniazid and Ethionamide in MycoBacterium Tuberculosis", Science, Jan. 14, 1994, 263:227-230.

Beckmann, et al., "Survey of Human and Rat Microsatellites", Genomics, 1992, 12:627-631.

Binladen, et al., "The Use of Coded PCR Primers Enables High-Throughput Sequencing of Multiple Homolog Amplification Products by 454 Parallel Sequencing", Plos One, 2007, 2(2): e197:1-9.

Bird, Adrian, "DNA Methylation Patterns and Epigenetic Memory", Genes Development, 2002, 16:6-21.

Caruthers, et al., "Chemical Synthesis of Deoxyoligonucleotides by the Phosphoramidite Method", Methods in Enzymology, 1987, 154:287-313.

Caruthers, Marvin H., "Gene Synthesis Machines: DNA Chemistry and Its Use", Science, Oct. 18, 1985, 230:281-285.

Caskey, et al., "Triplet Repeat Mutations in Human Disease", Science, May 8, 1992, 256(5058):784-789.

Chakrabarti, et al., "Sequence of Simian Immunodeficiency Virus from Macaque and Its Relationship to Other Human and Simian Retroviruses", Nature, Aug. 6, 1987, 328:543-547.

Chee, M., "Enzymatic Multiples DNA Sequencing", Nucleic Acids Research, 1991, 19(12):3301-3305.

Cook, et al., "Synthesis and Hybridization of a Series of Biotinylated Oligonucleotides", Nucleic Acids Research, 1988, 16:4077-4095.

Deisingh, et al., "Sequences of E. coli O157:H7 detected by a PCR-acoustic wave sensor combination", Analyst, 2001, 126(12):2153-2158.

(56)          References Cited

OTHER PUBLICATIONS

Ding, et al., "MS Analysis of Single-nucleotide Differences in Circulating Nucleic Acids: Application to Noninvasive Prenatal Diagnosis", PNAS, 2004, 101(29):10762-10767.
Ding, Chunming, "Qualitative and Quantitative DNA and RNA Analysis by Matrix-Assisted Laser Desorption/ionization Time-of-Flight Mass Spectrometry", Methods in Molecular Biology, 2006, 336:59-71.
Doktycz, et al., "Analysis of Polymerase Chain Reaction-Amplified DNA Products by Mass Spectrometry Using Matrix-Assisted Laser Desorption and Electrospray: Current Status", Analytical Biochemistry, 1995, 230:205-214.
Donovan, et al., "Increase in the Stability of Avidin Produced by Binding of Biotin. A Differential Scanning Calorimetric Study of Denaturation by Heat", Biochemistry, 1973, 12(3):512-517.
Dubiley, et al., "Polymorphism Analysis and Gene Detection by Minisequencing on an Array of Gel-Immobilized Primers", Nucleic Acids Research, 1999, 27(18):1-6.
Duffield, et al., "Simultaneous Determination of Multiple mRNA Levels Utilizing MALDI-TOF Mass Spectrometry and Biotinylated Dideoxynucleotides", RNA, Jun. 2010, 16(6):1285-1291.
Eckstein, "Oligonucleotides and Analogues: A Practical Approach", Oxford University Press, 1991, 56-57,137-139, 256-259.
Edwards, "Dinucleotide Repeat Polymorphism in Human GLUT2/liver Facilitative Glucose Transporter Gene on Chromosome 3", Nucleic Acids Research, 1991, 19(17):4791.
Fan, et al., "Parallel Genotyping of Human Snps Using Generic High-Density Oligonucleotide Tag Arrays 11", Genome Research, Jan. 1, 2000, 10(6):853-860.
Fitzgrald, et al., "Basic Matrices for the Matrix-Assisted Laser Desorption/Ionization Mass Spectrometry of Proteins and Oligonucleotides", Analytical Chemistry, 1993, 65:3204-3211.
Ganem, et al., "Detection of Oligonucleotide Duplex Forms by Ion-Spray Mass Spectrometry", Tetrahedron Letters, 1993, 34(9):1445-1448.
Gardner, et al., "Acyclic and Dideoxy Terminator Preferences Denote Divergent Sugar Recognition by Archaeon and Taq DNA Polymerases", Nucleic Acids Res., Jan. 15, 2002, 30(2):605-613.
German, et al., "Blood's Syndrome. XII. Report from the Registry for 1987", Clinical Genetics, 1989, 35:57-69.
Gust, et al., "Taxonomic Classification of Hepatitis a Virus", Intervirology, 1983, 20:1-7.
Guyader, et al., "Genome Organization and Transactivation of the Human Immunodeficiency Virus Type 2", Nature, Apr. 16, 1987, 326(6114):662-669.
Haff, et al., "Multiplex Genotyping of PCR Products with MassTag-Labeled Primers", Nucleic Acids Research, 1997, 25(18):3749-3750.
Haff, et al., "Single-Nucleotide Polymorphism Identification Assays Using a Thermostable DNA Polymerase and Delayed Extraction MALDI-TOF Mass Spectrometry", Genome Research, Apr. 1, 1997, 7(4):378-388.
Hartmer, et al., "RNase T1 Mediated Base-Specific Cleavage and MALDI-TOF MS for High-Throughput Comparative Sequence Analysis", Nucleic Acids Res., 2003, 31(9): e47:1-10.
Heym, et al., "Implications of Multidrug Resistance for the Future of Short-Course Chemotherapy of Tuberculosis: A Molecular Study", Lancet, 1994, 344(8918):293-298.
Hirsch, et al., "Easily Reversible Desthiobiotin Binding to Streptavidin, Avidin, and Other Biotin-Binding Proteins: Uses for Protein Labeling, Detection, and Isolation", Analytical Biochemistry, Sep. 2, 2015, 308(2):343-357.
Hirschhorn, et al., "SBE-TAGS: An Array-Based Method for Efficient Single-Nucleotide Polymorphism Genotyping 11", PNAS, Oct. 24, 2000, 97(22):12164-12169.
Hitchcock, et al., "Cleavage of Deoxyoxanosine-Containing Oligodeoxyribonucleotides by Bacterial Endonuclease V", Nucleic Acids Research, 2004, 32(13):4071-4080.

Holmberg, et al., "The Biotin-streptavidin Interaction can be Reversibly Broken Using Water at Elevated Temperatures", Electrophoresis, 2005, 26:501-510.
Jacobson, et al., "Applications of Mass Spectrometry to DNA Sequencing", Genet. Anal. Tech. Appl., 1991, 8(8):223-229.
Jeffreys, et al., "Hypervariable 'Minisatellite' Regions in Human DNA", Nature, Mar. 7, 1985, 314:67-73.
Khrapko, et al., "A Method for DNA Sequencing by Hybridization with Oligonucleotide Matrix", J. DNA Sequencing and Mapping, 1991, 1:375-388.
Kim, et al., "Digital Genotyping Using Molecular Affinity and Mass Spectrometry", Nature Review Genetics, 2003, 4:1001-1008.
Kim, et al., "Multiplex Genotyping of the Human Beta2-Adrenergic Receptor Gene Using Solid-Phase Capturable Dideoxynucleotides and Mass Spectrometry", Analytical Biochemistry, May 1, 2003, 316(2):251-258.
Kim, et al., "Solid Phase Capturable Dideoxynucleotides for Multiplex Genotyping Using Mass Spectrometry", Nucleic Acids Research, Aug. 15, 2002, 30(16): e85. (6 pages.).
Lefmann, et al., "Novel Mass Spectrometry-Based Tool for Genotypic Identification of Mycobacteria", Journal of Clinical Microbiology, Jan. 1, 2004, 42(1):339-346.
Leonard, et al., "High-Resolution Structure of Mutagenic Lesion in DNA", Proc. Nat. Acad. Sci. Biochemistry, 1990, 87:9573-9576.
Li, et al., "Single Nucleotide Polymorphism Determination Using Primer Extension and Time-of-flight Mass Spectrometry", Electrophoresis, Jun. 1999, 20(6):1258-1265.
Litt, et al., "Dinucleotide Repeat Polymorphism at the D11S35 Locus", Nucleic Acids Research, 1990, 18:5921.
Litt, et al., "Dinucleotide Repeat Polymorphism at the D6S89 Locus", Nucleic Acids Research, 1990, 18:4301.
Luty, et al., "Dinucleotide Repeat Polymorphism at the D14S45 Locus", Nucleic Acids Research, 1991, 19(15):4308.
Luty, et al., "Five Polymorphic Microsatellite VNTRs on the Human XChromosome", Am. J. Hum. Genet., 1990, 46:776-783.
Matthews, et al., "Analytical Strategies for the Use of DNA Probes", Analytical Chemistry, 1988, 169:1-25.
Mckinnon, P.J., "Ataxia-Telangiectasia: An Inherited Disorder of Ionizing-Radiation Sensitivity in Man", Human Genetics, 1987, 75(3):197-208.
Mizusawa, et al., "Improvement of the Dideoxy Chain Termination Method of DNA Sequencing by Use of Deoxy-7-Deazaguanosine Triphosphate in Place of DGTP", Nucleic Acids Research, 1986, 14(3):1319-1325.
Morris, et al., "Molecular Mechanisms of Multiple Drug Resistance in Clinical Isolates of Mycobacterium Tuberculosis", The Journal of Infectious Diseases, 1995, 171:954-960.
Morrison, et al., "Organic Chemistry", Published by Allyn and Bacon., Boston, Massachusetts, USA, 1973, 406-409.
Mosko, et al., "Ultrasensitive Detection of Multiplexed Somatic Mutations Using MALDI-TOF Mass Spectrometry", The Journal of Molecular Diagnostics, 2016, 18:23-31.
Muddiman, et al., "Length and Base Composition of PCR-Amplified Nucleic Acids. Using Mass Measurements from Electrospray Ionization Mass Spectrometry", Analytical Chemistry, Apr. 15, 1997, 69(8):1543-1549.
Mullis, "The Unusual Origin of the Polymerase Chain Reaction", Scientific American, 1990, 262(4):56-61.
Naito, et al., "Molecular Mass Measurement of Polymerase Chain Reaction Products Amplified from Human Blood DNA by Electrospray Ionization Mass Spectrometry", Rapid Communications in Mass Spectrometry, 1995, 9:1484-1486.
Nakamura, et al., "Variable Number of Tandem Repeat (VNTR) Markers for Human Gene Mapping", Science, 1987, 235:1616-1622.
Naomi, et al., "Rapid Mass Spectrometric Identification of Human Genomic Polymorphisms Using Multiplexed Photocleavable Mass-Tagged Probes and Solid Phase Capture", Organic and Biomolecular Chemistry, Jan. 1, 2007, 5(12):1878-1885.
Nguyen, et al., "Mild Conditions for Releasing Mono and Bis-Biotinylated Macromolecules from Immobilized Streptavidin", Biomolecular Engineering, Oct. 1, 2005, 22(4):147-150.

(56) References Cited

OTHER PUBLICATIONS

Nishimura, et al., "A Tetranucleotide Repeat for The F13B Locus", Nucleic Acids Research, 1992, 20(5):1167.

Nordhoff, et al., "Matrix-assisted Laser Desorption/Ionization Mass Spectrometry of Nucleic Acids with Wavelengths in the Ultraviolet and Infrared", Rapid Communications in Mass Spectrometry, Dec. 1992, 6(12):771-776.

Oeth, et al., "Sequenom® Application Note, Document No. 8876-006, R04", Nov. 10, 2006, 12 pages.

Overberg, et al., "Matrix-Assisted Laser Desorption of Large Biomolecules with a TEA-CO.sub.2-Laser", Rapid Communications in Mass Spectrometry, 1991, 5(3):128-131.

Palejwala, et al., "Quantitative Multiplex Sequence Analysis of Mutational Hot Spots. Frequency and Specificity of Mutations Induced by a Site-Specific Ethenocytosine in M13 Viral DNA", Biochemistry, 1993, 32:4105-4111.

Pieles, et al., "Matrix-assisted Laser Desorption Ionization Time-of-flight Mass Spectrometry: A Powerful Tool for The Mass and Sequence Analysis of Natural and Modified Oligonucleotides", Nucleic Acid Research, 1993, 21(14):3191-3196.

Pierce, et al., "Comparison of the GenMark Diagnostics eSensor Respiratory Viral Panel to Real-Time PCR for Detection of Respiratory Viruses in Children", Journal of Clinical Microbiology, Nov. 2012, 50(11):3458-3465.

Ploos, et al., "Tetranucleotide Repeat Polymorphism in the VWF Gene", Nucleic Acids Research, 1990, 18(16):4957.

Polymeropoulos, et al., "Trinucleotide Repeat Polymorphism at the Human Pancreatic Phospholipase A-2 Gene (PLA2)", Nucleic Acids Research, 1990, 18(24):7468.

Polymeropoulos, et al., "Tetranucleotide Repeat Polymorphism at the Human C-Fes/fps Proto-Oncogene (FES)", Nucleic Acids Research, 1991, 19(14):4018.

Polymeropoulos, et al., "Tetranucleotide Repeat Polymorphism at the Human Aromatase Cytochrome P-450 Gene (CYP19)", Nucleic Acids Research, 1991, 19(1):195.

Polymeropoulos, et al., "Tetranucleotide Repeat Polymorphism at the Human Coagulation Factor XIII a Subunit Gene(F13A1)", Nucleic Acids Research, 1991, 19(15):4306.

Ratner, et al., "Complete Nucleotide Sequence of AIDS Virus, HTLV-III", Nature, 1985, 313:227-284.

Reymer, et al., "A Lipoprotein Lipase Mutation (Asn291Ser) Is Associated with Reduced HDL Cholesterol Levels in Premature Atherosclerosis", Nature Genetics, 1995, 10(1):28-34.

Rosli, et al., "Quantitative Recovery of Biotinylated Proteins from Streptavidin-Based Affinity Chromatography Resins", Methods in Molecular Biology, 2008, 418:89-100.

Rybak, et al., "Purification of Biotinylated Proteins on Streptavidin Resin: A Protocol for Quantitative Elution", Proteomics, 2004, 4(8):2296-2299.

Sano, et al., "Intersubunit Contacts Made by Tryptophan 120 with Biotin Are Essential for Both Strong Biotin Binding and Biotin-Induced Tighter Subunit Association of Streptavidin", PNAS, 1995, 92(8):3180-3184.

Schächter, et al., "Genetic Associations with Human Longevity at the APOE and ACE loci", Nature Genetics, 1994, 6:29-32.

Schlesinger, "Macromolecular Sequencing and Synthesis: Selected Methods and Applications", Alan R. Liss, Inc., New York, 1988, 127-149.

Singer-Sam, "A Sensitive, Quantitative Assay for Measurement of Allele-specific Transcripts Differing by a Single Nucleotide", Genome Research, 1992, 1:160-163.

Si-Yuan, et al., "Principal and Development of SNP Genotyping Technology", Letters in Biotechnology, English Abstract Only, May 2003, 14(3):218-221.

Smith, et al., "Immobilization of Nucleic Acids Using Biotin-Strept(avidin) Systems", Topics in Current Chemistry, 2005, 261:63-90.

Stahl, et al., "Solid Phase DNA Sequencing Using the Biotin-Avidin System", Nucleic Acids Research, 1988, 16(7):3025-3039.

Stanssens, et al., "High-Throughput MALDI-TOF Discovery of Genomic Sequence Polymorphisms", Genome Research, 2004, 14(1):126-133.

Takenaka, et al., "Multiplex Single-Base 1-39 Extension Typing to Identify Nuclear Genes Required for RNA Editing in Plant Organelles", Nucleic Acid Research, Dec. 5, 2008, 37(2): e13.

Tautz, et al., "Hypervariability of Simple Sequences as a General Source for Polymorphic DNA Markers", Nucleic Acids Research, 1989, 17(16):6463-6471.

Thompson, et al., "Electrospray Ionisation-Cleavable Tandem Nucleic Acid Mass Tag-Peptide Nucleic Acid Conjugates: Synthesis and Applications to Quantitative Genomic Analysis Using Electrospray Ionisation-MS/MS", Nucleic Acid Research, Jan. 26, 2007, 35(4): e28 1-13.

Tost, et al., "Genotyping Single Nucleotide Polymorphisms by Mass Spectrometry", Mass Spectrometry Reviews, 2002, 21(6):388-418.

Trainor, "DNA Sequencing, Automation, and the Human Genome", Anal. Chem., 1990, 62:418-426.

Tsang, et al., "Mass Spectrometry-Based Detection of Hemoglobin E Mutation by Allele-Specific Base Extension Reaction", Clinical Chemistry, 2007, 53(12):2205-2209.

Tuschihashi, et al., "Progress in High Throughput SNP Genotyping Methods", The Pharmacogenomics Journal, Jan. 1, 2002, 2(2):103-110.

Uhlmann, et al., "Antisense Oligonucleotides: A New Therapeutic Principle, Chemical Reviews", Chemical Reviews, 1990, 90(4):544-583.

Vallone, et al., "Genotyping SNPs Using a UV-Photocleavable Oligonucleotide in MALDI-TOF MVALLON", Methods in Molecular Biology, 2005, 297:169-178.

Vivante, et al., "High-Throughput, Sensitive and Quantitative Assay for the Detection of BCR-ABL Kinase Domain Mutations", Leukemia, 2007, 21(6):1318-1321.

Wain, et al., "Nucleotide Sequence of the AIDS Virus, LAV", Cell, 1985, 40(1):9-17.

Wang, et al., "Large-Scale Identification, Mapping, and Genotyping of Single-Nucleotide Polymorphisms in the Human Genome", Science, 1998, 280(5366):1077-1082.

Weber, et al., "Abundant Class of Human DNA Polymorphisms Which Can Be Typed Using the Polymerase Chain Reaction", American Journal of Human Genetics, 1989, 44(3):388-396.

Weissenbach, et al., "A Second-Generation Linkage Map of the Human Genome", Nature, 1992, 359(6398):794-801.

Wenzel, et al., "Genosnip: SNP Genotyping by MALDI-TOF MS Using Photocleavable Oligonucleotides", Nucleosides, nucleotides nucleic acids, 2003, 22(5-8):1579-1581.

Wu, et al., "Matrix-Assisted Laser Desorption Time-of-Flight Mass Spectrometry of Oligonucleotides Using 3-Hydroxypicolinic Acid as an Ultraviolet-Sensitive Matrix", Rapid Communications in Mass Spectrometry, 1993, 7(2):142-146.

Wunschel, et al., "Analysis of Double-Stranded Polymerase Chain Reaction Products from the Bacillus Cereus Group by Electrospray Ionization Fourier Transform Ion Cyclotron Resonance Mass Spectrometry", Rapid Communications in Mass Spectrometry, 1996, 10(1):29-35.

Yao, et al., "Interaction of Deoxyinosine 3'-Endonuclease from *Escherichia coli* with DNA Containing Deoxyinosine", Journal of Biological Chemistry, 1995, 270(48):28609-28616.

Yao, et al., "Purification and Characterization of a Novel Deoxyinosine-Specific Enzyme, Deoxyinosine 3' Endonuclease, from *Escherichia coli*", Journal of Biological Chemistry, 1994, 269(23):16260-16268.

Yao, et al., "Strand-Specific Cleavage of Mismatch-Containing DNA by Deoxyinosine 3'-Endonuclease from *Escherichia coli*", Journal of Biological Chemistry, 1994, 269(50):31390-31396.

Ying, et al., "Design of a Reversible Biotin Analog and Applications in Protein Labeling, Detection, and Isolation", Chemical Communications, 2011, 47:8593-8595.

Yolov, et al., "Synthesis of RNA Using T7 RNA Polymerase and Immobilized DNA in a Stream Type Reactor", Biooraanicheskala Khhimia, Jun. 1991, 17(6):789-794.

Zuliani, et al., "Tetranucleotide Repeat Polymorphism in the LPL Gene", Nucleic Acids Research, 1990, 18(16):4958.

(56)                    References Cited

OTHER PUBLICATIONS

Office Action mailed on Jan. 9, 2001, in U.S. Appl. No. 09/431,613, filed Nov. 2, 1999.
Office Action mailed on May 8, 2002, in U.S. Appl. No. 09/783,881, filed Feb. 13, 2001.
Sanchez et al., "Typing of Y Chromosome SNPs With Multiplex PCR Methods", Methods in Molecular Biology, vol. 297, pp. 209-228.
Office Action in co-pending U.S. Appl. No. 18/142,512, dated Sep. 9, 2024, 7 pages.
Final Office Action in co-pending U.S. Appl. No. 18/142,512, dated Apr. 7, 2025, 6 pages.
Notice of Allowance in co-pending U.S. Appl. No. 18/142,512, dated Jul. 2, 2025, 6 pages.

* cited by examiner

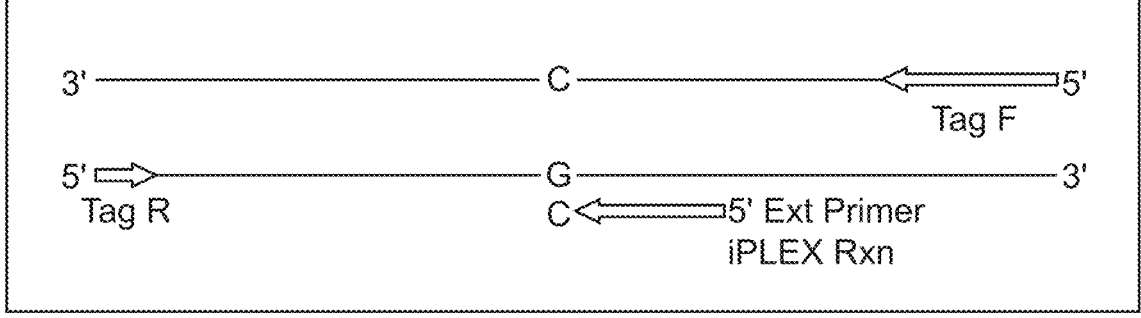
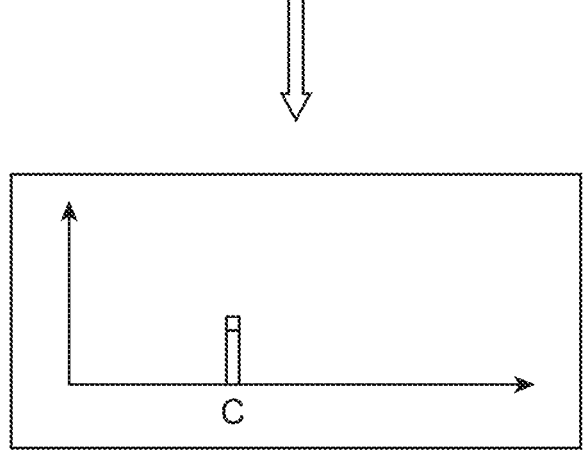
FIG. 3

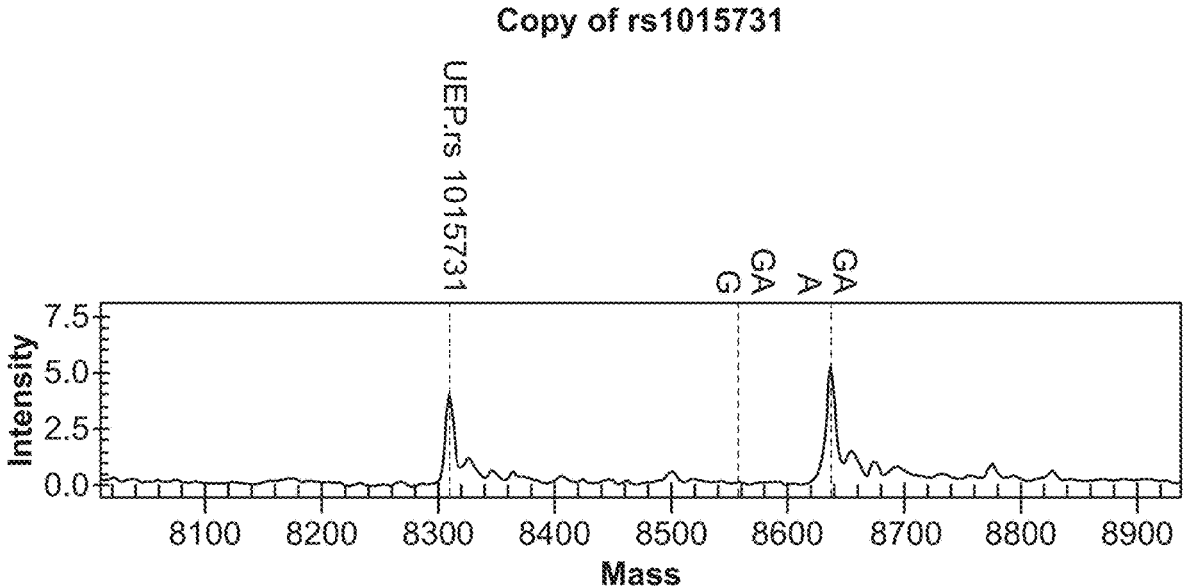
Uniplex PCR: A10
NA06987, 2/14/08,
2.5% Agarose gel
FIG. 5A

D1: 12 Plex
20080328

+M 1 2 3 4 5 6

| Y_ID | | SAMPLE_ID | CALL | DESCRIPTION |
|------|---|-----------|------|-------------|
| rs1000586 | ✓ | NA07057 | GA | A.Conservative |
| rs10012004 | ✓ | NA07057 | | D.Low Probablity |
| rs10014076 | ✓ | NA07057 | GA | A.Conservative |
| rs10027673 | ✓ | NA07057 | | D.Low Probablity |
| rs10028716 | ✓ | NA07057 | C | B.Moderate |
| rs10063237 | ✓ | NA07057 | | N.No-Alleles |
| rs1007716 | ✓ | NA07057 | GA | A.Conservative |
| rs10131894 | ✓ | NA07057 | C | B.Moderate |
| rs1014337 | ✓ | NA07057 | T | A.Conservative |
| rs1015731 | ✓ | NA07057 | G | B.Moderate |
| rs10164484 | ✓ | NA07057 | AG | B.Moderate |
| rs102511765 | ✓ | NA07057 | GT | A.Conservative |

FIG. 5B (Cont.)

calls

☐ software call
▨ manual call
▨ failed

| 12 plex | calls | % |
|---------|-------|---|
| software call | 9 | 75 |
| manual call | 2 | 16.66 |
| failed | 1 | 8.33 |

Results 2c : CONCEPT-2

Fig 5C continued:
B3:19 Plex, 20080501

| ASSAY_ID | SAMPLE_ID | CALL | DESCRIPTION |
|---|---|---|---|
| ☑ rs10014076 | NA06987 | A | A.Conservative |
| ☑ rs10028716 | NA06987 | C | A.Conservative |
| ☑ rs1007716 | NA06987 | | D.Low Probability |
| ☑ rs10131894 | NA06987 | CG | A.Conservative |
| ☑ rs1014337 | NA06987 | T | A.Conservative |
| ☑ rs10251765 | NA06987 | GT | B.Moderate |
| ☑ rs10499226 | NA06987 | GC | A.Conservative |
| ☑ rs1063087 | NA06987 | CA | A.Conservative |
| ☑ rs10742993 | NA06987 | C | A.Conservative |
| ☑ rs10882763 | NA06987 | G | A.Conservative |
| ☑ rs11033260 | NA06987 | A | A.Conservative |
| ☑ rs11240574 | NA06987 | CT | A.Conservative |
| ☑ rs11634405 | NA06987 | G | A.Conservative |
| ☑ rs1222958 | NA06987 | G | A.Conservative |
| ☑ rs12334756 | NA06987 | GA | B.Moderate |
| ☑ rs1266886 | NA06987 | T | A.Conservative |
| ☑ rs12825566 | NA06987 | A | A.Conservative |
| ☑ rs1393257 | NA06987 | T | B.Moderate |
| ☑ rs1400130 | NA06987 | | D.Low Probability |

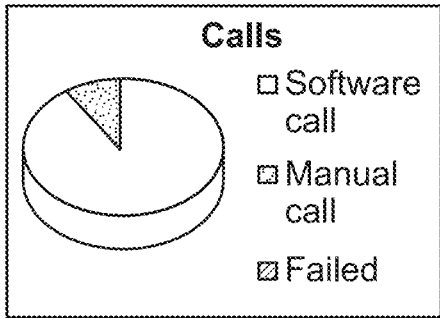

Calls
□ Software call
□ Manual call
☒ Failed

| 19plex | Calls | % |
|---|---|---|
| software call | 17 | 89.47 |
| manual call | 2 | 10.53 |
| failed | 0 | |

FIG. 5E

Results 2d : CONCEPT-2

Fig 5d continued:
B19: 35 Plex, 20080424

| ASSAY_ID | | | SAMPLE_ID | CALL | DESCRIPTION |
|---|---|---|---|---|---|
| ⊞ | ☑ | rs1000586 | NA06991 | | D.Low Probability |
| ⊞ | ☑ | rs10012004 | NA06991 | | N.No-Alleles |
| ⊞ | ☑ | rs10014076 | NA06991 | A | B.Moderate |
| ⊞ | ☑ | rs10027673 | NA06991 | | D.Low Probability |
| ⊞ | ☑ | rs10028716 | NA06991 | TC | C.Aggressive |
| ⊞ | ☑ | rs10063237 | NA06991 | | N.No-Alleles |
| ⊞ | ☑ | rs1007716 | NA06991 | A | B.Moderate |
| ⊞ | ☑ | rs10131894 | NA06991 | G | A.Conservative |
| ⊞ | ☑ | rs1014337 | NA06991 | GT | A.Conservative |
| ⊞ | ☑ | rs1015731 | NA06991 | | N.No-Alleles |
| ⊞ | ☑ | rs10164484 | NA06991 | | D.Low Probability |
| ⊞ | ☑ | rs10251765 | NA06991 | T | A.Conservative |
| ⊞ | ☑ | rs10265857 | NA06991 | | N.No-Alleles |
| ⊞ | ☑ | rs1032426 | NA06991 | | N.No-Alleles |
| ⊞ | ☑ | rs10495556 | NA06991 | | D.Low Probability |
| ⊞ | ☑ | rs10499226 | NA06991 | G | A.Conservative |
| ⊞ | ☑ | rs10505007 | NA06991 | | N.No-Alleles |
| ⊞ | ☑ | rs1063087 | NA06991 | C | B.Moderate |
| ⊞ | ☑ | rs10732346 | NA06991 | | D.Low Probability |
| ⊞ | ☑ | rs10742993 | NA06991 | TC | A.Conservative |
| ⊞ | ☑ | rs10882763 | NA06991 | GT | A.Conservative |
| ⊞ | ☑ | rs10911946 | NA06991 | | D.Low Probability |
| ⊞ | ☑ | rs11033260 | NA06991 | A | A.Conservative |
| ⊞ | ☑ | rs11240574 | NA06991 | CT | A.Conservative |
| ⊞ | ☑ | rs11599388 | NA06991 | A | C.Aggressive |
| ⊞ | ☑ | rs11634405 | NA06991 | GA | A.Conservative |
| ⊞ | ☑ | rs1222958 | NA06991 | A | A.Conservative |
| ⊞ | ☑ | rs12334756 | NA06991 | G | A.Conservative |
| ⊞ | ☑ | rs1266886 | NA06991 | C | A.Conservative |
| ⊞ | ☑ | rs12825566 | NA06991 | C | A.Conservative |
| ⊞ | ☑ | rs13023380 | NA06991 | | N.No-Alleles |
| ⊞ | ☑ | rs1393257 | NA06991 | C | A.Conservative |
| ⊞ | ☑ | rs1400130 | NA06991 | T | B.Moderate |
| ⊞ | ☑ | rs1490492 | NA06991 | T | B.Moderate |
| ⊞ | ☑ | rs1567603 | NA06991 | | D.Low Probability |

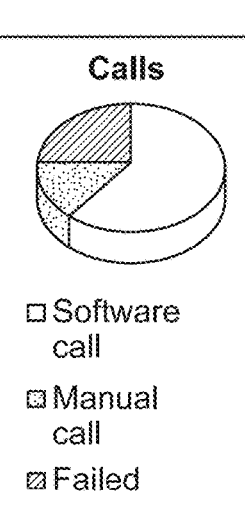

Calls

☐ Software call

☐ Manual call

☑ Failed

| 35plex | calls | % |
|---|---|---|
| software call | 21 | 60 |
| manual call | 5 | 14.29 |
| failed | 9 | 25.71 |

FIG. 5E (Cont.)

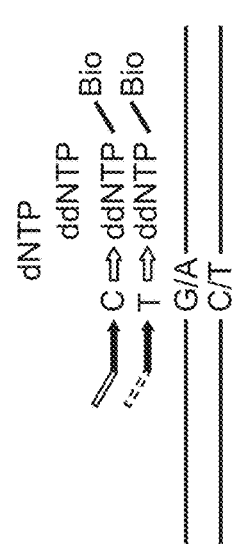
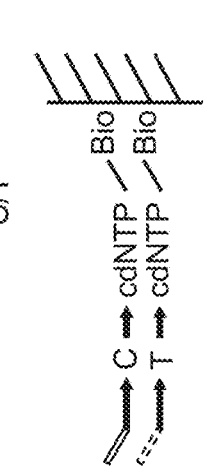
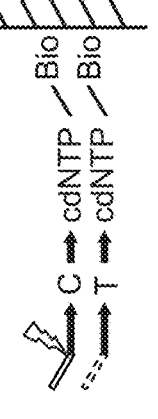
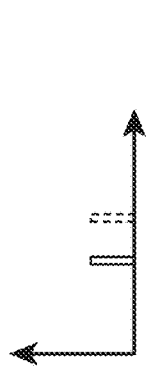
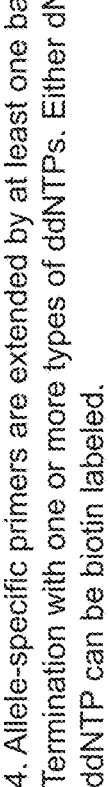

1. PCR amplification of region

2. SAP treatment to dephosphorylate unincorporated dNTPs

3. Allele-specific primers allele to PCR template

4. Allele-specific primers are extended by at least one base pair. Termination with one or more types of ddNTPs. Either dNTP or ddNTP can be biotin labeled.

5. Binding of extension product to solid support (e.g. streptavidin-coated beads), and subsequent removal of unextended oligos and reaction components.

6. Release of tag sequence 'mass tag' by cleavage of the primer

7. Allele specific mass tags identified by their mass difference in MA_DI-TOF MS

FIG. 6

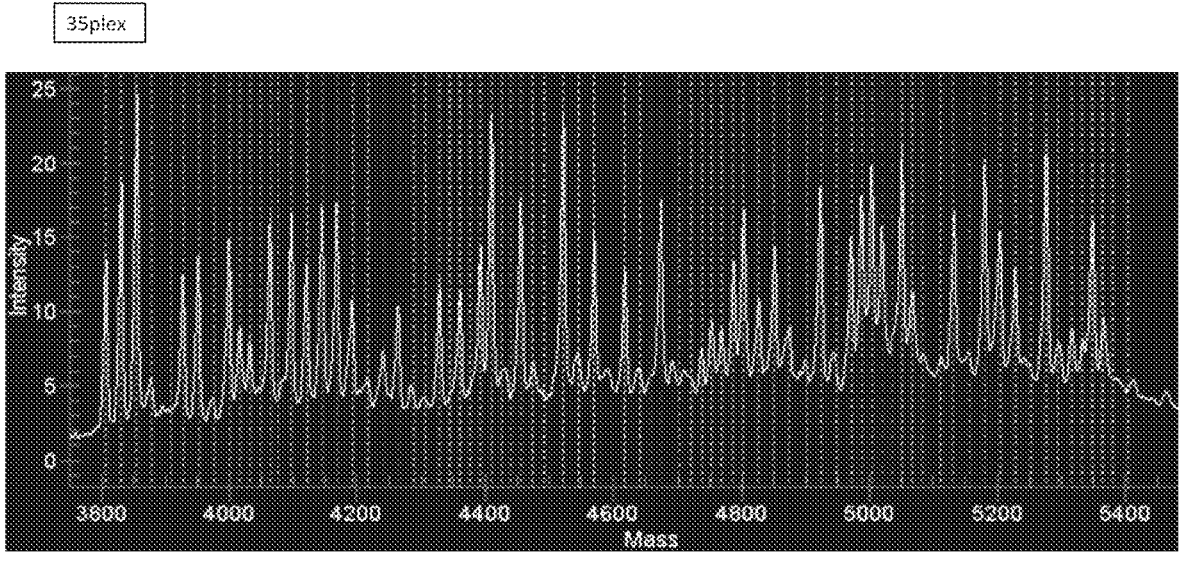
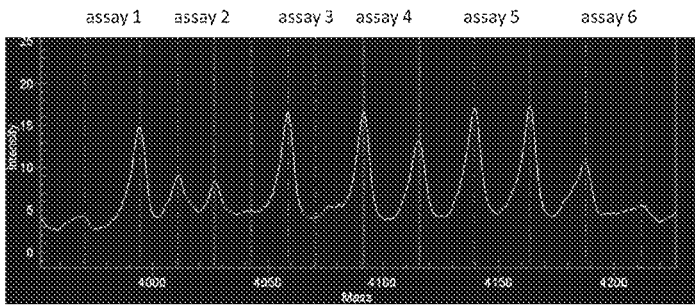
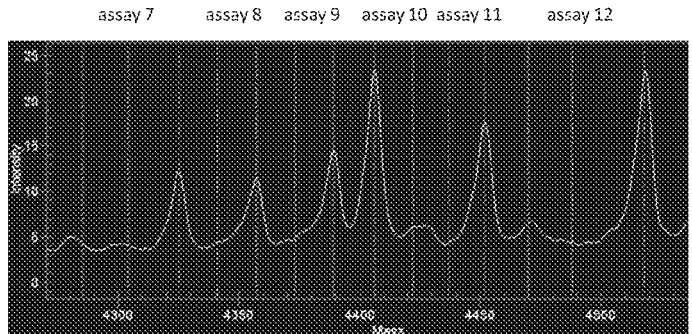
FIG. 7

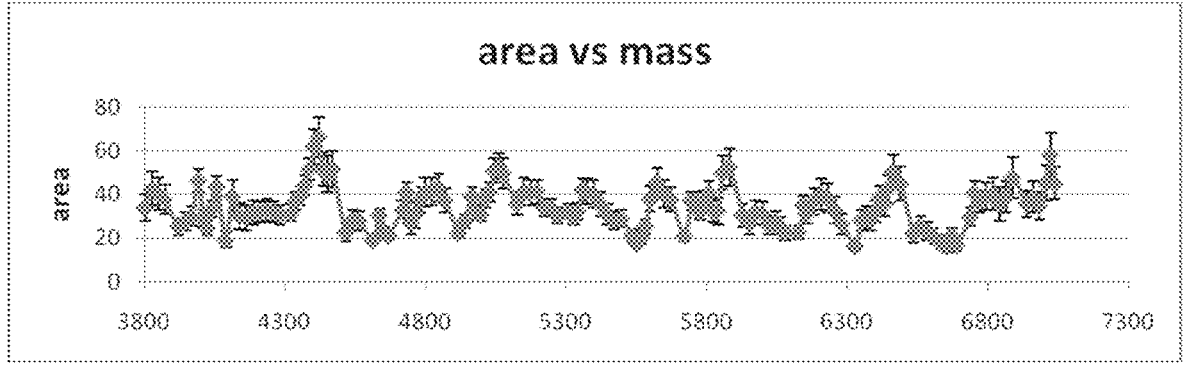
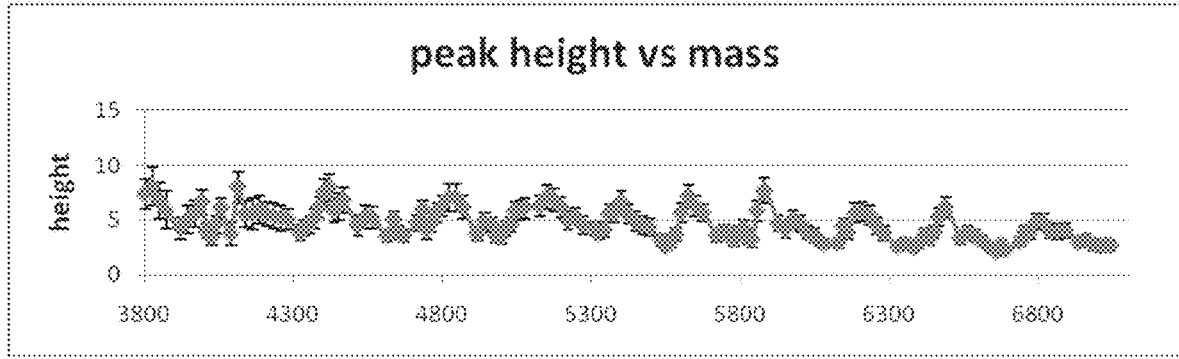
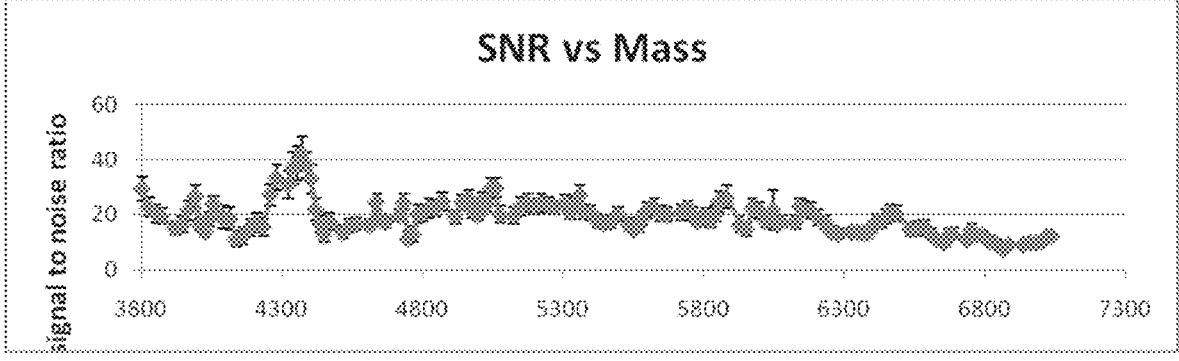
FIG. 9

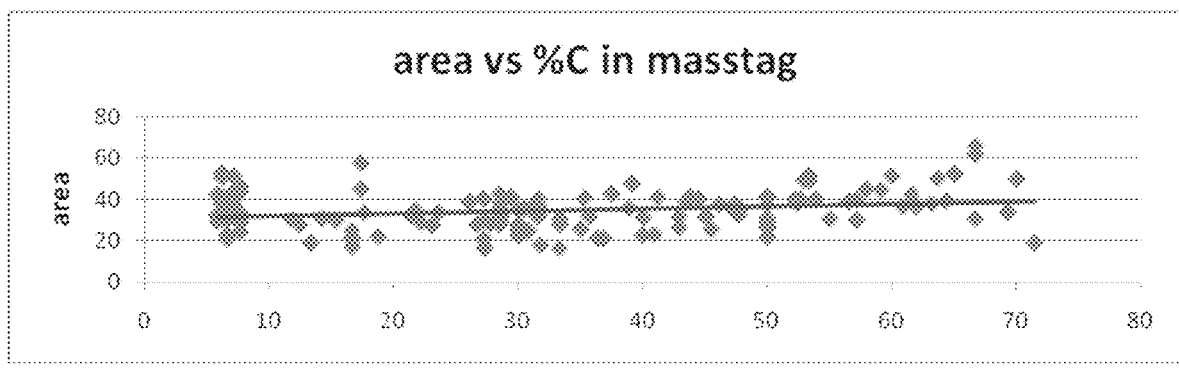
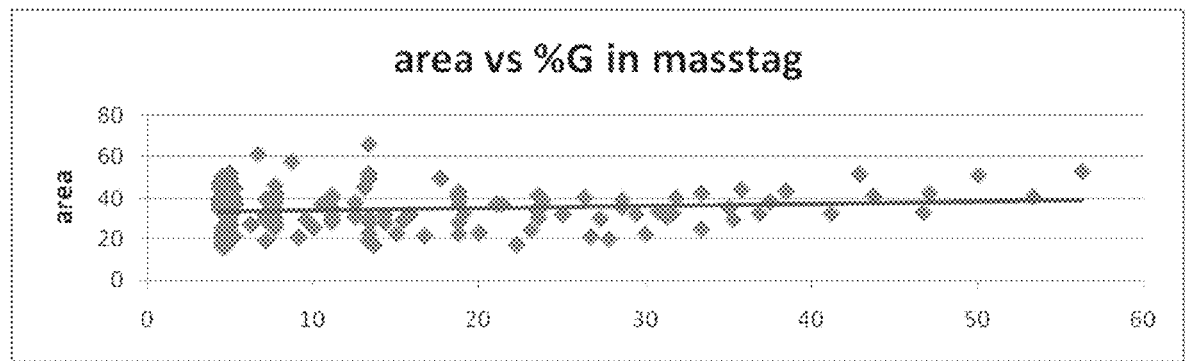
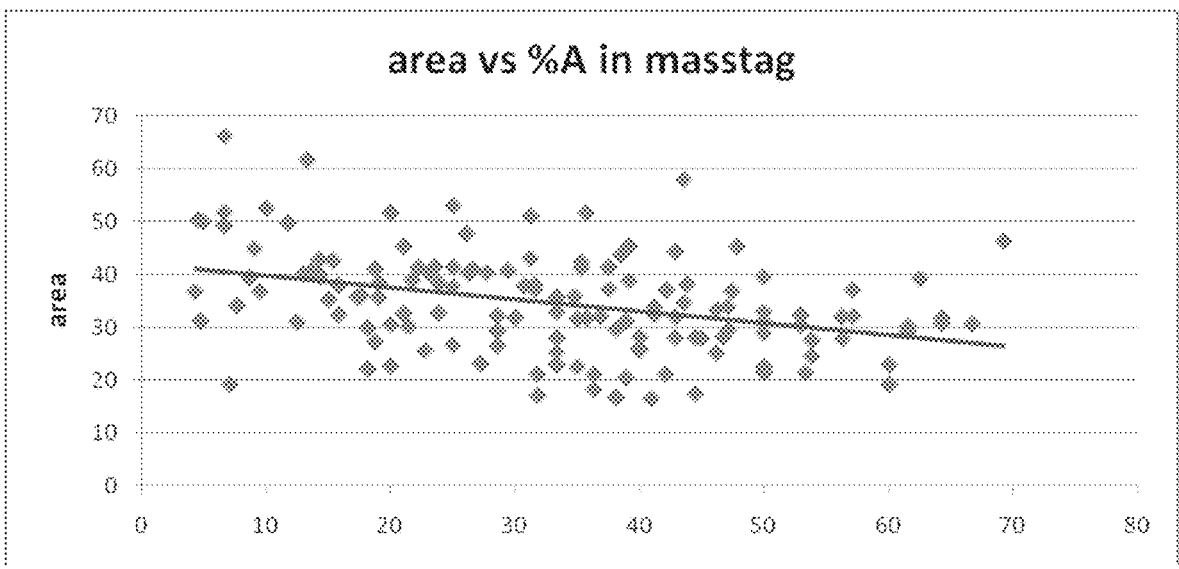
FIG. 10

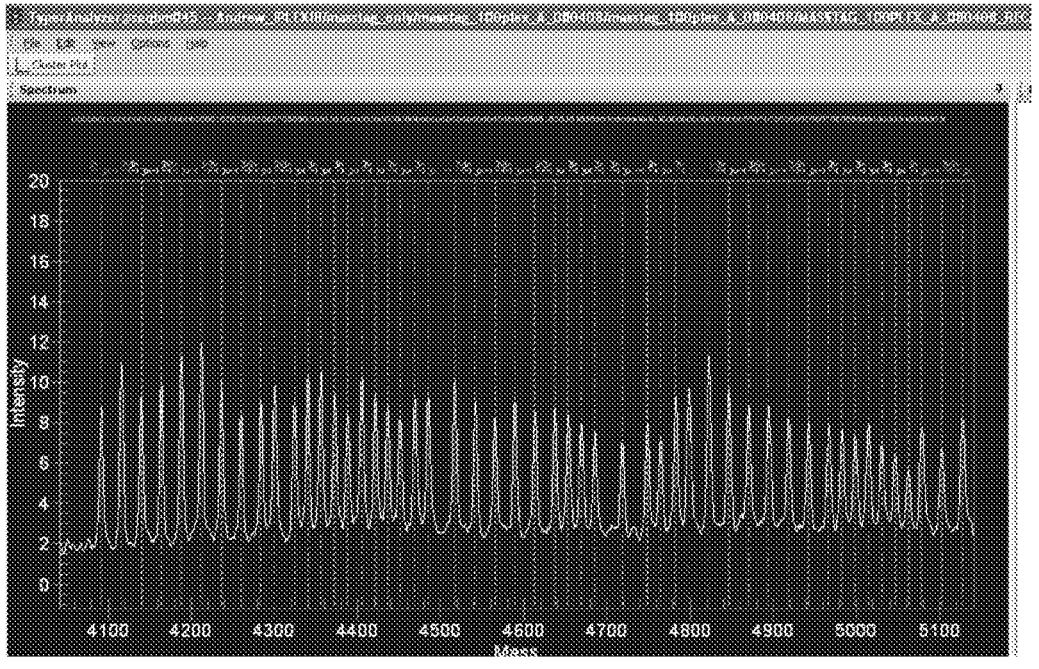
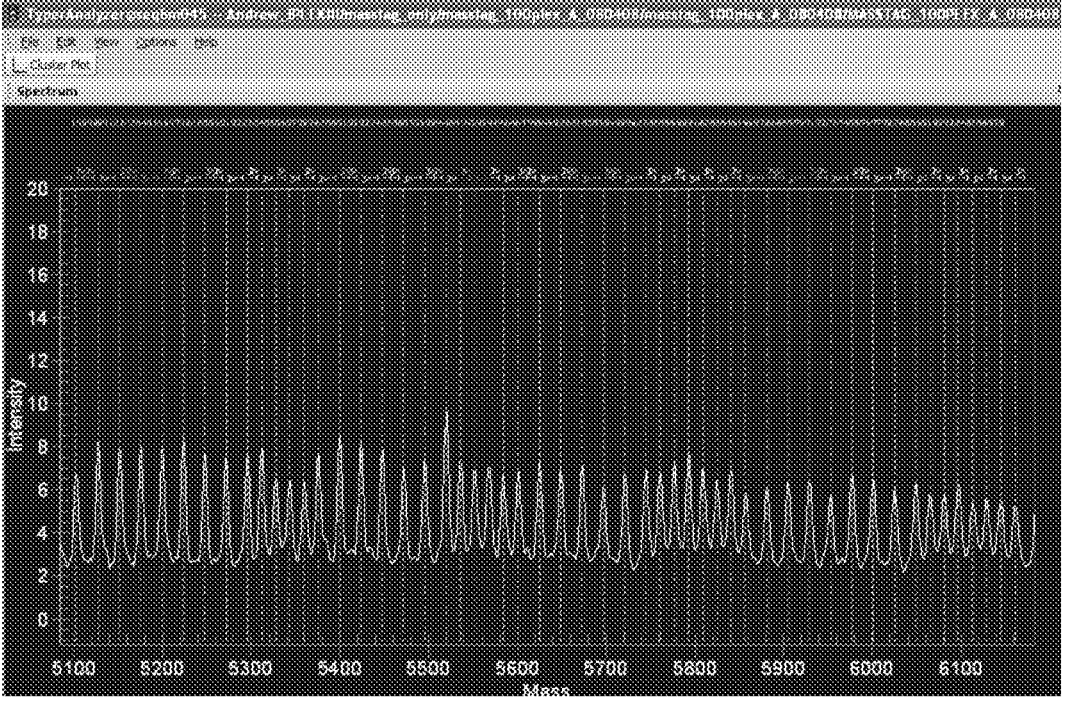
FIG. 11A

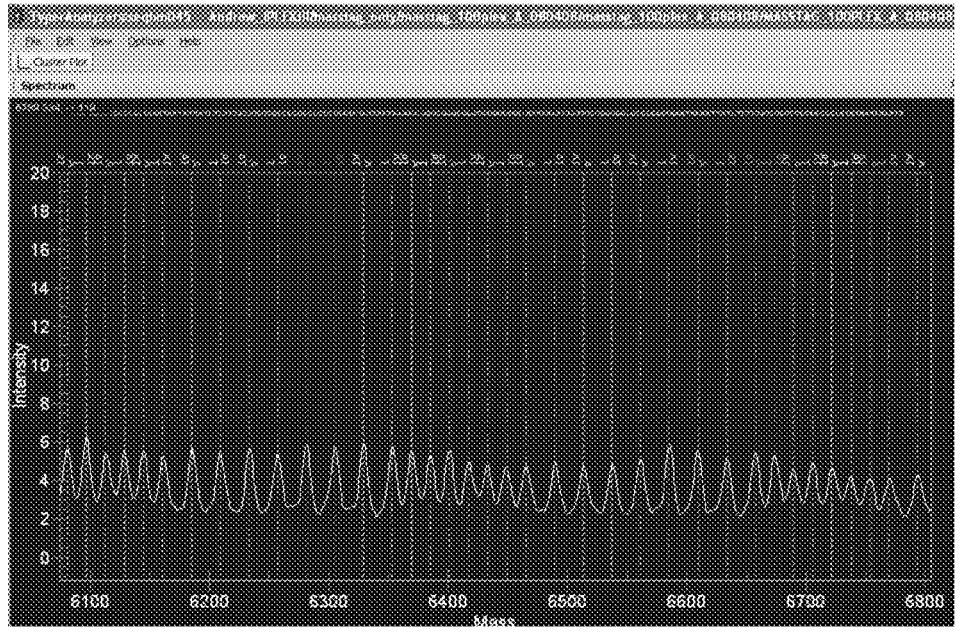
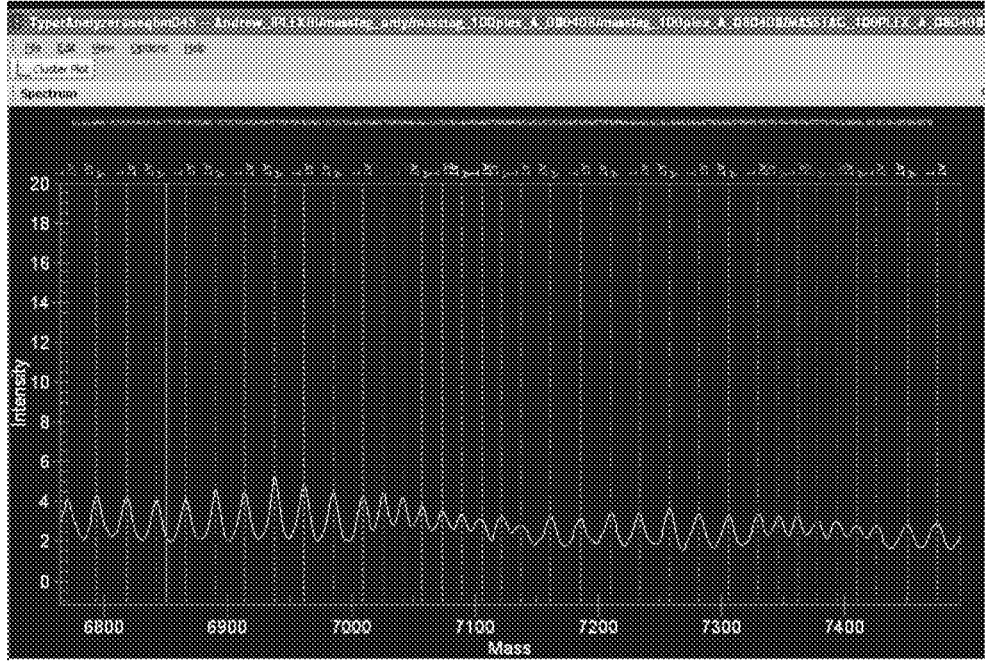
FIG. 11A (Cont.)

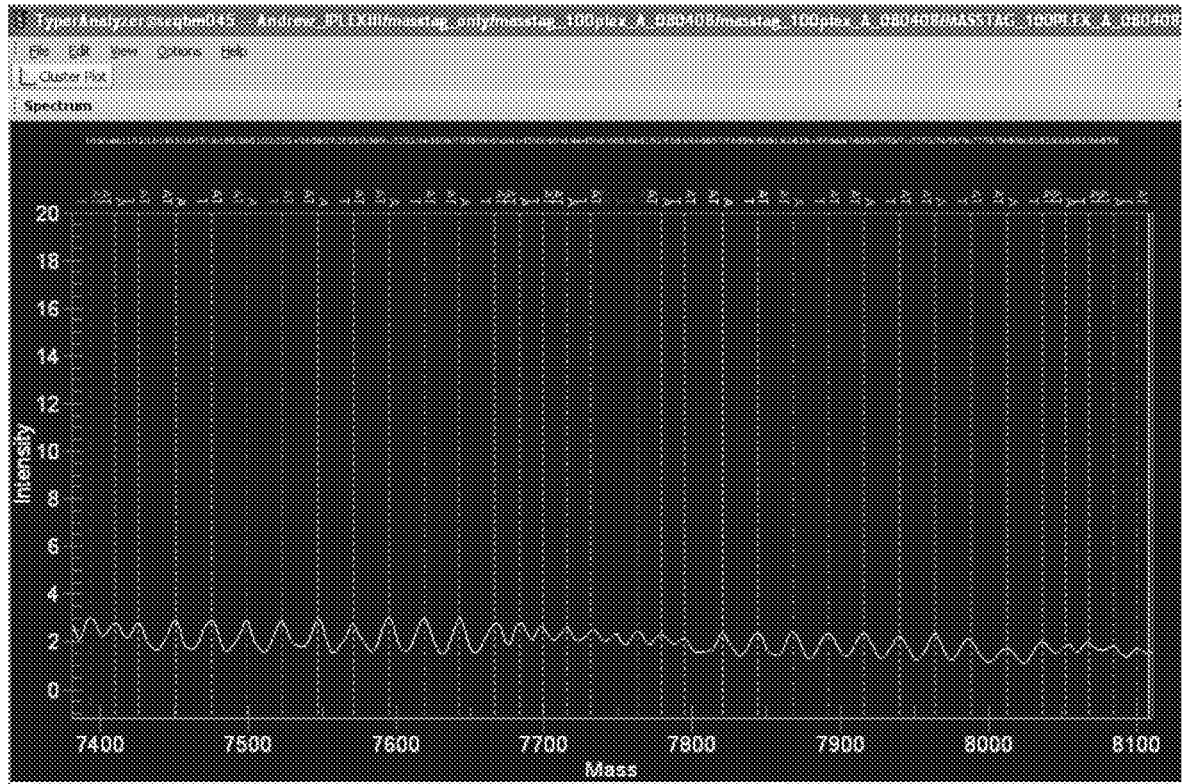
FIG. 11A (Cont. 1)

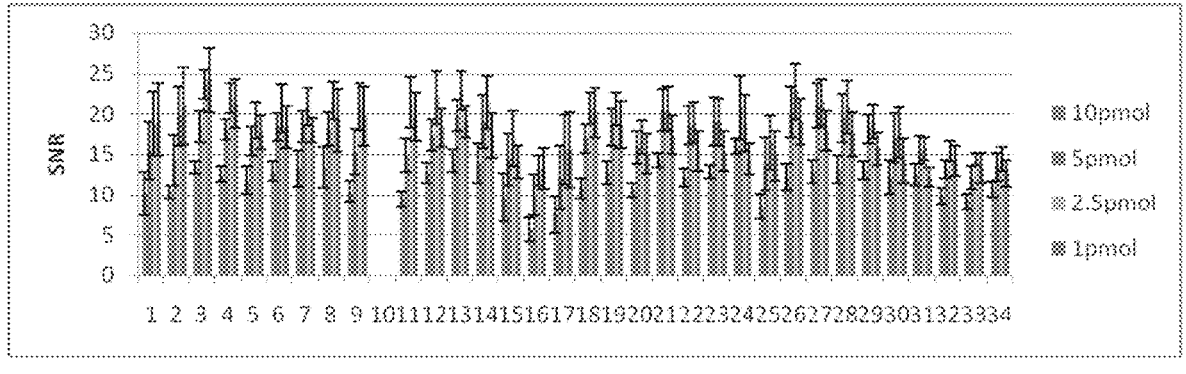
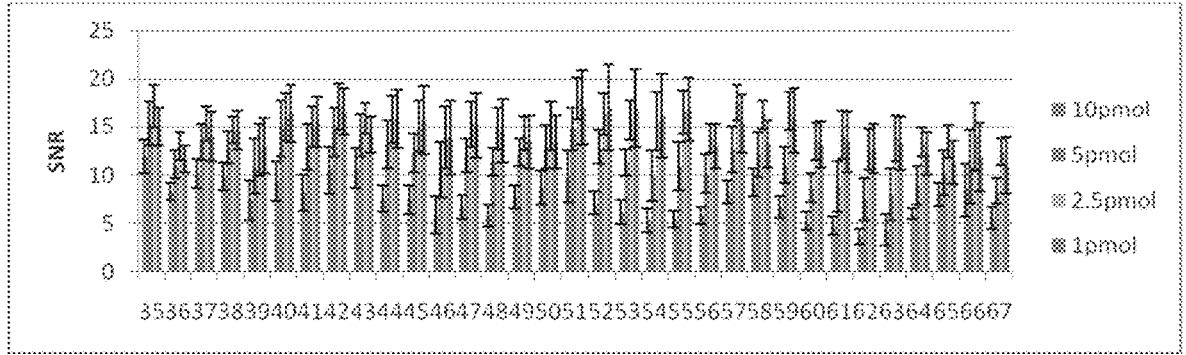
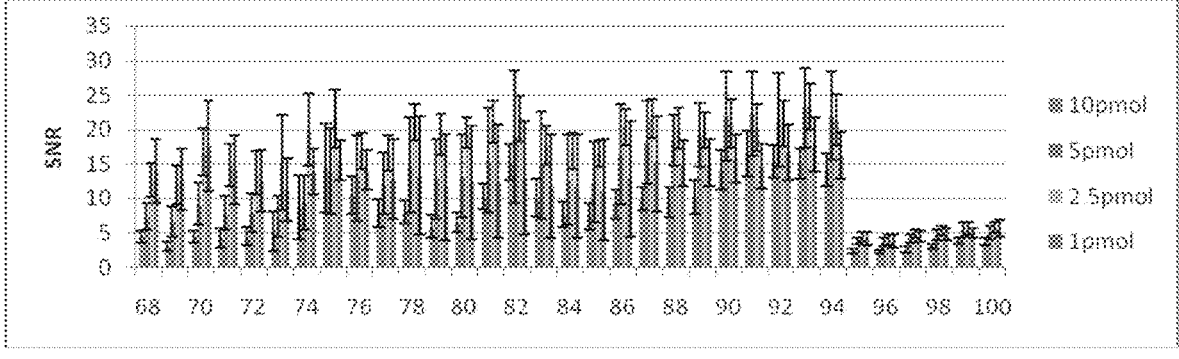
FIG. 11B

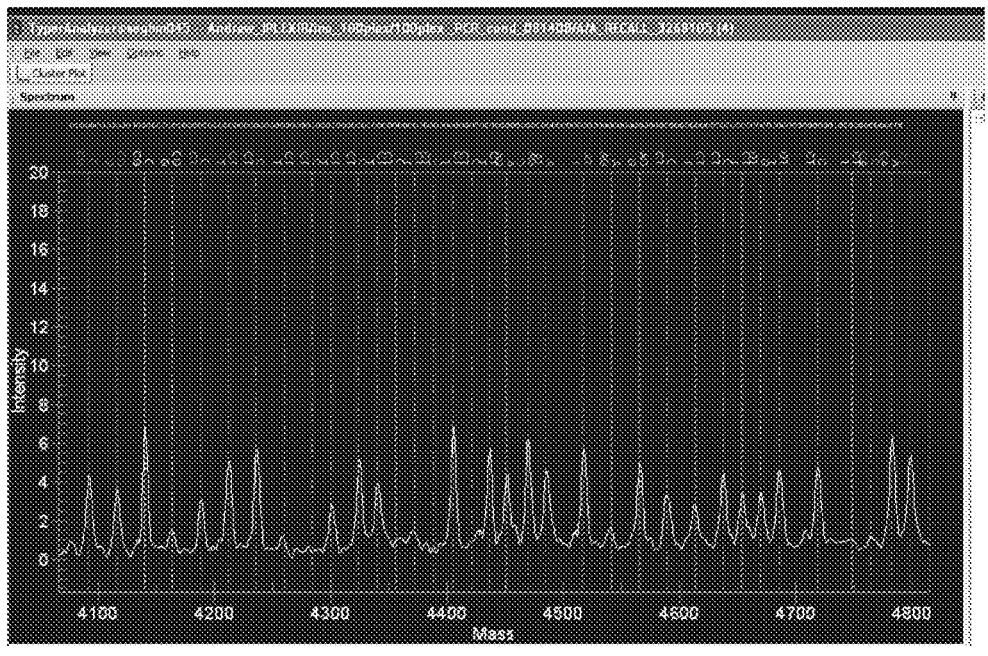
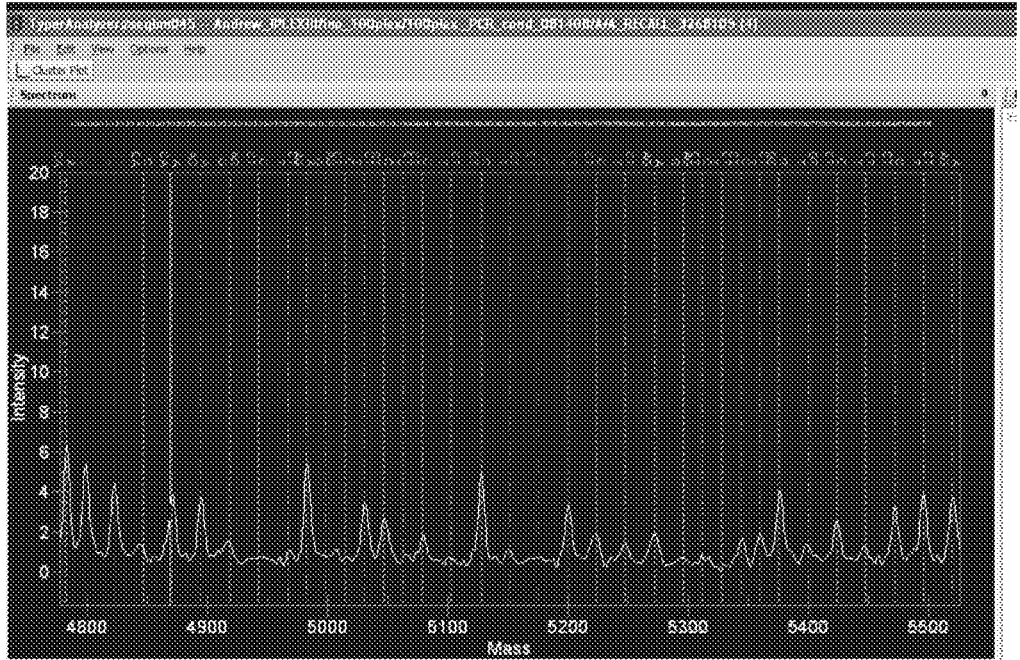
FIG. 11C

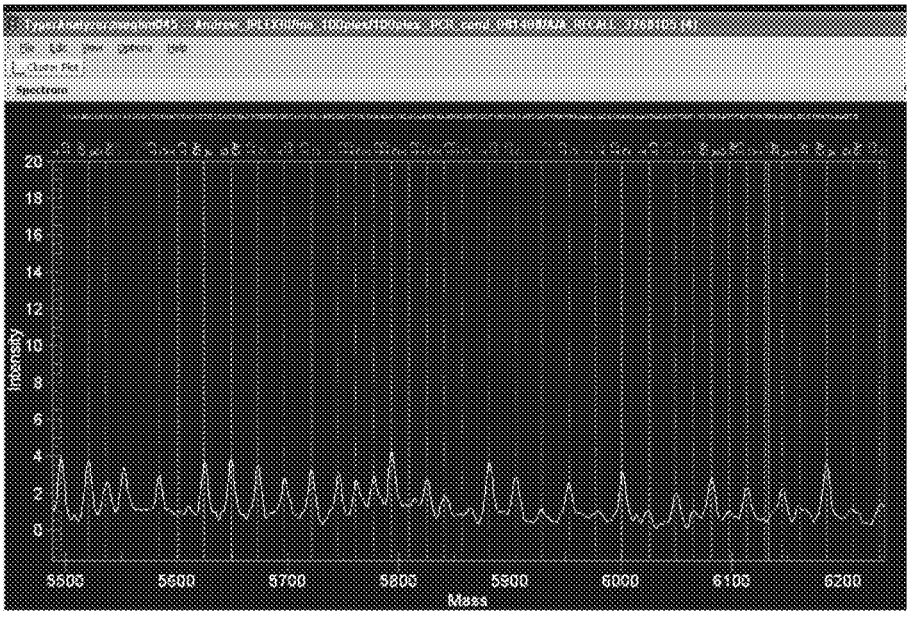
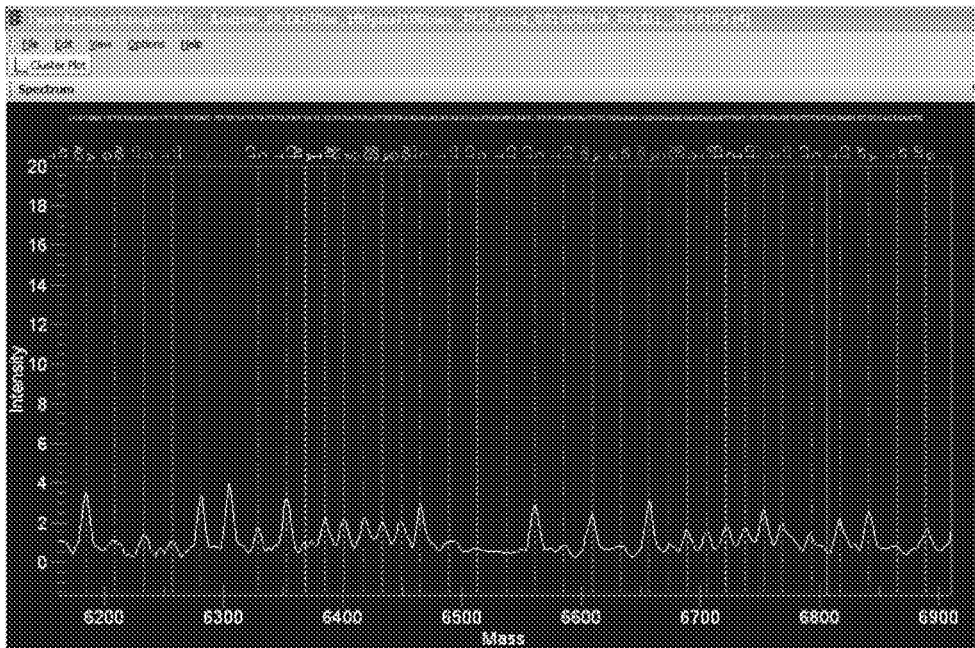
FIG. 11C (Cont.)

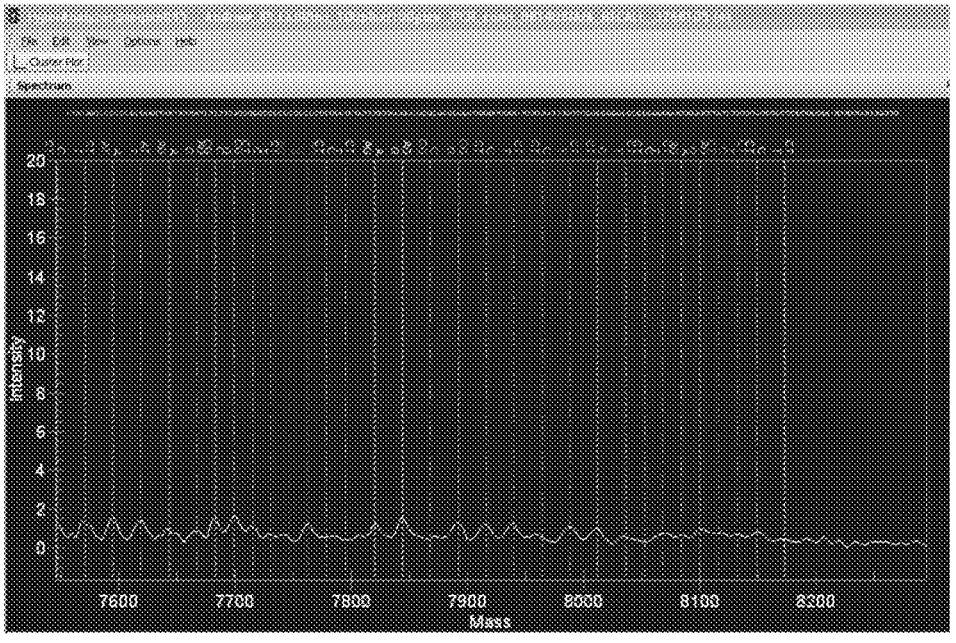
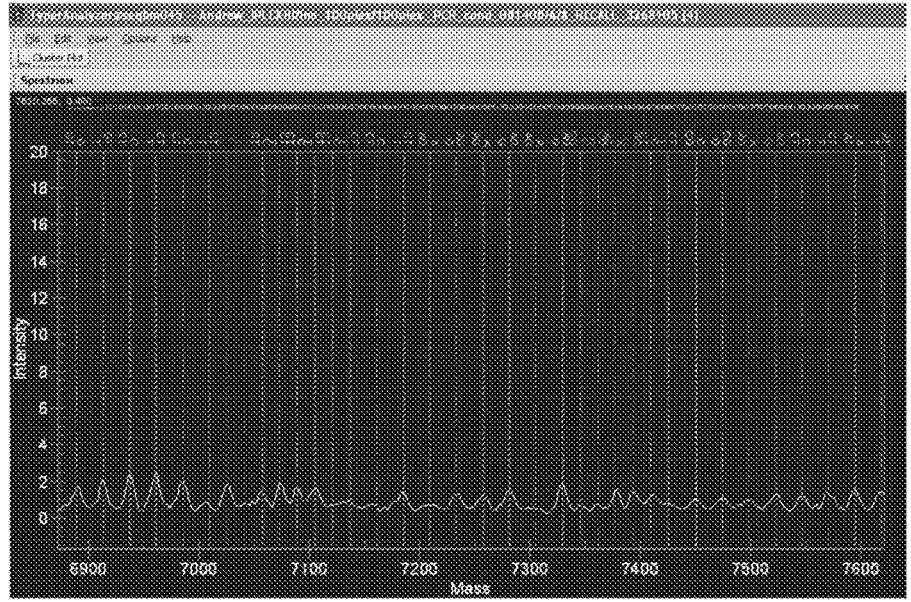
FIG. 11C (Cont. 1)

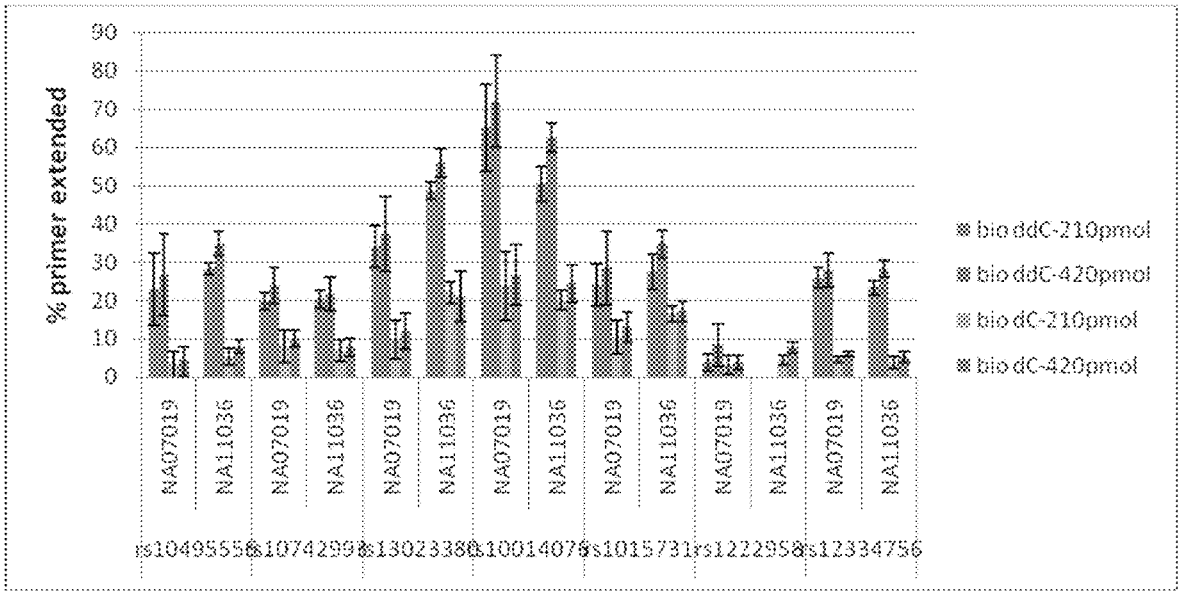
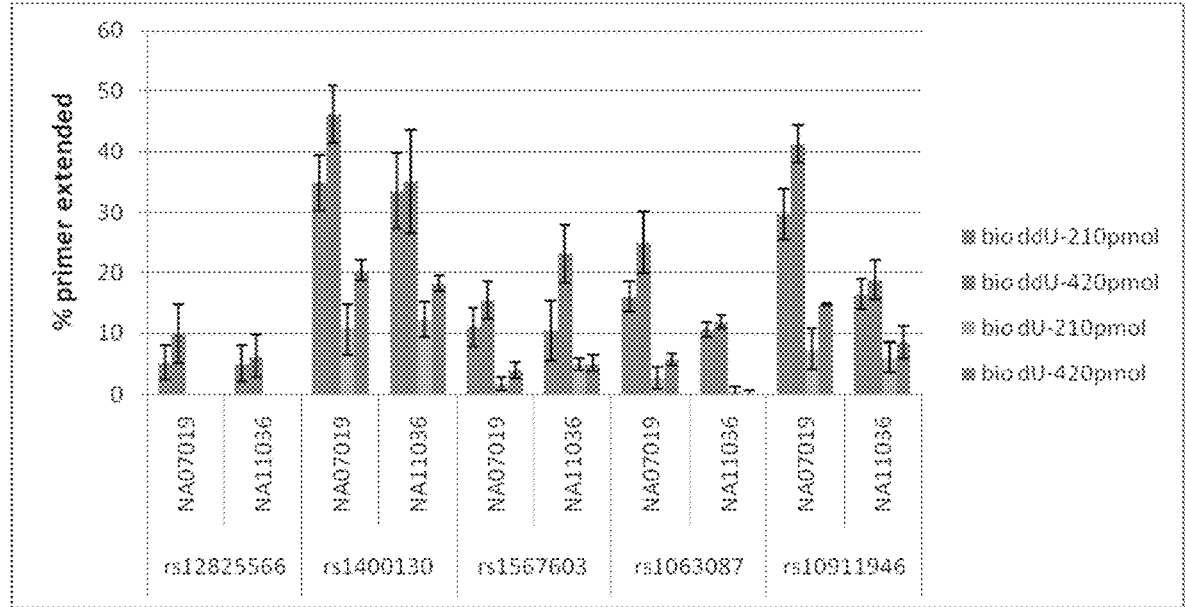
FIG. 13

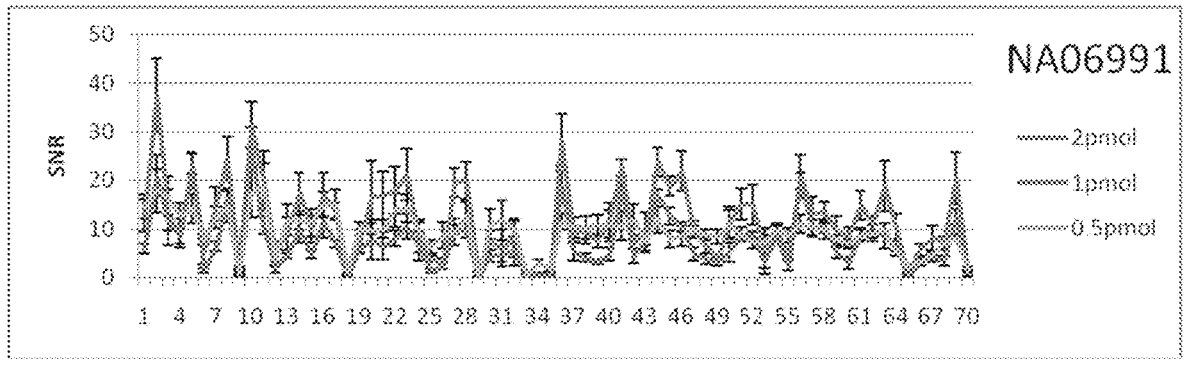
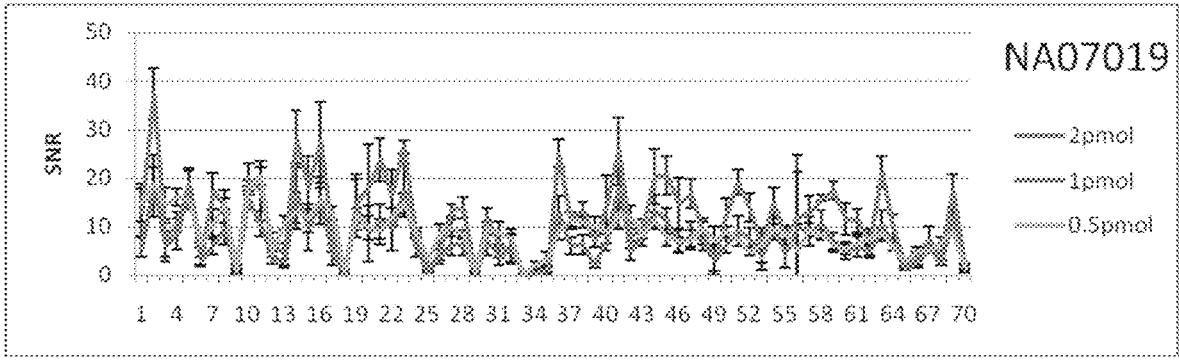
FIG. 18

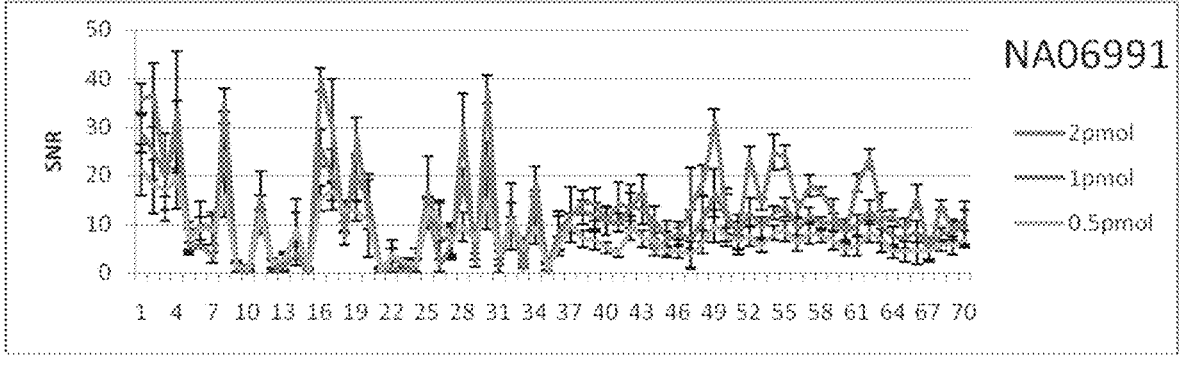
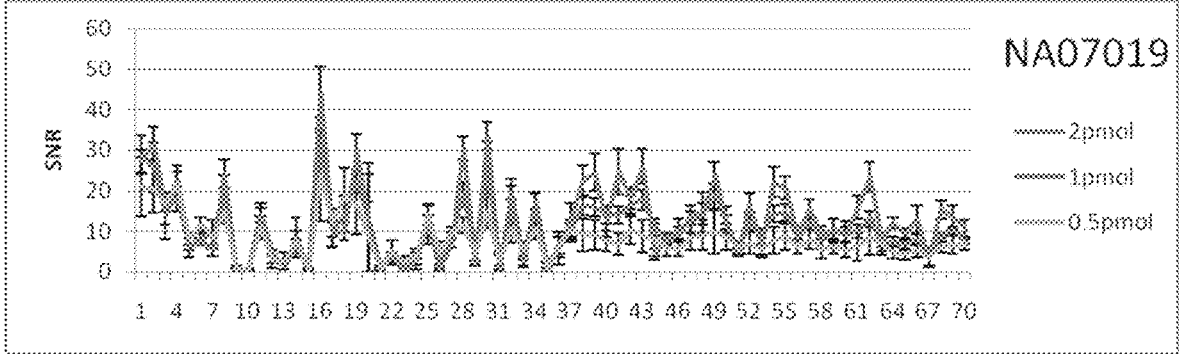
FIG. 19

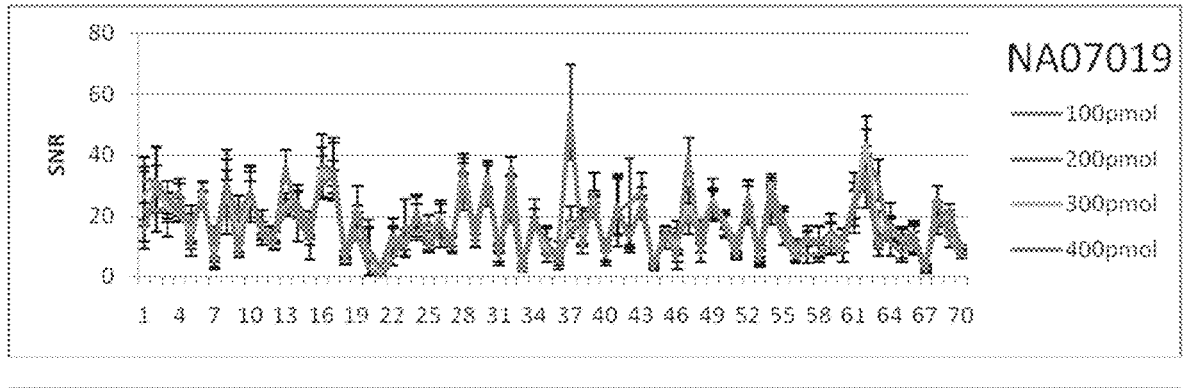
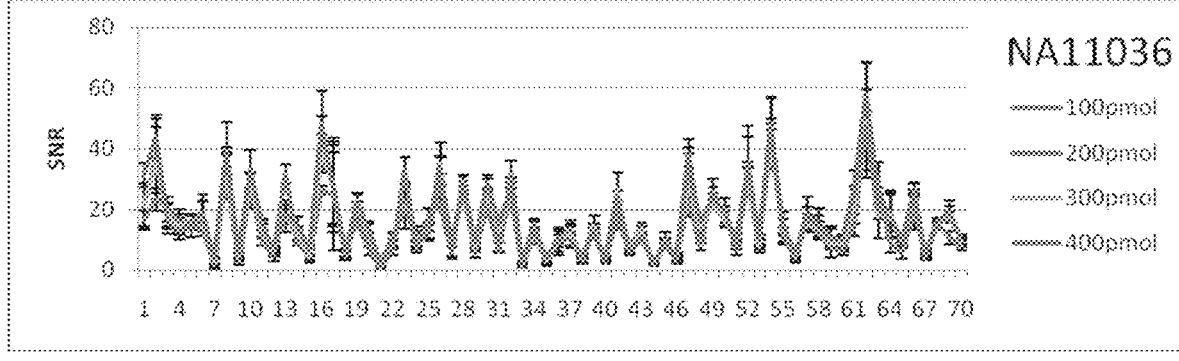
FIG. 20

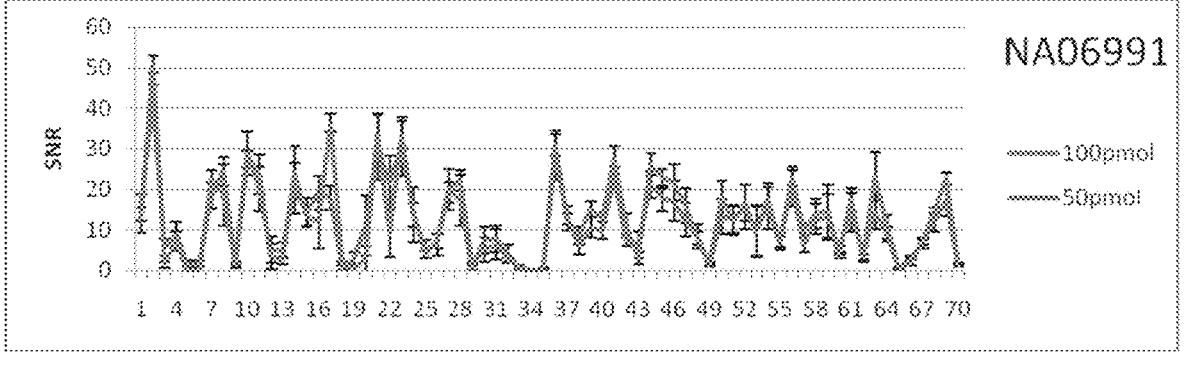
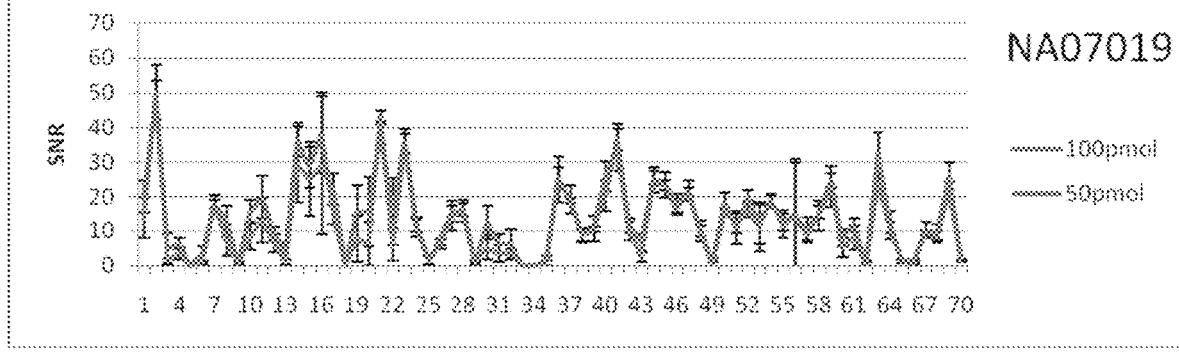
FIG. 21

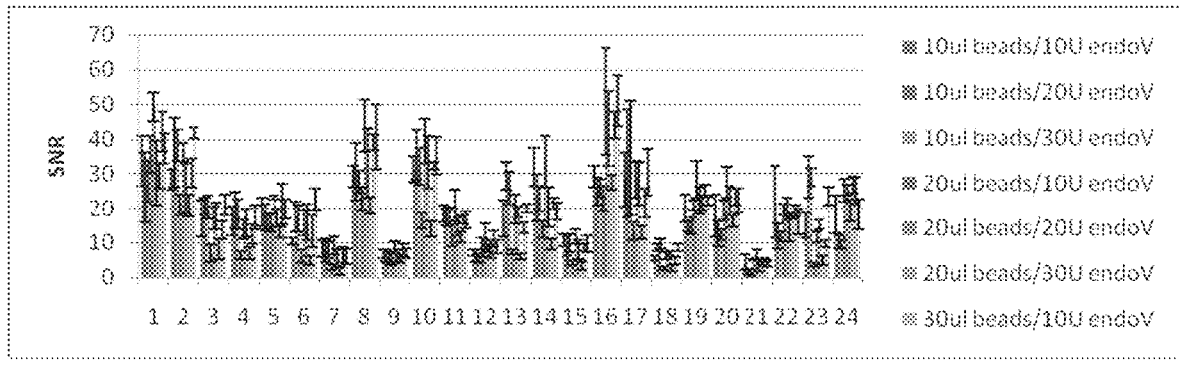
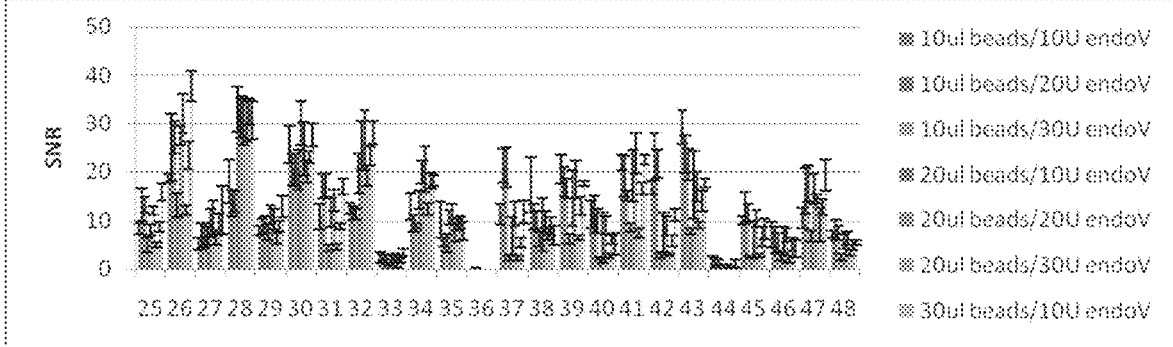
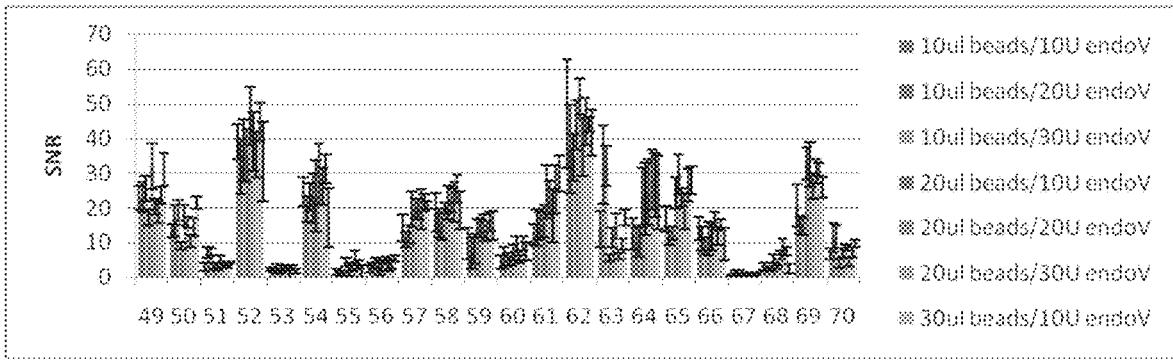
FIG. 24

Elute captured biotinylated extension product from the bead through competition with free biotin Magnet Removed purified eluant and dispense onto MassArray chip Detect mass of purified product through Matrix Assisted Laser Desorption Time of Flight mass spectrometry

FIG. 32A                    FIG. 32B

Competition assay with 1% rare allele :   Mutant – T, Competitor – A, WT – G

1% mutant – number of molecules (60 in 6000 molecules)
Assay: BRAF2 on cancer cell line sample 26D

SEQUENCE LISTING

```
Sequence total quantity: 339
SEQ ID NO: 1            moltype = DNA  length = 39
FEATURE                 Location/Qualifiers
misc_feature            1..39
                        note = Description of Artificial Sequence: Synthetic primer
source                  1..39
                        mol_type = other DNA
                        organism = synthetic construct
SEQUENCE: 1
ggaaacagct atgaccatgg taattgtact gtgagtggc                            39

SEQ ID NO: 2            moltype = DNA  length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 2
catgtcgttt tacaacgtcg tgc                                             23

SEQ ID NO: 3            moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 3
ggaaacagct atgaccatg                                                  19

SEQ ID NO: 4            moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 4
cacgacgttg taaaacgac                                                  19

SEQ ID NO: 5            moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 5
tcaaagaatt atatggctaa gg                                              22

SEQ ID NO: 6            moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 6
gagctgctgc accatattcc tgaac                                           25
```

```
SEQ ID NO: 7          moltype = DNA  length = 25
FEATURE               Location/Qualifiers
misc_feature          1..25
                      note = Description of Artificial Sequence: Synthetic primer
source                1..25
                      mol_type = other DNA
                      organism = synthetic construct
SEQUENCE: 7
gctctgaagg cggtgtatga catgg                                        25

SEQ ID NO: 8          moltype = DNA  length = 25
FEATURE               Location/Qualifiers
misc_feature          1..25
                      note = Description of Artificial Sequence: Synthetic primer
source                1..25
                      mol_type = other DNA
                      organism = synthetic construct
SEQUENCE: 8
gagctgctgc accatattcc tgaac                                        25

SEQ ID NO: 9          moltype = DNA  length = 25
FEATURE               Location/Qualifiers
misc_feature          1..25
                      note = Description of Artificial Sequence: Synthetic primer
source                1..25
                      mol_type = other DNA
                      organism = synthetic construct
SEQUENCE: 9
ccatgtcata caccgccttc agagc                                        25

SEQ ID NO: 10         moltype = DNA  length = 45
FEATURE               Location/Qualifiers
misc_feature          1..45
                      note = Description of Artificial Sequence: Synthetic primer
source                1..45
                      mol_type = other DNA
                      organism = synthetic construct
SEQUENCE: 10
gagctgctgc accatattcc tgaactctca aactccagag tggcc                  45

SEQ ID NO: 11         moltype = DNA  length = 47
FEATURE               Location/Qualifiers
misc_feature          1..47
                      note = Description of Artificial Sequence: Synthetic primer
source                1..47
                      mol_type = other DNA
                      organism = synthetic construct
SEQUENCE: 11
gagctgctgc accatattcc tgaacagcag tgcttcacac actttag                47

SEQ ID NO: 12         moltype = DNA  length = 46
FEATURE               Location/Qualifiers
misc_feature          1..46
                      note = Description of Artificial Sequence: Synthetic primer
source                1..46
                      mol_type = other DNA
                      organism = synthetic construct
SEQUENCE: 12
gagctgctgc accatattcc tgaacgtcct gatttctcct ccagag                 46

SEQ ID NO: 13         moltype = DNA  length = 48
FEATURE               Location/Qualifiers
misc_feature          1..48
                      note = Description of Artificial Sequence: Synthetic primer
source                1..48
                      mol_type = other DNA
                      organism = synthetic construct
SEQUENCE: 13
gagctgctgc accatattcc tgaacccctc ttgcataaaa tgttgcag              48

SEQ ID NO: 14         moltype = DNA  length = 53
FEATURE               Location/Qualifiers
misc_feature          1..53
                      note = Description of Artificial Sequence: Synthetic primer
source                1..53
                      mol_type = other DNA
                      organism = synthetic construct
SEQUENCE: 14
```

```
gagctgctgc accatattcc tgaaccatga agagaaatag ttctgaggtt tcc        53

SEQ ID NO: 15          moltype = DNA   length = 51
FEATURE                Location/Qualifiers
misc_feature           1..51
                       note = Description of Artificial Sequence: Synthetic primer
source                 1..51
                       mol_type = other DNA
                       organism = synthetic construct
SEQUENCE: 15
gagctgctgc accatattcc tgaacctgat agtaattgta ctgtgagtgg c          51

SEQ ID NO: 16          moltype = DNA   length = 62
FEATURE                Location/Qualifiers
misc_feature           1..62
                       note = Description of Artificial Sequence: Synthetic primer
source                 1..62
                       mol_type = other DNA
                       organism = synthetic construct
SEQUENCE: 16
gagctgctgc accatattcc tgaacctaaa aacttataat tttaatagag ggtgcattga  60
ag                                                                62

SEQ ID NO: 17          moltype = DNA   length = 45
FEATURE                Location/Qualifiers
misc_feature           1..45
                       note = Description of Artificial Sequence: Synthetic primer
source                 1..45
                       mol_type = other DNA
                       organism = synthetic construct
SEQUENCE: 17
gagctgctgc accatattcc tgaacacgta agcacacatc cccag               45

SEQ ID NO: 18          moltype = DNA   length = 52
FEATURE                Location/Qualifiers
misc_feature           1..52
                       note = Description of Artificial Sequence: Synthetic primer
source                 1..52
                       mol_type = other DNA
                       organism = synthetic construct
SEQUENCE: 18
gagctgctgc accatattcc tgaacgattt ctatcctcaa aaagcttatg gg         52

SEQ ID NO: 19          moltype = DNA   length = 56
FEATURE                Location/Qualifiers
misc_feature           1..56
                       note = Description of Artificial Sequence: Synthetic primer
source                 1..56
                       mol_type = other DNA
                       organism = synthetic construct
SEQUENCE: 19
gagctgctgc accatattcc tgaacgatga atcatcttac tctttagtat ggttgc     56

SEQ ID NO: 20          moltype = DNA   length = 46
FEATURE                Location/Qualifiers
misc_feature           1..46
                       note = Description of Artificial Sequence: Synthetic primer
source                 1..46
                       mol_type = other DNA
                       organism = synthetic construct
SEQUENCE: 20
gagctgctgc accatattcc tgaaccctgc cctttagaca ggaatc              46

SEQ ID NO: 21          moltype = DNA   length = 46
FEATURE                Location/Qualifiers
misc_feature           1..46
                       note = Description of Artificial Sequence: Synthetic primer
source                 1..46
                       mol_type = other DNA
                       organism = synthetic construct
SEQUENCE: 21
gagctgctgc accatattcc tgaaccatct gccttgatct cccttc              46

SEQ ID NO: 22          moltype = DNA   length = 46
FEATURE                Location/Qualifiers
misc_feature           1..46
                       note = Description of Artificial Sequence: Synthetic primer
source                 1..46
                       mol_type = other DNA
```

```
                      organism = synthetic construct
SEQUENCE: 22
gagctgctgc accatattcc tgaacccttc atgctcttct tcctgc                46

SEQ ID NO: 23             moltype = DNA  length = 78
FEATURE                   Location/Qualifiers
misc_feature              1..78
                          note = Description of Artificial Sequence: Synthetic primer
source                    1..78
                          mol_type = other DNA
                          organism = synthetic construct
SEQUENCE: 23
gagctgctgc accatattcc tgaacgctat ttttataata tttattattt taaataattc  60
aaaatacaaa agtaacac                                                78

SEQ ID NO: 24             moltype = DNA  length = 51
FEATURE                   Location/Qualifiers
misc_feature              1..51
                          note = Description of Artificial Sequence: Synthetic primer
source                    1..51
                          mol_type = other DNA
                          organism = synthetic construct
SEQUENCE: 24
gagctgctgc accatattcc tgaacctaga cattgggaat acataggagt g          51

SEQ ID NO: 25             moltype = DNA  length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 25
gagctgctgc accatattcc tgaacaactt gtacccagat gcagtc                46

SEQ ID NO: 26             moltype = DNA  length = 47
FEATURE                   Location/Qualifiers
misc_feature              1..47
                          note = Description of Artificial Sequence: Synthetic primer
source                    1..47
                          mol_type = other DNA
                          organism = synthetic construct
SEQUENCE: 26
gagctgctgc accatattcc tgaaccttct aaggcttcag ggatgac               47

SEQ ID NO: 27             moltype = DNA  length = 45
FEATURE                   Location/Qualifiers
misc_feature              1..45
                          note = Description of Artificial Sequence: Synthetic primer
source                    1..45
                          mol_type = other DNA
                          organism = synthetic construct
SEQUENCE: 27
gagctgctgc accatattcc tgaacgtact tgaaaagaag cccgg                 45

SEQ ID NO: 28             moltype = DNA  length = 47
FEATURE                   Location/Qualifiers
misc_feature              1..47
                          note = Description of Artificial Sequence: Synthetic primer
source                    1..47
                          mol_type = other DNA
                          organism = synthetic construct
SEQUENCE: 28
gagctgctgc accatattcc tgaacgatct ctctaccacc atcaggg               47

SEQ ID NO: 29             moltype = DNA  length = 48
FEATURE                   Location/Qualifiers
misc_feature              1..48
                          note = Description of Artificial Sequence: Synthetic primer
source                    1..48
                          mol_type = other DNA
                          organism = synthetic construct
SEQUENCE: 29
gagctgctgc accatattcc tgaacaggag tcactacatt cagggatg              48

SEQ ID NO: 30             moltype = DNA  length = 47
FEATURE                   Location/Qualifiers
misc_feature              1..47
                          note = Description of Artificial Sequence: Synthetic primer
```

```
source                    1..47
                          mol_type = other DNA
                          organism = synthetic construct
SEQUENCE: 30
gagctgctgc accatattcc tgaacgtgtc tcaggtgaaa gtgactc                    47

SEQ ID NO: 31             moltype = DNA   length = 49
FEATURE                   Location/Qualifiers
misc_feature              1..49
                          note = Description of Artificial Sequence: Synthetic primer
source                    1..49
                          mol_type = other DNA
                          organism = synthetic construct
SEQUENCE: 31
gagctgctgc accatattcc tgaaccttca ggattatact ggcagttgc                    49

SEQ ID NO: 32             moltype = DNA   length = 48
FEATURE                   Location/Qualifiers
misc_feature              1..48
                          note = Description of Artificial Sequence: Synthetic primer
source                    1..48
                          mol_type = other DNA
                          organism = synthetic construct
SEQUENCE: 32
gagctgctgc accatattcc tgaacgcttt gaatggtatc accctcac                    48

SEQ ID NO: 33             moltype = DNA   length = 45
FEATURE                   Location/Qualifiers
misc_feature              1..45
                          note = Description of Artificial Sequence: Synthetic primer
source                    1..45
                          mol_type = other DNA
                          organism = synthetic construct
SEQUENCE: 33
gagctgctgc accatattcc tgaacaaacg cagtcatcac tctcc                    45

SEQ ID NO: 34             moltype = DNA   length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 34
gagctgctgc accatattcc tgaacgggag cgggaatctt aaatcc                    46

SEQ ID NO: 35             moltype = DNA   length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 35
gagctgctgc accatattcc tgaacgcaac aggattcgac taaggc                    46

SEQ ID NO: 36             moltype = DNA   length = 54
FEATURE                   Location/Qualifiers
misc_feature              1..54
                          note = Description of Artificial Sequence: Synthetic primer
source                    1..54
                          mol_type = other DNA
                          organism = synthetic construct
SEQUENCE: 36
gagctgctgc accatattcc tgaaccatgt atatagtttg gctagcagtg aaag                    54

SEQ ID NO: 37             moltype = DNA   length = 50
FEATURE                   Location/Qualifiers
misc_feature              1..50
                          note = Description of Artificial Sequence: Synthetic primer
source                    1..50
                          mol_type = other DNA
                          organism = synthetic construct
SEQUENCE: 37
gagctgctgc accatattcc tgaacgaatc ctactcctaa ggtgatgttg                    50

SEQ ID NO: 38             moltype = DNA   length = 49
FEATURE                   Location/Qualifiers
misc_feature              1..49
```

```
                        note = Description of Artificial Sequence: Synthetic primer
source                  1..49
                        mol_type = other DNA
                        organism = synthetic construct
SEQUENCE: 38
gagctgctgc accatattcc tgaaccttca tcagcaagca actacattg                    49

SEQ ID NO: 39           moltype = DNA   length = 46
FEATURE                 Location/Qualifiers
misc_feature            1..46
                        note = Description of Artificial Sequence: Synthetic primer
source                  1..46
                        mol_type = other DNA
                        organism = synthetic construct
SEQUENCE: 39
gagctgctgc accatattcc tgaacgggtc caaaactgct catgtc                       46

SEQ ID NO: 40           moltype = DNA   length = 45
FEATURE                 Location/Qualifiers
misc_feature            1..45
                        note = Description of Artificial Sequence: Synthetic primer
source                  1..45
                        mol_type = other DNA
                        organism = synthetic construct
SEQUENCE: 40
gagctgctgc accatattcc tgaacttttt ccatggcttt tgggc                        45

SEQ ID NO: 41           moltype = DNA   length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 41
gagctgctgc accatattcc tgaactgtac aggcaggtct tagagatg                     48

SEQ ID NO: 42           moltype = DNA   length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 42
gagctgctgc accatattcc tgaacgtagc caattccttc agtgcag                      47

SEQ ID NO: 43           moltype = DNA   length = 45
FEATURE                 Location/Qualifiers
misc_feature            1..45
                        note = Description of Artificial Sequence: Synthetic primer
source                  1..45
                        mol_type = other DNA
                        organism = synthetic construct
SEQUENCE: 43
gagctgctgc accatattcc tgaacagggc ttgtttcagc ttgag                        45

SEQ ID NO: 44           moltype = DNA   length = 50
FEATURE                 Location/Qualifiers
misc_feature            1..50
                        note = Description of Artificial Sequence: Synthetic primer
source                  1..50
                        mol_type = other DNA
                        organism = synthetic construct
SEQUENCE: 44
gagctgctgc accatattcc tgaaccaaaa gttttgttta ggtgccttcc                   50

SEQ ID NO: 45           moltype = DNA   length = 50
FEATURE                 Location/Qualifiers
misc_feature            1..50
                        note = Description of Artificial Sequence: Synthetic primer
source                  1..50
                        mol_type = other DNA
                        organism = synthetic construct
SEQUENCE: 45
ggggagtgta ggttctggta cccaggctct gaaggcggtg tatgacatgg                   50

SEQ ID NO: 46           moltype = DNA   length = 76
FEATURE                 Location/Qualifiers
```

```
misc_feature          1..76
                      note = Description of Artificial Sequence: Synthetic primer
source                1..76
                      mol_type = other DNA
                      organism = synthetic construct
SEQUENCE: 46
catcacctat atcattattt actaaattat tttttcttca aactgactta ggctctgaag  60
gcggtgtatg acatgg                                                  76

SEQ ID NO: 47         moltype = DNA  length = 56
FEATURE               Location/Qualifiers
misc_feature          1..56
                      note = Description of Artificial Sequence: Synthetic primer
source                1..56
                      mol_type = other DNA
                      organism = synthetic construct
SEQUENCE: 47
cccttttttc ctaaaagccc ccaaactttt ggctctgaag gcggtgtatg acatgg       56

SEQ ID NO: 48         moltype = DNA  length = 53
FEATURE               Location/Qualifiers
misc_feature          1..53
                      note = Description of Artificial Sequence: Synthetic primer
source                1..53
                      mol_type = other DNA
                      organism = synthetic construct
SEQUENCE: 48
cttttgtgag ctggcttttg ctcatctcgc tctgaaggcg gtgtatgaca tgg          53

SEQ ID NO: 49         moltype = DNA  length = 59
FEATURE               Location/Qualifiers
misc_feature          1..59
                      note = Description of Artificial Sequence: Synthetic primer
source                1..59
                      mol_type = other DNA
                      organism = synthetic construct
SEQUENCE: 49
cctatttgag ttttgctttt ttgttttggt ctcggctctg aaggcggtgt atgacatgg    59

SEQ ID NO: 50         moltype = DNA  length = 56
FEATURE               Location/Qualifiers
misc_feature          1..56
                      note = Description of Artificial Sequence: Synthetic primer
source                1..56
                      mol_type = other DNA
                      organism = synthetic construct
SEQUENCE: 50
gatttagaca gagtcttact ctgtcaccag ggctctgaag gcggtgtatg acatgg       56

SEQ ID NO: 51         moltype = DNA  length = 58
FEATURE               Location/Qualifiers
misc_feature          1..58
                      note = Description of Artificial Sequence: Synthetic primer
source                1..58
                      mol_type = other DNA
                      organism = synthetic construct
SEQUENCE: 51
ctatactctt gctcgtggag ttaatctcag agggctctga aggcggtgta tgacatgg     58

SEQ ID NO: 52         moltype = DNA  length = 49
FEATURE               Location/Qualifiers
misc_feature          1..49
                      note = Description of Artificial Sequence: Synthetic primer
source                1..49
                      mol_type = other DNA
                      organism = synthetic construct
SEQUENCE: 52
ctcagaagtg tggaacagct gcccgctctg aaggcggtgt atgacatgg               49

SEQ ID NO: 53         moltype = DNA  length = 58
FEATURE               Location/Qualifiers
misc_feature          1..58
                      note = Description of Artificial Sequence: Synthetic primer
source                1..58
                      mol_type = other DNA
                      organism = synthetic construct
SEQUENCE: 53
cttgggactt caggtagact tagtttgaac atcgctctga aggcggtgta tgacatgg     58
```

```
SEQ ID NO: 54          moltype = DNA   length = 52
FEATURE                Location/Qualifiers
misc_feature           1..52
                       note = Description of Artificial Sequence: Synthetic primer
source                 1..52
                       mol_type = other DNA
                       organism = synthetic construct
SEQUENCE: 54
ccatctacat tagcttacca gggctgcgct ctgaaggcgg tgtatgacat gg           52

SEQ ID NO: 55          moltype = DNA   length = 53
FEATURE                Location/Qualifiers
misc_feature           1..53
                       note = Description of Artificial Sequence: Synthetic primer
source                 1..53
                       mol_type = other DNA
                       organism = synthetic construct
SEQUENCE: 55
ctctctaatg ttccagagaa accccagggc tctgaaggcg gtgtatgaca tgg          53

SEQ ID NO: 56          moltype = DNA   length = 52
FEATURE                Location/Qualifiers
misc_feature           1..52
                       note = Description of Artificial Sequence: Synthetic primer
source                 1..52
                       mol_type = other DNA
                       organism = synthetic construct
SEQUENCE: 56
cgttttctta tgtgtctggc ctcatccgct ctgaaggcgg tgtatgacat gg           52

SEQ ID NO: 57          moltype = DNA   length = 49
FEATURE                Location/Qualifiers
misc_feature           1..49
                       note = Description of Artificial Sequence: Synthetic primer
source                 1..49
                       mol_type = other DNA
                       organism = synthetic construct
SEQUENCE: 57
ggagcgctcc atgaaacaca acaggctctg aaggcggtgt atgacatgg              49

SEQ ID NO: 58          moltype = DNA   length = 54
FEATURE                Location/Qualifiers
misc_feature           1..54
                       note = Description of Artificial Sequence: Synthetic primer
source                 1..54
                       mol_type = other DNA
                       organism = synthetic construct
SEQUENCE: 58
gttgacagtt gattttgtaa tgcctccacg ctctgaaggc ggtgtatgac atgg         54

SEQ ID NO: 59          moltype = DNA   length = 54
FEATURE                Location/Qualifiers
misc_feature           1..54
                       note = Description of Artificial Sequence: Synthetic primer
source                 1..54
                       mol_type = other DNA
                       organism = synthetic construct
SEQUENCE: 59
cgatgtgatc ctgtgtcaaa taatgacggg ctctgaaggc ggtgtatgac atgg         54

SEQ ID NO: 60          moltype = DNA   length = 58
FEATURE                Location/Qualifiers
misc_feature           1..58
                       note = Description of Artificial Sequence: Synthetic primer
source                 1..58
                       mol_type = other DNA
                       organism = synthetic construct
SEQUENCE: 60
ctgaagggaa tggctggttt ttaatttgta gtggctctga aggcggtgta tgacatgg     58

SEQ ID NO: 61          moltype = DNA   length = 52
FEATURE                Location/Qualifiers
misc_feature           1..52
                       note = Description of Artificial Sequence: Synthetic primer
source                 1..52
                       mol_type = other DNA
                       organism = synthetic construct
SEQUENCE: 61
gaaggtggga ttacgcctaa ctttagggct ctgaaggcgg tgtatgacat gg           52
```

```
SEQ ID NO: 62            moltype = DNA   length = 45
FEATURE                  Location/Qualifiers
misc_feature             1..45
                         note = Description of Artificial Sequence: Synthetic primer
source                   1..45
                         mol_type = other DNA
                         organism = synthetic construct
SEQUENCE: 62
gacttcatgg ctggcagaaa gctctgaagg cggtgtatga catgg                       45

SEQ ID NO: 63            moltype = DNA   length = 51
FEATURE                  Location/Qualifiers
misc_feature             1..51
                         note = Description of Artificial Sequence: Synthetic primer
source                   1..51
                         mol_type = other DNA
                         organism = synthetic construct
SEQUENCE: 63
ctgcatttct actggtaaca tgcgccgctc tgaaggcggt gtatgacatg g               51

SEQ ID NO: 64            moltype = DNA   length = 67
FEATURE                  Location/Qualifiers
misc_feature             1..67
                         note = Description of Artificial Sequence: Synthetic primer
source                   1..67
                         mol_type = other DNA
                         organism = synthetic construct
SEQUENCE: 64
ctattcaggt gtcacttttta ttatgattat ctaaggtcag tggctctgaa ggcggtgtat   60
gacatgg                                                                 67

SEQ ID NO: 65            moltype = DNA   length = 54
FEATURE                  Location/Qualifiers
misc_feature             1..54
                         note = Description of Artificial Sequence: Synthetic primer
source                   1..54
                         mol_type = other DNA
                         organism = synthetic construct
SEQUENCE: 65
caggtccagt tcttgagttt catcctttcg ctctgaaggc ggtgtatgac atgg            54

SEQ ID NO: 66            moltype = DNA   length = 59
FEATURE                  Location/Qualifiers
misc_feature             1..59
                         note = Description of Artificial Sequence: Synthetic primer
source                   1..59
                         mol_type = other DNA
                         organism = synthetic construct
SEQUENCE: 66
cctctctgtt ttgttgagaa atccactctt ggtcgctctg aaggcggtgt atgacatgg      59

SEQ ID NO: 67            moltype = DNA   length = 56
FEATURE                  Location/Qualifiers
misc_feature             1..56
                         note = Description of Artificial Sequence: Synthetic primer
source                   1..56
                         mol_type = other DNA
                         organism = synthetic construct
SEQUENCE: 67
gcaaatgggt atggtttag ccagaaacat ggctctgaag gcggtgtatg acatgg          56

SEQ ID NO: 68            moltype = DNA   length = 45
FEATURE                  Location/Qualifiers
misc_feature             1..45
                         note = Description of Artificial Sequence: Synthetic primer
source                   1..45
                         mol_type = other DNA
                         organism = synthetic construct
SEQUENCE: 68
ggtgatggac ccactgcctg gctctgaagg cggtgtatga catgg                      45

SEQ ID NO: 69            moltype = DNA   length = 47
FEATURE                  Location/Qualifiers
misc_feature             1..47
                         note = Description of Artificial Sequence: Synthetic primer
source                   1..47
                         mol_type = other DNA
                         organism = synthetic construct
```

-continued

```
SEQUENCE: 69
gtgacctgac actggtggga tggctctgaa ggcggtgtat gacatgg                47

SEQ ID NO: 70          moltype = DNA   length = 54
FEATURE                Location/Qualifiers
misc_feature           1..54
                       note = Description of Artificial Sequence: Synthetic primer
source                 1..54
                       mol_type = other DNA
                       organism = synthetic construct
SEQUENCE: 70
gctttgtgtg caaatcacct attttcctgg ctctgaaggc ggtgtatgac atgg         54

SEQ ID NO: 71          moltype = DNA   length = 56
FEATURE                Location/Qualifiers
misc_feature           1..56
                       note = Description of Artificial Sequence: Synthetic primer
source                 1..56
                       mol_type = other DNA
                       organism = synthetic construct
SEQUENCE: 71
ggtgagagaa tatgaaagca aaacagcaac cgctctgaag gcggtgtatg acatgg       56

SEQ ID NO: 72          moltype = DNA   length = 53
FEATURE                Location/Qualifiers
misc_feature           1..53
                       note = Description of Artificial Sequence: Synthetic primer
source                 1..53
                       mol_type = other DNA
                       organism = synthetic construct
SEQUENCE: 72
gggctatgta gacacttcaa aggtgttcgc tctgaaggcg gtgtatgaca tgg          53

SEQ ID NO: 73          moltype = DNA   length = 53
FEATURE                Location/Qualifiers
misc_feature           1..53
                       note = Description of Artificial Sequence: Synthetic primer
source                 1..53
                       mol_type = other DNA
                       organism = synthetic construct
SEQUENCE: 73
gtttgctcta gctcaatggc ctcttaaggc tctgaaggcg gtgtatgaca tgg          53

SEQ ID NO: 74          moltype = DNA   length = 52
FEATURE                Location/Qualifiers
misc_feature           1..52
                       note = Description of Artificial Sequence: Synthetic primer
source                 1..52
                       mol_type = other DNA
                       organism = synthetic construct
SEQUENCE: 74
ccaacacagt catctgatcc catctccgct ctgaaggcgg tgtatgacat gg           52

SEQ ID NO: 75          moltype = DNA   length = 53
FEATURE                Location/Qualifiers
misc_feature           1..53
                       note = Description of Artificial Sequence: Synthetic primer
source                 1..53
                       mol_type = other DNA
                       organism = synthetic construct
SEQUENCE: 75
gtaggcaagg ctgttctttt ttgtgttggc tctgaaggcg gtgtatgaca tgg          53

SEQ ID NO: 76          moltype = DNA   length = 53
FEATURE                Location/Qualifiers
misc_feature           1..53
                       note = Description of Artificial Sequence: Synthetic primer
source                 1..53
                       mol_type = other DNA
                       organism = synthetic construct
SEQUENCE: 76
ccatatgcag tttttgtttt cccagtgcgc tctgaaggcg gtgtatgaca tgg          53

SEQ ID NO: 77          moltype = DNA   length = 67
FEATURE                Location/Qualifiers
misc_feature           1..67
                       note = Description of Artificial Sequence: Synthetic primer
source                 1..67
                       mol_type = other DNA
```

```
                       organism = synthetic construct
SEQUENCE: 77
caccataata gtttatctgc ttctactaaa attattattg gcgctctgaa ggcggtgtat   60
gacatgg                                                             67

SEQ ID NO: 78          moltype = DNA   length = 62
FEATURE                Location/Qualifiers
misc_feature           1..62
                       note = Description of Artificial Sequence: Synthetic primer
source                 1..62
                       mol_type = other DNA
                       organism = synthetic construct
SEQUENCE: 78
cctcagaatg aaatcatgct tttctgctaa tttgtaggct ctgaaggcgg tgtatgacat   60
gg                                                                  62

SEQ ID NO: 79          moltype = DNA   length = 54
FEATURE                Location/Qualifiers
misc_feature           1..54
                       note = Description of Artificial Sequence: Synthetic primer
source                 1..54
                       mol_type = other DNA
                       organism = synthetic construct
SEQUENCE: 79
ccttcagaca taccttggga aaatgtcagg ctctgaaggc ggtgtatgac atgg         54

SEQ ID NO: 80          moltype = DNA   length = 15
FEATURE                Location/Qualifiers
misc_feature           1..15
                       note = Description of Artificial Sequence: Synthetic primer
source                 1..15
                       mol_type = other DNA
                       organism = synthetic construct
SEQUENCE: 80
ccttcttcat ccccc                                                    15

SEQ ID NO: 81          moltype = DNA   length = 15
FEATURE                Location/Qualifiers
misc_feature           1..15
                       note = Description of Artificial Sequence: Synthetic primer
source                 1..15
                       mol_type = other DNA
                       organism = synthetic construct
SEQUENCE: 81
gcccataagc caaca                                                    15

SEQ ID NO: 82          moltype = DNA   length = 15
FEATURE                Location/Qualifiers
misc_feature           1..15
                       note = Description of Artificial Sequence: Synthetic primer
source                 1..15
                       mol_type = other DNA
                       organism = synthetic construct
SEQUENCE: 82
gtcccaaggg agagc                                                    15

SEQ ID NO: 83          moltype = DNA   length = 16
FEATURE                Location/Qualifiers
misc_feature           1..16
                       note = Description of Artificial Sequence: Synthetic primer
source                 1..16
                       mol_type = other DNA
                       organism = synthetic construct
SEQUENCE: 83
ggtaaagccc ctcgaa                                                   16

SEQ ID NO: 84          moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 84
ctccccacct gaccctg                                                  17

SEQ ID NO: 85          moltype = DNA   length = 17
FEATURE                Location/Qualifiers
misc_feature           1..17
```

```
                             note = Description of Artificial Sequence: Synthetic primer
source                       1..17
                             mol_type = other DNA
                             organism = synthetic construct
SEQUENCE: 85
ttatggtgtc tttcccc                                                        17

SEQ ID NO: 86                moltype = DNA   length = 17
FEATURE                      Location/Qualifiers
misc_feature                 1..17
                             note = Description of Artificial Sequence: Synthetic primer
source                       1..17
                             mol_type = other DNA
                             organism = synthetic construct
SEQUENCE: 86
caaagcaggt gcacgaa                                                        17

SEQ ID NO: 87                moltype = DNA   length = 18
FEATURE                      Location/Qualifiers
misc_feature                 1..18
                             note = Description of Artificial Sequence: Synthetic primer
source                       1..18
                             mol_type = other DNA
                             organism = synthetic construct
SEQUENCE: 87
acttcctccc ttcttact                                                       18

SEQ ID NO: 88                moltype = DNA   length = 18
FEATURE                      Location/Qualifiers
misc_feature                 1..18
                             note = Description of Artificial Sequence: Synthetic primer
source                       1..18
                             mol_type = other DNA
                             organism = synthetic construct
SEQUENCE: 88
ccctttggc ttcctggg                                                        18

SEQ ID NO: 89                moltype = DNA   length = 19
FEATURE                      Location/Qualifiers
misc_feature                 1..19
                             note = Description of Artificial Sequence: Synthetic primer
source                       1..19
                             mol_type = other DNA
                             organism = synthetic construct
SEQUENCE: 89
cccattttgc gccatttat                                                      19

SEQ ID NO: 90                moltype = DNA   length = 19
FEATURE                      Location/Qualifiers
misc_feature                 1..19
                             note = Description of Artificial Sequence: Synthetic primer
source                       1..19
                             mol_type = other DNA
                             organism = synthetic construct
SEQUENCE: 90
ggatcacatc gtgttagac                                                      19

SEQ ID NO: 91                moltype = DNA   length = 19
FEATURE                      Location/Qualifiers
misc_feature                 1..19
                             note = Description of Artificial Sequence: Synthetic primer
source                       1..19
                             mol_type = other DNA
                             organism = synthetic construct
SEQUENCE: 91
ggaagacgct tatcatggt                                                      19

SEQ ID NO: 92                moltype = DNA   length = 20
FEATURE                      Location/Qualifiers
misc_feature                 1..20
                             note = Description of Artificial Sequence: Synthetic primer
source                       1..20
                             mol_type = other DNA
                             organism = synthetic construct
SEQUENCE: 92
cccttgcatg catgcgcaca                                                     20

SEQ ID NO: 93                moltype = DNA   length = 20
FEATURE                      Location/Qualifiers
```

-continued

```
misc_feature            1..20
                        note = Description of Artificial Sequence: Synthetic primer
source                  1..20
                        mol_type = other DNA
                        organism = synthetic construct
SEQUENCE: 93
aggcaataga gggagtatca                                               20

SEQ ID NO: 94           moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 94
aaacttctcc ctcagcctac c                                             21

SEQ ID NO: 95           moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 95
cagaaataca tttgccacta t                                             21

SEQ ID NO: 96           moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 96
gcgctgtatc ctcagagagt a                                             21

SEQ ID NO: 97           moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 97
gggagaatgc atttcttttt cc                                            22

SEQ ID NO: 98           moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 98
ggatacttca agaatagtag ag                                            22

SEQ ID NO: 99           moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 99
cccactctat tcccacgtca gcc                                           23

SEQ ID NO: 100          moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 100
tttatttttc catcacacgt atg                                           23

SEQ ID NO: 101          moltype = DNA   length = 24
```

-continued

```
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 101
tttctaaatc cccacccggc gcag                                          24

SEQ ID NO: 102          moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 102
gctctcacca ttaactatac agca                                          24

SEQ ID NO: 103          moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 103
gttgacagtt ctccaagtcc agat                                          24

SEQ ID NO: 104          moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 104
ggattacaga tgccttcttg ggta                                          24

SEQ ID NO: 105          moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 105
caatcaaaga attatatggc taagg                                         25

SEQ ID NO: 106          moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 106
ccctttaaca cctatatggg tttttg                                        26

SEQ ID NO: 107          moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 107
gcagcacagc cttgcctaca atgaca                                        26

SEQ ID NO: 108          moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 108
gggcattctg aggaaaataa tgtatg                                        26
```

```
SEQ ID NO: 109          moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 109
ggacgagagg tctgagagtt tctgat                                             26

SEQ ID NO: 110          moltype = DNA   length = 27
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 110
acataactct cagataatta aagttgt                                            27

SEQ ID NO: 111          moltype = DNA   length = 27
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 111
atgttaacag aaagcacaat aaaaaca                                            27

SEQ ID NO: 112          moltype = DNA   length = 27
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 112
gggaggagag gaaccataag atattag                                            27

SEQ ID NO: 113          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 113
cctggttttg tcttccctat ttactgat                                           28

SEQ ID NO: 114          moltype = DNA   length = 28
FEATURE                 Location/Qualifiers
misc_feature            1..28
                        note = Description of Artificial Sequence: Synthetic primer
source                  1..28
                        mol_type = other DNA
                        organism = synthetic construct
SEQUENCE: 114
ggacaaaagt tctgaattat ttggtttg                                           28

SEQ ID NO: 115          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 115
acgttggatg aaaggctgat ccaggtcatc                                         30

SEQ ID NO: 116          moltype = DNA   length = 29
FEATURE                 Location/Qualifiers
misc_feature            1..29
                        note = Description of Artificial Sequence: Synthetic primer
source                  1..29
                        mol_type = other DNA
                        organism = synthetic construct
SEQUENCE: 116
acgttggatg ttgagacacg gcacagcgg                                          29
```

```
SEQ ID NO: 117            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 117
acgttggatg aaggtaggcc tttaggagag                                    30

SEQ ID NO: 118            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 118
acgttggatg atgcacaatc gtcctactcc                                    30

SEQ ID NO: 119            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 119
acgttggatg tgagccaggg atatcctaac                                    30

SEQ ID NO: 120            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 120
acgttggatg taatagaggg tgcattgaag                                    30

SEQ ID NO: 121            moltype = DNA   length = 29
FEATURE                   Location/Qualifiers
misc_feature              1..29
                          note = Description of Artificial Sequence: Synthetic primer
source                    1..29
                          mol_type = other DNA
                          organism = synthetic construct
SEQUENCE: 121
acgttggatg aaagagagag agatccctg                                     29

SEQ ID NO: 122            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 122
acgttggatg cactaataaa ggcagcctgt                                    30

SEQ ID NO: 123            moltype = DNA   length = 31
FEATURE                   Location/Qualifiers
misc_feature              1..31
                          note = Description of Artificial Sequence: Synthetic primer
source                    1..31
                          mol_type = other DNA
                          organism = synthetic construct
SEQUENCE: 123
acgttggatg ggctctgatc cctttttttta g                                 31

SEQ ID NO: 124            moltype = DNA   length = 31
FEATURE                   Location/Qualifiers
misc_feature              1..31
                          note = Description of Artificial Sequence: Synthetic primer
source                    1..31
                          mol_type = other DNA
                          organism = synthetic construct
SEQUENCE: 124
```

-continued

```
acgttggatg gcttttcctc ttctttggta g                         31

SEQ ID NO: 125       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
SEQUENCE: 125
acgttggatg tctcagttcc aactcatgcc                            30

SEQ ID NO: 126       moltype = DNA   length = 29
FEATURE              Location/Qualifiers
misc_feature         1..29
                     note = Description of Artificial Sequence: Synthetic primer
source               1..29
                     mol_type = other DNA
                     organism = synthetic construct
SEQUENCE: 126
acgttggatg agaatgtgcc aaagagcag                             29

SEQ ID NO: 127       moltype = DNA   length = 31
FEATURE              Location/Qualifiers
misc_feature         1..31
                     note = Description of Artificial Sequence: Synthetic primer
source               1..31
                     mol_type = other DNA
                     organism = synthetic construct
SEQUENCE: 127
acgttggatg ccttattgga ttctatgtcc c                          31

SEQ ID NO: 128       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
SEQUENCE: 128
acgttggatg acttggcgag tccccatttc                            30

SEQ ID NO: 129       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
SEQUENCE: 129
acgttggatg tcttgtctct tacctctcag                            30

SEQ ID NO: 130       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
SEQUENCE: 130
acgttggatg tgaggattaa aggatctggg                            30

SEQ ID NO: 131       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
SEQUENCE: 131
acgttggatg gaggctcctc tacacaaaag                            30

SEQ ID NO: 132       moltype = DNA   length = 30
FEATURE              Location/Qualifiers
misc_feature         1..30
                     note = Description of Artificial Sequence: Synthetic primer
source               1..30
                     mol_type = other DNA
                     organism = synthetic construct
```

-continued

```
SEQUENCE: 132
acgttggatg ttgctctaag gtggatgctg                                      30

SEQ ID NO: 133            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 133
acgttggatg gtttacaacc tgtggcagac                                      30

SEQ ID NO: 134            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 134
acgttggatg gaaagtgacc catcaagcag                                      30

SEQ ID NO: 135            moltype = DNA   length = 31
FEATURE                   Location/Qualifiers
misc_feature              1..31
                          note = Description of Artificial Sequence: Synthetic primer
source                    1..31
                          mol_type = other DNA
                          organism = synthetic construct
SEQUENCE: 135
acgttggatg ctatggggaa ctgaataagt g                                    31

SEQ ID NO: 136            moltype = DNA   length = 31
FEATURE                   Location/Qualifiers
misc_feature              1..31
                          note = Description of Artificial Sequence: Synthetic primer
source                    1..31
                          mol_type = other DNA
                          organism = synthetic construct
SEQUENCE: 136
acgttggatg caaactattg actggtcatg g                                    31

SEQ ID NO: 137            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 137
acgttggatg gcagaggttt gagaaaagag                                      30

SEQ ID NO: 138            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 138
acgttggatg gtatatgcct gtatgtggtc                                      30

SEQ ID NO: 139            moltype = DNA   length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 139
acgttggatg gagggaaaga cctgcttcta                                      30

SEQ ID NO: 140            moltype = DNA   length = 31
FEATURE                   Location/Qualifiers
misc_feature              1..31
                          note = Description of Artificial Sequence: Synthetic primer
source                    1..31
                          mol_type = other DNA
```

-continued

```
                            organism = synthetic construct
SEQUENCE: 140
acgttggatg gagaaggctt tccagaattt g                              31

SEQ ID NO: 141          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 141
acgttggatg caaaagccag ctcacaaaag                                30

SEQ ID NO: 142          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 142
acgttggatg ttttgggccc ctccatattc                                30

SEQ ID NO: 143          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 143
acgttggatg tggatatgct gaatttgagg                                30

SEQ ID NO: 144          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 144
acgttggatg cttttgtcca tgtttggcag                                30

SEQ ID NO: 145          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 145
acgttggatg aggacagttg tcgtgagatg                                30

SEQ ID NO: 146          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 146
acgttggatg ctgaggctgg gtaacttatc                                30

SEQ ID NO: 147          moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 147
acgttggatg gcccttggca catagtactg                                30

SEQ ID NO: 148          moltype = DNA  length = 30
FEATURE                 Location/Qualifiers
misc_feature            1..30
                        note = Description of Artificial Sequence: Synthetic primer
source                  1..30
```

```
                         mol_type = other DNA
                         organism = synthetic construct
SEQUENCE: 148
acgttggatg ttggttatag agcgtccctg                                  30

SEQ ID NO: 149          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 149
acgttggatg acccttact ccaataagtc                                   30

SEQ ID NO: 150          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 150
acgttggatg ttctcttcaa acctcccatc                                  30

SEQ ID NO: 151          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 151
acgttggatg ttttcctctt cctacccctc                                  30

SEQ ID NO: 152          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 152
acgttggatg tggcaacaca cgactgtact                                  30

SEQ ID NO: 153          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 153
acgttggatg tgcttcccag gtcactattg                                  30

SEQ ID NO: 154          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 154
acgttggatg tccatgagtg caggactacg                                  30

SEQ ID NO: 155          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 155
acgttggatg ctccacgagc aagagtatag                                  30

SEQ ID NO: 156          moltype = DNA   length = 30
FEATURE                 Location/Qualifiers
misc_feature            1..30
                        note = Description of Artificial Sequence: Synthetic primer
```

-continued

```
source                    1..30
                          mol_type = other DNA
                          organism = synthetic construct
SEQUENCE: 156
acgttggatg atcccatacg gccaagaaga                                    30

SEQ ID NO: 157            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 157
acgttggatg atgagtaacg cttggtgctg                                    30

SEQ ID NO: 158            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 158
acgttggatg tggtagcctc aagaatgctc                                    30

SEQ ID NO: 159            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 159
acgttggatg gaatgtgtaa aacaaaccag                                    30

SEQ ID NO: 160            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 160
acgttggatg tgagccatgt agagactcag                                    30

SEQ ID NO: 161            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 161
acgttggatg tctgcatccc ttaggttcac                                    30

SEQ ID NO: 162            moltype = DNA  length = 29
FEATURE                   Location/Qualifiers
misc_feature              1..29
                          note = Description of Artificial Sequence: Synthetic primer
source                    1..29
                          mol_type = other DNA
                          organism = synthetic construct
SEQUENCE: 162
acgttggatg accaagcact gtacttttc                                     29

SEQ ID NO: 163            moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 163
acgttggatg ttaatatagt ccccagccac                                    30

SEQ ID NO: 164            moltype = DNA  length = 30
FEATURE                   Location/Qualifiers
misc_feature              1..30
```

```
                      note = Description of Artificial Sequence: Synthetic primer
source                1..30
                      mol_type = other DNA
                      organism = synthetic construct
SEQUENCE: 164
acgttggatg ctgtgctgac tgagtagatg                                               30

SEQ ID NO: 165        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 165
acgttggatg atctttgaag gctcctctgg                                               30

SEQ ID NO: 166        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 166
acgttggatg gcatgtccct atgagatcag                                               30

SEQ ID NO: 167        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 167
acgttggatg ttaggcaccc caagtttcag                                               30

SEQ ID NO: 168        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 168
acgttggatg tgtagcatgt cagccatcag                                               30

SEQ ID NO: 169        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 169
acgttggatg gtagttgctt gtggttaccg                                               30

SEQ ID NO: 170        moltype = DNA  length = 29
FEATURE               Location/Qualifiers
misc_feature          1..29
                      note = Description of Artificial Sequence: Synthetic primer
source                1..29
                      mol_type = other DNA
                      organism = synthetic construct
SEQUENCE: 170
acgttggatg gagcaattca tttgtctcc                                                29

SEQ ID NO: 171        moltype = DNA  length = 30
FEATURE               Location/Qualifiers
misc_feature          1..30
                      note = Description of Artificial Sequence: Synthetic primer
source                1..30
                      mol_type = other DNA
                      organism = synthetic construct
SEQUENCE: 171
acgttggatg ttttgttgtt tgggcattgg                                               30

SEQ ID NO: 172        moltype = DNA  length = 30
FEATURE               Location/Qualifiers
```

-continued

```
misc_feature            1..30
                        note = Description of Artificial Sequence: Synthetic primer
source                  1..30
                        mol_type = other DNA
                        organism = synthetic construct
SEQUENCE: 172
acgttggatg gttcccatcc agtaatggag                                           30

SEQ ID NO: 173          moltype = DNA   length = 31
FEATURE                 Location/Qualifiers
misc_feature            1..31
                        note = Description of Artificial Sequence: Synthetic primer
source                  1..31
                        mol_type = other DNA
                        organism = synthetic construct
SEQUENCE: 173
acgttggatg ccaacagttt ttctttaagg g                                         31

SEQ ID NO: 174          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 174
acgttggatg agaagctccg agaaaaggtg                                           30

SEQ ID NO: 175          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 175
acgttggatg tatagccatt actgggcttg                                           30

SEQ ID NO: 176          moltype = DNA   length = 31
FEATURE                 Location/Qualifiers
misc_feature            1..31
                        note = Description of Artificial Sequence: Synthetic primer
source                  1..31
                        mol_type = other DNA
                        organism = synthetic construct
SEQUENCE: 176
acgttggatg ccctcttgca taaaatgttg c                                         31

SEQ ID NO: 177          moltype = DNA   length = 29
FEATURE                 Location/Qualifiers
misc_feature            1..29
                        note = Description of Artificial Sequence: Synthetic primer
source                  1..29
                        mol_type = other DNA
                        organism = synthetic construct
SEQUENCE: 177
acgttggatg ctccatgcaa ggctgtggc                                            29

SEQ ID NO: 178          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 178
acgttggatg cgttatcaag gactttgtgc                                           30

SEQ ID NO: 179          moltype = DNA   length = 31
FEATURE                 Location/Qualifiers
misc_feature            1..31
                        note = Description of Artificial Sequence: Synthetic primer
source                  1..31
                        mol_type = other DNA
                        organism = synthetic construct
SEQUENCE: 179
acgttggatg gaggttatct tattgtaacg c                                         31

SEQ ID NO: 180          moltype = DNA   length = 30
```

```
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 180
acgttggatg agactgtcct ttcccaggat                                      30

SEQ ID NO: 181           moltype = DNA  length = 30
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 181
acgttggatg tcatcagaag cagatgctgg                                      30

SEQ ID NO: 182           moltype = DNA  length = 30
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 182
acgttggatg ccatacgttc aaggattggg                                      30

SEQ ID NO: 183           moltype = DNA  length = 30
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 183
acgttggatg aggtgtgcaa gtgtcagaag                                      30

SEQ ID NO: 184           moltype = DNA  length = 30
FEATURE                  Location/Qualifiers
misc_feature             1..30
                         note = Description of Artificial Sequence: Synthetic primer
source                   1..30
                         mol_type = other DNA
                         organism = synthetic construct
SEQUENCE: 184
acgttggatg gtatatcatg tccagtgaag                                      30

SEQ ID NO: 185           moltype = DNA  length = 32
FEATURE                  Location/Qualifiers
misc_feature             1..32
                         note = Description of Artificial Sequence: Synthetic primer
modified_base            12
                         mod_base = OTHER
                         note = Deoxyinosine
source                   1..32
                         mol_type = other DNA
                         organism = synthetic construct
SEQUENCE: 185
ccaccgcctc cncctcccat ctccaccctc ta                                   32

SEQ ID NO: 186           moltype = DNA  length = 32
FEATURE                  Location/Qualifiers
misc_feature             1..32
                         note = Description of Artificial Sequence: Synthetic primer
modified_base            12
                         mod_base = OTHER
                         note = Deoxyinosine
source                   1..32
                         mol_type = other DNA
                         organism = synthetic construct
SEQUENCE: 186
ccaccgccta cncctcccat ctccaccctc tg                                   32

SEQ ID NO: 187           moltype = DNA  length = 32
FEATURE                  Location/Qualifiers
misc_feature             1..32
                         note = Description of Artificial Sequence: Synthetic primer
```

-continued

```
modified_base        12
                     mod_base = OTHER
                     note = Deoxyinosine
source               1..32
                     mol_type = other DNA
                     organism = synthetic construct
SEQUENCE: 187
ccacagccta cncttcctac ccctccagcc gc                              32

SEQ ID NO: 188       moltype = DNA  length = 32
FEATURE              Location/Qualifiers
misc_feature         1..32
                     note = Description of Artificial Sequence: Synthetic primer
modified_base        12
                     mod_base = OTHER
                     note = Deoxyinosine
source               1..32
                     mol_type = other DNA
                     organism = synthetic construct
SEQUENCE: 188
ccacagcata cncttcctac ccctccagcc gt                              32

SEQ ID NO: 189       moltype = DNA  length = 32
FEATURE              Location/Qualifiers
misc_feature         1..32
                     note = Description of Artificial Sequence: Synthetic primer
modified_base        12
                     mod_base = OTHER
                     note = Deoxyinosine
source               1..32
                     mol_type = other DNA
                     organism = synthetic construct
SEQUENCE: 189
caacagcaca anttgctatc cccacaatta cc                              32

SEQ ID NO: 190       moltype = DNA  length = 32
FEATURE              Location/Qualifiers
misc_feature         1..32
                     note = Description of Artificial Sequence: Synthetic primer
modified_base        12
                     mod_base = OTHER
                     note = Deoxyinosine
source               1..32
                     mol_type = other DNA
                     organism = synthetic construct
SEQUENCE: 190
caacagaaca anttgctatc cccacaatta ct                              32

SEQ ID NO: 191       moltype = DNA  length = 32
FEATURE              Location/Qualifiers
misc_feature         1..32
                     note = Description of Artificial Sequence: Synthetic primer
modified_base        12
                     mod_base = OTHER
                     note = Deoxyinosine
source               1..32
                     mol_type = other DNA
                     organism = synthetic construct
SEQUENCE: 191
caaaagaaca antgaaactg cagactcttc cc                              32

SEQ ID NO: 192       moltype = DNA  length = 32
FEATURE              Location/Qualifiers
misc_feature         1..32
                     note = Description of Artificial Sequence: Synthetic primer
modified_base        12
                     mod_base = OTHER
                     note = Deoxyinosine
source               1..32
                     mol_type = other DNA
                     organism = synthetic construct
SEQUENCE: 192
caaaagaaaa antgaaactg cagactcttc ct                              32

SEQ ID NO: 193       moltype = DNA  length = 32
FEATURE              Location/Qualifiers
misc_feature         1..32
                     note = Description of Artificial Sequence: Synthetic primer
modified_base        12
```

```
                            mod_base = OTHER
                            note = Deoxyinosine
source                      1..32
                            mol_type = other DNA
                            organism = synthetic construct
SEQUENCE: 193
aataagaaga ancgtctgat tggctttagt tc                                      32

SEQ ID NO: 194              moltype = DNA   length = 32
FEATURE                     Location/Qualifiers
misc_feature                1..32
                            note = Description of Artificial Sequence: Synthetic primer
modified_base               12
                            mod_base = OTHER
                            note = Deoxyinosine
source                      1..32
                            mol_type = other DNA
                            organism = synthetic construct
SEQUENCE: 194
gataagaaga ancgtctgat tggctttagt tt                                      32

SEQ ID NO: 195              moltype = DNA   length = 32
FEATURE                     Location/Qualifiers
misc_feature                1..32
                            note = Description of Artificial Sequence: Synthetic primer
modified_base               12
                            mod_base = OTHER
                            note = Deoxyinosine
source                      1..32
                            mol_type = other DNA
                            organism = synthetic construct
SEQUENCE: 195
aatagcgaga angctgtatc ctcagagagt ac                                      32

SEQ ID NO: 196              moltype = DNA   length = 32
FEATURE                     Location/Qualifiers
misc_feature                1..32
                            note = Description of Artificial Sequence: Synthetic primer
modified_base               12
                            mod_base = OTHER
                            note = Deoxyinosine
source                      1..32
                            mol_type = other DNA
                            organism = synthetic construct
SEQUENCE: 196
aatagcgaga gngctgtatc ctcagagagt at                                      32

SEQ ID NO: 197              moltype = DNA   length = 34
FEATURE                     Location/Qualifiers
misc_feature                1..34
                            note = Description of Artificial Sequence: Synthetic primer
modified_base               13
                            mod_base = OTHER
                            note = Deoxyinosine
source                      1..34
                            mol_type = other DNA
                            organism = synthetic construct
SEQUENCE: 197
ccaccccgc ccnttctccc acagtaaact tcca                                     34

SEQ ID NO: 198              moltype = DNA   length = 34
FEATURE                     Location/Qualifiers
misc_feature                1..34
                            note = Description of Artificial Sequence: Synthetic primer
modified_base               13
                            mod_base = OTHER
                            note = Deoxyinosine
source                      1..34
                            mol_type = other DNA
                            organism = synthetic construct
SEQUENCE: 198
ccaccaccgc ccnttctccc acagtaaact tccg                                    34

SEQ ID NO: 199              moltype = DNA   length = 34
FEATURE                     Location/Qualifiers
misc_feature                1..34
                            note = Description of Artificial Sequence: Synthetic primer
modified_base               13
                            mod_base = OTHER
```

-continued

```
                       note = Deoxyinosine
source                 1..34
                       mol_type = other DNA
                       organism = synthetic construct
SEQUENCE: 199
ccaccgcact acnctcttct gcttcatatt tcac                             34

SEQ ID NO: 200         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
source                 1..34
                       mol_type = other DNA
                       organism = synthetic construct
SEQUENCE: 200
ccacagcact acnctcttct gcttcatatt tcag                             34

SEQ ID NO: 201         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
source                 1..34
                       mol_type = other DNA
                       organism = synthetic construct
SEQUENCE: 201
caacagcacc acnttcatta tttcactcaa gcga                             34

SEQ ID NO: 202         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
source                 1..34
                       mol_type = other DNA
                       organism = synthetic construct
SEQUENCE: 202
caacagcaac acnttcatta tttcactcaa gcgg                             34

SEQ ID NO: 203         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
source                 1..34
                       mol_type = other DNA
                       organism = synthetic construct
SEQUENCE: 203
caacagctac aanaaacaaa ccagaaagtc acta                             34

SEQ ID NO: 204         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
source                 1..34
                       mol_type = other DNA
                       organism = synthetic construct
SEQUENCE: 204
caacagatac aanaaacaaa ccagaaagtc actg                             34

SEQ ID NO: 205         moltype = DNA  length = 34
FEATURE                Location/Qualifiers
misc_feature           1..34
                       note = Description of Artificial Sequence: Synthetic primer
modified_base          13
                       mod_base = OTHER
                       note = Deoxyinosine
```

```
source                   1..34
                         mol_type = other DNA
                         organism = synthetic construct
SEQUENCE: 205
caaaagatac aanatgtaga gactcagtct cttc                                    34

SEQ ID NO: 206           moltype = DNA   length = 34
FEATURE                  Location/Qualifiers
misc_feature             1..34
                         note = Description of Artificial Sequence: Synthetic primer
modified_base            13
                         mod_base = OTHER
                         note = Deoxyinosine
source                   1..34
                         mol_type = other DNA
                         organism = synthetic construct
SEQUENCE: 206
caaaagatag aanatgtaga gactcagtct cttg                                    34

SEQ ID NO: 207           moltype = DNA   length = 34
FEATURE                  Location/Qualifiers
misc_feature             1..34
                         note = Description of Artificial Sequence: Synthetic primer
modified_base            13
                         mod_base = OTHER
                         note = Deoxyinosine
source                   1..34
                         mol_type = other DNA
                         organism = synthetic construct
SEQUENCE: 207
caaaagagag aantgcaaat tagatttgtc aggc                                    34

SEQ ID NO: 208           moltype = DNA   length = 34
FEATURE                  Location/Qualifiers
misc_feature             1..34
                         note = Description of Artificial Sequence: Synthetic primer
modified_base            13
                         mod_base = OTHER
                         note = Deoxyinosine
source                   1..34
                         mol_type = other DNA
                         organism = synthetic construct
SEQUENCE: 208
cagaagagag aantgcaaat tagatttgtc aggt                                    34

SEQ ID NO: 209           moltype = DNA   length = 35
FEATURE                  Location/Qualifiers
misc_feature             1..35
                         note = Description of Artificial Sequence: Synthetic primer
modified_base            13
                         mod_base = OTHER
                         note = Deoxyinosine
source                   1..35
                         mol_type = other DNA
                         organism = synthetic construct
SEQUENCE: 209
cagaagagag agntatgtct tattcttctt cacca                                   35

SEQ ID NO: 210           moltype = DNA   length = 35
FEATURE                  Location/Qualifiers
misc_feature             1..35
                         note = Description of Artificial Sequence: Synthetic primer
modified_base            13
                         mod_base = OTHER
                         note = Deoxyinosine
source                   1..35
                         mol_type = other DNA
                         organism = synthetic construct
SEQUENCE: 210
caggagagag agntatgtct tattcttctt caccg                                   35

SEQ ID NO: 211           moltype = DNA   length = 36
FEATURE                  Location/Qualifiers
misc_feature             1..36
                         note = Description of Artificial Sequence: Synthetic primer
modified_base            14
                         mod_base = OTHER
                         note = Deoxyinosine
source                   1..36
```

-continued

```
                           mol_type = other DNA
                           organism = synthetic construct
SEQUENCE: 211
ccacccaccg cccntagtcc ccagccacta taaaac                              36

SEQ ID NO: 212            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
                          organism = synthetic construct
SEQUENCE: 212
ccacccgccg cccntagtcc ccagccacta taaaag                              36

SEQ ID NO: 213            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
                          organism = synthetic construct
SEQUENCE: 213
ccacccgccg ctcnttccca aagttgaggg acttac                              36

SEQ ID NO: 214            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
                          organism = synthetic construct
SEQUENCE: 214
ccactcgccg ctcnttccca aagttgaggg acttat                              36

SEQ ID NO: 215            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
                          organism = synthetic construct
SEQUENCE: 215
ccacgcgccc tacnaaggct cctctggggc acaagc                              36

SEQ ID NO: 216            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
                          organism = synthetic construct
SEQUENCE: 216
caacgcgcac tacnaaggct cctctggggc acaagt                              36

SEQ ID NO: 217            moltype = DNA  length = 36
FEATURE                   Location/Qualifiers
misc_feature              1..36
                          note = Description of Artificial Sequence: Synthetic primer
modified_base             14
                          mod_base = OTHER
                          note = Deoxyinosine
source                    1..36
                          mol_type = other DNA
```

```
                                organism = synthetic construct
SEQUENCE: 217
caacaagcac tacngggttt tgttgtgcca gtagaa                            36

SEQ ID NO: 218          moltype = DNA  length = 36
FEATURE                 Location/Qualifiers
misc_feature            1..36
                        note = Description of Artificial Sequence: Synthetic primer
modified_base           14
                        mod_base = OTHER
                        note = Deoxyinosine
source                  1..36
                        mol_type = other DNA
                        organism = synthetic construct
SEQUENCE: 218
caacaagcaa tacngggttt tgttgtgcca gtagag                            36

SEQ ID NO: 219          moltype = DNA  length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
SEQUENCE: 219
caagaagaaa taanctgcca attaatcatc aactctc                           37

SEQ ID NO: 220          moltype = DNA  length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
SEQUENCE: 220
aaagaagaaa taanctgcca attaatcatc aactctt                           37

SEQ ID NO: 221          moltype = DNA  length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
SEQUENCE: 221
gaagaagaca taanatgtca gccatcagcc tctcaca                           37

SEQ ID NO: 222          moltype = DNA  length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
SEQUENCE: 222
gaagaagaca tagnatgtca gccatcagcc tctcacg                           37

SEQ ID NO: 223          moltype = DNA  length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
```

-continued

```
SEQUENCE: 223
gaagaggacg tagngctctt atatctcata tgaacac                                37

SEQ ID NO: 224          moltype = DNA   length = 37
FEATURE                 Location/Qualifiers
misc_feature            1..37
                        note = Description of Artificial Sequence: Synthetic primer
modified_base           14
                        mod_base = OTHER
                        note = Deoxyinosine
source                  1..37
                        mol_type = other DNA
                        organism = synthetic construct
SEQUENCE: 224
gaggaggacg tagngctctt atatctcata tgaacag                                37

SEQ ID NO: 225          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 225
ccacgctcct ctacnacttt tcatggttat tctcagtc                               38

SEQ ID NO: 226          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 226
ccgcgctcct ctacnacttt tcatggttat tctcagtt                               38

SEQ ID NO: 227          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 227
ccacgcgcac caacntgttt tgtttgtttt gtttttc                                38

SEQ ID NO: 228          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 228
ccacgcgcgc caacntgttt tgtttgtttt gtttttt                                38

SEQ ID NO: 229          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 229
```

```
ccacgcgagt caacnccatc cagtaatgga gtacagtc                              38

SEQ ID NO: 230          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 230
ccacgagagt caacnccatc cagtaatgga gtacagtg                              38

SEQ ID NO: 231          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 231
ccacgagagt caacnagttt ttctttaagg ggagtaga                              38

SEQ ID NO: 232          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 232
caacgagagt aaacnagttt ttctttaagg ggagtagg                              38

SEQ ID NO: 233          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 233
caaagagaat aaacnggaca aagatgagtg cgtatatc                              38

SEQ ID NO: 234          moltype = DNA   length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 234
caaagagaat aaaanggaca aagatgagtg cgtatatt                              38

SEQ ID NO: 235          moltype = DNA   length = 39
FEATURE                 Location/Qualifiers
misc_feature            1..39
                        note = Description of Artificial Sequence: Synthetic primer
modified_base           15
                        mod_base = OTHER
                        note = Deoxyinosine
source                  1..39
                        mol_type = other DNA
                        organism = synthetic construct
SEQUENCE: 235
caaagagaat agaanggctt ggggtcccca ttaaagcga                             39
```

-continued

```
SEQ ID NO: 236          moltype = DNA  length = 39
FEATURE                 Location/Qualifiers
misc_feature            1..39
                        note = Description of Artificial Sequence: Synthetic primer
modified_base           15
                        mod_base = OTHER
                        note = Deoxyinosine
source                  1..39
                        mol_type = other DNA
                        organism = synthetic construct
SEQUENCE: 236
cagagagaat agaanggctt ggggtcccca ttaaagcgg                          39

SEQ ID NO: 237          moltype = DNA  length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 237
aagagcgaga gagantacta aagacgctta tcatggtc                           38

SEQ ID NO: 238          moltype = DNA  length = 38
FEATURE                 Location/Qualifiers
misc_feature            1..38
                        note = Description of Artificial Sequence: Synthetic primer
modified_base           15
                        mod_base = OTHER
                        note = Deoxyinosine
source                  1..38
                        mol_type = other DNA
                        organism = synthetic construct
SEQUENCE: 238
aggagcgaga gagantacta aagacgctta tcatggtt                           38

SEQ ID NO: 239          moltype = DNA  length = 39
FEATURE                 Location/Qualifiers
misc_feature            1..39
                        note = Description of Artificial Sequence: Synthetic primer
modified_base           15
                        mod_base = OTHER
                        note = Deoxyinosine
source                  1..39
                        mol_type = other DNA
                        organism = synthetic construct
SEQUENCE: 239
cggagagaga ggagntgcaa ggctgtggct ggacaagac                          39

SEQ ID NO: 240          moltype = DNA  length = 39
FEATURE                 Location/Qualifiers
misc_feature            1..39
                        note = Description of Artificial Sequence: Synthetic primer
modified_base           15
                        mod_base = OTHER
                        note = Deoxyinosine
source                  1..39
                        mol_type = other DNA
                        organism = synthetic construct
SEQUENCE: 240
cggagaggga ggagntgcaa ggctgtggct ggacaagat                          39

SEQ ID NO: 241          moltype = DNA  length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 241
cccgctccgc cagtcnattc tatattagaa caactctctt c                       41
```

-continued

```
SEQ ID NO: 242          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 242
ccacgcgcgc cagtcnattc tatattagaa caactctctt t                         41

SEQ ID NO: 243          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 243
ccacgcgcga cagacntaac gcatatgcac atgcacacat c                         41

SEQ ID NO: 244          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 244
ccacgcgaga cagacntaac gcatatgcac atgcacacat t                         41

SEQ ID NO: 245          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 245
caacgcgaga cagacntgtc ctttcccagg atgctcaaag c                         41

SEQ ID NO: 246          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 246
caacgcgaga cagaantgtc ctttcccagg atgctcaaag t                         41

SEQ ID NO: 247          moltype = DNA   length = 41
FEATURE                 Location/Qualifiers
misc_feature            1..41
                        note = Description of Artificial Sequence: Synthetic primer
modified_base           16
                        mod_base = OTHER
                        note = Deoxyinosine
source                  1..41
                        mol_type = other DNA
                        organism = synthetic construct
SEQUENCE: 247
caacgagaga cagtanagca gatgctggcc ccatgcttca g                         41

SEQ ID NO: 248          moltype = DNA   length = 41
```

```
FEATURE              Location/Qualifiers
misc_feature         1..41
                     note = Description of Artificial Sequence: Synthetic primer
modified_base        16
                     mod_base = OTHER
                     note = Deoxyinosine
source               1..41
                     mol_type = other DNA
                     organism = synthetic construct
SEQUENCE: 248
caacgagaga aagtanagca gatgctggcc ccatgcttca t                     41

SEQ ID NO: 249       moltype = DNA  length = 41
FEATURE              Location/Qualifiers
misc_feature         1..41
                     note = Description of Artificial Sequence: Synthetic primer
modified_base        16
                     mod_base = OTHER
                     note = Deoxyinosine
source               1..41
                     mol_type = other DNA
                     organism = synthetic construct
SEQUENCE: 249
caaggagaga aagaantaat agtacaacag ctatcaatta c                     41

SEQ ID NO: 250       moltype = DNA  length = 41
FEATURE              Location/Qualifiers
misc_feature         1..41
                     note = Description of Artificial Sequence: Synthetic primer
modified_base        16
                     mod_base = OTHER
                     note = Deoxyinosine
source               1..41
                     mol_type = other DNA
                     organism = synthetic construct
SEQUENCE: 250
caaggagaga gagaantaat agtacaacag ctatcaatta t                     41

SEQ ID NO: 251       moltype = DNA  length = 41
FEATURE              Location/Qualifiers
misc_feature         1..41
                     note = Description of Artificial Sequence: Synthetic primer
modified_base        16
                     mod_base = OTHER
                     note = Deoxyinosine
source               1..41
                     mol_type = other DNA
                     organism = synthetic construct
SEQUENCE: 251
caaggagaga gagagntgtg caagtgtcag aagatgaaca a                     41

SEQ ID NO: 252       moltype = DNA  length = 41
FEATURE              Location/Qualifiers
misc_feature         1..41
                     note = Description of Artificial Sequence: Synthetic primer
modified_base        16
                     mod_base = OTHER
                     note = Deoxyinosine
source               1..41
                     mol_type = other DNA
                     organism = synthetic construct
SEQUENCE: 252
cgaggagaga gagagntgtg caagtgtcag aagatgaaca g                     41

SEQ ID NO: 253       moltype = DNA  length = 42
FEATURE              Location/Qualifiers
misc_feature         1..42
                     note = Description of Artificial Sequence: Synthetic primer
modified_base        17
                     mod_base = OTHER
                     note = Deoxyinosine
source               1..42
                     mol_type = other DNA
                     organism = synthetic construct
SEQUENCE: 253
ccacctacca ccagtcngaa gaaataagaa acattgagac ac                    42

SEQ ID NO: 254       moltype = DNA  length = 42
FEATURE              Location/Qualifiers
```

```
misc_feature            1..42
                        note = Description of Artificial Sequence: Synthetic primer
modified_base           17
                        mod_base = OTHER
                        note = Deoxyinosine
source                  1..42
                        mol_type = other DNA
                        organism = synthetic construct
SEQUENCE: 254
ccacatacca ccagtcngaa gaaataagaa acattgagac at                           42

SEQ ID NO: 255          moltype = DNA  length = 13
FEATURE                 Location/Qualifiers
misc_feature            1..13
                        note = Description of Artificial Sequence: Synthetic
                         oligonucleotide
modified_base           12
                        mod_base = OTHER
                        note = Deoxyinosine
source                  1..13
                        mol_type = other DNA
                        organism = synthetic construct
SEQUENCE: 255
ccaccgcctc cnc                                                           13

SEQ ID NO: 256          moltype = DNA  length = 13
FEATURE                 Location/Qualifiers
misc_feature            1..13
                        note = Description of Artificial Sequence: Synthetic
                         oligonucleotide
modified_base           12
                        mod_base = OTHER
                        note = Deoxyinosine
source                  1..13
                        mol_type = other DNA
                        organism = synthetic construct
SEQUENCE: 256
ccaccgccta cnc                                                           13

SEQ ID NO: 257          moltype = DNA  length = 13
FEATURE                 Location/Qualifiers
misc_feature            1..13
                        note = Description of Artificial Sequence: Synthetic
                         oligonucleotide
modified_base           12
                        mod_base = OTHER
                        note = Deoxyinosine
source                  1..13
                        mol_type = other DNA
                        organism = synthetic construct
SEQUENCE: 257
ccacagccta cnc                                                           13

SEQ ID NO: 258          moltype = DNA  length = 13
FEATURE                 Location/Qualifiers
misc_feature            1..13
                        note = Description of Artificial Sequence: Synthetic
                         oligonucleotide
modified_base           12
                        mod_base = OTHER
                        note = Deoxyinosine
source                  1..13
                        mol_type = other DNA
                        organism = synthetic construct
SEQUENCE: 258
ccacagcata cnc                                                           13

SEQ ID NO: 259          moltype = DNA  length = 13
FEATURE                 Location/Qualifiers
misc_feature            1..13
                        note = Description of Artificial Sequence: Synthetic
                         oligonucleotide
modified_base           12
                        mod_base = OTHER
                        note = Deoxyinosine
source                  1..13
                        mol_type = other DNA
                        organism = synthetic construct
SEQUENCE: 259
```

```
caacagcaca ant                                                              13

SEQ ID NO: 260      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
                    note = Deoxyinosine
source              1..13
                    mol_type = other DNA
                    organism = synthetic construct
SEQUENCE: 260
caacagaaca ant                                                              13

SEQ ID NO: 261      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
                    note = Deoxyinosine
source              1..13
                    mol_type = other DNA
                    organism = synthetic construct
SEQUENCE: 261
caaaagaaca ant                                                              13

SEQ ID NO: 262      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
                    note = Deoxyinosine
source              1..13
                    mol_type = other DNA
                    organism = synthetic construct
SEQUENCE: 262
caaaagaaaa ant                                                              13

SEQ ID NO: 263      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
                    note = Deoxyinosine
source              1..13
                    mol_type = other DNA
                    organism = synthetic construct
SEQUENCE: 263
aataagaaga anc                                                              13

SEQ ID NO: 264      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
                    note = Deoxyinosine
source              1..13
                    mol_type = other DNA
                    organism = synthetic construct
SEQUENCE: 264
gataagaaga anc                                                              13

SEQ ID NO: 265      moltype = DNA   length = 13
FEATURE             Location/Qualifiers
misc_feature        1..13
                    note = Description of Artificial Sequence: Synthetic
                    oligonucleotide
modified_base       12
                    mod_base = OTHER
```

```
                            note = Deoxyinosine
source                      1..13
                            mol_type = other DNA
                            organism = synthetic construct
SEQUENCE: 265
aatagcgaga ang                                                              13

SEQ ID NO: 266              moltype = DNA  length = 13
FEATURE                     Location/Qualifiers
misc_feature               1..13
                            note = Description of Artificial Sequence: Synthetic
                            oligonucleotide
modified_base              12
                            mod_base = OTHER
                            note = Deoxyinosine
source                      1..13
                            mol_type = other DNA
                            organism = synthetic construct
SEQUENCE: 266
aatagcgaga gng                                                              13

SEQ ID NO: 267              moltype = DNA  length = 14
FEATURE                     Location/Qualifiers
misc_feature               1..14
                            note = Description of Artificial Sequence: Synthetic
                            oligonucleotide
modified_base              13
                            mod_base = OTHER
                            note = Deoxyinosine
source                      1..14
                            mol_type = other DNA
                            organism = synthetic construct
SEQUENCE: 267
ccaccccgc ccnt                                                              14

SEQ ID NO: 268              moltype = DNA  length = 14
FEATURE                     Location/Qualifiers
misc_feature               1..14
                            note = Description of Artificial Sequence: Synthetic
                            oligonucleotide
modified_base              13
                            mod_base = OTHER
                            note = Deoxyinosine
source                      1..14
                            mol_type = other DNA
                            organism = synthetic construct
SEQUENCE: 268
ccaccaccgc ccnt                                                             14

SEQ ID NO: 269              moltype = DNA  length = 14
FEATURE                     Location/Qualifiers
misc_feature               1..14
                            note = Description of Artificial Sequence: Synthetic
                            oligonucleotide
modified_base              13
                            mod_base = OTHER
                            note = Deoxyinosine
source                      1..14
                            mol_type = other DNA
                            organism = synthetic construct
SEQUENCE: 269
ccaccgcact acnc                                                             14

SEQ ID NO: 270              moltype = DNA  length = 14
FEATURE                     Location/Qualifiers
misc_feature               1..14
                            note = Description of Artificial Sequence: Synthetic
                            oligonucleotide
modified_base              13
                            mod_base = OTHER
                            note = Deoxyinosine
source                      1..14
                            mol_type = other DNA
                            organism = synthetic construct
SEQUENCE: 270
ccacagcact acnc                                                             14

SEQ ID NO: 271              moltype = DNA  length = 14
FEATURE                     Location/Qualifiers
```

-continued

```
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
SEQUENCE: 271
caacagcacc acnt                                                            14

SEQ ID NO: 272         moltype = DNA  length = 14
FEATURE                Location/Qualifiers
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
SEQUENCE: 272
caacagcaac acnt                                                            14

SEQ ID NO: 273         moltype = DNA  length = 14
FEATURE                Location/Qualifiers
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
SEQUENCE: 273
caacagctac aana                                                            14

SEQ ID NO: 274         moltype = DNA  length = 14
FEATURE                Location/Qualifiers
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
SEQUENCE: 274
caacagatac aana                                                            14

SEQ ID NO: 275         moltype = DNA  length = 14
FEATURE                Location/Qualifiers
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
SEQUENCE: 275
caaaagatac aana                                                            14

SEQ ID NO: 276         moltype = DNA  length = 14
FEATURE                Location/Qualifiers
misc_feature           1..14
                       note = Description of Artificial Sequence: Synthetic
                        oligonucleotide
modified_base          13
                       mod_base = OTHER
                       note = Deoxyinosine
source                 1..14
                       mol_type = other DNA
                       organism = synthetic construct
```

-continued

```
SEQUENCE: 276
caaaagatag aana                                                          14

SEQ ID NO: 277        moltype = DNA   length = 14
FEATURE               Location/Qualifiers
misc_feature          1..14
                      note = Description of Artificial Sequence: Synthetic
                      oligonucleotide
modified_base         13
                      mod_base = OTHER
                      note = Deoxyinosine
source                1..14
                      mol_type = other DNA
                      organism = synthetic construct
SEQUENCE: 277
caaaagagag aant                                                          14

SEQ ID NO: 278        moltype = DNA   length = 14
FEATURE               Location/Qualifiers
misc_feature          1..14
                      note = Description of Artificial Sequence: Synthetic
                      oligonucleotide
modified_base         13
                      mod_base = OTHER
                      note = Deoxyinosine
source                1..14
                      mol_type = other DNA
                      organism = synthetic construct
SEQUENCE: 278
cagaagagag aant                                                          14

SEQ ID NO: 279        moltype = DNA   length = 14
FEATURE               Location/Qualifiers
misc_feature          1..14
                      note = Description of Artificial Sequence: Synthetic
                      oligonucleotide
modified_base         13
                      mod_base = OTHER
                      note = Deoxyinosine
source                1..14
                      mol_type = other DNA
                      organism = synthetic construct
SEQUENCE: 279
cagaagagag agnt                                                          14

SEQ ID NO: 280        moltype = DNA   length = 14
FEATURE               Location/Qualifiers
misc_feature          1..14
                      note = Description of Artificial Sequence: Synthetic
                      oligonucleotide
modified_base         13
                      mod_base = OTHER
                      note = Deoxyinosine
source                1..14
                      mol_type = other DNA
                      organism = synthetic construct
SEQUENCE: 280
caggagagag agnt                                                          14

SEQ ID NO: 281        moltype = DNA   length = 15
FEATURE               Location/Qualifiers
misc_feature          1..15
                      note = Description of Artificial Sequence: Synthetic
                      oligonucleotide
modified_base         14
                      mod_base = OTHER
                      note = Deoxyinosine
source                1..15
                      mol_type = other DNA
                      organism = synthetic construct
SEQUENCE: 281
ccacccaccg cccnt                                                         15

SEQ ID NO: 282        moltype = DNA   length = 15
FEATURE               Location/Qualifiers
misc_feature          1..15
                      note = Description of Artificial Sequence: Synthetic
                      oligonucleotide
modified_base         14
```

```
                        mod_base = OTHER
                        note = Deoxyinosine
source                  1..15
                        mol_type = other DNA
                        organism = synthetic construct
SEQUENCE: 282
ccacccgccg cccnt                                                   15

SEQ ID NO: 283          moltype = DNA  length = 15
FEATURE                 Location/Qualifiers
misc_feature            1..15
                        note = Description of Artificial Sequence: Synthetic
                         oligonucleotide
modified_base           14
                        mod_base = OTHER
                        note = Deoxyinosine
source                  1..15
                        mol_type = other DNA
                        organism = synthetic construct
SEQUENCE: 283
ccacccgccg ctcnt                                                   15

SEQ ID NO: 284          moltype = DNA  length = 15
FEATURE                 Location/Qualifiers
misc_feature            1..15
                        note = Description of Artificial Sequence: Synthetic
                         oligonucleotide
modified_base           14
                        mod_base = OTHER
                        note = Deoxyinosine
source                  1..15
                        mol_type = other DNA
                        organism = synthetic construct
SEQUENCE: 284
ccactcgccg ctcnt                                                   15

SEQ ID NO: 285          moltype = DNA  length = 15
FEATURE                 Location/Qualifiers
misc_feature            1..15
                        note = Description of Artificial Sequence: Synthetic
                         oligonucleotide
modified_base           14
                        mod_base = OTHER
                        note = Deoxyinosine
source                  1..15
                        mol_type = other DNA
                        organism = synthetic construct
SEQUENCE: 285
ccacgcgccc tacna                                                   15

SEQ ID NO: 286          moltype = DNA  length = 15
FEATURE                 Location/Qualifiers
misc_feature            1..15
                        note = Description of Artificial Sequence: Synthetic
                         oligonucleotide
modified_base           14
                        mod_base = OTHER
                        note = Deoxyinosine
source                  1..15
                        mol_type = other DNA
                        organism = synthetic construct
SEQUENCE: 286
caacgcgcac tacna                                                   15

SEQ ID NO: 287          moltype = DNA  length = 15
FEATURE                 Location/Qualifiers
misc_feature            1..15
                        note = Description of Artificial Sequence: Synthetic
                         oligonucleotide
modified_base           14
                        mod_base = OTHER
                        note = Deoxyinosine
source                  1..15
                        mol_type = other DNA
                        organism = synthetic construct
SEQUENCE: 287
caacaagcac tacng                                                   15

SEQ ID NO: 288          moltype = DNA  length = 15
```

-continued

```
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 288
caacaagcaa tacng                                                     15

SEQ ID NO: 289           moltype = DNA  length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 289
caagaagaaa taanc                                                     15

SEQ ID NO: 290           moltype = DNA  length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 290
aaagaagaaa taanc                                                     15

SEQ ID NO: 291           moltype = DNA  length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 291
gaagaagaca taana                                                     15

SEQ ID NO: 292           moltype = DNA  length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 292
gaagaagaca tagna                                                     15

SEQ ID NO: 293           moltype = DNA  length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
```

-continued

```
                             organism = synthetic construct
SEQUENCE: 293
gaagaggacg tagng                                                        15

SEQ ID NO: 294           moltype = DNA   length = 15
FEATURE                  Location/Qualifiers
misc_feature             1..15
                         note = Description of Artificial Sequence: Synthetic
                          oligonucleotide
modified_base            14
                         mod_base = OTHER
                         note = Deoxyinosine
source                   1..15
                         mol_type = other DNA
                         organism = synthetic construct
SEQUENCE: 294
gaggaggacg tagng                                                        15

SEQ ID NO: 295           moltype = DNA   length = 16
FEATURE                  Location/Qualifiers
misc_feature             1..16
                         note = Description of Artificial Sequence: Synthetic
                          oligonucleotide
modified_base            15
                         mod_base = OTHER
                         note = Deoxyinosine
source                   1..16
                         mol_type = other DNA
                         organism = synthetic construct
SEQUENCE: 295
ccacgctcct ctacna                                                       16

SEQ ID NO: 296           moltype = DNA   length = 16
FEATURE                  Location/Qualifiers
misc_feature             1..16
                         note = Description of Artificial Sequence: Synthetic
                          oligonucleotide
modified_base            15
                         mod_base = OTHER
                         note = Deoxyinosine
source                   1..16
                         mol_type = other DNA
                         organism = synthetic construct
SEQUENCE: 296
ccgcgctcct ctacna                                                       16

SEQ ID NO: 297           moltype = DNA   length = 16
FEATURE                  Location/Qualifiers
misc_feature             1..16
                         note = Description of Artificial Sequence: Synthetic
                          oligonucleotide
modified_base            15
                         mod_base = OTHER
                         note = Deoxyinosine
source                   1..16
                         mol_type = other DNA
                         organism = synthetic construct
SEQUENCE: 297
ccacgcgcac caacnt                                                       16

SEQ ID NO: 298           moltype = DNA   length = 16
FEATURE                  Location/Qualifiers
misc_feature             1..16
                         note = Description of Artificial Sequence: Synthetic
                          oligonucleotide
modified_base            15
                         mod_base = OTHER
                         note = Deoxyinosine
source                   1..16
                         mol_type = other DNA
                         organism = synthetic construct
SEQUENCE: 298
ccacgcgcgc caacnt                                                       16

SEQ ID NO: 299           moltype = DNA   length = 16
FEATURE                  Location/Qualifiers
misc_feature             1..16
                         note = Description of Artificial Sequence: Synthetic
                          oligonucleotide
```

-continued

```
modified_base          15
                       mod_base = OTHER
                       note = Deoxyinosine
source                 1..16
                       mol_type = other DNA
                       organism = synthetic construct
SEQUENCE: 299
ccacgcgagt caacnc                                                                16

SEQ ID NO: 300         moltype = DNA  length = 16
FEATURE                Location/Qualifiers
misc_feature           1..16
                       note = Description of Artificial Sequence: Synthetic
                        oligonucleotide
modified_base          15
                       mod_base = OTHER
                       note = Deoxyinosine
source                 1..16
                       mol_type = other DNA
                       organism = synthetic construct
SEQUENCE: 300
ccacgagagt caacnc                                                                16

SEQ ID NO: 301         moltype = DNA  length = 16
FEATURE                Location/Qualifiers
misc_feature           1..16
                       note = Description of Artificial Sequence: Synthetic
                        oligonucleotide
modified_base          15
                       mod_base = OTHER
                       note = Deoxyinosine
source                 1..16
                       mol_type = other DNA
                       organism = synthetic construct
SEQUENCE: 301
ccacgagagt caacna                                                                16

SEQ ID NO: 302         moltype = DNA  length = 16
FEATURE                Location/Qualifiers
misc_feature           1..16
                       note = Description of Artificial Sequence: Synthetic
                        oligonucleotide
modified_base          15
                       mod_base = OTHER
                       note = Deoxyinosine
source                 1..16
                       mol_type = other DNA
                       organism = synthetic construct
SEQUENCE: 302
caacgagagt aaacna                                                                16

SEQ ID NO: 303         moltype = DNA  length = 16
FEATURE                Location/Qualifiers
misc_feature           1..16
                       note = Description of Artificial Sequence: Synthetic
                        oligonucleotide
modified_base          15
                       mod_base = OTHER
                       note = Deoxyinosine
source                 1..16
                       mol_type = other DNA
                       organism = synthetic construct
SEQUENCE: 303
caaagagaat aaacng                                                                16

SEQ ID NO: 304         moltype = DNA  length = 16
FEATURE                Location/Qualifiers
misc_feature           1..16
                       note = Description of Artificial Sequence: Synthetic
                        oligonucleotide
modified_base          15
                       mod_base = OTHER
                       note = Deoxyinosine
source                 1..16
                       mol_type = other DNA
                       organism = synthetic construct
SEQUENCE: 304
caaagagaat aaaang                                                                16
```

-continued

```
SEQ ID NO: 305            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
                          mol_type = other DNA
                          organism = synthetic construct
SEQUENCE: 305
caaagagaat agaang                                                    16

SEQ ID NO: 306            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
                          mol_type = other DNA
                          organism = synthetic construct
SEQUENCE: 306
cagagagaat agaang                                                    16

SEQ ID NO: 307            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
                          mol_type = other DNA
                          organism = synthetic construct
SEQUENCE: 307
aagagcgaga gagant                                                    16

SEQ ID NO: 308            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
                          mol_type = other DNA
                          organism = synthetic construct
SEQUENCE: 308
aggagcgaga gagant                                                    16

SEQ ID NO: 309            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
                          mol_type = other DNA
                          organism = synthetic construct
SEQUENCE: 309
cggagagaga ggagnt                                                    16

SEQ ID NO: 310            moltype = DNA   length = 16
FEATURE                   Location/Qualifiers
misc_feature              1..16
                          note = Description of Artificial Sequence: Synthetic
                          oligonucleotide
modified_base             15
                          mod_base = OTHER
                          note = Deoxyinosine
source                    1..16
```

```
                      mol_type = other DNA
                      organism = synthetic construct
SEQUENCE: 310
cggagaggga ggagnt                                                      16

SEQ ID NO: 311        moltype = DNA   length = 17
FEATURE               Location/Qualifiers
misc_feature          1..17
                      note = Description of Artificial Sequence: Synthetic
                       oligonucleotide
modified_base         16
                      mod_base = OTHER
                      note = Deoxyinosine
source                1..17
                      mol_type = other DNA
                      organism = synthetic construct
SEQUENCE: 311
cccgctccgc cagtcna                                                     17

SEQ ID NO: 312        moltype = DNA   length = 17
FEATURE               Location/Qualifiers
misc_feature          1..17
                      note = Description of Artificial Sequence: Synthetic
                       oligonucleotide
modified_base         16
                      mod_base = OTHER
                      note = Deoxyinosine
source                1..17
                      mol_type = other DNA
                      organism = synthetic construct
SEQUENCE: 312
ccacgcgcgc cagtcna                                                     17

SEQ ID NO: 313        moltype = DNA   length = 17
FEATURE               Location/Qualifiers
misc_feature          1..17
                      note = Description of Artificial Sequence: Synthetic
                       oligonucleotide
modified_base         16
                      mod_base = OTHER
                      note = Deoxyinosine
source                1..17
                      mol_type = other DNA
                      organism = synthetic construct
SEQUENCE: 313
ccacgcgcga cagacnt                                                     17

SEQ ID NO: 314        moltype = DNA   length = 17
FEATURE               Location/Qualifiers
misc_feature          1..17
                      note = Description of Artificial Sequence: Synthetic
                       oligonucleotide
modified_base         16
                      mod_base = OTHER
                      note = Deoxyinosine
source                1..17
                      mol_type = other DNA
                      organism = synthetic construct
SEQUENCE: 314
ccacgcgaga cagacnt                                                     17

SEQ ID NO: 315        moltype = DNA   length = 17
FEATURE               Location/Qualifiers
misc_feature          1..17
                      note = Description of Artificial Sequence: Synthetic
                       oligonucleotide
modified_base         16
                      mod_base = OTHER
                      note = Deoxyinosine
source                1..17
                      mol_type = other DNA
                      organism = synthetic construct
SEQUENCE: 315
caacgcgaga cagacnt                                                     17

SEQ ID NO: 316        moltype = DNA   length = 17
FEATURE               Location/Qualifiers
misc_feature          1..17
                      note = Description of Artificial Sequence: Synthetic
```

```
                        oligonucleotide
modified_base           16
                        mod_base = OTHER
                        note = Deoxyinosine
source                  1..17
                        mol_type = other DNA
                        organism = synthetic construct
SEQUENCE: 316
caacgcgaga cagaant                                          17

SEQ ID NO: 317          moltype = DNA  length = 17
FEATURE                 Location/Qualifiers
misc_feature            1..17
                        note = Description of Artificial Sequence: Synthetic
                        oligonucleotide
modified_base           16
                        mod_base = OTHER
                        note = Deoxyinosine
source                  1..17
                        mol_type = other DNA
                        organism = synthetic construct
SEQUENCE: 317
caacgagaga cagtana                                          17

SEQ ID NO: 318          moltype = DNA  length = 17
FEATURE                 Location/Qualifiers
misc_feature            1..17
                        note = Description of Artificial Sequence: Synthetic
                        oligonucleotide
modified_base           16
                        mod_base = OTHER
                        note = Deoxyinosine
source                  1..17
                        mol_type = other DNA
                        organism = synthetic construct
SEQUENCE: 318
caacgagaga aagtana                                          17

SEQ ID NO: 319          moltype = DNA  length = 17
FEATURE                 Location/Qualifiers
misc_feature            1..17
                        note = Description of Artificial Sequence: Synthetic
                        oligonucleotide
modified_base           16
                        mod_base = OTHER
                        note = Deoxyinosine
source                  1..17
                        mol_type = other DNA
                        organism = synthetic construct
SEQUENCE: 319
caaggagaga aagaant                                          17

SEQ ID NO: 320          moltype = DNA  length = 17
FEATURE                 Location/Qualifiers
misc_feature            1..17
                        note = Description of Artificial Sequence: Synthetic
                        oligonucleotide
modified_base           16
                        mod_base = OTHER
                        note = Deoxyinosine
source                  1..17
                        mol_type = other DNA
                        organism = synthetic construct
SEQUENCE: 320
caaggagaga gagaant                                          17

SEQ ID NO: 321          moltype = DNA  length = 17
FEATURE                 Location/Qualifiers
misc_feature            1..17
                        note = Description of Artificial Sequence: Synthetic
                        oligonucleotide
modified_base           16
                        mod_base = OTHER
                        note = Deoxyinosine
source                  1..17
                        mol_type = other DNA
                        organism = synthetic construct
SEQUENCE: 321
caaggagaga gagagnt                                          17
```

-continued

```
SEQ ID NO: 322          moltype = DNA   length = 17
FEATURE                 Location/Qualifiers
misc_feature            1..17
                        note = Description of Artificial Sequence: Synthetic
                         oligonucleotide
modified_base           16
                        mod_base = OTHER
                        note = Deoxyinosine
source                  1..17
                        mol_type = other DNA
                        organism = synthetic construct
SEQUENCE: 322
cgaggagaga gagagnt                                                   17

SEQ ID NO: 323          moltype = DNA   length = 18
FEATURE                 Location/Qualifiers
misc_feature            1..18
                        note = Description of Artificial Sequence: Synthetic
                         oligonucleotide
modified_base           17
                        mod_base = OTHER
                        note = Deoxyinosine
source                  1..18
                        mol_type = other DNA
                        organism = synthetic construct
SEQUENCE: 323
ccacctacca ccagtcng                                                  18

SEQ ID NO: 324          moltype = DNA   length = 18
FEATURE                 Location/Qualifiers
misc_feature            1..18
                        note = Description of Artificial Sequence: Synthetic
                         oligonucleotide
modified_base           17
                        mod_base = OTHER
                        note = Deoxyinosine
source                  1..18
                        mol_type = other DNA
                        organism = synthetic construct
SEQUENCE: 324
ccacatacca ccagtcng                                                  18

SEQ ID NO: 325          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 325
acgttggatg taccagaacc tacactcccc                                     30

SEQ ID NO: 326          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 326
acgttggatg acgtaagcac acatccccag                                     30

SEQ ID NO: 327          moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 327
acgttggatg tctcaaactc cagagtggcc                                     30

SEQ ID NO: 328          moltype = DNA   length = 30
FEATURE                 Location/Qualifiers
misc_feature            1..30
                        note = Description of Artificial Sequence: Synthetic primer
source                  1..30
                        mol_type = other DNA
```

```
                         organism = synthetic construct
SEQUENCE: 328
acgttggatg agctgttcca cacttctgag                                        30

SEQ ID NO: 329           moltype = DNA  length = 21
FEATURE                  Location/Qualifiers
misc_feature             1..21
                         note = Description of Artificial Sequence: Synthetic primer
source                   1..21
                         mol_type = other DNA
                         organism = synthetic construct
misc_feature             1..8
                         note = DNA
misc_feature             9
                         note = RNA
misc_feature             10..21
                         note = DNA
SEQUENCE: 329
tttctcccca cctgaccctg c                                                 21

SEQ ID NO: 330           moltype = DNA  length = 22
FEATURE                  Location/Qualifiers
misc_feature             1..22
                         note = Description of Artificial Sequence: Synthetic primer
source                   1..22
                         mol_type = other DNA
                         organism = synthetic construct
misc_feature             1..9
                         note = DNA
misc_feature             10
                         note = RNA
misc_feature             11..22
                         note = DNA
SEQUENCE: 330
ttttctcccc acctgaccct gt                                                22

SEQ ID NO: 331           moltype = DNA  length = 28
FEATURE                  Location/Qualifiers
misc_feature             1..28
                         note = Description of Artificial Sequence: Synthetic primer
source                   1..28
                         mol_type = other DNA
                         organism = synthetic construct
misc_feature             1..11
                         note = DNA
misc_feature             12
                         note = RNA
misc_feature             13..28
                         note = DNA
SEQUENCE: 331
ttattcccag gtgcatgcat gcgcacac                                          28

SEQ ID NO: 332           moltype = DNA  length = 29
FEATURE                  Location/Qualifiers
misc_feature             1..29
                         note = Description of Artificial Sequence: Synthetic primer
source                   1..29
                         mol_type = other DNA
                         organism = synthetic construct
misc_feature             1..12
                         note = DNA
misc_feature             13
                         note = RNA
misc_feature             14..29
                         note = DNA
SEQUENCE: 332
ttatttccca ggtgcatgca tgcgcacag                                         29

SEQ ID NO: 333           moltype =   length =
SEQUENCE: 333
000

SEQ ID NO: 334           moltype = DNA  length = 10
FEATURE                  Location/Qualifiers
misc_feature             1..10
                         note = Description of Artificial Sequence: Synthetic
                          oligonucleotide
source                   1..10
                         mol_type = other DNA
```

-continued

```
                          organism = synthetic construct
misc_feature             1..9
                          note = DNA
misc_feature             10
                          note = RNA
SEQUENCE: 334
ttttctcccc                                                          10

SEQ ID NO: 335           moltype = DNA   length = 12
FEATURE                  Location/Qualifiers
misc_feature             1..12
                          note = Description of Artificial Sequence: Synthetic
                           oligonucleotide
source                   1..12
                          mol_type = other DNA
                          organism = synthetic construct
misc_feature             1..11
                          note = DNA
misc_feature             12
                          note = RNA
SEQUENCE: 335
ttattcccag gt                                                       12

SEQ ID NO: 336           moltype = DNA   length = 13
FEATURE                  Location/Qualifiers
misc_feature             1..13
                          note = Description of Artificial Sequence: Synthetic
                           oligonucleotide
source                   1..13
                          mol_type = other DNA
                          organism = synthetic construct
misc_feature             1..12
                          note = DNA
misc_feature             13
                          note = RNA
SEQUENCE: 336
ttatttccca ggt                                                      13

SEQ ID NO: 337           moltype = DNA   length = 20
FEATURE                  Location/Qualifiers
misc_feature             1..20
                          note = Description of Artificial Sequence: Synthetic
                           oligonucleotide
source                   1..20
                          mol_type = other DNA
                          organism = synthetic construct
SEQUENCE: 337
acccactcca tcgagatttc                                               20

SEQ ID NO: 338           moltype = DNA   length = 21
FEATURE                  Location/Qualifiers
misc_feature             1..21
                          note = Description of Artificial Sequence: Synthetic
                           oligonucleotide
source                   1..21
                          mol_type = other DNA
                          organism = synthetic construct
SEQUENCE: 338
acccactcca tcgagatttc t                                             21

SEQ ID NO: 339           moltype = DNA   length = 21
FEATURE                  Location/Qualifiers
misc_feature             1..21
                          note = Description of Artificial Sequence: Synthetic
                           oligonucleotide
source                   1..21
                          mol_type = other DNA
                          organism = synthetic construct
SEQUENCE: 339
acccactcca tcgagatttc a                                             21
```

PRODUCTS AND PROCESSES FOR MULTIPLEX NUCLEIC ACID IDENTIFICATION

RELATED PATENT APPLICATIONS

This patent application is a continuation of U.S. patent application Ser. No. 16/793,732 filed on Feb. 18, 2020, now issued U.S. Pat. No. 11,667,958, entitled PRODUCTS AND PROCESSES FOR MULTIPLEX NUCLEIC ACID IDENTIFICATION, naming Christiane Honisch, Dirk J. Van Den Boom, Michael Mosko, and Anders Nygren as inventors, and designated by which is a continuation of U.S. patent application Ser. No. 13/551,486 filed on Jul. 17, 2012, now issued U.S. Pat. No. 10,604,791, entitled PRODUCTS AND PROCESSES FOR MULTIPLEX NUCLEIC ACID IDENTIFICATION, naming Christiane Honisch, Dirk J. Van Den Boom, Michael Mosko, and Anders Nygren as inventors, and designated by which is a continuation application of international patent application no. PCT/US2012/038710 filed on May 18, 2012, entitled PRODUCTS AND PROCESSES FOR MULTIPLEX NUCLEIC ACID IDENTIFICATION, naming Christiane Honisch, Dirk Johannes Van Den Boom, Michael Mosko, and Anders Nygren as inventors and designated by which claims the benefit of U.S. Provisional Patent Application No. 61/488,082 filed on May 19, 2011, entitled PRODUCTS AND PROCESSES FOR MULTIPLEX NUCLEIC ACID IDENTIFICATION, naming Christiane Honisch, Dirk Johannes Van Den Boom, and Michael Mosko as inventors, and designated by and this patent application is related to U.S. patent application Ser. No. 13/126,684 filed on Oct. 27, 2009, entitled PRODUCTS AND PROCESSES FOR MULTIPLEX NUCLEIC ACID IDENTIFICATION, naming Dirk Johannes Van Den Boom, Christiane Honisch, Andrew Timms and Smita Chitnis as inventors, and designated by which is a national phase application of international patent application number PCT/US2009/062239, filed on Oct. 27, 2009, entitled PRODUCTS AND PROCESSES FOR MULTIPLEX NUCLEIC ACID IDENTIFICATION, naming Dirk Johannes Van Den Boom, Christiane Honisch, Andrew Timms and Smita Chitnis as applicants and inventors, and designated by which claims the benefit of U.S. Provisional Patent Application No. 61/109,885 filed on Oct. 30, 2008, entitled PRODUCTS AND PROCESSES FOR MULTIPLEX NUCLEIC ACID IDENTIFICATION, naming Dirk Johannes Van Den Boom, Christiane Honisch, Andrew Timms and Smita Chitnis as inventors. The entire content of the foregoing patent applications hereby is incorporated by reference, including all text, tables and drawings.

SEQUENCE LISTING

The instant application contains a Sequence Listing which has been submitted in XML format via PatentCenter and is hereby incorporated by reference in its entirety. Said XML copy, created on Jun. 21, 2023, is named AGB-602000N3 SL.xml and is 526,632 bytes in size.

FIELD

The technology relates in part to nucleic acid identification procedures in which multiple target nucleic acids can be detected in one procedure. The technology also in part relates to identification of nucleic acid modifications.

BACKGROUND

The detection of specific nucleic acids is an important tool for diagnostic medicine and molecular biology research.

Nucleic acid assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species, for example.

SUMMARY

Provided in some embodiments is a method for determining the presence or absence of a plurality of target nucleic acids in a composition, which includes: (a) preparing amplicons of the target nucleic acids by amplifying the target nucleic acids, or portions thereof, under amplification conditions; (b) contacting the amplicons in solution with a set of oligonucleotides under hybridization conditions, where each oligonucleotide in the set includes a hybridization sequence capable of specifically hybridizing to one amplicon under the hybridization conditions when the amplicon is present in the solution; (c) generating extended oligonucleotides that include a capture agent by extending oligonucleotides hybridized to the amplicons by one or more nucleotides, wherein one of the one of more nucleotides is a terminating nucleotide and one or more of the nucleotides added to the oligonucleotides includes the capture agent; (d) contacting the extended oligonucleotides with a solid phase under conditions in which the capture agent interacts with the solid phase; (e) releasing the extended oligonucleotides that have interacted with the solid phase by competition with a competitor; and (f) detecting the extended oligonucleotides released in (e); whereby the presence or absence of each target nucleic acid is determined by the presence or absence of the corresponding extended oligonucleotide. In certain embodiments, (i) the mass of one oligonucleotide species detectably differs from the masses of the other oligonucleotide species in the set; and (ii) each oligonucleotide species specifically corresponds to a specific amplicon and thereby specifically corresponds to a specific target nucleic acid. In some embodiments, (i) each oligonucleotide in the set includes a mass distinguishable tag located 5' of the hybridization sequence, (ii) the mass of the mass distinguishable tag of one oligonucleotide detectably differs from the masses of mass distinguishable tags of the other oligonucleotides in the set; and (iii) each mass distinguishable tag specifically corresponds to a specific amplicon and thereby specifically corresponds to a specific target nucleic acid, the mass of the mass distinguishable tag is detected by mass spectrometry, and the presence or absence of each target nucleic acid is determined by the presence or absence of the corresponding mass distinguishable tag. In some embodiments, detecting the mass distinguishable tag detects the extended oligonucleotide. In certain embodiments, the extended oligonucleotides released in (e), or the mass distinguishable tags associated or cleaved from the released extended oligonucleotides, are detected by mass spectrometry.

Provided also in certain embodiments is a method for determining the presence or absence of a plurality of target nucleic acids in a composition, which includes: (a) preparing amplicons of the target nucleic acids by amplifying the target nucleic acids, or portions thereof, under amplification conditions; (b) contacting the amplicons in solution with a set of oligonucleotides under hybridization conditions, where: (i) each oligonucleotide in the set includes a hybridization sequence capable of specifically hybridizing to one amplicon under the hybridization conditions when the amplicon is present in the solution, (ii) each oligonucleotide in the set includes a mass distinguishable tag located 5' of the hybridization sequence, (iii) the mass of the mass distinguishable tag of one oligonucleotide detectably differs from the masses of mass distinguishable tags of the other oligonucleotides in the set; and (iv) each mass distinguishable tag specifically corresponds to a specific amplicon and thereby specifically corresponds to a specific target nucleic acid; (c) generating extended oligonucleotides that include a capture agent by extending oligonucleotides hybridized to the amplicons by one or more nucleotides, wherein one of the one of more nucleotides is a terminating nucleotide and one or more of the nucleotides added to the oligonucleotides includes the capture agent; (d) contacting the extended oligonucleotides with a solid phase under conditions in which the capture agent interacts with the solid phase; (e) releasing the extended oligonucleotides that have interacted with the solid phase by competition with a competitor; and (f) detecting the mass distinguishable tags released in (e); whereby the presence or absence of each target nucleic acid is determined by the presence or absence of the corresponding mass distinguishable tag. In certain embodiments, the extended oligonucleotides released in (e), or the mass distinguishable tags associated or cleaved from the released extended oligonucleotides, are detected by mass spectrometry.

In some embodiments, the mass distinguishable tag is not cleaved and released from the extended oligonucleotide, and in certain embodiments, the mass distinguishable tag is cleaved and released from the extended oligonucleotide. In some embodiments, the mass distinguishable tag is the extended oligonucleotide. In certain embodiments, the extension in (c) is performed once yielding one extended oligonucleotide. In some embodiments, the extension in (c) is performed multiple times (e.g., under amplification conditions) yielding multiple copies of the extended oligonucleotide. In certain embodiments, a solution containing amplicons (e.g., amplicons produced in (a)) is treated with an agent that removes terminal phosphates from any nucleotides not incorporated into the amplicons. The terminal phosphate sometimes is removed by contacting the amplicons with a phosphatase, and in certain embodiments the phosphatase is alkaline phosphatase (e.g., shrimp alkaline phosphatase).

Also provided in some embodiments is a method for determining the presence or absence of a plurality of target nucleic acids in a composition, which comprises (a) contacting target nucleic acids in solution with a set of oligonucleotides under hybridization conditions, where (i) each oligonucleotide in the set comprises a hybridization sequence capable of specifically hybridizing to one target nucleic acid species under the hybridization conditions when the target nucleic acid species is present in the solution; (b) generating extended oligonucleotides that comprise a capture agent by extending oligonucleotides hybridized to the amplicons by one or more nucleotides under amplification conditions, wherein one of the one of more nucleotides is a terminating nucleotide and one or more of the nucleotides added to the oligonucleotides comprises the capture agent; (c) contacting the extended oligonucleotides with a solid phase under conditions in which the capture agent interacts with the solid phase; (d) releasing the extended oligonucleotides that have interacted with the solid phase by competition with a competitor; and (e) detecting the extended oligonucleotides released in (d); whereby the presence or absence of each target nucleic acid is determined by the presence or absence of the corresponding extended oligonucleotide. In certain embodiments, (i) the mass of one oligonucleotide species detectably differs from the masses of the other oligonucleotide species in the set; and (ii) each oligonucleotide species specifically corresponds to a specific amplicon and thereby specifically corresponds to a specific target nucleic acid. In some embodiments, (i) each oligonucleotide in the set includes a mass distinguishable tag located 5' of the hybridization sequence, (ii) the mass of the mass distinguishable tag of one oligonucleotide detectably differs from the masses of mass distinguishable tags of the other oligonucleotides in the set; and (iii) each mass distinguishable tag specifically corresponds to a specific amplicon and thereby specifically corresponds to a specific target nucleic acid, the mass of the mass distinguishable tag is detected by mass spectrometry, and the presence or absence of each target nucleic acid is determined by the presence or absence of the corresponding mass distinguishable tag. In some embodiments, detecting the mass distinguishable tag detects the extended oligonucleotide. In some embodiments, detecting the mass distinguishable tag detects the extended oligonucleotide. In certain embodiments, the extended oligonucleotides released in (d), or the mass distinguishable tags associated or cleaved from the released extended oligonucleotides, are detected by mass spectrometry.

Any suitable amplification procedure can be utilized in multiplex detection assays described herein, and sometimes the following procedure is utilized in some embodiments, which comprises: (a) contacting the target nucleic acids with a set of first polynucleotides, where each first polynucleotide comprises (1) a first complementary sequence that hybridizes to the target nucleic acid and (2) a first tag located 5' of the complementary sequence; (b) preparing extended first polynucleotides by extending the first polynucleotide; (c) joining a second polynucleotide to the 3' end of the extended first polynucleotides, where the second polynucleotide comprises a second tag; (d) contacting the product of (c) with a primer and extending the primer, where the primer hybridizes to the first tag or second tag; and (e) amplifying the product of (c) with a set of primers under amplification conditions, where one primer in the set hybridizes to one of the tags and another primer in the set hybridizes to the complement of the other tag. In certain embodiments linear amplification is performed with one set of primers. In some embodiments, the second polynucleotide comprises a nucleotide sequence that hybridizes to the target nucleic acid. The nucleotide sequence of the first tag and the nucleotide sequence of the second tag are different in some embodiments, and are identical, or are complementary to one another, in other embodiments. In certain embodiments, the first tag and the second tag are included in each of the amplification products produced in (e). Such an amplification process can further comprise (f) contacting the amplicons in solution with a set of oligonucleotides under hybridization conditions, where each oligonucleotide in the set comprises a hybridization sequence capable of specifically hybridizing to one amplicon under the hybridization conditions when the amplicon is present in the solution; (g) generating extended oligonucleotides that comprise a capture agent by extending oligonucleotides hybridized to the amplicons by one or more nucleotides, where one of the one of more nucleotides is a terminating nucleotide and one or more of the nucleotides added to the oligonucleotides comprises the capture agent; (h) contacting the extended oligonucleotides with a solid phase under conditions in which the capture agent interacts with the solid phase; (i) releasing the extended oligonucleotides that have interacted with the solid phase by competition with a competitor; and (j) detecting the released extended oligonucleotides in (i); whereby the presence or absence of each target nucleic acid is determined by the presence or absence of the extended oligonucleotide. In certain embodiments, the extension in (g) is performed once yielding one extended oligonucleotide. In some embodiments, the extension in (g) is performed multiple times (e.g., under amplification conditions) yielding multiple copies of the extended oligonucleotide. In certain embodiments, (i) the mass of one oligonucleotide species detectably differs from the masses of the other oligonucleotide species in the set; and (ii) each oligonucleotide species specifically corresponds to a specific amplicon and thereby specifically corresponds to a specific target nucleic acid. In some embodiments, (i) each oligonucleotide in the set includes a mass distinguishable tag located 5' of the hybridization sequence, (ii) the mass of the mass distinguishable tag of one oligonucleotide detectably differs from the masses of mass distinguishable tags of the other oligonucleotides in the set; and (iii) each mass distinguishable tag specifically corresponds to a specific amplicon and thereby specifically corresponds to a specific target nucleic acid, the mass of the mass distinguishable tag is detected by mass spectrometry, and the presence or absence of each target nucleic acid is determined by the presence or absence of the corresponding mass distinguishable tag. In some embodiments, detecting the mass distinguishable tag detects the extended oligonucleotide. In some embodiments, detecting the mass distinguishable tag detects the extended oligonucleotide.

In some embodiments, competition with a competitor includes contacting the solid phase with a competitor. In certain embodiments, the nucleotide that includes the capture agent is a capture agent conjugated to a nucleotide triphosphate. In some embodiments, the nucleotide triphosphate is a dideoxynucleotide triphosphate.

In certain embodiments, the capture agent includes a member of a binding pair. In some embodiments, the capture agent includes biotin or a biotin analogue, and on certain embodiments, the solid phase includes avidin or streptavidin. In some embodiments, the capture agent includes avidin or streptavidin, and in certain embodiments, the solid phase includes biotin. In some embodiments, releasing the mass distinguishable tags by competition with a competitor is carried out under elevated temperature conditions. In certain embodiments, the elevated temperature conditions include treatment for between about 1 minute to about 10 minutes (e.g., about 1 minute, about 2 minutes about 3 minutes, about 4 minutes, about 5 minutes, about 6 minutes, about 7 minutes, about 8 minutes, about 9 minutes or about 10 minutes) at a temperature of between about 80 degrees Celsius to about 100 degrees Celsius (e.g., about 80 degrees Celsius (° C.), about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or 100° C.). In some embodiments, the elevated temperature conditions comprise treatment for about 5 minutes at about 90 degrees Celsius. In certain embodiments, (c) (e.g., generating extended oligonucleotides that include a capture agent by extending oligonucleotides hybridized to the amplicons by one or more nucleotides, wherein one of the one of more nucleotides is a terminating nucleotide and one or more of the nucleotides added to the oligonucleotides includes the capture agent) is carried out in one container and the method further comprises transferring the released mass distinguishable tags to another container between (e) and (f).

In some embodiments, the solution containing amplicons produced in (a) is treated with an agent that removes terminal phosphates from any nucleotides not incorporated into the amplicons. In certain embodiments, the terminal phosphate is removed by contacting the solution with a phosphatase. In some embodiments, the phosphatase is alkaline phosphatase, and in certain embodiments, the alkaline phosphatase is shrimp alkaline phosphatase.

In some embodiments, the terminal nucleotides in the extended oligonucleotides comprise the capture agent. In certain embodiments, one or more non-terminal nucleotides in the extended oligonucleotides comprise the capture agent. In some embodiments, the hybridization sequence is about 5 to about 200 nucleotides in length. In some embodiments, the hybridization sequence in each oligonucleotide is about 5 to about 50 nucleotides in length. In certain embodiments, terminal nucleotides in the extended oligonucleotides comprise the capture agent, and sometimes one or more non-terminal nucleotides in the extended oligonucleotides comprise the capture agent. In some embodiments, the capture agent comprises biotin, or alternatively avidin or streptavidin, in which case the solid phase comprises avidin or streptavidin, or biotin, respectively.

The distinguishable tag is distinguished in part by mass in certain embodiments (i.e., a mass distinguishable tag where a distinguishing feature is mass). The distinguishable tag in some embodiments consists of nucleotides, and sometimes the tag is about 5 nucleotides to about 50 nucleotides in length. The distinguishable tag in certain embodiments is a nucleotide compomer, which sometimes is about 5 nucleotides to about 35 nucleotides in length. In some embodiments, the distinguishable tag is a peptide, which sometimes is about 5 amino acids to about 100 amino acids in length. The distinguishable tag in certain embodiments is a concatemer of organic molecule units. In some embodiments, the tag is a trityl molecule concatemer.

In certain embodiments, the solid phase is selected from a flat surface, a silicon chip, a bead, sphere or combination of the foregoing. A solid phase sometimes is paramagnetic. In some embodiments, the solid phase is a paramagnetic bead, and in certain embodiments, the solid phase includes a capture agent.

In certain embodiments, the presence or absence of about 50 or more target nucleic acid species is detected by a method described herein. In some embodiments, about 100 or more, 150 or more, 200 or more, 250 or more, 300 or more, 325 or more, 350 or more, 375 or more, 400, or more, 425 or more, 450 or more, 475 or more or 500 or more target nucleic acids is detected. In some embodiments, the presence, absence or amount of about 2 to 500 target nucleic acid species is detected by a method described herein (e.g., about 5, 10, 25, 50, 75, 100, 150, 200, 250, 300, 350, 400, 450 target nucleic acid species). The target nucleic acids in certain embodiments are genomic DNA (e.g., human, microbial, viral, fungal or plant genomic DNA; any eukaryotic or prokaryotic nucleic acid (RNA and DNA)). In some embodiments, the oligonucleotides are RNA or DNA.

In some embodiments, the mass spectrometry is matrix-assisted laser desorption ionization (MALDI) mass spectrometry. In certain embodiments, the mass spectrometry is electrospray (ES) mass spectrometry. In some embodiments, the presence or absence of about 1 to about 50 or more target nucleic acids is detected. In certain embodiments, the mass distinguishable tag consists of nucleotides. In some embodiments, the mass distinguishable tag is a nucleotide compomer. In certain embodiments, the nucleotide compomer is about 5 nucleotides to about 150 nucleotides in length. In some embodiments, the target nucleic acids are genomic DNA, and in certain embodiments, the genomic DNA is human genomic DNA.

In some embodiments, detecting comprises an increased signal to noise ratio when releasing comprises competition with a competitor as compared to releasing that does not comprise competition with a competitor. In some embodiments, the detecting is with a signal to noise ratio greater than a signal to noise ratio for detecting after releasing without competition with a competitor. In some embodiments, a signal to noise ratio for extending only a mutant is greater than a signal to noise ratio for extending a wild type and a mutant allele. In some embodiments, the sensitivity of detecting a mutant allele is greater for extending only a mutant allele than for extending a wild type allele and a mutant allele. In some embodiments, the detecting comprises a signal to noise ratio greater than the signal to noise ratio for a method in which releasing does not comprise competition with a competitor.

In some embodiments provided is a method for detecting the presence, absence or amount of a plurality of genetic variants in a composition, comprising: (a) preparing a plurality of amplicons derived from a plurality of target nucleic acid species, or portions thereof, where each target nucleic acid species comprises a first variant and a second variant; (b) hybridizing the amplicons to oligonucleotide species, where each oligonucleotide species hybridizes to an amplicon derived from a target nucleic acid species, thereby generating hybridized oligonucleotide species; and (c) contacting the hybridized oligonucleotide species with an extension composition comprising one or more terminating nucleotides under extension conditions; where (i) at least one of the one or more terminating nucleotides comprises a capture agent, and (ii) the hybridized oligonucleotide species that hybridize to the first variant are extended by a terminating nucleotide and the hybridized oligonucleotide species that hybridize to the second variant are not extended by a terminating nucleotide, thereby generating extended oligonucleotide species; (d) capturing the extended oligonucleotide species to a solid phase that captures the capture agent; (e) releasing the extended oligonucleotide species bound to the solid phase in (d) from the solid phase; and (f) detecting the mass of each extended oligonucleotide species released from the solid phase in (e) by mass spectrometry; whereby the presence, absence or amount of the genetic variants is detected. In some embodiments, the extended oligonucleotide species of the second variant is not detected. In some embodiments, each oligonucleotide species comprises a mass distinguishable tag located 5' of the hybridization sequence. In some embodiments a method comprises a first variant and a second variant where the first variant is a lower abundance variation and the second variant is a higher abundance variation. In some embodiments the genetic variants are single nucleotide polymorphism (SNP) variants, the first variant is a lower abundance allele and the second variant is a higher abundance allele. In some embodiments the one or more terminating nucleotides consist of one terminating nucleotide. In some embodiments the one or more terminating nucleotides consist of two terminating nucleotides. In some embodiments the one or more terminating nucleotides consist of three terminating nucleotides. In some embodiments the one or more terminating nucleotides independently are selected from ddATP, ddGTP, ddCTP, ddTTP and ddUTP. In some embodiments the extension composition comprises a non-terminating nucleotide. In some embodiments the extension composition comprises one or more extension nucleotides, which extension nucleotides comprise no capture agent. In some embodiments releasing the extended oligonucleotide species comprises contacting the solid phase with a releasing agent. In some embodiments the capture agent comprises biotin or a biotin analogue, the solid phase comprises streptavidin and the releasing agent comprises free biotin or a biotin analogue. In some embodiments, free biotin or a biotin analogue is the releasing agent. In some embodiments, free biotin or a biotin analogue is added at a concentration of about 10 to about 100 ug/ml. In some embodiments, free biotin or a biotin analogue is added at a concentration of about 25 ug/ml. In some embodiments the releasing agent has a higher affinity for the solid phase than the capture agent. In some embodiments releasing the extended oligonucleotide species comprises heating from about 30° C. to about 100° C. In some embodiments releasing the extended oligonucleotide species comprises heating from about 60° C. to about 100° C. In some embodiments releasing the extended oligonucleotide species comprises heating from 89° C. to about 100° C. In some embodiments releasing the extended oligonucleotide species comprises heating to about 90° C. In some embodiments, the solid phase is washed after an extended oligonucleotide is captured. In some embodiments, the washing removes salts that produce interfering adducts in mass spectrometry analysis. In some embodiments, an extended oligonucleotide is not contacted with a resin (e.g. an ion exchange resin).

In some embodiments a plurality of target nucleic acid species is 20 or more target nucleic acid species. In some embodiments a plurality of target nucleic acid species is 200 or more target nucleic acid species. In some embodiments a plurality of target nucleic acid species is 200 to 300 target nucleic acid species.

In some embodiments the extension conditions comprise cycling 20 to 300 times. In some embodiments the extension conditions comprise cycling 200 to 300 times.

In some embodiments, a composition comprising a plurality of genetic variants comprises a synthetic template. In some embodiments, a composition comprising a plurality of genetic variants comprises a synthetic template and the amount and/or percentage of a first variant in the composition is determined wherein the synthetic template comprises a variant different than in the first variant and second variant and hybridizes to the same oligonucleotides species. In some embodiments, a plurality of amplicons comprise a synthetic template and the amount and/or percentage of a first variant in a composition is determined wherein the synthetic template comprises a variant different than in the first variant and second variant and hybridizes to the same oligonucleotides species.

Certain embodiments are described further in the following description, claims and drawings.

BRIEF DESCRIPTION OF THE DRAWINGS

The drawings illustrate certain non-limiting embodiments of the technology and are not necessarily drawn to scale.

FIG. 3 shows the universal PCR products from both Approach 1 and 2 procedures from FIGS. 1 and 2, which can be identified using a post-PCR reaction (iPLEX Gold, SEQUENOM).

FIG. 5A shows MALDI-TOF MS spectra for genotyping of rs1015731 using an Approach 2 protocol.

FIG. 5E shows the genotypes acquired from MALDI-TOF MS spectra from FIG. 5C (19 plex) and FIG. 5D (35 plex).

FIG. 6 shows PCR amplification and post-PCR primer extension with allele-specific extension primers containing allele-specific mass tags.

FIG. 7 shows MALDI-TOF MS spectra for 35 plex genotyping using post-PCR primer extension with allele-specific extension primers containing allele-specific mass tags as a readout.

FIG. 9 shows oligonucleotides mass tags corresponding to a 70 plex assay. All oligonucleotides were diluted to a final total concentration of 10 pmol and spotted on a 384 well chip. Values for area, peak height and signal-to-noise ratio were collected from Typer 3.4 (SEQUENOM).

FIG. 10 shows peak areas for oligonucleotides mass tags corresponding to 70 plex assay sorted by nucleotide composition. All oligonucleotides were diluted to a final total concentration of 10 pmol and spotted on a 384 well chip. Area values were collected from Typer 3.4 (SEQUENOM).

FIG. 11A shows a MALDI-TOF MS spectrum (zoomed views) of oligonucleotide tags corresponding to a 100 plex assay. FIG. 11B shows signal to noise ratios of oligonucleotide tags corresponding to a 100 plex assay. All oligonucleotides were diluted to a final total concentration of 10, 5, 2.5 or 1pmol, with 8 replicates spotted on a 384 well chip. Values for signal-to-noise ratio were collected from Typer 3.4 (SEQUENOM). FIG. 11C shows a MALDI-TOF MS spectrum (zoomed views) of a 100 plex assay after PCR amplification and post-PCR primer extension with allele-specific extension primers containing allele-specific mass tags.

FIG. 13 shows extension rates for 7 plex and 5 plex reactions over two DNAs. Results compare extension by a single biotinylated ddNTP or a biotinylated dNTP terminated by an unmodified ddNTP, and final amounts of biotinylated dNTP or ddNTP of 210 or 420 pmol added to the reaction. Extension rates were calculated by dividing the area of extended product by the total area (extended product and unextended oligonucleotide) in Typer 3.4. All experiments include two replicates of two Centre de'Etude du Polymorphisme Humain (CEPH) DNAs, NA07019 and NA11036.

FIGS. 16, 17, 18 and 19 show a comparison of extension oligonucleotide concentration in extension reactions using a 70 plex assay. All assays followed the same protocol except for the amount of extension oligonucleotide used. All experiments include four replicates of the two CEPH DNAs NA06991 and NA07019. The results compare the signal-to-noise ratios of the extension products from Typer 3.4 (SEQUENOM).

FIGS. 20 and 21 show a comparison of biotinylated ddNTP concentration in extension reactions using a 70 plex assay. All assays followed the same protocol except for the amount of biotinylated ddNTP used (value indicates final amount of each biotinylated nucleotide). All experiments include four replicates of the two CEPH DNAs NA06991 and NA07019. The results compare the signal-to-noise ratios of the extension products from Typer 3.4 (SEQUENOM).

FIG. 24 shows a comparison of magnetic streptavidin beads and endonuclease V concentration using a 70 plex assay. All assays were conducted using the same conditions except for the amount of magnetic streptavidin beads and endonuclease V. All experiments include four replicates of the CEPH DNA NA11036. The results compare the signal-to-noise ratio from Typer 3.4.

In FIG. 27A, a region of interest is PCR amplified (e.g., using uniplex or multiplex methods) with subsequent dephosphorylation of the amplified products with shrimp alkaline phosphatase (not shown in diagram). FIG. 27B illustrates single base extension of biotinylated dideoxynucleotides over the residue of interest in the product amplified in panel A. FIG. 27C illustrates the capture of the biotinylated extension products by streptavidin coated magnetic beads. FIG. 27D illustrates a washing step to remove unused reaction components followed by a capture step, to capture the streptavidin coated magnetic beads to which the biotinylated extension products are bound. FIG. 27E illustrates release of the biotinylated extension products from the streptavidin coated magnetic bead by competition with free biotin. FIG. 27F illustrates the purified biotinylated extension products, which can be further analyzed using a variety of methods, including matrix assisted laser desorption/time of flight (MALDI-TOF) mass spectrometry (MS). For use in MALDI-TOF mass spectrometry, the isolated extension products can be dispensed onto a SpectroCHIP® (SEQUENOM), for example. FIG. 27G illustrates a representative mass spectrum from MALDI-TOF MS analysis of a biotinylated extension product generated as described herein. See Example 12 for experimental details and results.

FIG. 28 discloses SEQ ID NOS 337-339, respectively, in order of appearance.

FIG. 32A shows the results of a biotin competition using Dynal C1 streptavidin beads for capture and free-biotin for the competition. The concentration of the biotinylated oligonucleotide and reference oligonucleotide (i.e. quantification oligonucleotide) tested was 0.031 uM. FIG. 32B shows the results of an inosine cleavage release using Dynal C1 streptavidin beads for capture and endonuclease V for the release. The concentration of the biotinylated oligonucleotide and reference oligonucleotide (i.e. quantification oligonucleotide) tested was 0.031 uM.

FIG. 34A shows results using Dynal C1 beads. FIG. 34B shows results using Solulink Beads. FIG. 34C shows results using Dynal M270 beads.

DETAILED DESCRIPTION

Figures 1A, 1B, 1C, 1D:
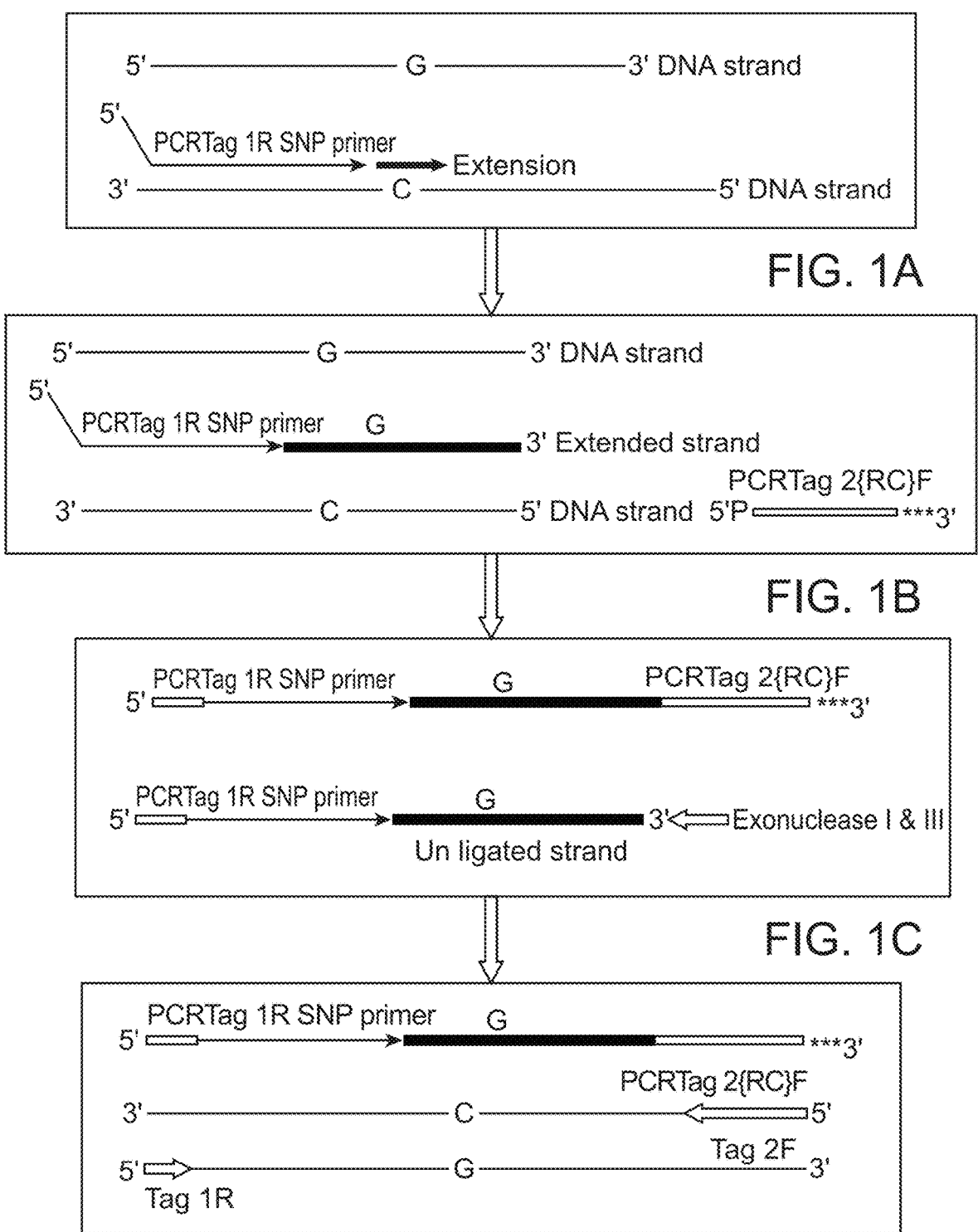
FIGS. 1A-1D show amplification of a gene of interest using extension of a gene specific primer with a universal PCR tag and a subsequent single strand ligation to a second universal tag followed by exonuclease clean-up and amplification utilizing tag 1 and 2 (Approach 1).

Methods for determining the presence or absence of a plurality of target nucleic acids in a composition described herein find multiple uses by the person of ordinary skill in the art (hereafter referred to herein as the "person of ordinary skill"). Such methods can be utilized, for example, to:

(a) rapidly determine whether a particular target sequence (e.g. a target sequence comprising a genetic variation) is present in a sample; (b) perform mixture analysis, e.g., identify a mixture and/or its composition or determine the frequency of a target sequence in a mixture (e.g., mixed communities, quasispecies); (c) detect sequence variations (e.g., mutations, single nucleotide polymorphisms) in a sample; (d) perform haplotyping determinations; (e) perform microorganism (e.g., pathogen) typing; (f) detect the presence or absence of a microorganism target sequence in a sample; (g) identify disease markers; (h) detect microsatellites; (i) identify short tandem repeats; (j) identify an organism or organisms; (k) detect allelic variations; (l) determine allelic frequency; (m) determine methylation patterns; (n) perform epigenetic determinations; (o) re-sequence a region of a biomolecule; (p) perform analyses in human clinical research and medicine (e.g. cancer marker detection, sequence variation detection; detection of sequence signatures favorable or unfavorable for a particular drug administration), (q) perform HLA typing; (r) perform forensics analyses; (s) perform vaccine quality control analyses; (t) monitor treatments; (u) perform vector identity analyses; (v) perform vaccine or production strain quality control and (w) test strain identity (x) plants. Such methods also may be utilized, for example, in a variety of fields, including, without limitation, in commercial, education, medical, agriculture, environmental, disease monitoring, military defense, and forensics fields.

Target Nucleic Acids

As used herein, the term "nucleic acid" refers to an oligonucleotide or polynucleotide, including, without limitation, natural nucleic acids (e.g., deoxyribonucleic acid (DNA), ribonucleic acid (RNA)), synthetic nucleic acids, non-natural nucleic acids (e.g., peptide nucleic acid (PNA)), unmodified nucleic acids, modified nucleic acids (e.g., methylated DNA or RNA, labeled DNA or RNA, DNA or RNA having one or more modified nucleotides). Reference to a nucleic acid as a "polynucleotide" refers to two or more nucleotides or nucleotide analogs linked by a covalent bond. Nucleic acids may be any type of nucleic acid suitable for use with processes described herein. A nucleic acid in certain embodiments can be DNA (e.g., complementary DNA (cDNA), genomic DNA (gDNA), plasmids and vector DNA and the like), RNA (e.g., viral RNA, message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A nucleic acid in some embodiments is from a single chromosome (e.g., a nucleic acid sample may be from one chromosome of a sample obtained from a diploid organism). In the case of fetal nucleic acid, the nucleic acid may be from the paternal allele, the maternal allele or the maternal and paternal allele.

The term "species," as used herein with reference to a target nucleic acid, amplicon, primer, sequence tag, polynucleotide, or oligonucleotide, refers to one nucleic acid having a nucleotide sequence that differs by one or more nucleotides from the nucleotide sequence of another nucleic acid when the nucleotide sequences are aligned. Thus, a first nucleic acid species differs from a second nucleic acid species when the sequences of the two species, when aligned, differ by one or more nucleotides (e.g., about 1, 2, 3, 4, 5, 10, 15, 20, 25, 30, 35, 40, 45, 50, 55, 60, 65, 70, 75, 80, 90, 95, 100 or more than 100 nucleotide differences). In certain embodiments, the number of nucleic acid species, such as target nucleic acid species, amplicon species or extended oligonucleotide species, includes, but is not limited to about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 nucleic acid species.

In some embodiments an oligonucleotide species is hybridized to a nucleic acid template (e.g. an amplicon) thereby forming a double stranded nucleic acid and the oligonucleotide species that is hybridized to the template is referred to herein as a hybridized oligonucleotide species. In some embodiments a hybridized oligonucleotide species can comprise one or more nucleotides that are not hybridized to the template. For example, a hybridized oligonucleotide species can comprise one or more mismatched nucleotides (e.g. non-complementary nucleotides) and sometimes a 5' and/or 3' region of nucleotides that do not hybridize. In some embodiments a hybridized oligonucleotide species comprises a tag (e.g. a mass distinguishable tag, a sequence tag, a light emitting tag or a radioactive tag). In some embodiments a hybridized oligonucleotide species comprises a capture agent (e.g. biotin, or any member of binding pair). In some embodiments a hybridized oligonucleotide species comprises a terminating nucleotide.

As used herein, the term "nucleotides" refers to natural and non-natural nucleotides. Nucleotides include, but are not limited to, naturally occurring nucleoside mono-, di-, and triphosphates: deoxyadenosine mono-, di- and triphosphate; deoxyguanosine mono-, di- and triphosphate; deoxythymidine mono-, di- and triphosphate; deoxycytidine mono-, di- and triphosphate; deoxyuridine mono-, di- and triphosphate; and deoxyinosine mono-, di- and triphosphate (referred to herein as dA, dG, dT, dC, dU and dI, or A, G, T, C, U and I respectively). Nucleotides also include, but are not limited to, modified nucleotides and nucleotide analogs. Modified nucleotides and nucleotide analogs include, without limitation, deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyldeoxycytidine triphosphate, $^{13}C/^{15}N$ labeled nucleotides and deoxyinosine mono-, di- and triphosphate. Modified nucleotides, isotopically enriched nucleotides, depleted nucleotides, tagged and labeled nucleotides and nucleotide analogs can be obtained using a variety of combinations of functionality and attachment positions.

The term "composition" as used herein with reference to nucleic acids refers to a tangible item that includes one or more nucleic acids. A composition sometimes is a sample extracted from a source, but also a composition of all samples at the source, and at times is the source of one or more nucleic acids. A composition can comprise nucleic acids. In some embodiments, a composition can comprise genomic DNA. In some embodiments, a composition can comprise maternal DNA, fetal DNA or a mixture of maternal and fetal DNA. In some embodiments, a composition can comprise fragments of genomic DNA. In some embodiments a composition can comprise nucleic acids derived from a virus, bacteria, yeast, fungus, mammal or mixture thereof.

A nucleic acid sample may be derived from one or more sources. A sample may be collected from an organism, mineral or geological site (e.g., soil, rock, mineral deposit, fossil), or forensic site (e.g., crime scene, contraband or suspected contraband), for example. Thus, a source may be environmental, such as geological, agricultural, combat theater or soil sources, for example. A source also may be from any type of organism such as any plant, fungus, protistan, moneran, virus or animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable nucleic acids. Sources also can refer to different parts of an organism such as internal parts, external parts, living or non-living cells, tissue, fluid and the like. A sample therefore may be a "biological sample," which refers to any material obtained from a living source or formerly-living source, for example, an animal such as a human or other mammal, a plant, a bacterium, a fungus, a protist or a virus. A source can be in any form, including, without limitation, a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, hair, cerebral spinal fluid and synovial fluid and organs. A sample also may be isolated at a different time point as compared to another sample, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19, 20, 25, 50, 75, 100, 200, 300, 400, 500, 600, 700, 800, 900 or 1000 or more samples).

Nucleic acids may be treated in a variety of manners. For example, a nucleic acid may be reduced in size (e.g., sheared, digested by nuclease or restriction enzyme, de-phosphorylated, de-methylated), increased in size (e.g., phosphorylated, reacted with a methylation-specific reagent, attached to a detectable label), treated with inhibitors of nucleic acid cleavage and the like.

Nucleic acids may be provided for conducting methods described herein without processing, in certain embodiments. In some embodiments, nucleic acid is provided for conducting methods described herein after processing. For example, a nucleic acid may be extracted, isolated, purified or amplified from a sample. The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species).

Nucleic acids may be processed by a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information.

As used herein, the term "target nucleic acid" or "target nucleic acid species" refers to any nucleic acid species of interest in a sample. A target nucleic acid includes, without limitation, (i) a particular allele amongst two or more possible alleles, and (ii) a nucleic acid having, or not having, a particular mutation, nucleotide substitution, sequence variation, repeat sequence, marker or distinguishing sequence. As used herein, the term "different target nucleic acids" refers to nucleic acid species that differ by one or more features. As used herein, the term "genetic variation" refers to nucleic acid species that differ by one or more features. As used herein, the term "variant" refers to nucleic acid species that differ by one or more features. Features include, without limitation, one or more methyl groups or a methylation state, one or more phosphates, one or more acetyl groups, and one or more deletions, additions or substitutions of one or more nucleotides. Examples of one or more deletions, additions or substitutions of one or more nucleotides include, without limitation, the presence or absence of a particular mutation, presence or absence of a nucleotide substitution (e.g., single nucleotide polymorphism (SNP)), presence or absence of a repeat sequence (e.g., di-, tri-, tetra-, penta-nucleotide repeat), presence or absence of a marker (e.g., microsatellite) and presence of absence of a distinguishing sequence (e.g., a sequence that distinguishes one organism from another (e.g., a sequence that distinguishes one viral strain from another viral strain)). Different target nucleic acids may be distinguished by any known method, for example, by mass, binding, distinguishable tags and the like, as described herein.

As used herein, the term "plurality of target nucleic acids" or "plurality of target nucleic acid species" refers to more than one target nucleic acid species. A plurality of target nucleic acids can be about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 nucleic acid species, in certain embodiments. Detection or identification of nucleic acids results in detection of the target and can indicate the presence or absence of a particular mutation, sequence variation (mutation or polymorphism) or genetic variation (e.g. sequence variation, sequence difference or polymorphism). Within the plurality of target nucleic acids, there may be detection of the same or different target nucleic acids. The plurality of target nucleic acids may also be identified quantitatively as well as qualitatively in terms of identification. Also refer to multiplexing below.

Amplification and Extension

A nucleic acid (e.g., a target nucleic acid) can be amplified in certain embodiments. As used herein, the term "amplifying," and grammatical variants thereof, refers to a process of generating copies of a template nucleic acid. For example, nucleic acid template may be subjected to a process that linearly or exponentially generates two or more nucleic acid amplicons (copies) having the same or substantially the same nucleotide sequence as the nucleotide sequence of the template, or a portion of the template. Nucleic acid amplification often is specific (e.g., amplicons have the same or substantially the same sequence), and can be non-specific (e.g., amplicons have different sequences) in certain embodiments. Nucleic acid amplification sometimes is beneficial when the amount of target sequence present in a sample is low. By amplifying the target sequences and detecting the amplicon synthesized, sensitivity of an assay can be improved, since fewer target sequences are needed at the beginning of the assay for detection of a target nucleic acid. A target nucleic acid sometimes is not amplified prior to hybridizing an extension oligonucleotide, in certain embodiments.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term "cycling" refers to amplification (e.g. an amplification reaction or extension reaction) utilizing a single primer or multiple primers where temperature cycling is used. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

A strand of a single-stranded nucleic acid target can be amplified and one or two strands of a double-stranded nucleic acid target can be amplified. An amplification product (amplicon), in some embodiments, is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Polymerase-based amplification can be effected, in certain embodiments, by employing universal primers. In such processes, hybridization regions that hybridize to one or more universal primers are incorporated into a template nucleic acid. Such hybridization regions can be incorporated into (i) a primer that hybridizes to a target nucleic acid and is extended, and/or (ii) an oligonucleotide that is joined (e.g., ligated using a ligase enzyme) to a target nucleic acid or a product of (i), for example. Amplification processes that involve universal primers can provide an advantage of amplifying a plurality of target nucleic acids using only one or two amplification primers, for example.

FIG. 1 shows certain embodiments of amplification processes. In certain embodiments, only one primer is utilized for amplification (e.g., FIG. 1A). In certain embodiments, two primers are utilized. Under amplification conditions at least one primer has a complementary distinguishable tag. The gene specific extend primer has a 5' universal PCRTag1R (e.g., FIG. 1A). It may be extended on any nucleic acid, for example genomic DNA. The DNA or the PCR Tag1R gene specific extend primer may be biotinylated, to facilitate clean up of the reaction. The extended strand then is ligated by a single strand ligase to a universal phosphorylated oligonucleotide, which has a sequence that is the reverse complement of Tag2F (universal PCR primer; FIG. 1B). To facilitate cleanup in the next step, the phosphorylated oligonucleotide can include exonuclease resistant nucleotides at its 3' end. During the exonuclease treatment, all non-ligated extended strands are degraded, whereas ligated products are protected and remain in the reaction (e.g., FIG. 1C). A universal PCR then is performed, using Tag1R and the Tag2F primers, to amplify multiple targets (e.g., FIG. 1D).

Figure 2:
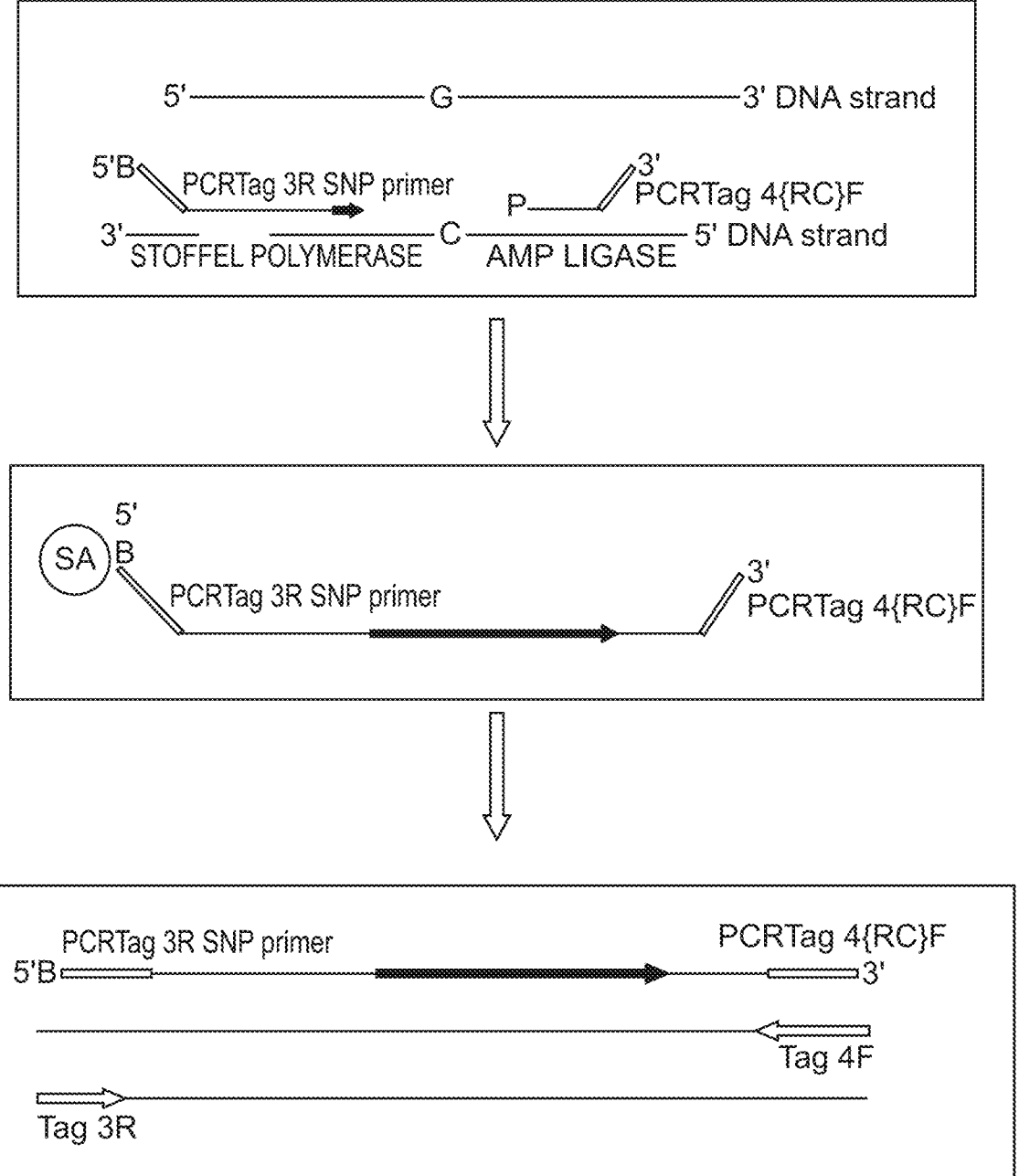
FIG. 2 shows amplification of a gene of interest using a gene specific biotinylated primer with a universal tag 3 that is extended on a template then ligated downstream to a gene specific phosphorylated oligonucleotide tag 4 on the same strand. This product is subsequently amplified utilizing tag 3 and 4 (Concept2).

FIG. 2 also shows certain embodiments of amplification processes. In some embodiments, a method involving primer extension and ligation takes place in the same reaction (e.g., FIG. 2A). Biotinylated PCRTag3R gene-specific primer is an extension primer. The phosphorylated oligonucleotide has a gene-specific sequence and binds about 40 bases (e.g., 4 to 100 or more) away from the primer extension site, to the same strand of DNA. Thus a DNA polymerase, such as Stoffel polymerase, extends the strand, until it reaches the phosphorylated oligonucleotide. A ligase enzyme ligates the gene specific sequence of the phosphorylated oligonucleotide to the extended strand. The 3' end of phosphorylated oligonucleotide has PCRTag4(RC)F as its universal tag. The biotinylated extended strands then are bound to streptavidin beads. This approach facilitates cleanup of the reaction (e.g., FIG. 2B). DNA, such as genomic DNA, and the gene specific phosphorylated oligonucleotides are washed away. A universal PCR then is performed, using Tag3R and Tag4F as primers, to amplify different genes of interest (e.g., FIG. 2C).

Certain nucleic acids can be extended in certain embodiments. The term "extension," and grammatical variants thereof, as used herein refers to elongating one strand of a nucleic acid. For example, an oligonucleotide that hybridizes to a target nucleic acid or an amplicon generated from a target nucleic acid can be extended in certain embodiments. An extension reaction is conducted under extension conditions, and a variety of such conditions are known and selected for a particular application. Extension conditions include certain reagents, including without limitation, one or more oligonucleotides, extension nucleotides (e.g., nucleotide triphosphates (dNTPs)), terminating nucleotides (e.g., one or more dideoxynucleotide triphosphates (ddNTPs)), one or more salts (e.g., magnesium-containing salt), one or more buffers (e.g., with beta-NAD, Triton X-100), and one or more polymerizing agents (e.g., DNA polymerase, RNA polymerase). Extension can be conducted under isothermal conditions or under non-isothermal conditions (e.g., thermocycled conditions), in certain embodiments. One or more nucleic acid species can be extended in an extension reaction, and one or more molecules of each nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 100, 200, 300, 400, 500 or 600 or more times. In some embodiments the extension reaction is cycled 20 to times. In some embodiments the extension reaction is cycled 20 to 100 times. In some embodiments the extension reaction is cycled 20 to 300 times. In some embodiments the extension reaction is cycled 200 to 300 times.

In some embodiments a target nucleic acid (e.g. target nucleic acid species, oligonucleotide species, hybridized oligonucleotide species or amplicon) is extended in the presence of an extension composition where the target nucleic acid is extended by one nucleotide. An extension composition can comprise one or more buffers, salts, enzymes (e.g. polymerases, Klenow, etc.), water, templates (e.g. DNA, RNA, amplicons, etc.), primers (e.g. oligonucleotides), nucleotide triphosphates, glycerol, macromolecular exclusion molecules and any other additives used in the art. An extension composition can comprise terminating nucleotides (e.g. dideoxynucleotides (e.g. ddNTPs)), non-terminating or extension nucleotides (e.g. dNTPs) or a mixture of terminating nucleotides and non-terminating nucleotides. An extension composition consisting essentially of a particular terminating nucleotide or terminating nucleotides, can contain any other component of an extension composition (e.g. buffers, salts, templates, primers, etc.), but does not contain any other terminating nucleotide or nucleotide triphosphate (e.g. dNTP) except those specified. For example an extension composition consisting essentially of ddTTP and ddCTP does not contain ddATP, ddGTP or any other dNTP. In some embodiments the nucleotides in an extension composition are only terminating nucleotides and the target nucleic acid is extended by one nucleotide (i.e. sometimes there are no extension nucleotides in the extension composition). In some embodiments an extension composition consists essentially of terminating nucleotides (e.g. ddNTPs). In some embodiments, a terminating nucleotide comprises one or more (e.g. 1, 2, 3, 4, 5, 6, 7, 8, 9, 10, 11, 12, 13, 14, 15, 20, or more) capture agents. In some embodiments, a terminating nucleotide comprises one or more (e.g. 1, 2, 3, 4, 5, 6, 7, 8, 9, 10, 11, 12, 13, 14, 15, 20, or more) different capture agents. In some embodiments, a terminating nucleotide comprises (e.g. is covalently bound to) one or more (e.g. 1, 2, 3, 4, 5, 6, 7, 8, 9, 10, 11, 12, 13, 14, 15, 20, or more) capture agent molecules. In some embodiments, a terminating nucleotide comprises one capture agent molecule. In some embodiments, a first terminating nucleotide comprises a capture agent and a second terminating nucleotide comprises a different capture agent. In some embodiments, an extension composition comprises one or more terminating nucleotides where each terminating nucleotide comprises a different capture agent. In some embodiments, an extension composition comprises one or more terminating nucleotides where each terminating nucleotide comprises a capture agent and the capture agent is the same. In some embodiments, an extension composition comprises a terminating nucleotide and an extension nucleotide and one or more of the nucleotides (e.g. terminating nucleotides and/or extension nucleotides) include a capture agent. In some embodiments a terminating nucleotide comprises a capture agent and the capture agent is biotin or a biotin analogue. In some embodiments, the extension composition consists essentially of terminating nucleotides that are bound to one or more capture agents. In some embodiments the capture agent is biotin or a biotin analogue. A biotin analogue can be any modified biotin that effects the binding properties of biotin to avidin or streptavidin (e.g. 9-methylbiotin, biotin methyl ester (MEBio), desthiobiotin (DEBio), 2'-iminobiotin (IMBio), e-N-Biotinyl-L-lysine, diaminobiotin (DABio), including all biotin analogues disclosed in Lai-Qiang et.al. (Lai-Qiang Ying and Bruce P. Branchaud, Chemical Communications, 2011, 47, 8593-8595)). In some embodiments the capture agent is avidin, streptavidin or a modified form of avidin or streptavidin (e.g. nitroavidin, nitrostreptavidin, NeutrAvidin, CaptAvidin and derivatives thereof).

Any suitable extension reaction can be selected and utilized. An extension reaction can be utilized, for example, to discriminate SNP alleles by the incorporation of deoxynucleotides and/or dideoxynucleotides to an extension oligonucleotide that hybridizes to a region adjacent to the SNP site in a target nucleic acid. The primer often is extended with a polymerase. In some embodiments, the oligonucleotide is extended by only one deoxynucleotide or dideoxynucleotide complementary to the SNP site. In some embodiments, an oligonucleotide may be extended by dNTP incorporation and terminated by a ddNTP, or terminated by ddNTP incorporation without dNTP extension in certain embodiments. One or more dNTP and/or ddNTP used during the extension reaction are labeled with a moiety allowing immobilization to a solid support, such as biotin, in some embodiments. Extension may be carried out using unmodified extension oligonucleotides and unmodified dideoxynucleotides, unmodified extension oligonucleotides and biotinylated dideoxynucleotides, extension oligonucleotides containing a deoxyinosine and unmodified dideoxynucleotides, extension oligonucleotides containing a deoxyinosine and biotinylated dideoxynucleotides, extension by biotinylated dideoxynucleotides, or extension by biotinylated deoxynucleotide and/or unmodified dideoxynucleotides, in some embodiments.

In some embodiments an oligonucleotide species can hybridize, under hybridization conditions, to a template (e.g. a target nucleic acid species) adjacent to a genetic variation or variant (e.g. the 3' end of the oligonucleotide species may be located 5' of the genetic variation site and may be 0 to nucleotides away from the 5' end of the genetic variation site). Several variant may exist at a site of genetic variation in a target nucleic acid. A genetic variant sometimes is a single nucleotide polymorphism (SNP) or single nucleotide variant. Several single nucleotide variants may exist at a single base position on a template target located 3' of a hybridized oligonucleotide. Several single nucleotide variants may differ by a single base located at a position on a template target that is 3' of a hybridized oligonucleotide species. In some embodiments an oligonucleotide species is extended by one nucleotide at the variant position. The oligonucleotide can be extended by any one of five terminating nucleotides (e.g. ddATP, ddUTP, ddTTP, ddGTP, ddCTP), depending on the number of variants present, in some embodiments. A target nucleic acid species and its variants, or a corresponding amplicon, can act as the template and can, in part, determine which terminating nucleotide is added to the oligonucleotide in the extension reaction. A target nucleic acid species may have two or more variants. In some embodiments a target nucleic acid species comprises two variants. In some embodiments a target nucleic acid species comprises three variants. In some embodiments a target nucleic acid species comprises four variants. In some embodiments a target nucleic acid species comprises no variants.

In some embodiments the amount of molecules of a target mutant variant (e.g. low abundant variant) present in an assay where the wild type (e.g. high abundance species) extension product is not generated is determined by the use of a synthetic template included in the extension reaction. In some embodiments the amount of target (e.g. copy number, concentration, percentage) mutant variant (i.e. mutant extension products) and/or percentage of target mutant variant in the sample is quantified by including a known amount of synthetic template in the extension reaction. In some embodiments the synthetic template can hybridize to an oligonucleotide species and contain a base substitution at the mutant position located just 3' of the oligonucleotide species to be extended. In some embodiments, the base substitution is different than the wild type or target mutant variant (e.g. first variant, low abundant variant, SNP). In some embodiments, the base substitution present in the template is not present in the sample prior to introduction of the template. In some embodiments a ddNTP (e.g. a biotin-ddNTP) that is complementary to the base substitution in the synthetic template is also introduced into the reaction. In some embodiments, oligonucleotide species that hybridize to the target mutant variant are co-amplified (e.g. co-extended) with oligonucleotide species that hybridize to the synthetic template. In some embodiments, multiple reactions, that include serial dilutions of a synthetic template, are performed to determine the amount and/or percentage of the target mutant variant. In some embodiments, the amount and/or percentage of the target mutant variant is determined by the amount of synthetic template that yields equal extension product as the target mutant variant.

In some embodiments, one variant can be in greater abundance than other variants. In some embodiments, the variant of greatest abundance is referred to as the wild type variant. In some embodiments a target nucleic acid species comprises a first and second variant where the second variant is represented in greater abundance (i.e. more template is present). In some embodiments a target nucleic acid species comprises a first, second and third variant where the second variant is represented in greater abundance over the first and third variant. In some embodiments a target nucleic acid species comprises a first, second, third and fourth variant where the second variant is represented in greater abundance over the first, third and fourth variant. A variant that is represented in a greater abundance generally is present at a higher concentration or is represented by a greater number of molecules (e.g. copies) when compared to another variant. A higher concentration can be 2-fold or more. In some embodiments, a higher concentration is 10-fold or more. In some embodiments, a higher concentration is a 100-fold, a 1000-fold or 10000-fold or more. In some embodiments, a second variant represents a wild type sequence and is present at a 100-fold or higher concentration than a first variant. In some embodiments, a first variant is represented at a significantly lower concentration than a second variant (e.g. a wild type) where the first variant represents less of the target nucleic acid species. In some embodiments a first variant represents less than 30%, 20%, 15%, 10%, 8%, 5%, 4%, 3%, 2%, 1%, 0.8%, 0.75%, 0.1%, 0.05%, 0.01% or less of the target nucleic acid species. In some embodiments a first variant represents between about 5% to about 0.75% of the target nucleic acid species. In some embodiments a first variant represents less than 30%, 20%, 15%, 10%, 8%, 5%, 4%, 3%, 2%, 1%, 0.75%, 0.5%, 0.1%, 0.05%, 0.01% or less of the total nucleic acid in a composition.

In some embodiments, a terminating nucleotide that is present (or, in some embodiments absent) in an extension composition determines which terminating nucleotide is added to an oligonucleotide. In some embodiments, an extension composition comprises one or more terminating nucleotides (e.g. ddNTPs). In some embodiments, an extension composition comprises one or more terminating nucleotides and one or more non-terminating nucleotides (e.g. dNTPs). In some embodiments, an extension composition comprises only terminating nucleotides that correspond to a specific variant (e.g. a first variant or a less abundant variant) and therefore only allow extension of that specific variant. In some embodiments, a terminating nucleotide that would allow extension of a second variant (e.g. a wild type or more abundant variant) can be excluded from an extension composition thereby preventing extension of the second variant. In some embodiments, an extension composition comprises only terminating nucleotides that correspond to a first and third variant and therefore only allow extension of those specific variants.

In some embodiments, an extension composition comprises only terminating nucleotides that correspond to a first, third and fourth variant and therefore only allow extension of the first, third and fourth variants. In some embodiments, an extension composition consists essentially of terminating nucleotides that correspond to a first variant. In some embodiments, a method comprises contacting hybridized oligonucleotide species with an extension composition comprising one or more terminating nucleotides under extension conditions where (i) at least one of the one or more terminating nucleotides comprises a capture agent, and (ii) the hybridized oligonucleotide species that hybridize to the first variant (e.g. a less abundant variant, (e.g., less abundant SNP variant)) are extended by a terminating nucleotide and the hybridized oligonucleotide species that hybridize to the second variant (e.g. wild type or more abundant variant) are not extended by a terminating nucleotide, thereby generating extended oligonucleotide species. In some embodiments an extended oligonucleotide species of a second variant is not detected.

The term "signal to noise ratio" as used herein refers to the quantitative measurement of the quality of a signal by quantifying the ratio of intensity of a signal relative to noise when using a detection process (e.g. mass spectrometry). In some embodiments, an intensive peak on one spectrum has a greater signal to noise ratio than a low intensity peak generated by the same analyte (e.g. an extended oligonucleotide species) on another spectrum. In some embodiments, noise is generated by extended oligonucleotide species derived from abundant variants (e.g. wild type alleles, second variants, wild type variants). In some embodiments, the signal generated from an extended oligonucleotide species derived from a less abundant variant (e.g. a first variant, third variant, fourth variant, mutant variant, mutant allele, SNP) is obscured by the noise generated by a more abundant extended oligonucleotide species (e.g. a second variant, wild type variant, wild type allele) when using mass spectrometry. The term "signal" as used in the phrase "signal to noise ratio" herein refers to the intensity of a signal peak of an extended oligonucleotide species. In some embodiments, the term "signal" as used in the phrase "signal to noise ratio" herein generally refers to the intensity of a signal peak of an extended oligonucleotide species derived from a less abundant variant (e.g. a first variant, mutant variant, mutant allele, SNP). In some embodiments, a terminating nucleotide that would allow extension of a second variant (e.g. a wild type or more abundant variant) is excluded from an extension composition thereby preventing extension of the second variant and increasing the signal to noise ratio for a less abundant variant (e.g. a first variant, mutant variant, mutant allele, SNP). In some embodiments, a method comprises contacting hybridized oligonucleotide species with an extension composition comprising one or more terminating nucleotides under extension conditions where (i) at least one of the one or more terminating nucleotides comprises a capture agent, and (ii) the hybridized oligonucleotide species that hybridize to the first variant (e.g. a less abundant variant, (e.g., less abundant SNP variant)) are extended by a terminating nucleotide and the hybridized oligonucleotide species that hybridize to the second variant (e.g. wild type or more abundant variant) are not extended by a terminating nucleotide, thereby generating extended oligonucleotide species and increasing the signal to noise ratio compared to a condition where both the first and second variants are extended. In some embodiments the detecting in (f) is with a signal to noise ratio greater than a signal to noise ratio for detecting after releasing without competition with a competitor. In some embodiments the detecting in (f) comprises an increase in a signal to noise ratio when the releasing step (e) comprises competition with a competitor as compared to a releasing step that does not comprise competition with a competitor. In some embodiments a signal to noise ratio for extending only a mutant allele is greater than a signal to noise ratio for extending a wild type and a mutant allele.

The term "sensitivity" as used herein refers to an amount of analyte that can be detected at a given signal-to-noise ratio when using a detection process (e.g. mass spectrometry). In some embodiments, sensitivity can be improved by decreasing the background or noise level. In some embodiments, noise is generated by extended oligonucleotide species derived from abundant variants (e.g. wild type alleles, second variants, wild type variants). In some embodiments, sensitivity is increased when the signal generated from an extended oligonucleotide species derived from a more abundant extended oligonucleotide species (e.g. a second variant, wild type variant, wild type allele) is reduced or eliminated. In some embodiments, a terminating nucleotide that would allow extension of a second variant (e.g. a wild type or more abundant variant) is excluded from an extension composition thereby preventing extension of the second variant and increasing the sensitivity for detection of a less abundant variant (e.g. a first variant, mutant variant, mutant allele, SNP). In some embodiments, a method comprises contacting hybridized oligonucleotide species with an extension composition comprising one or more terminating nucleotides under extension conditions where (i) at least one of the one or more terminating nucleotides comprises a capture agent, and (ii) the hybridized oligonucleotide species that hybridize to the first variant (e.g. a less abundant variant, (e.g., less abundant SNP variant)) are extended by a terminating nucleotide and the hybridized oligonucleotide species that hybridize to the second variant (e.g. wild type or more abundant variant) are not extended by a terminating nucleotide, thereby generating extended oligonucleotide species and increasing the sensitivity for detection of the first variant compared to a condition where both the first and second variants are extended. In some embodiments the sensitivity of detecting a mutant allele in (f) is greater for extending only a mutant allele than for extending a wild type and a mutant allele.

Any suitable type of nucleotides can be incorporated into an amplification product or an extension product. Nucleotides may be naturally occurring nucleotides, terminating nucleotides, or non-naturally occurring nucleotides (e.g., nucleotide analog or derivative), in some embodiments. Certain nucleotides can comprise a detectable label and/or a member of a binding pair (e.g., the other member of the binding pair may be linked to a solid phase), in some embodiments. A solution containing amplicons produced by an amplification process, or a solution containing extension products produced by an extension process, can be subjected to further processing. For example, a solution can be contacted with an agent that removes phosphate moieties from free nucleotides that have not been incorporated into an amplicon or extension product. An example of such an agent is a phosphatase (e.g., alkaline phosphatase). Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

The term "oligonucleotide" as used herein refers to two or more nucleotides or nucleotide analogs linked by a covalent bond. An oligonucleotide is of any convenient length, and in some embodiments is about 5 to about 200 nucleotides in length, about 5 to about 150 nucleotides in length, about 5 to about 100 nucleotides in length, about 5 to about 75 nucleotides in length or about 5 to about 50 nucleotides in length, and sometimes is about 5, 6, 7, 8, 9, 10, 11, 12, 13, 14, 16, 17, 18, 19, 20, 25, 30, 35, 40, 45, 50, 55, 60, 65, 70, 75, 80, 80, 85, 90, 95, 100, 125, 150, 175, or 200 nucleotides in length. Oligonucleotides may include deoxyribonucleic acid (DNA), ribonucleic acid (RNA), naturally occurring and/or non-naturally occurring nucleotides or combinations thereof and any chemical or enzymatic modification thereof (e.g. methylated DNA, DNA of modified nucleotides). The length of an oligonucleotide sometimes is shorter than the length of an amplicon or target nucleic acid, but not necessarily shorter than a primer or polynucleotide used for amplification. An oligonucleotide often comprises a nucleotide subsequence or a hybridization sequence that is complementary, or substantially complementary, to an amplicon, target nucleic acid or complement thereof (e.g., about 95%, 96%, 97%, 98%, 99% or greater than 99% identical to the amplicon or target nucleic acid complement when aligned). An oligonucleotide may contain a nucleotide subsequence not complementary to, or not substantially complementary to, an amplicon, target nucleic acid or complement thereof (e.g., at the 3' or 5' end of the nucleotide subsequence in the primer complementary to or substantially complementary to the amplicon). An oligonucleotide in certain embodiments, may contain a detectable molecule (e.g., a tag, fluorophore, radioisotope, colormetric agent, particle, enzyme and the like) and/or a member of a binding pair, in certain embodiments (e.g., biotin/avidin, biotin/streptavidin).

The term "in solution" as used herein refers to a liquid, such as a liquid containing one or more nucleic acids, for example. Nucleic acids and other components in solution may be dispersed throughout, and a solution often comprises water (e.g., aqueous solution). A solution may contain any convenient number of oligonucleotide species, and there often are at least the same number of oligonucleotide species as there are amplicon species or target nucleic acid species to be detected.

The term "hybridization sequence" as used herein refers to a nucleotide sequence in an oligonucleotide capable of specifically hybridizing to an amplicon, target nucleic acid or complement thereof. The hybridization sequence is readily designed and selected and can be of a length suitable for hybridizing to an amplicon, target sequence or complement thereof in solution as described herein. In some embodiments, the hybridization sequence in each oligonucleotide is about 5 to about 200 nucleotides in length (e.g., about 5 to 10, about 10 to 15, about 15 to 20, about 20 to 25, about 25 to 30, about 30 to 35, about 35 to 40, about 40 to 45, or about 45 to 50, about 50 to 70, about 80 to 90, about 90 to 110, about 100 to 120, about 110 to 130, about 120 to 140, about 130 to 150, about 140 to 160, about 150 to 170, about 160 to 180, about 170 to 190, about 180 to 200 nucleotides in length).

The term "hybridization conditions" as used herein refers to conditions under which two nucleic acids having complementary nucleotide sequences can interact with one another. Hybridization conditions can be high stringency, medium stringency or low stringency, and conditions for these varying degrees of stringency are known. Hybridization conditions often are selected that allow for amplification and/or extension depending on the application of interest.

The term "specifically hybridizing to one amplicon or target nucleic acid" as used herein refers to hybridizing substantially to one amplicon species or target nucleic acid species and not substantially hybridizing to other amplicon species or target nucleic acid species in the solution. Specific hybridization rules out mismatches so that, for example, an oligonucleotide may be designed to hybridize specifically to a certain allele and only to that allele. An oligonucleotide that is homogenously matched or complementary to an allele will specifically hybridize to that allele, whereas if there is one or more base mismatches then no hybridization may occur.

The term "hybridization location" as used herein refers to a specific location on an amplicon or target nucleic acid to which another nucleic acid hybridizes. In certain embodiments, the terminus of an oligonucleotide is adjacent to or substantially adjacent to a site on an amplicon species or target nucleic acid species that has a different sequence than another amplicon species or target nucleic acid species. The terminus of an oligonucleotide is "adjacent" to a site when there are no nucleotides between the site and the oligonucleotide terminus. The terminus of an oligonucleotide is "substantially adjacent" to a site when there are 1, 2, 3, 4, 5, 6, 7, 8, 9 or 10 nucleotides between the site and the oligonucleotide terminus, in certain embodiments.

Capture Agents and Solid Phases

One or more capture agents may be utilized for the methods described herein. There are several different types of capture agents available for processes described herein, including, without limitation, members of a binding pair, for example. Examples of binding pairs, include, without limitation, (a) non-covalent binding pairs (e.g., antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, receptor/ligand or binding portion thereof, and vitamin B12/intrinsic factor); and (b) covalent attachment pairs (e.g., sulfhydryl/maleimide, sulfhydryl/haloacetyl derivative, amine/isotriocyanate, amine/succinimidyl ester, and amine/sulfonyl halides), and the like. In some embodiments, one member of a binding pair is in association with an extended oligonucleotide or amplification product and another member in association with a solid phase. The term "in association with" as used herein refers to an interaction between at least two units, where the two units are bound or linked to one another, for example.

The term "competitor" as used herein refers to any molecule that competes with the capture agent for interaction with (e.g., binding to) the solid phase. Non-limiting examples of competitors include free capture agent (e.g., one or the other member of a binding pair, free biotin, free avidin/streptavidin), a competing fragment of a capture agent (e.g., a competing fragment of biotin or avidin/streptavidin), a competing multimer of the capture agent (e.g., a biotin multimer), another competing molecule or fragment or multimer thereof, a molecule that competes specifically for binding to the solid phase, elevated salt conditions, elevated temperature conditions, or combinations thereof. In some embodiments, a multimer of a capture agent comprises between about 2 and about 50 monomers. In some embodiments, a multimer of a capture agent comprises between about 2 and about 10 monomers. In some embodiments, a multimer of a capture agent comprises about 2, 3, 4, 5, 6, 7, 8, 9, 10, 11, 12, 13, 14, 15, 16, 17, 18, 19, or 20 monomers. In some embodiments, a capture agent comprising a multimer of capture agents comprises monomers that are covalently bound to each other. In some embodiments, a capture agent comprising a multimer of capture agents comprises monomers that are not covalently bound to each other. The term "free capture agent" as used herein refers to a capture agent that is not in association with a solid phase or extended oligonucleotide. In some embodiments, a free capture agent can be biotin or a competing portion or fragment thereof. In certain embodiments, a free capture agent can be avidin, streptavidin, or a competing portion or fragment thereof. The term "competing portion or fragment" refers to capture agent that is less than full size, yet still retains the functionality of the intact capture agent (e.g., the same, less or more of the capture agent interaction activity with the solid support) with respect to interaction with the other member of a binding pair (e.g., a fragment or portion of biotin that still can bind to avidin or streptavidin, a fragment or portion of avidin or streptavidin that still can bind to biotin). In some embodiments, a fragment of a free capture agent (e.g. a fragment of biotin), is any size that still retains the functionality of the intact capture agent. In some embodiments, a free capture agent (e.g. a fragment of biotin), is any size that still retains some of the functionality of the intact capture agent. In some embodiments, a free capture agent (e.g. a fragment of biotin), is a size that retains between about 30% and about 100% of the functionality of the intact capture agent. In some embodiments, a free capture agent (e.g. a fragment of biotin), is a size that retains about 30%, 40%, 50%, 60%, 70%, 80%, 90% or 100% of the functionality of the intact capture agent.

In some embodiments, free capture agent (e.g. free biotin) is added at a concentration from about to about 5000 ug/ml.

In some embodiments, free capture agent (e.g. free biotin) is added at a concentration of about 0.1, 0.25, 0.5, 1, 2.5, 5, 10, 20, 25, 30, 40, 50, 60, 70, 80, 90, 100, 200, 400, 800, 1000, 2000, 4000, 5000 ug/ml or higher. In some embodiments, free capture agent (e.g. free biotin) is added at a concentration from about 10 to about 100 ug/ml. In some embodiments, free capture agent (e.g. free biotin) is added at a concentration of about 10, 20, 21, 22, 23, 24, 25, 26, 27, 28, 29, or 30 ug/ml. In some embodiments, free capture agent (e.g. free biotin) is added to a composition comprising an extended oligonucleotides species at a concentration of about 25 ug/ml.

The term "solid support" or "solid phase" as used herein refers to an insoluble material with which nucleic acid can be associated. Examples of solid supports for use with processes described herein include, without limitation, arrays, beads (e.g., paramagnetic beads, magnetic beads, microbeads, nanobeads) and particles (e.g., microparticles, nanoparticles). Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 microm-eters; about 1, 5, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 85, 90, 95, 100, 200, 300, 400, 500 micrometers. The term "paramagnetic" as used herein refers to magnetism that generally occurs only in the presence of an externally applied magnetic field. Thus, a paramagnetic bead can be attracted to an externally applied magnetic source, but typically does not exert its own magnetic field in the absence of an externally applied magnetic field. Mag-netic beads comprising a ferrous core, generally exert their own magnetic field.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, poly-amide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads® and SoluLink. A solid phase (e.g. a bead) can comprise a member of a binding pair (e.g. avidin, streptavidin or derivative thereof). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 pmoles of free capture agent (e.g. free biotin) per mg solid support. In some embodiments the binding capacity of solid phase comprising a member of a binding pair is greater than about 800, 900, 1000, 1100, 1200, 1250, 1300, 1350, 1400, 1450, 1500, 1600, 1800, 2000 pmoles of free capture agent per mg solid support.

A solid support may be provided in a collection of solid supports. A solid support collection comprises two or more different solid support species. The term "solid support species" as used herein refers to a solid support in associa-tion with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads). Each solid support species in a collection of solid supports sometimes is labeled with a specific identification tag. An identification tag for a particular solid support species sometimes is a nucleic acid (e.g., "solid phase nucleic acid") having a unique sequence in certain embodiments. An identification tag can be any molecule that is detectable and distinguish-able from identification tags on other solid support species.

Solid phase nucleic acid often is single-stranded and is of any type suitable for hybridizing nucleic acid (e.g., DNA, RNA, analogs thereof (e.g., peptide nucleic acid (PNA)), chimeras thereof (e.g., a single strand comprises RNA bases and DNA bases) and the like). Solid phase nucleic acid is associated with the solid support in any manner known by the person of ordinary skill and suitable for hybridization of solid phase nucleic acid to nucleic acid. Solid phase nucleic acid may be in association with a solid support by a covalent linkage or a non-covalent interaction. Non-limiting examples of non-covalent interactions include hydrophobic interactions (e.g., C18 coated solid support and tritylated nucleic acid), polar interactions, and the like. Solid phase nucleic acid may be associated with a solid support by different methodology known to the person of ordinary skill, which include without limitation (i) sequentially synthesiz-ing nucleic acid directly on a solid support, and (ii) synthe-sizing nucleic acid, providing the nucleic acid in solution phase and linking the nucleic acid to a solid support. Solid phase nucleic acid may be linked covalently at various sites in the nucleic acid to the solid support, such as (i) at a 1', 2', 3', 4' or 5' position of a sugar moiety or (ii) a pyrimidine or purine base moiety, of a terminal or non-terminal nucleotide of the nucleic acid, for example. The 5' terminal nucleotide of the solid phase nucleic acid is linked to the solid support in certain embodiments.

After extended oligonucleotides are associated with a solid phase (i.e. post capture), unextended oligonucleotides and/or unwanted reaction components that do not bind often are washed away or degraded. In some embodiments, a solid phase is washed after extended oligonucleotide species are captured. In some embodiments, a solid phase is washed after extended oligonucleotide species are captured and prior to releasing the extended oligonucleotide species. In some embodiments, washing a solid phase removes salts. In some embodiments, washing a solid phase removes salts that produce interfering adducts in mass spectrometry. In some embodiments, washing a solid phase removes salts that interfere with mass spectrometry. In some embodiments, extended oligonucleotide species are contacted with an anion exchange resin after washing the solid phase. In some embodiments, extended oligonucleotide species are not con-tacted with an anion exchange resin after washing the solid phase. In some embodiments, extended oligonucleotide species are captured on a solid phase, washed one or more times, released from the solid phase and are not contacted with an anion exchange resin. Extended oligonucleotides may be treated by one or more procedures prior to detection. For example, extended oligonucleotides may be conditioned prior to detection (e.g., homogenizing the type of cation and/or anion associated with captured nucleic acid by ion exchange). Extended oligonucleotides may be released from a solid phase prior to detection in certain embodiments.

In some embodiments, an extended oligonucleotide (e.g. an extended oligonucleotide species) is in association with a capture agent comprising one member of a binding pair (e.g., biotin or avidin/streptavidin). In certain embodiments, an extended oligonucleotide comprising a capture agent is captured by contacting a binding pair member with a solid phase comprising the other member of the binding pair (e.g., avidin/streptavidin or biotin). In certain embodiments an extended oligonucleotide is biotinylated, and the biotin moiety with extended oligonucleotide product is captured by contacting the biotin moiety with an avidin or streptavidin coated solid phase. In some embodiments, an extended oligonucleotide comprises a mass distinguishable tag, and in certain embodiments, detecting the mass distinguishable tag comprises detecting the presence or absence of an extended oligonucleotide. In some embodiments, the extended oligonucleotide is extended by one, two, three, or more nucleotides. In some embodiments, an extended oligonucleotide bound to a solid phase is released from the solid phase by competition with a competitor and the extended oligonucleotide is detected. In some embodiments, an extended oligonucleotide bound to a solid phase is released from the solid phase by competition with a competitor and a distinguishable label in, or associated with, the extended oligonucleotide is detected. In some embodiments, an extended oligonucleotide bound to a solid phase is released from the solid phase by competition with a competitor, a distinguishable label is released from the extended oligonucleotide, and the released distinguishable label is detected.

Distinguishable Labels and Release

As used herein, the terms "distinguishable labels" and "distinguishable tags" refer to types of labels or tags that can be distinguished from one another and used to identify the nucleic acid to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments, label composition of the distinguishable labels and tags can be selected and/or designed to result in optimal flight behavior in a mass spectrometer and to allow labels and tags to be distinguished at high multiplexing levels.

For methods used herein, a particular target nucleic acid species, amplicon species and/or extended oligonucleotide species often is paired with a distinguishable detectable label species, such that the detection of a particular label or tag species directly identifies the presence of a particular target nucleic acid species, amplicon species and/or extended oligonucleotide species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target species. When the presence of a label species is detected, then the presence of the target nucleic acid species associated with that label species thereby is detected, in certain embodiments.

The term "species," as used herein with reference to a distinguishable tag or label (collectively, "label"), refers to one label that is detectably distinguishable from another label. In certain embodiments, the number of label species, includes, but is not limited to, about 2 to about 10000 label species, about 2 to about 500,000 label species, about 2 to about 100,000, about 2 to about 50000, about 2 to about 10000, and about 2 to about 500 label species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000 or 500000 label species.

The term "mass distinguishable label" as used herein refers to a label that is distinguished by mass as a feature. A variety of mass distinguishable labels can be selected and used, such as for example a compomer, amino acid and/or a concatemer. Different lengths and/or compositions of nucleotide strings (e.g., nucleic acids; compomers), amino acid strings (e.g., peptides; polypeptides; compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by $B_n$ (i.e.: $A_aC_cG_gT_t$, with $A_0C_0G_0T_0$ representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of a, c, g or t equals 1 or more (e.g., $A_0C_0G_1T_0$, $A_1C_0G_1T_0$, $A_2C_1G_1T_2$, $A_3C_2G_1T_5$). For purposes of comparing sequences to determine sequence variations, in the methods provided herein, "unnatural" compomers containing negative numbers of monomeric units can be generated by an algorithm utilized to process data.

For polypeptides, a compomer refers to the amino acid composition of a polypeptide fragment, with the number of each type of amino acid similarly denoted. A compomer species can correspond to multiple sequences. For example, the compomer $A_2G_3$ corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., $A_0C_0G_5T_0$ and $A_0C_5G_0T_0$ are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish compomer species.

The terms "concatemer" and "concatemer" are used herein synonymously (collectively "concatemer") and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-nitroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

In certain embodiments, a distinguishable label or tag is not cleaved from an extended oligonucleotide, and in some embodiments, the distinguishable label or tag comprises a capture agent. In certain embodiments, detecting a distinguishable feature includes detecting the presence or absence of an extended oligonucleotide, and in some embodiments an extended oligonucleotide includes a capture agent. In some embodiments an extended oligonucleotide is released from a solid phase by competition with a competitor, and in certain embodiments competition with a competitor comprises contacting a solid phase with a competitor. In some embodiments, releasing an extended oligonucleotide from a solid phase is carried out under elevated temperature conditions. In certain embodiments, the elevated temperature conditions are between about 80 degrees Celsius and about 100 degrees Celsius. In some embodiments, releasing the extend oligonucleotides from the capture agent occurs under elevated temperature conditions for between about 1 minute and about 10 minutes. In certain embodiments, releasing an extended oligonucleotides from a solid phase includes treatment with a competitor (e.g., free capture agent, competing fragment of free capture agent, multimer of free capture agent, any molecule that specifically competes for binding to the solid phase, the like and combinations thereof) for about 5 minutes at about 90 degrees Celsius. In some embodiments, a competitor is biotin and a solid phase comprises avidin/streptavidin, and in certain embodiments a competitor is avidin/streptavidin and a solid phase comprises biotin.

In certain embodiments, a multiplex assay includes some oligonucleotides that are extended and some oligonucleotides that are not extended after extension. In such embodiments, oligonucleotides that are not extended often do not bind to a solid phase, and in some embodiments, oligonucleotides that are not extended can interact with a solid phase.

In some embodiments, the ratio of competitor to capture agent attached to a nucleotide or nucleic acid (e.g., extended oligonucleotide with incorporated capture agent (e.g., biotin)) can be 1:1. In certain embodiments, a competitor may be used in excess of capture agent associated with an oligonucleotide, and in some embodiments, capture agent associated with an oligonucleotide may be in excess of competitor. In such embodiments, the excess sometimes is about a 5-fold excess to about a 50,000-fold excess (e.g., about a 10-fold excess, about a 100-fold excess, about a 1,000-fold excess, or about a 10,000-fold excess).

Detection and Degree of Multiplexing

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorbtion, and/or light scattering labels).

Methods provided herein allow for high-throughput detection or discovery of target nucleic acid species in a plurality of target nucleic acids. Multiplexing refers to the simultaneous detection of more than one target nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of target nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction. Multiplexing is applicable when the genotype at a polymorphic locus is not known, and in some embodiments, the genotype at a locus is known.

In certain embodiments, the number of target nucleic acid species multiplexed include, without limitation, about 2 to 1,000 species, and sometimes about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501 species or more. Design methods for achieving resolved mass spectra with multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, only more primers are involved for multiplex reactions. In addition, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given SNP strand, in some embodiments. In such embodiments, the length often is between limits that can be, for example, user-specified (e.g., 17 to 24 bases or 17-26 bases) and often do not contain bases that are uncertain in the target sequence. Hybridization strength sometimes is gauged by calculating the sequence-dependent melting (or hybridization/dissociation) temperature, $T_m$. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER (SEQUENOM).

As used herein, the term "call rate" or "calling rate" refers to the number of calls (e.g., genotypes determined) obtained relative to the number of calls attempted to be obtained. In other words, for a 12-plex reaction, if 10 genotypes are ultimately determined from conducting methods provided herein, then 10 calls have been obtained with a call rate of 10/12. Different events can lead to failure of a particular attempted assay, and lead to a call rate lower than 100%.

Occasionally, in the case of a mix of dNTPs and ddNTPs for termination, inappropriate extension products can occur by pausing of a polymerase after incorporation of one non-terminating nucleotide (i.e., dNTP), resulting in a prematurely terminated extension primer, for example. The mass difference between this falsely terminated and a correctly terminated primer mass extension reaction at the polymorphic site sometimes is too small to resolve consistently and can lead to miscalls if an inappropriate termination mix is used. The mass differences between a correct termination and a false termination (i.e., one caused by pausing) as well between a correct termination and salt adducts as well as a correct termination and an unspecific incorporation often is maximized to reduce the number of miscalls.

Multiplex assay accuracy may be determined by assessing the number of calls obtained (e.g., correctly or accurately assessed) and/or the number of false positive and/or false negative events in one or more assays. Accuracy also may be assessed by comparison with the accuracy of corresponding uniplex assays for each of the targets assessed in the multiplex assay. In certain embodiments, one or more methods may be used to determine a call rate. For example, a manual method may be utilized in conjunction with an automated or computer method for making calls, and in some embodiments, the rates for each method may be summed to calculate an overall call rate. In certain embodiments, accuracy or call rates, when multiplexing two or more target nucleic acids (e.g., fifty or more target nucleic acids), can be about 99% or greater, 98%, 97%, 96%, 95%, 94%, 93%, 92%, 91%, 90%, 89%, 87-88%, 85-86%, 83-84%, 81-82%, 80%, 78-79% or 76-77%, for example. In some embodiments, a call rate for each target species in a multiplex assay that includes about 2 to 200 target species is greater than or equal to 80% or more (e.g., 81%, 82%, 83%, 84%, 85%, 86%, 87%, 88%, 89%, 90%, 91%, 92%, 93%, 94%, 95%, 96%, 97%, 98%, 99% or greater).

In certain embodiments the error rate may be determined based on the call rate or rate of accuracy. For example, the error rate may be the number of calls made in error. In some embodiments, for example, the error rate may be 100% less the call rate or rate of accuracy. The error rate may also be referred to as the "fail rate." Identification of false positives and/or false negatives can readjust both the call and error rates. In certain embodiments running more assays can also help in identifying false positives and/or false negatives, thereby adjusting the call and/or error rates. In certain embodiments, error rates, when multiplexing two or more target nucleic acids (e.g., fifty or more target nucleic acids), can be about 1% or less, 2%, 3%, 4,%, 5%, 6%, 7%, 8%, 9%, 10%, 11%, 12%, 13%, 14%, 15%, 16%, 17%, 18%, 19%, 20%, 21%, 22%, 23%, 24% or 25%, for example.

Applications

Following are examples of non-limiting applications of multiplex technology described herein.

1. Detection of Sequence Variations (e.g. Genetic Variants)

Provided are improved methods for identifying the genomic basis of disease and markers thereof. The sequence variation (e.g. genetic variant) candidates that can be identified by the methods provided herein include sequences containing sequence variations that are polymorphisms. Polymorphisms include both naturally occurring, somatic sequence variations and those arising from mutation. Polymorphisms include but are not limited to: sequence micro-variants where one or more nucleotides in a localized region vary from individual to individual, insertions and deletions which can vary in size from one nucleotides to millions of bases, and microsatellite or nucleotide repeats which vary by numbers of repeats. Nucleotide repeats include homogeneous repeats such as dinucleotide, trinucleotide, tetranucleotide or larger repeats, where the same sequence in repeated multiple times, and also heteronucleotide repeats where sequence motifs are found to repeat. For a given locus the number of nucleotide repeats can vary depending on the individual.

A polymorphic marker or site is the locus at which divergence occurs. Such a site can be as small as one base pair (an SNP). Polymorphic markers include, but are not limited to, restriction fragment length polymorphisms (RFLPs), variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different Mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Furthermore, numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transportation. Accordingly, it is highly desirable to develop rapid, sensitive, and accurate methods for determining the identity of allelic variants of polymorphic regions of genes or genetic lesions. A method or a kit as provided herein can be used to genotype a subject by determining the identity of one or more allelic variants of one or more polymorphic regions in one or more genes or chromosomes of the subject. Genotyping a subject using a method as provided herein can be used for forensic or identity testing purposes and the polymorphic regions can be present in mitochondrial genes or can be short tandem repeats.

Single nucleotide polymorphisms (SNPs) are generally biallelic systems, that is, there are two alleles that an individual can have for any particular marker. This means that the information content per SNP marker is relatively low when compared to microsatellite markers, which can have upwards of 10 alleles. SNPs also tend to be very population-specific; a marker that is polymorphic in one population can not be very polymorphic in another. SNPs, found approximately every kilobase (see Wang et al. (1998) Science 280:1077-1082), offer the potential for generating very high density genetic maps, which will be extremely useful for developing haplotyping systems for genes or regions of interest, and because of the nature of SNPs, they can in fact be the polymorphisms associated with the disease phenotypes under study. The low mutation rate of SNPs also makes them excellent markers for studying complex genetic traits.

Much of the focus of genomics has been on the identification of SNPs, which are important for a variety of reasons. They allow indirect testing (association of haplotypes) and direct testing (functional variants). They are the most abundant and stable genetic markers. Common diseases are best explained by common genetic alterations, and the natural variation in the human population aids in understanding disease, therapy and environmental interactions.

Sensitive detection of somatic mutations is especially valuable to the cancer research community whose interest is the identification of genetic determinants for the initiation and proliferation of tumors. The information gained from a sensitive approach can also be used for profiling mutations to predict patient outcomes and inform a relevant treatment option. In some embodiments, a sensitive detection method, that can detect a genetic variant that represents less than or equal to 5% of its counterpart wild type sequence, is needed. In some embodiments, a detection method that can detect less than or equal to 1% of wild type is implemented. In some embodiments, a detection method that can detect less than or equal to 5%, 4%, 3%, 2%, 1%, 0.8%, 0.75%, 0.5%, 0.05%, or 0.01% of wild type is implemented. Additionally, within pre-natal diagnostics, this type of method could elucidate paternally derived mutations in utero.

In some embodiments, allelic analysis can be performed by generating extended oligonucleotides from nucleic acid targets carrying one or more somatic mutations (e.g., SNPs, disease markers, the like and combinations thereof) of interest. Detecting the presence or absence of a released, extended oligonucleotide representing an allele carrying a somatic mutation can be utilized as a rapid method of screening for the presence or absence of a particular mutation in a target population, in some embodiments. In certain embodiments involving generating an extended oligonucleotide from a mutant allele, the extended oligonucleotide can be detected as the appropriate mutant allele gives rise to an extended oligonucleotide product.

2. Identifying Disease Markers

Provided herein are methods for the rapid and accurate identification of sequence variations that are genetic markers of disease, which can be used to diagnose or determine the prognosis of a disease. Diseases characterized by genetic markers can include, but are not limited to, atherosclerosis, obesity, diabetes, autoimmune disorders, and cancer. Diseases in all organisms have a genetic component, whether inherited or resulting from the body's response to environmental stresses, such as viruses and toxins. The ultimate goal of ongoing genomic research is to use this information to develop new ways to identify, treat and potentially cure these diseases. The first step has been to screen disease tissue and identify genomic changes at the level of individual samples. The identification of these "disease" markers is dependent on the ability to detect changes in genomic markers in order to identify errant genes or sequence variants. Genomic markers (all genetic loci including single nucleotide polymorphisms (SNPs), microsatellites and other noncoding genomic regions, tandem repeats, introns and exons) can be used for the identification of all organisms, including humans. These markers provide a way to not only identify populations but also allow stratification of populations according to their response to disease, drug treatment, resistance to environmental agents, and other factors. A disease marker sometimes is a mutation, and can be a relatively rare allele such as, for example, a somatic mutation against the background of a wild type allele (e.g., cancer tissue versus normal tissue, mutant viral type versus normal viral type (e.g. HIV)), in some embodiments. In some embodiments the rare allele or mutation represents less than 5%, 4%, 3%, 2%, 1%, 0.8%, 0.75%, 0.1%, 0.05%, or 0.01% of the wild type. In some embodiment, the rare allele or mutation can represent less than 1% of the wild type.

38

3. Microbial Identification

Provided herein is a process or method for identifying genera, species, strains, clones or subtypes of microorganisms and viruses. The microorganism(s) and viruses are selected from a variety of organisms including, but not limited to, bacteria, fungi, protozoa, ciliates, and viruses. The microorganisms are not limited to a particular genus, species, strain, subtype or serotype or any other classification. The microorganisms and viruses can be identified by determining sequence variations in a target microorganism sequence relative to one or more reference sequences or samples. The reference sequence(s) can be obtained from, for example, other microorganisms from the same or different genus, species strain or serotype or any other classification, or from a host prokaryotic or eukaryotic organism or any mixed population.

Identification and typing of pathogens (e.g., bacterial or viral) is critical in the clinical management of infectious diseases. Precise identity of a microbe is used not only to differentiate a disease state from a healthy state, but is also fundamental to determining the source of the infection and its spread and whether and which antibiotics or other antimicrobial therapies are most suitable for treatment. In addition treatment can be monitored. Traditional methods of pathogen typing have used a variety of phenotypic features, including growth characteristics, color, cell or colony morphology, antibiotic susceptibility, staining, smell, serotyping, biochemical typing and reactivity with specific antibodies to identify microbes (e.g., bacteria). All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. Some organisms cannot be maintained in culture or exhibit prohibitively slow growth rates (e.g., up to 6-8 weeks for *Mycobacterium tuberculosis*).

In many cases, the pathogens are present in minor amounts and/or are very similar to the organisms that make up the normal flora, and can be indistinguishable from the innocuous strains by the methods cited above. In these cases, determination of the presence of the pathogenic strain can require the higher resolution afforded by the molecular typing methods provided herein.

4. Detecting the Presence of Viral or Bacterial Nucleic Acid Sequences Indicative of an Infection The methods provided herein can be used to determine the presence of viral or bacterial nucleic acid sequences indicative of an infection by identifying sequence variations that are present in the viral or bacterial nucleic acid sequences relative to one or more reference sequences. The reference sequence(s) can include, but are not limited to, sequences obtained from an infectious organism, related non-infectious organisms, or sequences from host organisms. Viruses, bacteria, fungi and other infectious organisms contain distinct nucleic acid sequences, including sequence variants, which are different from the sequences contained in the host cell. A target DNA sequence can be part of a foreign genetic sequence such as the genome of an invading microorganism, including, for example, bacteria and their phages, viruses, fungi, protozoa, and the like. The processes provided herein are particularly applicable for distinguishing between different variants or strains of a microorganism (e.g., pathogenic, less pathogenic, resistant versus non-resistant and the like) in order, for example, to choose an appropriate thera-
peutic intervention. Examples of disease-causing viruses
that infect humans and animals and that can be detected by
a disclosed process include but are not limited to Retroviri-
dae (e.g., human immunodeficiency viruses such as HIV-1
(also referred to as HTLV-III, LAV or HTLV-III/LAV; Ratner
et al., Nature, 313:227-284 (1985); Wain Hobson et al., Cell,
40:9-17 (1985), HIV-2 (Guyader et al., Nature, 328:662-669
(1987); European Patent Publication No. 0 269 520;
Chakrabarti et al., Nature, 328:543-547 (1987); European
Patent Application No. 0 655 501), and other isolates such
as HIV-LP (International Publication No. WO 94/00562);
Picornaviridae (e.g., polioviruses, hepatitis A virus, (Gust et
al., Intervirology, 20:1-7 (1983)); enteroviruses, human cox-
sackie viruses, rhinoviruses, echoviruses); Calcivirdae (e.g.
strains that cause gastroenteritis); Togaviridae (e.g., equine
encephalitis viruses, rubella viruses); Flaviridae (e.g., den-
gue viruses, encephalitis viruses, yellow fever viruses);
Coronaviridae (e.g., coronaviruses); Rhabdoviridae (e.g.,
vesicular stomatitis viruses, rabies viruses); Filoviridae
(e.g., ebola viruses); Paramyxoviridae (e.g., parainfluenza
viruses, mumps virus, measles virus, respiratory syncytial
virus); Orthomyxoviridae (e.g., influenza viruses); Bunga-
viridae (e.g., Hantaan viruses, bunga viruses, phleboviruses
and Nairo viruses); Arenaviridae (hemorrhagic fever
viruses); Reoviridae (e.g., reoviruses, orbiviruses and rota-
viruses); Birnaviridae; Hepadnaviridae (Hepatitis B virus);
Parvoviridae (parvoviruses); Parvoviridae (most adenovi-
ruses); Papovaviridae (papilloma viruses, polyoma viruses);
Adenoviridae (most adenoviruses); Herpesviridae (herpes
simplex virus type 1 (HSV-1) and HSV-2, varicella zoster
virus, cytomegalovirus, herpes viruses; Poxviridae (variola
viruses, vaccinia viruses, pox viruses); Iridoviridae (e.g.,
African swine fever virus); and unclassified viruses (e.g., the
etiological agents of Spongiform encephalopathies, the
agent of delta hepatitis (thought to be a defective satellite of
hepatitis B virus), the agents of non-A, non-B hepatitis
(class 1=internally transmitted; class 2=parenterally trans-
mitted, i.e., Hepatitis C); Norwalk and related viruses, and
astroviruses.

Examples of infectious bacteria include but are not lim-
ited to *Helicobacter pyloris*, *Borelia burgdorferi*, *Legionella
pneumophilia*, *Mycobacteria* sp. (e.g. *M. tuberculosis*, *M.
avium*, *M. intracellulare*, *M. kansaii*, *M. gordonae*), *Salmo-
nella*, *Staphylococcus aureus*, *Neisseria gonorrheae*, *Neis-
seria meningitidis*, *Listeria monocytogenes*, *Streptococcus
pyogenes* (Group A *Streptococcus*), *Streptococcus agalac-
tiae* (Group B *Streptococcus*), *Streptococcus* sp. (*viridans*
group), *Streptococcus faecalis*, *Streptococcus bovis*, *Strep-
tococcus* sp. (*anaerobic* species), *Streptococcus pneumo-
niae*, pathogenic *Campylobacter* sp., *Enterococcus* sp., *Hae-
mophilus influenzae*, *Bacillus anthracis*, *Corynebacterium
diphtheriae*, *Corynebacterium* sp., *Erysipelothrix rhu-
siopathiae*, *Clostridium perfringens*, *Clostridium tetani*,
*Escherichia coli*, *Enterobacter aerogenes*, *Klebsiella pneu-
moniae*, *Pasteurella multocida*, *Bacteroides* sp., *Fusobacte-
rium nucleatum*, *Streptobacillus moniliformis*, *Treponema
pallidium*, *Treponema pertenue*, *Leptospira*, and *Actinomy-
ces israeli* and any variants including antibiotic resistance
variants Examples of infectious fungi include but are not limited
to *Cryptococcus neoformans*, *Histoplasma capsulatum*,
*Coccidioides immitis*, *Blastomyces dermatitidis*, *Chlamydia
trachomatis*, *Candida albicans*. Other infectious organisms
include protists such as *Plasmodium falciparum* and *Toxo-
plasma gondii*.

5. Antibiotic Profiling

Methods provided herein can improve the speed and
accuracy of detection of nucleotide changes involved in drug
resistance, including antibiotic resistance. Genetic loci
involved in resistance to isoniazid, rifampin, streptomycin,
fluoroquinolones, and ethionamide have been identified
[Heym et al., Lancet 344:293 (1994) and Morris et al., J.
Infect. Dis. 171:954 (1995)]. A combination of isoniazid
(inh) and rifampin (rif) along with pyrazinamide and etham-
butol or streptomycin, is routinely used as the first line of
attack against confirmed cases of *M. tuberculosis* [Banerjee
et al., Science 263:227 (1994)]. The increasing incidence of
such resistant strains necessitates the development of rapid
assays to detect them and thereby reduce the expense and
community health hazards of pursuing ineffective, and pos-
sibly detrimental, treatments. The identification of some of
the genetic loci involved in drug resistance has facilitated
the adoption of mutation detection technologies for rapid
screening of nucleotide changes that result in drug resis-
tance. In addition, the technology facilitates treatment moni-
toring and tracking or microbial population structures as
well as surveillance monitoring during treatment. In addi-
tion, correlations and surveillance monitoring of mixed
populations can be performed.

6. Haplotyping

The methods provided herein can be used to detect
haplotypes. In any diploid cell, there are two haplotypes at
any gene or other chromosomal segment that contain at least
one distinguishing variance. In many well-studied genetic
systems, haplotypes are more powerfully correlated with
phenotypes than single nucleotide variations. Thus, the
determination of haplotypes is valuable for understanding
the genetic basis of a variety of phenotypes including
disease predisposition or susceptibility, response to thera-
peutic interventions, and other phenotypes of interest in
medicine, animal husbandry, and agriculture.

Haplotyping procedures as provided herein permit the
selection of a portion of sequence from one of an individu-
al's two homologous chromosomes and to genotype linked
SNPs on that portion of sequence. The direct resolution of
haplotypes can yield increased information content, improv-
ing the diagnosis of any linked disease genes or identifying
linkages associated with those diseases.

7. Microsatellites

Methods provided herein allow for rapid, unambiguous
detection of microsatellite sequence variations. Microsatel-
lites (sometimes referred to as variable number of tandem
repeats or VNTRs) are short tandemly repeated nucleotide
units of one to seven or more bases, the most prominent
among them being di-, tri-, and tetranucleotide repeats.
Microsatellites are present every 100,000 bp in genomic
DNA (J. L. Weber and P. E. Can, Am. J. Hum. Genet. 44, 388
(1989); J. Weissenbach et al., Nature 359, 794 (1992)). CA
dinucleotide repeats, for example, make up about of the
human extra-mitochondrial genome; CT and AG repeats
together make up about 0.2%. CG repeats are rare, most
probably due to the regulatory function of CpG islands.
Microsatellites are highly polymorphic with respect to
length and widely distributed over the whole genome with a
main abundance in non-coding sequences, and their function
within the genome is unknown. Microsatellites can be
important in forensic applications, as a population will
maintain a variety of microsatellites characteristic for that
population and distinct from other populations which do not
interbreed.

Many changes within microsatellites can be silent, but
some can lead to significant alterations in gene products or
expression levels. For example, trinucleotide repeats found in the coding regions of genes are affected in some tumors (C. T. Caskey et al., Science 256, 784 (1992) and alteration of the microsatellites can result in a genetic instability that results in a predisposition to cancer (P. J. McKinnen, Hum. Genet. 1 75, 197 (1987); J. German et al., Clin. Genet. 35, 57 (1989)).

8. Short Tandem Repeats

The methods provided herein can be used to identify short tandem repeat (STR) regions in some target sequences of the human genome relative to, for example, reference sequences in the human genome that do not contain STR regions. STR regions are polymorphic regions that are not related to any disease or condition. Many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International PCT application No. WO 9213969 A1, Edwards et al., Nucl. Acids Res. 19:4791 (1991); Beckmann et al. (1992) Genomics 12:627-631). Nearly half of these STR loci are polymorphic, providing a rich source of genetic markers. Variation in the number of repeat units at a particular locus is responsible for the observed sequence variations reminiscent of variable nucleotide tandem repeat (VNTR) loci (Nakamura et al. (1987) Science 235:1616-1622); and minisatellite loci (Jeffreys et al. (1985) Nature 314:67-73), which contain longer repeat units, and microsatellite or dinucleotide repeat loci (Luty et al. (1991) Nucleic Acids Res. 19:4308; Litt et al. (1990) Nucleic Acids Res. 18:4301; Litt et al. (1990) Nucleic Acids Res. 18:5921; Luty et al. (1990) Am. J. Hum. Genet. 46:776-783; Tautz (1989) Nucl. Acids Res. 17:6463-6471; Weber et al. (1989) Am. J. Hum. Genet. 44:388-396; Beckmann et al. (1992) Genomics 12:627-631). VNTR typing is a very established tool in microbial typing e.g. *M. tuberculosis* (MIRU typing).

Examples of STR loci include, but are not limited to, pentanucleotide repeats in the human CD4 locus (Edwards et al., Nucl. Acids Res. 19:4791 (1991)); tetranucleotide repeats in the human aromatase cytochrome P-450 gene (CYP19; Polymeropoulos et al., Nucl. Acids Res. 19:195 (1991)); tetranucleotide repeats in the human coagulation factor XIII A subunit gene (F13A1; Polymeropoulos et al., Nucl. Acids Res. 19:4306 (1991)); tetranucleotide repeats in the F13B locus (Nishimura et al., Nucl. Acids Res. 20:1167 (1992)); tetranucleotide repeats in the human c-les/fps, proto-oncogene (FES; Polymeropoulos et al., Nucl. Acids Res. 19:4018 (1991)); tetranucleotide repeats in the LFL gene (Zuliani et al., Nucl. Acids Res. 18:4958 (1990)); trinucleotide repeat sequence variations at the human pancreatic phospholipase A-2 gene (PLA2; Polymeropoulos et al., Nucl. Acids Res. 18:7468 (1990)); tetranucleotide repeat sequence variations in the VWF gene (Ploos et al., Nucl. Acids Res. 18:4957 (1990)); and tetranucleotide repeats in the human thyroid peroxidase (hTPO) locus (Anker et al., Hum. Mol. Genet. 1:137 (1992)).

9. Organism Identification

Polymorphic STR loci and other polymorphic regions of genes are sequence variations that are extremely useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains, microbes and other material in forensic medicine. Such loci also are useful markers in commercial animal breeding and pedigree analysis and in commercial plant breeding. Traits of economic importance in plant crops and animals can be identified through linkage analysis using polymorphic DNA markers. Efficient and accurate methods for determining the identity of such loci are provided herein.

Detecting Allelic Variation

The methods provided herein allow for high-throughput, fast and accurate detection of allelic variants. Studies of allelic variation involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant can be detected by the use of a primer that is perfectly matched with only one of the possible alleles; the mismatch to the other allele acts to prevent the extension of the primer, thereby preventing the amplification of that sequence. The methods herein also are applicable to association studies, copy number variations, detection of disease marker and SNP sets for typing and the like.

11. Determining Allelic Frequency

The methods herein described are valuable for identifying one or more genetic markers whose frequency changes within the population as a function of age, ethnic group, sex or some other criteria. For example, the age-dependent distribution of ApoE genotypes is known in the art (see, e.g., Schechter et al. (1994) Nature Genetics 6:29-32). The frequencies of sequence variations known to be associated at some level with disease can also be used to detect or monitor progression of a disease state. For example, the N291S polymorphism (N291S) of the Lipoprotein Lipase gene, which results in a substitution of a serine for an asparagine at amino acid codon 291, leads to reduced levels of high density lipoprotein cholesterol (HDL-C) that is associated with an increased risk of males for arteriosclerosis and in particular myocardial infarction (see, Reymer et al. (1995) Nature Genetics 10:28-34). In addition, determining changes in allelic frequency can allow the identification of previously unknown sequence variations and ultimately a gene or pathway involved in the onset and progression of disease.

12. Epigenetics

The methods provided herein can be used to study variations in a target nucleic acid or protein relative to a reference nucleic acid or protein that are not based on sequence, e.g., the identity of bases or amino acids that are the naturally occurring monomeric units of the nucleic acid or protein. For example, methods provided herein can be used to recognize differences in sequence-independent features such as methylation patterns, the presence of modified bases or amino acids, or differences in higher order structure between the target molecule and the reference molecule, to generate fragments that are cleaved at sequence-independent sites. Epigenetics is the study of the inheritance of information based on differences in gene expression rather than differences in gene sequence. Epigenetic changes refer to mitotically and/or meiotically heritable changes in gene function or changes in higher order nucleic acid structure that cannot be explained by changes in nucleic acid sequence. Examples of features that are subject to epigenetic variation or change include, but are not limited to, DNA methylation patterns in animals, histone modification and the Polycomb-trithorax group (Pc-G/tx) protein complexes (see, e.g., Bird, A., Genes Dev., 16:6-21 (2002)).

Epigenetic changes usually, although not necessarily, lead to changes in gene expression that are usually, although not necessarily, inheritable. For example, as discussed further below, changes in methylation patterns is an early event in cancer and other disease development and progression. In many cancers, certain genes are inappropriately switched off or switched on due to aberrant methylation. The ability of methylation patterns to repress or activate transcription can be inherited. The Pc-G/trx protein complexes, like methylation, can repress transcription in a heritable fashion. The Pc-G/trx multiprotein assembly is targeted to specific regions of the genome where it effectively freezes the embryonic gene expression status of a gene, whether the gene is active or inactive, and propagates that state stably through development. The ability of the Pc-G/trx group of proteins to target and bind to a genome affects only the level of expression of the genes contained in the genome, and not the properties of the gene products. The methods provided herein can be used with specific cleavage reagents or specific extension reactions that identify variations in a target sequence relative to a reference sequence that are based on sequence-independent changes, such as epigenetic changes.

13. Methylation Patterns

The methods provided herein can be used to detect sequence variations that are epigenetic changes in the target sequence, such as a change in methylation patterns in the target sequence. Analysis of cellular methylation is an emerging research discipline. The covalent addition of methyl groups to cytosine is primarily present at CpG dinucleotides (microsatellites). Although the function of CpG islands not located in promoter regions remains to be explored, CpG islands in promoter regions are of special interest because their methylation status regulates the transcription and expression of the associated gene. Methylation of promoter regions leads to silencing of gene expression. This silencing is permanent and continues through the process of mitosis. Due to its significant role in gene expression, DNA methylation has an impact on developmental processes, imprinting and X-chromosome inactivation as well as tumor genesis, aging, and also suppression of parasitic DNA. Methylation is thought to be involved in the cancerogenesis of many widespread tumors, such as lung, breast, and colon cancer, and in leukemia. There is also a relation between methylation and protein dysfunctions (long Q-T syndrome) or metabolic diseases (transient neonatal diabetes, type 2 diabetes).

Bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the sequence of a target nucleic acid that is not treated with bisulfite with the sequence of the nucleic acid that is treated with bisulfite in the methods provided herein, the degree of methylation in a nucleic acid as well as the positions where cytosine is methylated can be deduced.

Methylation analysis via restriction endonuclease reaction is made possible by using restriction enzymes which have methylation-specific recognition sites, such as HpaII and MSPI. The basic principle is that certain enzymes are blocked by methylated cytosine in the recognition sequence. Once this differentiation is accomplished, subsequent analysis of the resulting fragments can be performed using the methods as provided herein.

These methods can be used together in combined bisulfite restriction analysis (COBRA). Treatment with bisulfite causes a loss in BstUI recognition site in amplified PCR product, which causes a new detectable fragment to appear on analysis compared to untreated sample. Methods provided herein can be used in conjunction with specific cleavage of methylation sites to provide rapid, reliable information on the methylation patterns in a target nucleic acid sequence.

14. Resequencing

The dramatically growing amount of available genomic sequence information from various organisms increases the need for technologies allowing large-scale comparative sequence analysis to correlate sequence information to function, phenotype, or identity. The application of such technologies for comparative sequence analysis can be widespread, including SNP discovery and sequence-specific identification of pathogens. Therefore, resequencing and high-throughput mutation screening technologies are critical to the identification of mutations underlying disease, as well as the genetic variability underlying differential drug response.

Several approaches have been developed in order to satisfy these needs. Current technology for high-throughput DNA sequencing includes DNA sequencers using electrophoresis and laser-induced fluorescence detection. Electrophoresis-based sequencing methods have inherent limitations for detecting heterozygotes and are compromised by GC compressions. Thus a DNA sequencing platform that produces digital data without using electrophoresis can overcome these problems. Matrix-assisted laser desorption/ionization time-of-flight mass spectrometry (MALDI-TOF MS) measures nucleic acid fragments with digital data output. Methods provided herein allow for high-throughput, high speed and high accuracy in the detection of sequence identity and sequence variations relative to a reference sequence. This approach makes it possible to routinely use MALDI-TOF MS sequencing for accurate mutation detection, such as screening for founder mutations in BRCA1 and BRCA2, which are linked to the development of breast cancer.

15. Disease Outbreak Monitoring

In times of global transportation and travel outbreaks of pathogenic endemics require close monitoring to prevent their worldwide spread and enable control. DNA based typing by high-throughput technologies enable a rapid sample throughput in a comparatively short time, as required in an outbreak situation (e.g. monitoring in the hospital environment, early warning systems). Monitoring is dependent of the microbial marker region used, but can facilitate monitoring to the genus, species, strain or subtype specific level. Such approaches can be useful in biodefense, in clinical and pharmaceutical monitoring and metagenomics applications (e.g. analysis of gut flora). Such monitoring of treatment progress or failure is described in U.S. Pat. Nos. 7,255,992, 7,217,510, 7,226,739 and 7,108,974 which are incorporated by reference herein.

16. Vaccine Quality Control and Production Clone Quality Control

Methods provided herein can be used to control the identity of recombinant production clones (not limited to vaccines), which can be vaccines or e.g. insulin or any other production clone or biological or medical product.

17. Microbial Monitoring in Pharmacology for Production Control and Quality

Methods provided herein can be used to control the quality of pharmacological products by, for example, detecting the presence or absence of certain microorganism target nucleic acids in such products.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. One or more of the following components, for example, may be included in a kit: (i) one or more nucleotides (e.g. terminating nucleotides and/or non-terminating nucleotides); (ii) one or more nucleotides comprising a capture agent; (iii) one or more oligonucleotides (e.g. oligonucleotide primers, one or more extension oligonucleotides, oligonucleotides comprising a tag, oligonucleotides comprising a capture agent); (iv) free capture agent (e.g. free biotin); (v) a solid phase (e.g. a bead) comprising a member of a binding pair (viii); (ix) one or more enzymes (e.g. a polymerase, endonuclease, restriction enzyme, etc.); (x) controls components (e.g. control genomic DNA, primers, synthetic templates, target nucleic acids, etc.) (xi) one or more buffers and (xii) printed matter (e.g. directions, labels, etc).

A kit sometimes is utilized in conjunction with a process, and can include instructions for performing one or more processes and/or a description of one or more compositions. A kit may be utilized to carry out a process (e.g., using a solid phase) described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

EXAMPLES

The examples set forth below illustrate, and do not limit, the technology.

Example 1: Pre-PCR Reaction

The presented process provides an alternative biochemistry to the regular PCR, which usually has two gene specific primers amplifying the same target. The process is suited for the amplification of target regions e.g. containing a SNP.

Approach 1: This method uses only one primer to extend, see FIG. 1. The gene specific extend primer has a 5' universal PCRTag1R. It is extended on the genomic DNA. The DNA or the PCR Tag1R gene specific extend primer may be biotinylated, to facilitate clean up of the reaction. The extended strand is then ligated to a universal phosphorylated oligonucleotide, which has sequence which is reverse complement of Tag2F (universal PCR primer). To facilitate clean up in the next step, the phosphorylated oligonucleotide has exonuclease resistant nucleotides at its 3' end. During the exonuclease treatment, all non-ligated extend strands are digested, whereas ligated products are protected and remain in the reaction. A universal PCR is then performed using Tag1R and the Tag2F primers, to amplify multiple targets. An overview of concept-1 is outlined in FIG. 1.

Approach 2: In this method, primer extension and ligation takes place in the same reaction. FIG. 2 shows the use of a biotinylated PCRTag3R gene specific primer as an extension primer. The phosphorylated oligonucleotide has a gene specific sequence and binds around 40 bases away from the primer extension site, to the same strand of DNA. Thus, Stoffel DNA polymerase extends the strand, until it reaches the phosphorylated oligonucleotide. Amp ligase (Epicentre) ligates the gene specific sequence of the phosphorylated oligonucleotide to the extended strand. The 3' end of Phospho oligonucleotide has PCRTag4(RC)F as its universal tag. The biotinylated extended strands are then bound to streptavidin beads. This facilitates clean up of the reaction. Genomic DNA and the gene specific phosphorylated oligonucleotides will get washed away. A universal PCR is then performed using Tag3R and Tag4F as primers, to amplify different genes of interest. An overview of concept-2 is as shown in FIG. 2.

The universal PCR products from both the Approach 1 and 2 can be identified using the post-PCR reaction, as shown in FIG. 3. SAP was used to clean up the PCR reaction. Post-PCR reactions were performed using gene specific oligonucleotides binding just before the SNP and the single base extended products were spotted on a chip array and analyzed on mass spectrometry. Alternatively the methods provided herein can be used for post-PCR read-out.

Example 2: Pre-PCR Reaction Materials from Example 1

Approach 1:

1a) Extension: A 90 ul reaction was performed with 18 ng plasmid insert, 1× Qiagen PCR buffer with Mg, 2.82 mM of total MgCl2, 10 mM Tris, pH 9.5, 50 uM dNTPs, 0.5 uM 5' PCR tag1R gene specific extension primer, 5.76 U Thermosequenase. The thermo cycling conditions used were 2 minutes at 94° C. followed by 45 cycles of 10 second denaturation at 94° C.; 10 seconds annealing at 56° C.; 20 seconds extension at 72° C.

1b) Ligation: 5 ul of extended product was ligated with 500 pmols of a phospho oligonucleotide (reverse complement of the Tag2F primer) which is exonuclease resistant at its 3'end. The extension product and phospho-oligonucleotide were denatured at 65° C./10 minutes, cooled before volume made to 50 ul with 50 mM Tris-HCl, pH 7.8, 10 mM MgCl2, 10 mM DTT, 1 mM ATP and 50 U T4 RNA Ligase1. Incubation was carried out at 37° C./4 hours, 65° C./20 minutes.

1c) Exonuclease treatment: 10 ul of the ligated product was denatured at 95° C./5 minutes, cooled and diluted with 0.5× exonuclease III buffer containing 20 U exonuclease I and 100 U exonuclease III in a total volume of 20 ul. The reaction was incubated at 37° C./4 hours, 80° C./20 minutes.

1d) Universal PCR: 2 ul of the exonuclease treated product was amplified with 0.4 uM each of M13 forward and reverse primers in a 25 ul reaction containing 1× Qiagen buffer containing 1.5 mM MgCl2, 200 uM dNTP and 0.625 U Hot star DNA polymerase. The thermo cycling conditions used were 15 minutes at 94° C., followed by 45 cycles of 30 second denaturation at 94° C.; 30 seconds annealing at 55° C. and one minute extension at 72° C.

The primers and PCR tag sequences used were:

Universal Tag 1R (rs10063237)=5' GGAAACAGC-TATGACCATG—(GTAATTGTACTGTGAGTGGC) gene specific sequence 3' (SEQ ID NO: 1), Universal Tag2 (RC) F=5'P-CATGICGTITTACAACGTCG*T*G*ddC 3' (SEQ ID NO: 2) (The * represents exonuclease resistant linkages between the nucleotides) Tag1R (M13R)=5' GGAAACAGCTATGACCATG 3' (SEQ ID NO: 3) Tag2F (M13F)=5' CACGACGTTGTAAAACGAC 3' (SEQ ID NO: 4) rs10063237_E1 (for post-PCR reaction): 5'TCAAAGAATTATATGGCTAAGG 3' (SEQ ID NO: 5)

Figure 4:
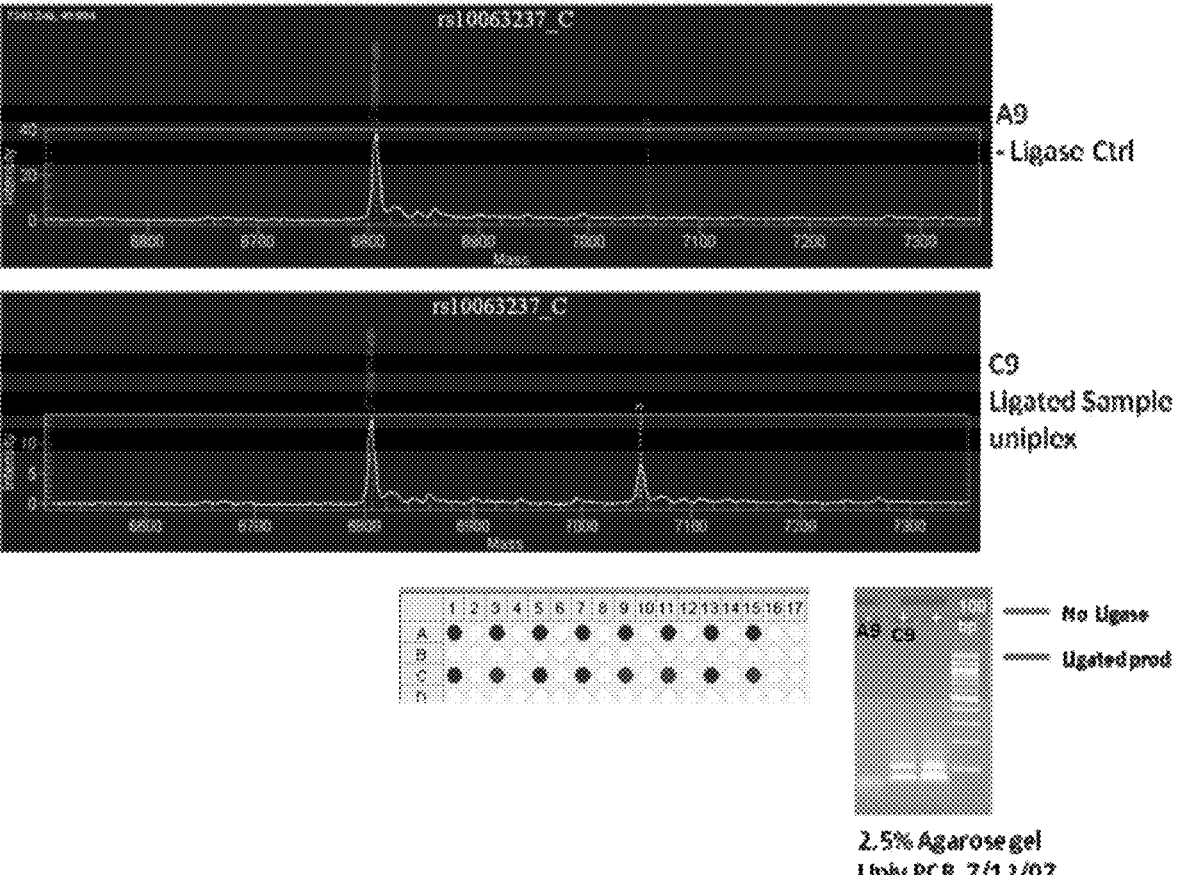
FIG. 4 shows MALDI-TOF MS spectra for genotyping of a single nucleotide polymorphism (dbSNP #rs10063237) using an Approach 1 protocol.

Results from Approach 1 can be seen in FIG. 4.

Approach 2:

2a) Extension and Ligation: The 20 ul reaction was carried out with 16-35 ng genomic DNA, 1× Amp ligase buffer (Epicentre), 200 uM dNTP, 10 nM biotinylated extension primer, 50 nM gene specific phospho oligonucleotide, 1 U Stoffel fragment DNA polymerase and 4 U Amp ligase (Epicentre). The thermo cycling conditions used: 5 minutes at 94° C. followed by 19 cycles of 30 second denaturation at 94° C.; 150 seconds annealing at 58.5° C., with a decrease in temperature by at every cycle; 45 seconds extension at 72° C. The extension and ligation reaction was treated with 40 ug of proteinase K at 60° C. for 20 minutes.

2b) Bead Clean up: 15 ul of Dyna beads M-280 streptavidin beads were washed three times with 1× binding buffer (5 mM Tris-HCl pH 7.5, 1 M NaCl, 0.5 mM EDTA). During all washes, the beads were bound to the magnet and the supernatant then discarded. Two extension reactions were pooled and diluted to get a 1× binding buffer concentration and then mixed with the beads. The beads were incubated at room temperature for 20 minutes, with gentle agitation. The beads were then washed 3 times with 1× wash buffer (10 mM Tris, pH 81 mM EDTA) and 2 times with water. The beads were then treated with 0.1N NaOH at room temperature for 10 minutes. The beads were then washed 2 times with 1× wash buffer and 2 times with water. The beads were finally suspended in 15 ul water.

2c) Universal PCR: 2 ul beads were added to a 25 ul PCR reaction containing 1×PCR Gold buffer (Applied Biosystems), 250 uM dNTP, 2.5 mM MgCl$_2$, and 0.4 uM each of Tag4F and Tag3R primers, 1.25 U AmpliTaq Gold DNA polymerase and 0.05% Tween 20. The thermo cycling conditions used were 12 minutes at 94° C. followed by 60 cycles of 30 second denaturation at 94° C.; 30 seconds annealing at 68° C.; 45 seconds extension at 72° C., with a final extension of 72° C. for 2 minutes.

The primers and Tag sequences used were:

```
Universal Tag 3R =
                                    (SEQ ID NO: 6)
5' GAGCTGCTGCACCATATTCCTGAAC-gene specific sequence
3', Universal Tag4 (RC) F =
                                    (SEQ ID NO: 7)
5'P-gene specific sequence-GCTCTGAAGGCGGTGTATGACATG
G 3'

Tag3R =
                                    (SEQ ID NO: 8)
5' GAGCTGCTGCACCATATTCCTGAAC 3'

Tag4F =
                                    (SEQ ID NO: 9)
5' CCATGTCATACACCGCCTTCAGAGC 3'
```

Figure 5B:
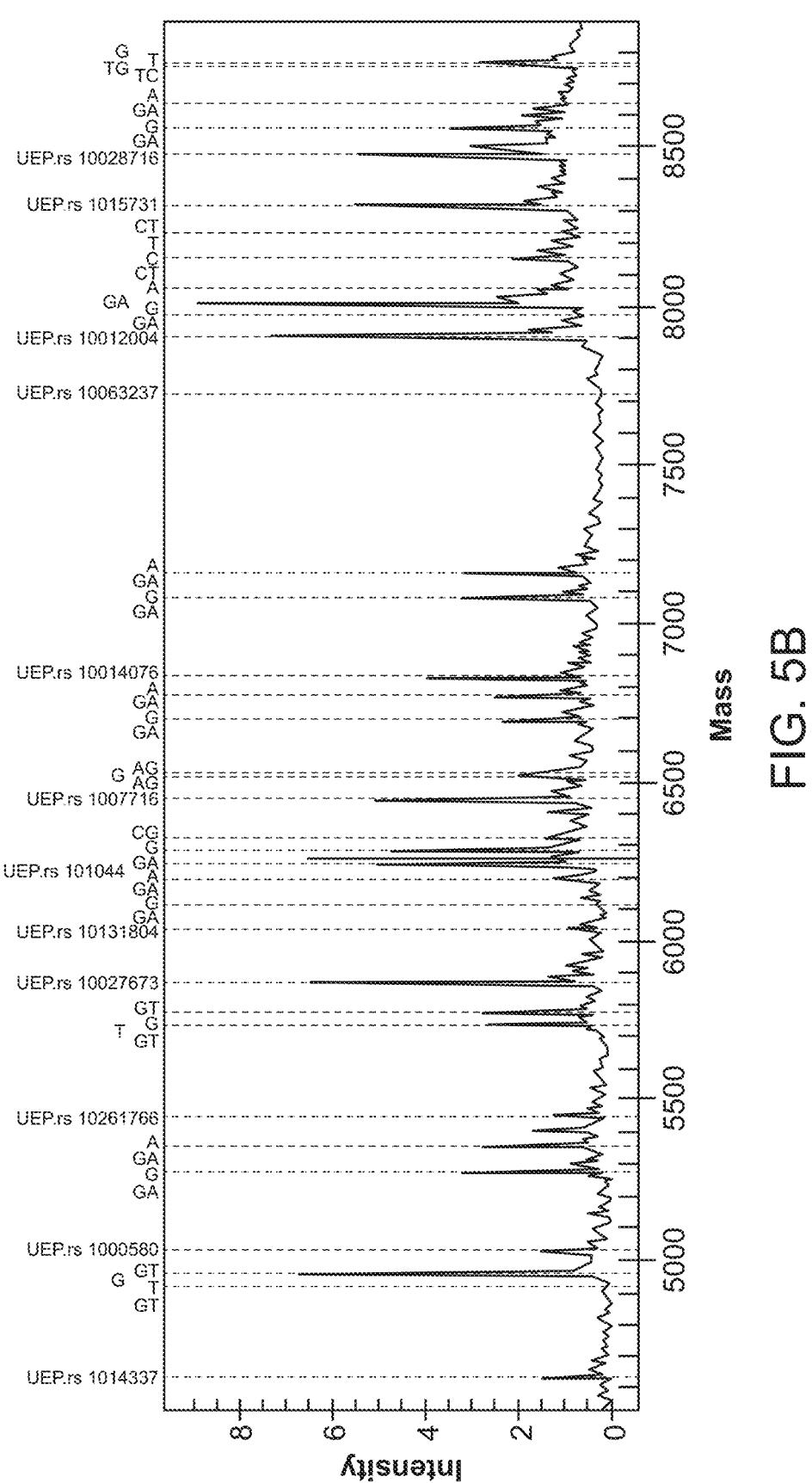
FIG. 5B shows MALDI-TOF MS spectra for genotyping 12 targets (e.g., a 12 plex reaction) using an Approach 2 protocol.
Figure 5C:
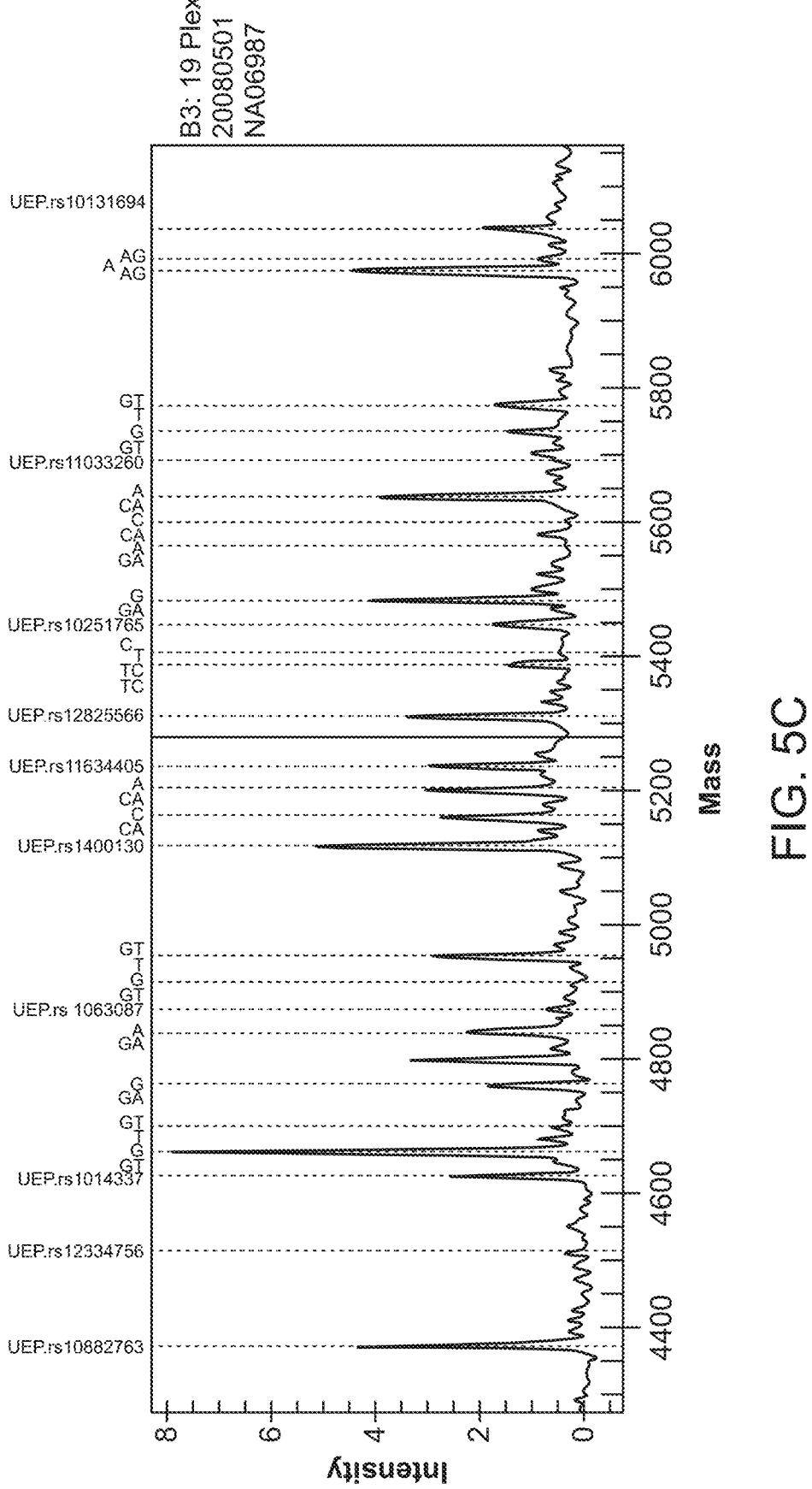
FIG. 5C shows MALDI-TOF MS spectra for genotyping a 19 plex reaction using an Approach 2 protocol.
Figure 5C:
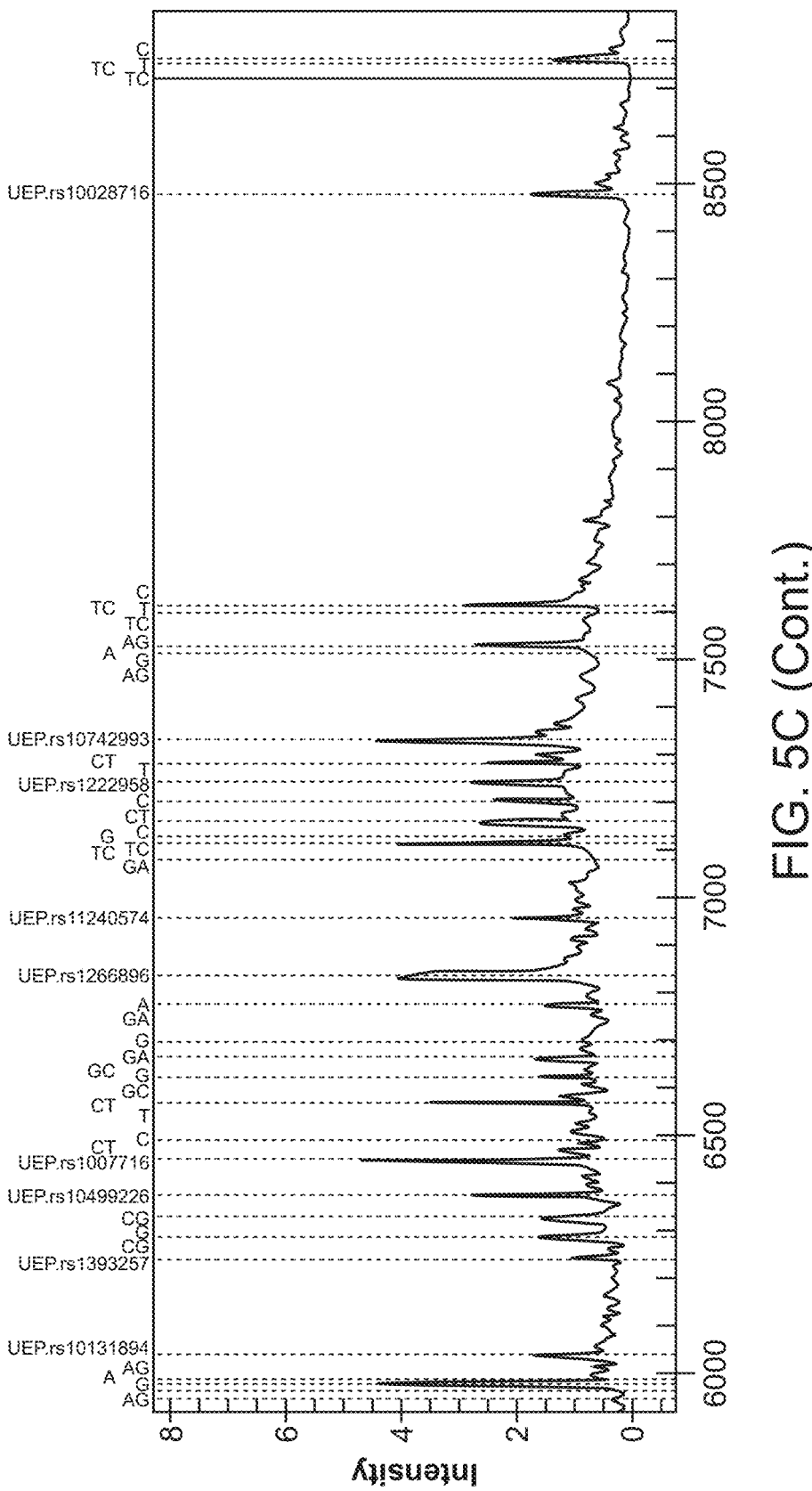
Figure 5D:
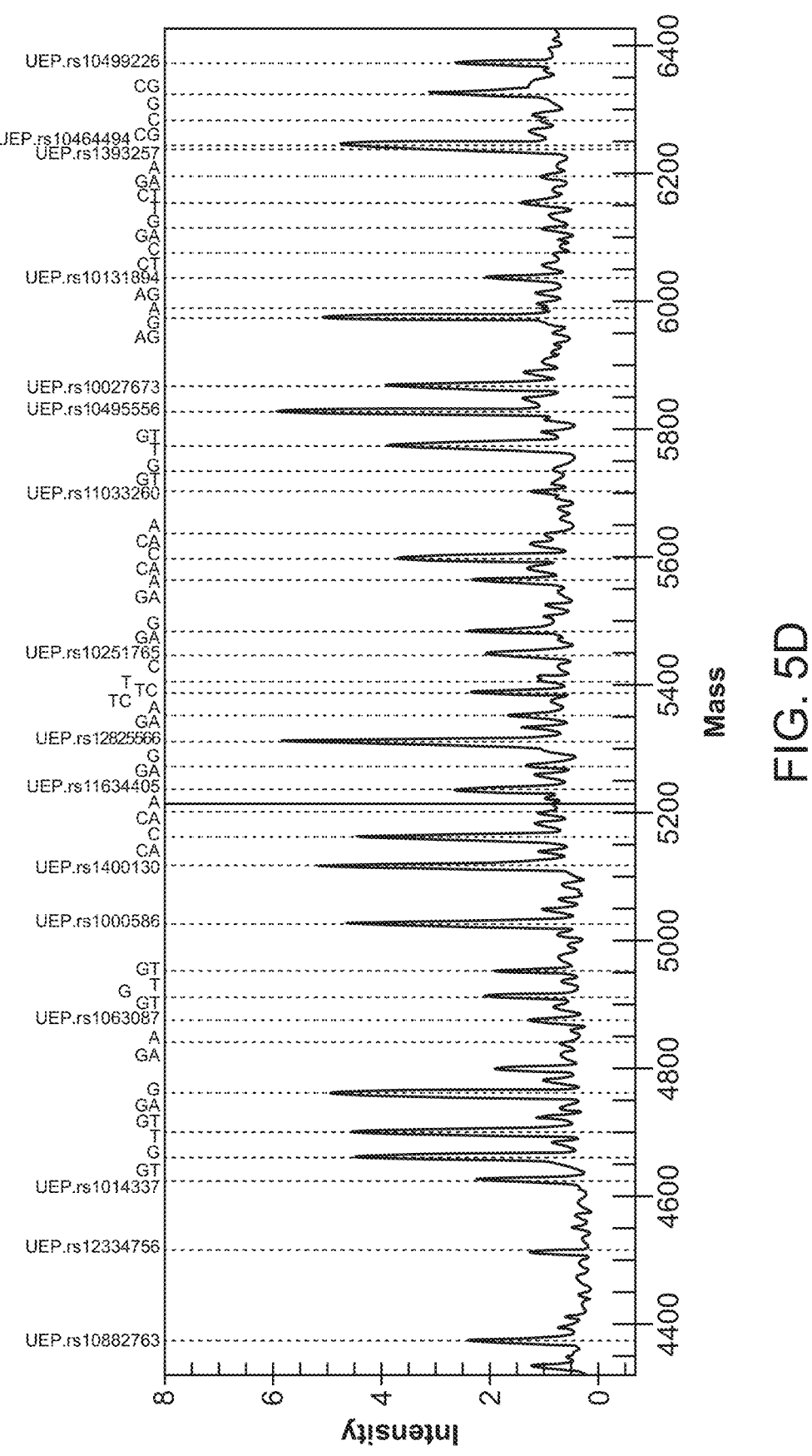
FIG. 5D shows MALDI-TOF MS spectra for genotyping a 35 plex reaction using an Approach 2 protocol.
Figure 5D:
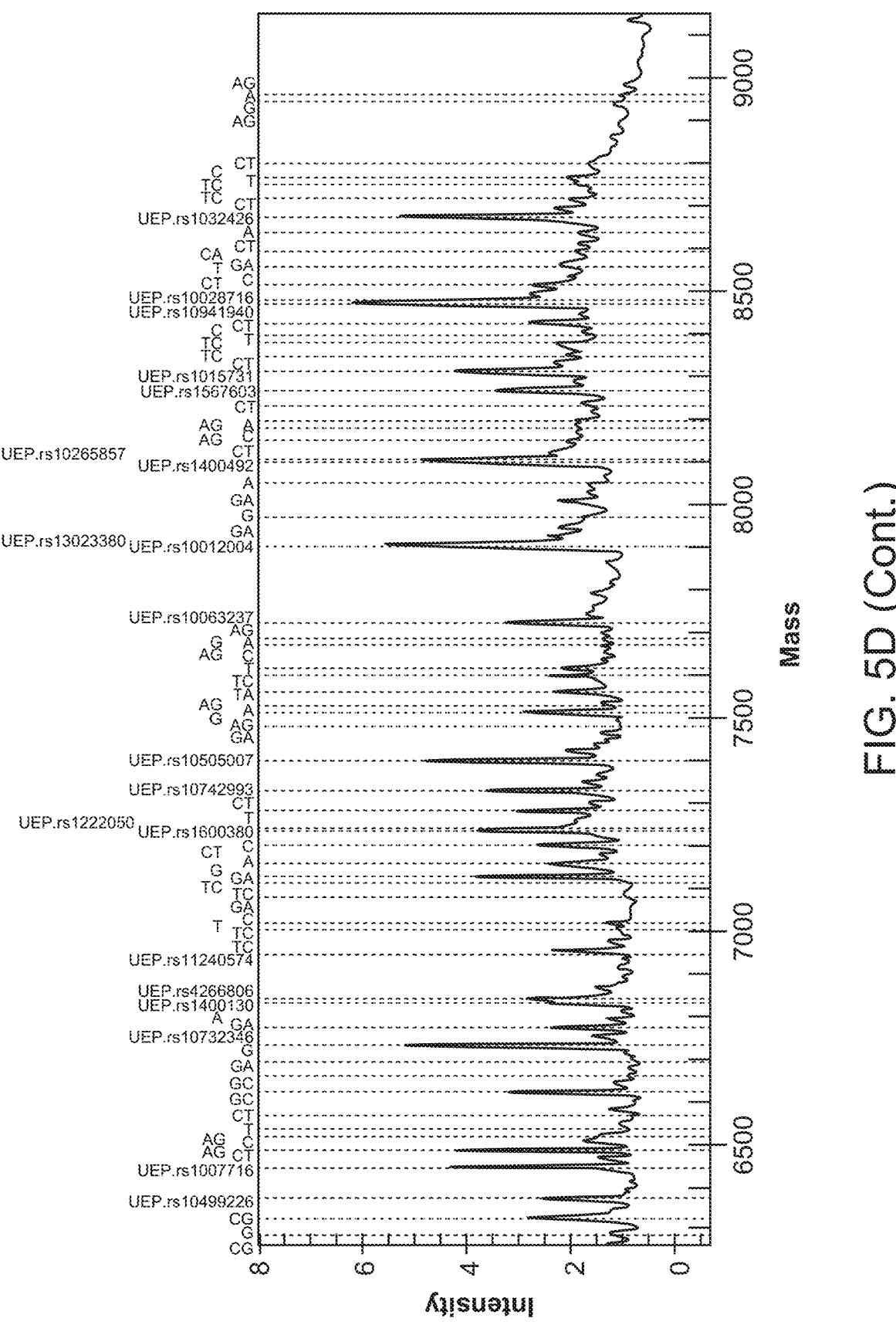

Approach 2 gene specific extend primers, phospho oligonucleotides and post-PCR reaction extension primers are listed in Tables 1, 2 and 3 respectively. For Table 1, the PCR tag region is underlined. In Approach 2, 5'-Biotinylated and PCR-tagged gene specific-primer is extended on genomic DNA by Stoffel DNA polymerase and simultaneously ligated to a downstream gene specific PCR-tagged phospho oligonucleotide bound on the same strand, by Amp Ligase (Epicentre). Results from Approach 2 are shown in FIGS. 5A-5.

TABLE 1

Extension primers used to extend genomic DNA in the extension ligation reaction (non-hybridizing regions are underlined)

| Primer Name | 5'Biotin-primer seq | SEQ ID NO: |
|---|---|---|
| 5'BiotinUF rs1000586 | 5'Biotin-GAGCTGCTGCACCATATTCCTGAACTCTCAAACTCCAGAGTGGCC | 10 |
| 5'BiotinUF rs10012004 | 5'Biotin-GAGCTGCTGCACCATATTCCTGAACAGCAGTGCTTCACACACTTTAG | 11 |
| 5'BiotinUF rs10014076 | 5'Biotin-GAGCTGCTGCACCATATTCCTGAACGTCCTGATTTCTCCTCCAGAG | 12 |
| 5'BiotinUF rs10027673 | 5'Biotin-GAGCTGCTGCACCATATTCCTGAACCCCTCTTGCATAAAATGTTGCAG | 13 |
| 5'BiotinUF rs10028716 | 5'Biotin-GAGCTGCTGCACCATATTCCTGAACCATGAAGAGAAATAGTTCTGAGGTTTCC | 14 |
| 5'BiotinNewUF rs10063237 | 5'Biotin-GAGCTGCTGCACCATATTCCTGAACCTGATAGTAATTGTACTGTGAGTGGC | 15 |
| 5'BiotinUF rs1007716 | 5'Biotin-GAGCTGCTGCACCATATTCCTGAACCTAAAAACTTATAATTTTAATAGAGGGTGCATTGAAG | 16 |
| 5'BiotinUF rs10131894 | 5'Biotin-GAGCTGCTGCACCATATTCCTGAACACGTAAGCACACATCCCCAG | 17 |
| 5'BiotinUF rs1014337 | 5'Biotin-GAGCTGCTGCACCATATTCCTGAACGATTTCTATCCTCAAAAAGCTTATGGG | 18 |
| 5'BiotinUF rs1015731 | 5'Biotin-GAGCTGCTGCACCATATTCCTGAACGATGAATCATCTTACTCTTTAGTATGGTTGC | 19 |
| 5'BiotinUF rs10164484 | 5'Biotin-GAGCTGCTGCACCATATTCCTGAACCCTGCCCTTTAGACAGGAATC | 20 |
| 5'BiotinUF rs10251765 | 5'Biotin-GAGCTGCTGCACCATATTCCTGAACCATCTGCCTTGATCTCCCTTC | 21 |
| 5'BiotinUF rs10265857 | 5'Biotin-GAGCTGCTGCACCATATTCCTGAACCCTTCATGCTCTTCTTCCTGC | 22 |

TABLE 1-continued

Extension primers used to extend genomic DNA in the extension ligation
reaction (non-hybridizing regions are underlined)

| Primer Name | 5'Biotin-primer seq | SEQ ID NO: |
|---|---|---|
| 5'BiotinUF rs1032426 | 5'Biotin-GAGCTGCTGCACCATATTCCTGAACGCTATTTTTATAATATTTATTATTTT AAATAATTCAAAATACAAAAGTAACAC | 23 |
| 5'BiotinUF rs10495556 | 5'Biotin-GAGCTGCTGCACCATATTCCTGAACCTAGACATTGGGAATACATAGGAGTG | 24 |
| 5'BiotinUF rs10499226 | 5'Biotin-GAGCTGCTGCACCATATTCCTGAACAACTTGTACCCAGATGCAGTC | 25 |
| 5'BiotinUF rs10505007 | 5'Biotin-GAGCTGCTGCACCATATTCCTGAACCTTCTAAGGCTTCAGGGATGAC | 26 |
| 5'BiotinUF rs1063087 | 5'Biotin-GAGCTGCTGCACCATATTCCTGAACGTACTTGAAAAGAAGCCCGG | 27 |
| 5'BiotinUF rs10732346 | 5'Biotin-GAGCTGCTGCACCATATTCCTGAACGATCTCTCTACCACCATCAGGG | 28 |
| 5'BiotinNewUF rs10742993 | 5'Biotin-GAGCTGCTGCACCATATTCCTGAACAGGAGTCACTACATTCAGGGATG | 29 |
| 5'BiotinUF rs10882763 | 5'Biotin-GAGCTGCTGCACCATATTCCTGAACGTGTCTCAGGTGAAAGTGACTC | 30 |
| 5'BiotinNewUF rs10911946 | 5'Biotin-GAGCTGCTGCACCATATTCCTGAACCTTCAGGATTATACTGGCAGTTGC | 31 |
| 5'BioinUF rs11033260 | 5'Biotin-GAGCTGCTGCACCATATTCCTGAACGCTTTGAATGGTATCACCCTCAC | 32 |
| 5'BiotinUF rs11240574 | 5'Biotin-GAGCTGCTGCACCATATTCCTGAACAAACGCAGTCATCACTCTCC | 33 |
| 5'BiotinUF rs11599388 | 5'Biotin-GAGCTGCTGCACCATATTCCTGAACGGGAGCGGGAATCTTAAATCC | 34 |
| 5'BiotinUF rs11634405 | 5'Biotin-GAGCTGCTGCACCATATTCCTGAACGCAACAGGATTCGACTAAGGC | 35 |
| 5'BiotinUF rs1222958 | 5'Biotin-GAGCTGCTGCACCATATTCCTGAACCATGTATATAGTTTGGCTAGCAGTGAAAG | 36 |
| 5'BiotinUF rs12334756 | 5'Biotin-GAGCTGCTGCACCATATTCCTGAACGAATCCTACTCCTAAGGTGATGTTG | 37 |
| 5'BiotinUF rs1266886 | 5'Biotin-GAGCTGCTGCACCATATTCCTGAACCTTCATCAGCAAGCAACTACATTG | 38 |
| 5'BiotinNewUF rs12825566 | 5'Biotin-GAGCTGCTGCACCATATTCCTGAACGGGTCCAAAACTGCTCATGTC | 39 |
| 5'BiotinUF13023380 | 5'Biotin-GAGCTGCTGCACCATATTCCTGAACTTTTTCCATGGCTTTTGGGC | 40 |
| 5'BiotinUF rs1393257 | 5'Biotin-GAGCTGCTGCACCATATTCCTGAACTGTACAGGCAGGTCTTAGAGATG | 41 |
| 5'BiotinUF rs1400130 | 5'Biotin-GAGCTGCTGCACCATATTCCTGAACGTAGCCAATTCCTTCAGTGCAG | 42 |
| 5'BiotinNewUF rs1490492 | 5'Biotin-GAGCTGCTGCACCATATTCCTGAACAGGGCTTGTTTCAGCTTGAG | 43 |
| 5'BiotinUF rs1567603 | 5'Biotin-GAGCTGCTGCACCATATTCCTGAACCAAAAGTTTTGTTTAGGTGCCTTCC | 44 |

TABLE 2

Gene-specific phospho oligonucleotides used to ligate the extended strand
in the extension ligation reaction (non-hybridizing regions are underlined)

| Primer name | 5'P-Primer Sequence | SEQ ID NO: |
|---|---|---|
| 5'P rs1000586 | GGGGAGTGTAGGTTCTGGTACCCAGGCTCTGAAGGCGGTGTATGACATGG | 45 |
| 5'P rs10012004 | CATCACCTATATCATTATTTACTAAATTATTTTTTCTTCAAACTGACTTAGGCTCTGAA GGCGGTGTATGACATGG | 46 |
| 5'P rs10014076 | CCCTTTTTTCCTAAAAGCCCCCAAACTTTTGGCTCTGAAGGCGGTGTATGACATGG | 47 |
| 5'P rs10027673 | CTTTTGTGAGCTGGCTTTTGCTCATCTCGCTCTGAAGGCGGTGTATGACATGG | 48 |
| 5'P rs10028716 | CCTATTTGAGTTTTGCTTTTTTGTTTTGGTCTCGGCTCTGAAGGCGGTGTATGACATGG | 49 |
| 5'P rs1006237long | GATTTAGACAGAGTCTTACTCTGTCACCAGGGCTCTGAAGGCGGTGTATGACATGG | 50 |
| 5'P rs1007716 | CTATACTCTTGCTCGTGGAGTTAATCTCAGAGGGCTCTGAAGGCGGTGTATGACATGG | 51 |

TABLE 2-continued

Gene-specific phospho oligonucleotides used to ligate the extended strand
in the extension ligation reaction (non-hybridizing regions are underlined)

| Primer name | 5'P-Primer Sequence | SEQ ID NO: |
|---|---|---|
| 5'P rs10131894 | CTCAGAAGTGTGGAACAGCTGCCCGCTCTGAAGGCGGTGTATGACATGG | 52 |
| 5'P rs1014337 | CTTGGGACTTCAGGTAGACTTAGTTTGAACATCGCTCTGAAGGCGGTGTATGACATGG | 53 |
| 5'P rs1015731 | CCATCTACATTAGCTTACCAGGGCTGCGCTCTGAAGGCGGTGTATGACATGG | 54 |
| 5'P rs10164484 | CTCTCTAATGTTCCAGAGAAACCCCAGGGCTCTGAAGGCGGTGTATGACATGG | 55 |
| 5'P rs10251765 | CGTTTTCTTATGTGTCTGGCCTCATCCGCTCTGAAGGCGGTGTATGACATGG | 56 |
| 5'P rs10265857 | GGAGCGCTCCATGAAACACAACAGGCTCTGAAGGCGGTGTATGACATGG | 57 |
| 5'P rs1032426 | GTTGACAGTTGATTTTGTAATGCCTCCACGCTCTGAAGGCGGTGTATGACATGG | 58 |
| 5'P rs10495556 | CGATGTGATCCTGTGTCAAATAATGACGGGCTCTGAAGGCGGTGTATGACATGG | 59 |
| 5'P rs10499226 | CTGAAGGGAATGGCTGGTTTTTAATTTGTAGTGGCTCTGAAGGCGGTGTATGACATGG | 60 |
| 5'P rs10505007 | GAAGGTGGGATTACGCCTAACTTTAGGGCTCTGAAGGCGGTGTATGACATGG | 61 |
| 5'P rs1063087 | GACTTCATGGCTGGCAGAAAGCTCTGAAGGCGGTGTATGACATGG | 62 |
| 5'P rs10732346 | CTGCATTTCTACTGGTAACATGCGCCGCTCTGAAGGCGGTGTATGACATGG | 63 |
| 5'PNew rs10742993 | CTATTCAGGTGTCACTTTTATTATGATTATCTAAGGTCAGTGGCTCTGAAGGCGGTGTATGACATGG | 64 |
| 5'P rs10882763 | CAGGTCCAGTTCTTGAGTTTCATCCTTTCGCTCTGAAGGCGGTGTATGACATGG | 65 |
| 5'P rs109119461ong | CCTCTCTGTTTTGTTGAGAAATCCACTCTTGGTCGCTCTGAAGGCGGTGTATGACATGG | 66 |
| 5'P rs11033260 | GCAAAATGGGTATGGTTTAGCCAGAAACATGGCTCTGAAGGCGGTGTATGACATGG | 67 |
| 5'P rs11240574 | GGTGATGGACCCACTGCCTGGCTCTGAAGGCGGTGTATGACATGG | 68 |
| 5'P rs11599388 | GTGACCTGACACTGGTGGGATGGCTCTGAAGGCGGTGTATGACATGG | 69 |
| 5'P rs11634405 | GCTTTGTGTGCAAATCACCTATTTTCCTGGCTCTGAAGGCGGTGTATGACATGG | 70 |
| 5'P rs1222958 | GGTGAGAGAATATGAAAGCAAAACAGCAACCGCTCTGAAGGCGGTGTATGACATGG | 71 |
| 5'P rs12334756 | GGGCTATGTAGACACTTCAAAGGTGTTCGCTCTGAAGGCGGTGTATGACATGG | 72 |
| 5'P rs1266886 | GTTTGCTCTAGCTCAATGGCCTCTTAAGGCTCTGAAGGCGGTGTATGACATGG | 73 |
| 5'PNew rs12825566 | CCAACACAGTCATCTGATCCCATCTCCGCTCTGAAGGCGGTGTATGACATGG | 74 |
| 5'P rs13023380 | GTAGGCAAGGCTGTTCTTTTTTGTGTTGGCTCTGAAGGCGGTGTATGACATGG | 75 |
| 5'P rs1393257 | CCATATGCAGTTTTTGTTTTCCCAGTGCGCTCTGAAGGCGGTGTATGACATGG | 76 |
| 5'P rs1400130 | CACCATAATAGTTTATCTGCTTCTACTAAAATTATTATTGGCGCTCTGAAGGCGGTGTATGACATGG | 77 |
| 5'PNew rs1490492 | CCTCAGAATGAAATCATGCTTTTCTGCTAATTTGTAGGCTCTGAAGGCGGTGTATGACATGG | 78 |
| 5'P rs1567603 | CCTTCAGACATACCTTGGGAAAATGTCAGGCTCTGAAGGCGGTGTATGACATGG | 79 |

TABLE 3

Standard post-PCR primers used in the post-PCR assay for the universal PCR readout

| | TERM | SNP_ID | UEP_DIR | UEP_MASS | UEP_SEQ 5'-3' | SEQ ID NO: | EXT1_CALL | EXT1_MASS | EXT2_CALL | EXT2_MASS |
|---|---|---|---|---|---|---|---|---|---|---|
| L1 | goldPLEX | rs10882763 | F | 4374.9 | CCTTCTTCATCCCCC | 80 | G | 4662.1 | T | 4701.9 |
| L2 | goldPLEX | rs12334756 | R | 4515 | GCCCATAAGCCAACA | 81 | G | 4762.2 | A | 4842.1 |

TABLE 3-continued

| | | | | | | SEQ ID NO: | EXT1_ CALL | EXT1_ MASS | EXT2_ CALL | EXT2_ MASS |
|---|---|---|---|---|---|---|---|---|---|---|
| | | | | | Standard post-PCR primers used in the post-PCR assay for the universal PCR readout | | | | | |
| | TERM | SNP_ID | UEP_ DIR | UEP_ MASS | UEP_SEQ 5'-3' | | | | | |
| L3 | goldPLEX | rs1014337 | F | 4627 | GTCCCAAGGGAGAGC | 82 | G | 4914.2 | T | 4954.1 |
| L4 | goldPLEX | rs1063087 | R | 4875.2 | GGTAAAGCCCCTCGAA | 83 | C | 5162.4 | A | 5202.3 |
| L5 | goldPLEX | rs1000586 | R | 5027.3 | CTCCCCACCTGACCCTG | 84 | G | 5274.5 | A | 5354.4 |
| L6 | goldPLEX | rs1400130 | R | 5118.3 | TTATGGTGTCTTTCCCC | 85 | T | 5389.5 | C | 5405.5 |
| L7 | goldPLEX | rs11634405 | R | 5237.4 | CAAAGCAGGTGCACGAA | 86 | G | 5484.6 | A | 5564.5 |
| L8 | goldPLEX | rs12825566 | R | 5311.5 | ACTTCCTCCCTTCTTACT | 87 | C | 5598.7 | A | 5638.6 |
| L9 | goldPLEX | rs10251765 | F | 5448.5 | CCCTTTTGGCTTCCTGGG | 88 | G | 5735.7 | T | 5775.6 |
| L10 | goldPLEX | rs11033260 | F | 5704.7 | CCCATTTTGCGCCATTTAT | 89 | A | 5975.9 | G | 5991.9 |
| L11 | goldPLEX | rs10495556 | F | 5827.8 | GGATCACATCGTGTTAGAC | 90 | C | 6075 | T | 6154.9 |
| L12 | goldPLEX | rs10027673 | R | 5867.8 | ggAAGACGCTTATCATGGT | 91 | G | 6115 | A | 6194.9 |
| M1 | goldPLEX | rs10131894 | F | 6037.9 | ccctTGCATGCATGCGCACA | 92 | C | 6285.1 | G | 6325.1 |
| M2 | goldPLEX | rs1393257 | F | 6239.1 | agGCAATAGAGGGAGTATCA | 93 | C | 6486.3 | T | 6566.2 |
| M3 | goldPLEX | rs10164484 | F | 6246.1 | aaactTCTCCCTCAGCCTACC | 94 | A | 6517.3 | G | 6533.3 |
| M4 | goldPLEX | rs10499226 | R | 6373.2 | CAGAAATACATTTGCCACTAT | 95 | G | 6620.4 | C | 6660.4 |
| M5 | goldPLEX | rs1007716 | R | 6446.2 | gcGCTGTATCCTCAGAGAGTA | 96 | G | 6693.4 | A | 6773.3 |
| M6 | goldPLEX | rs10732346 | R | 6731.4 | GGGAGAATGCATTTCTTTTTC C | 97 | T | 7002.6 | C | 7018.6 |
| M7 | goldPLEX | rs10014076 | R | 6831.5 | GGATACTTCAAGAATAGTAGA G | 98 | G | 7078.7 | A | 7158.6 |
| M8 | goldPLEX | rs1266886 | R | 6840.4 | cccacTCTATTCCCACGTCAG CC | 99 | T | 7111.7 | C | 7127.7 |
| M9 | goldPLEX | rs11240574 | F | 6954.5 | tttaTTTTTCCATCACACGTA TG | 100 | C | 7201.7 | T | 7281.6 |
| M10 | goldPLEX | rs11599388 | R | 7233.7 | tttcTAAATCCCCACCCGGCG CAG | 101 | G | 7480.9 | A | 7560.8 |
| M11 | goldPLEX | rs1222958 | F | 7240.7 | gCTCTCACCATTAACTATACA GCA | 102 | A | 7511.9 | G | 7527.9 |
| M12 | goldPLEX | rs10742993 | R | 7327.8 | gttgACAGTTCTCCAAGTCCA GAT | 103 | T | 7599 | C | 7615 |
| H1 | goldPLEX | rs10505007 | F | 7398.8 | ggattACAGATGCCTTCTTGG GTA | 104 | A | 7670 | G | 7686 |
| H2 | goldPLEX | rs10063237 | R | 7722.1 | CAATCAAAGAATTATATGGCT AAGG | 105 | G | 7969.2 | A | 8049.2 |
| H3 | goldPLEX | rs10012004 | F | 7902.1 | ccdtTAACACCTATATGGGTT TTTG | 106 | C | 8149.3 | T | 8229.2 |
| H4 | goldPLEX | rs13023380 | F | 7909.2 | gcagcACAGCCTTGCCTACAA TGACA | 107 | A | 8180.4 | G | 8196.4 |
| H5 | goldPLEX | rs1490492 | F | 8098.3 | gggCATTCTGAGGAAAATAAT GTATG | 108 | C | 8345.5 | T | 8425.4 |
| H6 | goldPLEX | rs10265857 | R | 8106.3 | ggacGAGAGGTCTGAGAGTTT CTGAT | 109 | T | 8377.5 | C | 8393.5 |
| H7 | goldPLEX | rs1567603 | F | 8265.4 | acATAACTCTCAGATAATTAA AGTTGT | 110 | C | 8512.6 | T | 8592.5 |

TABLE 3-continued

| | | | | | SEQ | EXT1_ | EXT1_ | EXT2_ | EXT2_ |
|---|---|---|---|---|---|---|---|---|---|
| | | | | Standard post-PCR primers used in the post-PCR assay for the universal PCR readout | | | | | |
| | TERM | SNP_ID | UEP_DIR | UEP_MASS | UEP_SEQ 5'-3' | SEQ ID NO: | EXT1_CALL | EXT1_MASS | EXT2_CALL | EXT2_MASS |
| H8 | goldPLEX | rs1015731 | R | 8310.5 | atgtTAACAGAAAGCACAATA AAAACA | 111 | G | 8557.7 | A | 8637.6 |
| H9 | goldPLEX | rs10911946 | F | 8470.5 | gggagGAGAGGAACCATAAGA TATTAG | 112 | C | 8717.7 | T | 8797.6 |
| H10 | goldPLEX | rs10028716 | R | 8477.5 | cctggTTTTGTCTTCCCTATT TACTGAT | 113 | T | 8748.7 | C | 8764.7 |
| H11 | goldPLEX | rs1032426 | F | 8672.7 | ggacAAAAGTTCTGAATTATT TGGTTTG | 114 | A | 8943.9 | G | 8959.9 |

Example 3: Post-PCR Reaction after Examples 1 and 2

SAP/Post-PCR Reaction: 5 ul Univ PCR was dispensed in a 384 well plate and 2 ul SAP reaction containing 0.6 U SAP (shrimp alkaline phosphatase) were added with incubation at 37° C. for 40 minutes and finally inactivation of the enzyme at 85° C. for 5 minutes. Extension reagents were added in 2 ul amounts containing 0.9 mM acyclic terminators and 1.353 U post-PCR enzyme. The extension oligonucleotide mixture differed in concentration according to its mass: 0.5 uM of low mass: 4000-5870 daltons, 1.0 uM of medium mass: 6000-7350 daltons and 1.5 uM of high mass: 7400-8700 daltons were added in a final volume of 9 ul. The cycling conditions used for post-PCR reaction were 94° C./30 sec and 40 cycles of an 11 temperature cycle (94° C./5 secs and 5 internal cycles of (52° C./5 sec and 80° C./5 sec) and final extension at 72° C./3 minutes.

MALDI-TOF MS: The extension reaction was diluted with 16 ul water and 6 mg CLEAN Resin (SEQUENOM) was added to desalt the reaction. It was rotated for 2 hours at room temperature. 15 nl of the post-PCR reaction were dispensed robotically onto silicon chips preloaded with matrix (SpectroCHIP®, SEQUENOM). Mass spectra were acquired using a Mass ARRAY Compact Analyzer (MALDI-TOF mass spectrometer, SEQUENOM).

Example 4: Post-PCR Reaction to Increase Multiplexing and Flexibility in SNP Genotyping The presented process provides a concept for an alternative goldPLEX primer extension post-PCR format to increase multiplexing and flexibility of SNP genotyping. It utilizes allele specific extension primers, with two extension primers per SNP designed to hybridize on the SNP site. Each primer contains a gene and allele specific 3' nucleotide for specific hybridization to the SNP site of interest and a varied defined 5' nucleotide sequence which corresponds to a mass tag. The specificity of the assay is determined by the match of the 3' end of the primer to the template, which will only be extended by DNA polymerase if corresponding to the specific SNP. An overview of the process is outlined in FIG. 6.

The extension primers are extended by dNTP incorporation and terminated by a ddNTP or alternatively terminated by ddNTP incorporation without dNTP extension. One or more dNTP and/or ddNTP used during the extension reaction are labeled with a moiety allowing immobilization to a solid support, such as biotin.

The extension product is subsequently immobilized on a solid support, such as streptavidin coated beads, where only extended/terminated products will bind. Unextended primers and unwanted reaction components do not bind and are washed away.

The 5' nucleotide sequence or an alternative group which corresponds to a mass tag is cleaved from the extension product, leaving the 3' section of the extension product bound to the solid support. The cleavage can be achieved with a variety of methods including enzymatic, chemical and physical treatments. The possibility outlined in this example utilizes Endonuclease V to cleave a deoxyinosine within the primer. The reaction cleaves the second phosphodiester bonds 3' to deoxyinosine releasing an oligonucleotide mass tag.

The 5' nucleotide sequence (mass tag) is then transferred to a chip array and analyzed by mass spectrometry (e.g. MALDI-TOF MS). The presence of a mass signal matching the tag's mass indicates an allele specific primer was extended and therefore the presence of that specific allele.

Example 5: Endonuclease V Cleavage of Deoxyinosine

Prior to the extension reaction a 35 plex PCR was carried out in a 5 μl reaction volume using the following reagents; 5 ng DNA, 1×PCR buffer, 500 μM each dNTP, 100 nM each PCR primer (as listed in Table 4), 3 mM $MgCl_2$, and 0.15 U Taq (SEQUENOM). Thermocycling was carried out using the following conditions: 7 minutes at 95° C.; followed by 45 cycles of 20 seconds at 95° C., 30 seconds at 56° C. and 1 minute at 72° C.; and concludes with 3 minutes at 72° C.

The PCR reaction was treated with SAP (shrimp alkaline phosphatase) to dephosphorylate unincorporated dNTPs. A 2 μl mixture containing 0.6 U SAP was added to the PCR product and then subjected to 40 minutes at 37° C. and 5 minutes at 85° C.

Extension reaction reagents were combined in a 3 μl volume, which was added to the SAP treated PCR product. The total extension reaction contained the following reagents; 1× goldPLEX buffer, 17 μM each biotin ddNTP, 0.8 μM each extension primer (listed in Table 5) and 1× post-goldPLEX enzyme.

Thermocycling was carried out using a 200 cycle program consisting of 2 minutes at 94° C.; followed by 40 cycles of 5 seconds at 94° C., followed by 5 cycles of 5 seconds at 52° C., and 5 seconds at 72° C.; and concludes with 3 minutes at 72° C. Extension primer sequences containing the mass tags and resulting masses of the cleaved products corresponding to specific alleles are listed in Table 5.

Solulink magnetic streptavidin beads were conditioned by washing three times with 50 mM Tris-HCl pH 7.5, 1M NaCl, 0.5 mM EDTA, pH 7.5. The extension reaction was then combined with 300 μg conditioned beads. Beads were incubated at room temperature for 30 minutes with gentle agitation and then pelleted using a magnetic rack. The supernatant was removed. Subsequently the beads were washed 3 times with 50 mM Tris-HCl, 1M NaCl, 0.5 mM EDTA, pH 7.5 and 3 times with water. For each wash step the beads were pelleted and the supernatant removed. The mass tags were cleaved from the extension product by addition of a solution containing 30 U Endonuclease V and 0.4× buffer 4(NEB) and incubation at 37° C. for 1 hour. After incubation the magnetic beads were pelleted using a magnetic rack and the supernatant containing the mass tag products was removed.

Desalting was achieved by the addition of 6 mg CLEAN Resin (SEQUENOM). 15 nl of the cleavage reactions were dispensed robotically onto silicon chips preloaded with matrix (SpectroCHIP®, SEQUENOM). Mass spectra were acquired using a MassARRAY Compact Analyser (MALDI-TOF mass spectrometer (SEQUENOM). FIG. 7 shows MALDI-TOF MS spectra for 35 plex genotyping using the post-PCR readout as presented herein.

TABLE 4

| | | | | |
|---|---|---|---|---|
| | | PCR primers used in this study | | |
| SNP ID | Forward Primer | SEQ ID NO: | Reverse Primer | SEQ ID NO: |
| rs11155591 | ACGTTGGATGAAAGGCTGATCCAGGTCATC | 115 | ACGTTGGATGTTCTCTTCAAACCTCCCATC | 150 |
| rs12554258 | ACGTTGGATGTTGAGACACGGCACAGCGG | 116 | ACGTTGGATGTTTTCCTCTTCCTACCCCTC | 151 |
| rs12162441 | ACGTTGGATGAAGGTAGGCCTTTAGGAGAG | 117 | ACGTTGGATGTGGCAACACACGACTGTACT | 152 |
| rs11658800 | ACGTTGGATGATGCACAATCGTCCTACTCC | 118 | ACGTTGGATGTGCTTCCCAGGTCACTATTG | 153 |
| rs13194159 | ACGTTGGATGTGAGCCAGGGATATCCTAAC | 119 | ACGTTGGATGTCCATGAGTGCAGGACTACG | 154 |
| rs1007716 | ACGTTGGATGTAATAGAGGGTGCATTGAAG | 120 | ACGTTGGATGCTCCACGAGCAAGAGTATAG | 155 |
| rs11637827 | ACGTTGGATGAAAGAGAGAGAGATCCCTG | 121 | ACGTTGGATGATCCCATACGGCCAAGAAGA | 156 |
| rs13188128 | ACGTTGGATGCACTAATAAAGGCAGCCTGT | 122 | ACGTTGGATGATGAGTAACGCTTGGTGCTG | 157 |
| rs1545444 | ACGTTGGATGGGCTCTGATCCCTTTTTTTAG | 123 | ACGTTGGATGTGGTAGCCTCAAGAATGCTC | 158 |
| rs1544928 | ACGTTGGATGGCTTTTCCTCTTCTTTGGTAG | 124 | ACGTTGGATGGAATGTGTAAAACAAACCAG | 159 |
| rs11190684 | ACGTTGGATGTCTCAGTTCCAACTCATGCC | 125 | ACGTTGGATGTGAGCCATGTAGAGACTCAG | 160 |
| rs12147286 | ACGTTGGATGAGAATGTGCCAAAGAGCAG | 126 | ACGTTGGATGTCTGCATCCCTTAGGTTCAC | 161 |
| rs11256200 | ACGTTGGATGCCTTATTGGATTCTATGTCCC | 127 | ACGTTGGATGACCAAGCACTGTACTTTTC | 162 |
| rs1124181 | ACGTTGGATGACTTGGCGAGTCCCCATTTC | 128 | ACGTTGGATGTTAATATAGTCCCCAGCCAC | 163 |
| rs1392592 | ACGTTGGATGTCTTGTCTCTTACCTCTCAG | 129 | ACGTTGGATGCTGTGCTGACTGAGTAGATG | 164 |
| rs1507157 | ACGTTGGATGTGAGGATTAAAGGATCTGGG | 130 | ACGTTGGATGATCTTTGAAGGCTCCTCTGG | 165 |
| rs1569907 | ACGTTGGATGGGAGGCTCCTCTACACAAAG | 131 | ACGTTGGATGGCATGTCCCTATGAGATCAG | 166 |
| rs1339007 | ACGTTGGATGTTGCTCTAAGGTGGATGCTG | 132 | ACGTTGGATGTTAGGCACCCCAAGTTTCAG | 167 |
| rs1175500 | ACGTTGGATGGTTTACAACCTGTGGCAGAC | 133 | ACGTTGGATGTGTAGCATGTCAGCCATCAG | 168 |
| rs11797485 | ACGTTGGATGGAAAGTGACCCATCAAGCAG | 134 | ACGTTGGATGGTAGTTGCTTGTGGTTACCG | 169 |
| rs1475270 | ACGTTGGATGCTATGGGGAACTGAATAAGTG | 135 | ACGTTGGATGGAGCAATTCATTTGTCTCC | 170 |
| rs12631412 | ACGTTGGATGCAAACTATTGACTGGTCATGG | 136 | ACGTTGGATGTTTTGTTGTTTGGGCATTGG | 171 |
| rs1456076 | ACGTTGGATGGCAGAGGTTTGAGAAAAGAG | 137 | ACGTTGGATGGTTCCCATCCAGTAATGGAG | 172 |
| rs12958106 | ACGTTGGATGGTATATGCCTGTATGTGGTC | 138 | ACGTTGGATGCCAACAGTTTTTCTTTAAGGG | 173 |
| rs1436633 | ACGTTGGATGGAGGGAAAGACCTGCTTCTA | 139 | ACGTTGGATGAGAAGCTCCGAGAAAAGGTG | 174 |
| rs1587543 | ACGTTGGATGGAGAAGGCTTTCCAGAATTTG | 140 | ACGTTGGATGTATAGCCATTACTGGGCTTG | 175 |
| rs10027673 | ACGTTGGATGCAAAAGCCAGCTCACAAAAG | 141 | ACGTTGGATGCCCTCTTGCATAAAATGTTGC | 176 |
| rs12750459 | ACGTTGGATGTTTTGGGCCCCTCCATATTC | 142 | ACGTTGGATGCTCCATGCAAGGCTGTGGC | 177 |
| rs13144228 | ACGTTGGATGTGGATATGCTGAATTTGAGG | 143 | ACGTTGGATGCGTTATCAAGGACTTTGTGC | 178 |

TABLE 4-continued

PCR primers used in this study

| SNP ID | Forward Primer | SEQ ID NO: | Reverse Primer | SEQ ID NO: |
|---|---|---|---|---|
| rs11131052 | ACGTTGGATGCTTTTGTCCATGTTTGGCAG | 144 | ACGTTGGATGGAGGTTATCTTATTGTAACGC | 179 |
| rs1495805 | ACGTTGGATGAGGACAGTTGTCGTGAGATG | 145 | ACGTTGGATGAGACTGTCCTTTCCCAGGAT | 180 |
| rs1664131 | ACGTTGGATGCTGAGGCTGGGTAACTTATC | 146 | ACGTTGGATGTCATCAGAAGCAGATGCTGG | 181 |
| rs1527448 | ACGTTGGATGGCCCTTGGCACATAGTACTG | 147 | ACGTTGGATGCCATACGTTCAAGGATTGGG | 182 |
| rs11062992 | ACGTTGGATGTTGGTTATAGAGCGTCCCTG | 148 | ACGTTGGATGAGGTGTGCAAGTGTCAGAAG | 183 |
| rs12518099 | ACGTTGGATGACCCCTTACTCCAATAAGTC | 149 | ACGTTGGATGGTATATCATGTCCAGTGAAG | 184 |

TABLE 5

Extension primers and mass tags released after cleavage*

| SNP ID | Extension Primer Sequence | SEQ ID NO: | Mass Tag Sequence | SEQ ID NO: | Mass |
|---|---|---|---|---|---|
| rs11155591_a | CCACCGCCTCCICCTCCCATCTCCACCCTCTA | 185 | CCACCGCCTCCIC | 255 | 3802.49 |
| rs11155591_g | CCACCGCCTACICCTCCCATCTCCACCCTCTG | 186 | CCACCGCCTACIC | 256 | 3826.52 |
| rs12554258_c | CCACAGCCTACICTTCCTACCCCTCCAGCCGC | 187 | CCACAGCCTACIC | 257 | 3850.54 |
| rs12554258_t | CCACAGCATACICTTCCTACCCCTCCAGCCGT | 188 | CCACAGCATACIC | 258 | 3874.57 |
| rs12162441_c | CAACAGCACAAITTGCTATCCCCACAATTACC | 189 | CAACAGCACAAIT | 259 | 3922.62 |
| rs12162441_t | CAACAGAACAAITTGCTATCCCCACAATTACT | 190 | CAACAGAACAAIT | 260 | 3946.64 |
| rs11658800_c | CAAAAGAACAAITGAAACTGCAGACTCTTCCC | 191 | CAAAAGAACAAIT | 261 | 3970.67 |
| rs11658800_t | CAAAAGAAAAAITGAAACTGCAGACTCTTCCT | 192 | CAAAAGAAAAAIT | 262 | 3994.69 |
| rs13194159_c | AATAAGAAGAAICGTCTGATTGGCTTTAGTTC | 193 | AATAAGAAGAAIC | 263 | 4010.69 |
| rs13194159_t | GATAAGAAGAAICGTCTGATTGGCTTTAGTTT | 194 | GATAAGAAGAAIC | 264 | 4026.69 |
| rs1007716_c | AATAGCGAGAAIGCTGTATCCTCAGAGAGTAC | 195 | AATAGCGAGAAIG | 265 | 4042.69 |
| rs1007716_t | AATAGCGAGAGIGCTGTATCCTCAGAGAGTAT | 196 | AATAGCGAGAGIG | 266 | 4058.69 |
| rs11637827_a | CCACCCCGCCCITTCTCCCACAGTAAACTTCCA | 197 | CCACCCCGCCCIT | 267 | 4091.68 |
| rs11637827_g | CCACCACCGCCCITTCTCCCACAGTAAACTTCCG | 198 | CCACCACCGCCCIT | 268 | 4115.70 |
| rs13188128_c | CCACCGCACTACICTCTTCTGCTTCATATTTCAC | 199 | CCACCGCACTACIC | 269 | 4139.73 |
| rs13188128_g | CCACAGCACTACICTCTTCTGCTTCATATTTCAG | 200 | CCACAGCACTACIC | 270 | 4163.75 |
| rs1545444_a | CAACAGCACCACITTCATTATTTCACTCAAGCGA | 201 | CAACAGCACCACIT | 271 | 4187.78 |
| rs1545444_g | CAACAGCAACACITTCATTATTTCACTCAAGCGG | 202 | CAACAGCAACACIT | 272 | 4211.80 |
| rs1544928_a | CAACAGCTACAAIAAACAAACCAGAAAGTCACTA | 203 | CAACAGCTACAAIA | 273 | 4235.83 |
| rs1544928_g | CAACAGATACAAIAAACAAACCAGAAAGTCACTG | 204 | CAACAGATACAAIA | 274 | 4259.85 |
| rs11190684_c | CAAAAGATACAAIATGTAGAGACTCAGTCTCTTC | 205 | CAAAAGATACAAIA | 275 | 4283.88 |
| rs11190684_g | CAAAAGATAGAAIATGTAGAGACTCAGTCTCTTG | 206 | CAAAAGATAGAAIA | 276 | 4323.90 |
| rs12147286_c | CAAAAGAGAGAAITGCAAATTAGATTTGTCAGGC | 207 | CAAAAGAGAGAAIT | 277 | 4339.90 |
| rs12147286_t | CAGAAGAGAGAAITGCAAATTAGATTTGTCAGGT | 208 | CAGAAGAGAGAAIT | 278 | 4355.90 |
| rs11256200_a | CAGAAGAGAGAGITATGTCTTATTCTTCTTCACCA | 209 | CAGAAGAGAGAGIT | 279 | 4371.90 |
| rs11256200_g | CAGGAGAGAGAGITATGTCTTATTCTTCTTCACCG | 210 | CAGGAGAGAGAGIT | 280 | 4387.90 |

TABLE 5-continued

Extension primers and mass tags released after cleavage*

| SNP ID | Extension Primer Sequence | SEQ ID NO: | Mass Tag Sequence | SEQ ID NO: | Mass |
|---|---|---|---|---|---|
| rs1124181_c | CCACCCACCGCCCITAGTCCCCAGCCACTATAAAAC | 211 | CCACCCACCGCCCIT | 281 | 4404.89 |
| rs1124181_g | CCACCCGCCGCCCITAGTCCCCAGCCACTATAAAAG | 212 | CCACCCGCCGCCCIT | 282 | 4420.89 |
| rs1392592_c | CCACCCGCCGCTCITTCCCAAAGTTGAGGGACTTAC | 213 | CCACCCGCCGCTCIT | 283 | 4435.90 |
| rs1392592_t | CCACTCGCCGCTCITTCCCAAAGTTGAGGGACTTAT | 214 | CCACTCGCCGCTCIT | 284 | 4450.91 |
| rs1507157_c | CCACGCGCCCTACIAAGGCTCCTCTGGGGCACAAGC | 215 | CCACGCGCCCTACIA | 285 | 4468.94 |
| rs1507157_t | CAACGCGCACTACIAAGGCTCCTCTGGGGCACAAGT | 216 | CAACGCGCACTACIA | 286 | 4516.99 |
| rs1569907_a | CAACAAGCACTACIGGGTTTTGTTGTGCCAGTAGAA | 217 | CAACAAGCACTACIG | 287 | 4541.01 |
| rs1569907_g | CAACAAGCAATACIGGGTTTTGTTGTGCCAGTAGAG | 218 | CAACAAGCAATACIG | 288 | 4565.04 |
| rs1339007_c | CAAGAAGAAATAAICTGCCAATTAATCATCAACTCTC | 219 | CAAGAAGAAATAAIC | 289 | 4613.09 |
| rs1339007_t | AAAGAAGAAATAAICTGCCAATTAATCATCAACTCTT | 220 | AAAGAAGAAATAAIC | 290 | 4637.11 |
| rs1175500_a | GAAGAAGACATAAIATGTCAGCCATCAGCCTCTCACA | 221 | GAAGAAGACATAAIA | 291 | 4653.11 |
| rs1175500_g | GAAGAAGACATAGIATGTCAGCCATCAGCCTCTCACG | 222 | GAAGAAGACATAGIA | 292 | 4669.11 |
| rs11797485_c | GAAGAGGACGTAGIGCTCTTATATCTCATATGAACAC | 223 | GAAGAGGACGTAGIG | 293 | 4717.11 |
| rs11797485_g | GAGGAGGACGTAGIGCTCTTATATCTCATATGAACAG | 224 | GAGGAGGACGTAGIG | 294 | 4733.11 |
| rs1475270_c | CCACGCTCCTCTACIACTTTTCATGGTTATTCTCAGTC | 225 | CCACGCTCCTCTACIA | 295 | 4748.12 |
| rs1475270_t | CCGCGCTCCTCTACIACTTTTCATGGTTATTCTCAGTT | 226 | CCGCGCTCCTCTACIA | 296 | 4764.12 |
| rs12631412_c | CCACGCGCACCAACITGTTTTGTTTGTTTTGTTTTTTC | 227 | CCACGCGCACCAACIT | 297 | 4782.15 |
| rs12631412_t | CCACGCGCGCCAACITGTTTTGTTTGTTTTGTTTTTTT | 228 | CCACGCGCGCCAACIT | 298 | 4798.15 |
| rs1456076_c | CCACGCGAGTCAACICCATCCAGTAATGGAGTACAGTC | 229 | CCACGCGAGTCAACIC | 299 | 4822.17 |
| rs1456076_g | CCACGAGAGTCAACICCATCCAGTAATGGAGTACAGTG | 230 | CCACGAGAGTCAACIC | 300 | 4846.20 |
| rs12958106_a | CCACGAGAGTCAACIAGTTTTTCTTTAAGGGGAGTAGA | 231 | CCACGAGAGTCAACIA | 301 | 4870.22 |
| rs12958106_g | CAACGAGAGTAAACIAGTTTTTCTTTAAGGGGAGTAGG | 232 | CAACGAGAGTAAACIA | 302 | 4918.27 |
| rs1436633_c | CAAAGAGAATAAACIGGACAAAGATGAGTGCGTATATC | 233 | CAAAGAGAATAAACIG | 303 | 4942.30 |
| rs1436633_a | CAAAGAGAATAAAIGGACAAAGATGAGTGCGTATATT | 234 | CAAAGAGAATAAAIG | 304 | 4966.32 |
| rs1587543_a | CAAAGAGAATAGAAIGGCTTGGGGTCCCCATTAAAGCGA | 235 | CAAAGAGAATAGAAIG | 305 | 4982.32 |
| rs1587543_g | CAGAGAGAATAGAAIGGCTTGGGGTCCCCATTAAAGCGG | 236 | CAGAGAGAATAGAAIG | 306 | 4998.32 |
| rs10027673_c | AAGAGCGAGAGAGAITACTAAAGACGCTTATCATGGTC | 237 | AAGAGCGAGAGAGAIT | 307 | 5014.32 |
| rs10027673_t | AGGAGCGAGAGAGAITACTAAAGACGCTTATCATGGTT | 238 | AGGAGCGAGAGAGAIT | 308 | 5030.32 |
| rs12750459_c | CGGAGAGAGAGGAGITGCAAGGCTGTGGCTGGACAAGAC | 239 | CGGAGAGAGAGGAGIT | 309 | 5046.32 |
| rs12750459_t | CGGAGAGGGAGGAGITGCAAGGCTGTGGCTGGACAAGAT | 240 | CGGAGAGGGAGGAGIT | 310 | 5062.31 |
| rs13144228_c | CCCGCTCCGCCAGTCIATTCTATATTAGAACAACTCTCTTC | 241 | CCCGCTCCGCCAGTCIA | 311 | 5078.31 |
| rs13144228_t | CCACGCGCGCCAGTCIATTCTATATTAGAACAACTCTCTTT | 242 | CCACGCGCGCCAGTCIA | 312 | 5127.35 |
| rs11131052_c | CCACGCGCGACAGACITAACGCATATGCACATGCACACATC | 243 | CCACGCGCGACAGACIT | 313 | 5151.38 |
| rs11131052_t | CCACGCGAGACAGACITAACGCATATGCACATGCACACATT | 244 | CCACGCGAGACAGACIT | 314 | 5175.40 |
| rs1495805_c | CAACGCGAGACAGACITGTCCTTTCCCAGGATGCTCAAAGC | 245 | CAACGCGAGACAGACIT | 315 | 5199.43 |
| rs1495805_t | CAACGCGAGACAGAAITGTCCTTTCCCAGGATGCTCAAAGT | 246 | CAACGCGAGACAGAAIT | 316 | 5223.45 |
| rs1664131_g | CAACGAGAGACAGTAIAGCAGATGCTGGCCCCATGCTTCAG | 247 | CAACGAGAGACAGTAIA | 317 | 5247.48 |

TABLE 5-continued

| | | SEQ ID NO: | Mass Tag Sequence | SEQ ID NO: | Mass |
|---|---|---|---|---|---|
| SNP ID | Extension Primer Sequence | | | | |
| rs1664131_t | CAACGAGAGAAAGTAIAGCAGATGCTGGCCCCATGCTTCAT | 248 | CAACGAGAGAAAGTAIA | 318 | 5271.50 |
| rs1527448_c | CAAGGAGAGAAAGAAITAATAGTACAACAGCTATCAATTAC | 249 | CAAGGAGAGAAAGAAIT | 319 | 5311.53 |
| rs1527448_t | CAAGGAGAGAGAGAAITAATAGTACAACAGCTATCAATTAT | 250 | CAAGGAGAGAGAGAAIT | 320 | 5327.53 |
| rs11062992_a | CAAGGAGAGAGAGAGITGTGCAAGTGTCAGAAGATGAACAA | 251 | CAAGGAGAGAGAGAGIT | 321 | 5343.53 |
| rs11062992_g | CGAGGAGAGAGAGAGITGTGCAAGTGTCAGAAGATGAACAG | 252 | CGAGGAGAGAGAGAGIT | 322 | 5359.53 |
| rs12518099_c | CCACCTACCACCAGTCIGAAGAAATAAGAAACATTGAGACAC | 253 | CCACCTACCACCAGTCIG | 323 | 5375.52 |
| rs12518099_t | CCACATACCACCAGTCIGAAGAAATAAGAAACATTGAGACAT | 254 | CCACATACCACCAGTCIG | 324 | 5399.55 |

*SNP specific nucleotides are underlined, mass tags are underlined and "I" refers to deoxyinosine.

Example 6: RNase A Cleavage of Ribonucleotide

Materials and Methods

Prior to the extension reaction a 2-plex PCR was carried out in a 5 μl reaction volume using the following reagents; 2 ng DNA, 1.25× HotStar Taq buffer, 500 μM each dNTP, 100 nM each PCR primer (as listed in Table 1), 3.5 mM MgCl$_2$, and 0.15 U HotStar Taq (Qiagen). Thermocycling was carried out using the following conditions: 15 minutes at 95° C.; followed by 45 cycles of 20 seconds at 95° C., 30 seconds at 56° C. and 1 minute at 72° C.; and concludes with 3 minutes at 72° C. The PCR reaction was treated with SAP (shrimp alkaline phosphatase) to dephosphorylate unincorporated dNTPs. A 2 μl mixture containing 0.3 U SAP was added to the PCR product and then subjected to 40 minutes at 37° C. and 5 minutes at 85° C.

TABLE 6

| | | SEQ | | SEQ |
|---|---|---|---|---|
| | Forward | ID | Reverse | ID |
| SNP ID | Primer | NO: | Primer | NO: |
| rs1000586 | ACGTTGGATGTA CCAGAACCTACA CTCCCC | 325 | ACGTTGGATGTC TCAAACTCCAGA GTGGCC | 327 |
| rs10131894 | ACGTTGGATGAC GTAAGCACACAT CCCCAG | 326 | ACGTTGGATGAG CTGTTCCACACT TCTGAG | 328 |

PCR primers used

Extension reaction reagents were combined in a 2 μl volume, which was added to the SAP treated PCR product. The extension reaction contained the following reagents; 21 μM each biotin ddNTP, 1 μM each extension primer including a ribonucleotide for subsequent RNase A cleavage (listed in Table 7) and 1.25 U Thermo Sequenase. Thermocycling was carried out using the following cycling conditions: 2 minutes at 94° C.; followed by 100 cycles of 5 seconds at 94° C., 5 seconds at 52° C., and 5 seconds at 72° C.; and concludes with 3 minutes at 72° C. Removal of unbound nucleotides was carried out using the QIAquick Nucleotide Removal Kit (Qiagen) as recommended by the manufacturer.

The eluted extension reaction was then combined with 30 μg prepared Dynabeads M-280 Streptavidin beads (Dynal) (washed three times with 5 mM Tris-HCl pH 7.5, 1M NaCl, 0.5 mM EDTA). Beads were incubated at room temperature for 15 minutes with gentle agitation and then pelleted using a magnetic rack. The supernatant was removed. Subsequently the beads were washed 6 times with 5 mM Tris-HCl pH 7.5, 1 M NaCl, 0.5 mM EDTA. For each wash step the beads were pelleted and the supernatant removed.

The mass tags were cleaved from the extension product by addition of RNase A and incubation at 37° C. for 1 hour. After incubation the magnetic beads were pelleted using a magnetic rack and the supernatant containing the mass tag products was removed. Desalting was achieved by the addition of 6 mg CLEAN Resin (SEQUENOM).

15 nl of the cleavage reactions were dispensed robotically onto silicon chips preloaded with matrix (SpectroCHIP®, SEQUENOM). Mass spectra were acquired using a MassARRAY Compact Analyser (MALDI-TOF mass spectrometer, SEQUENOM).

Figure 8:
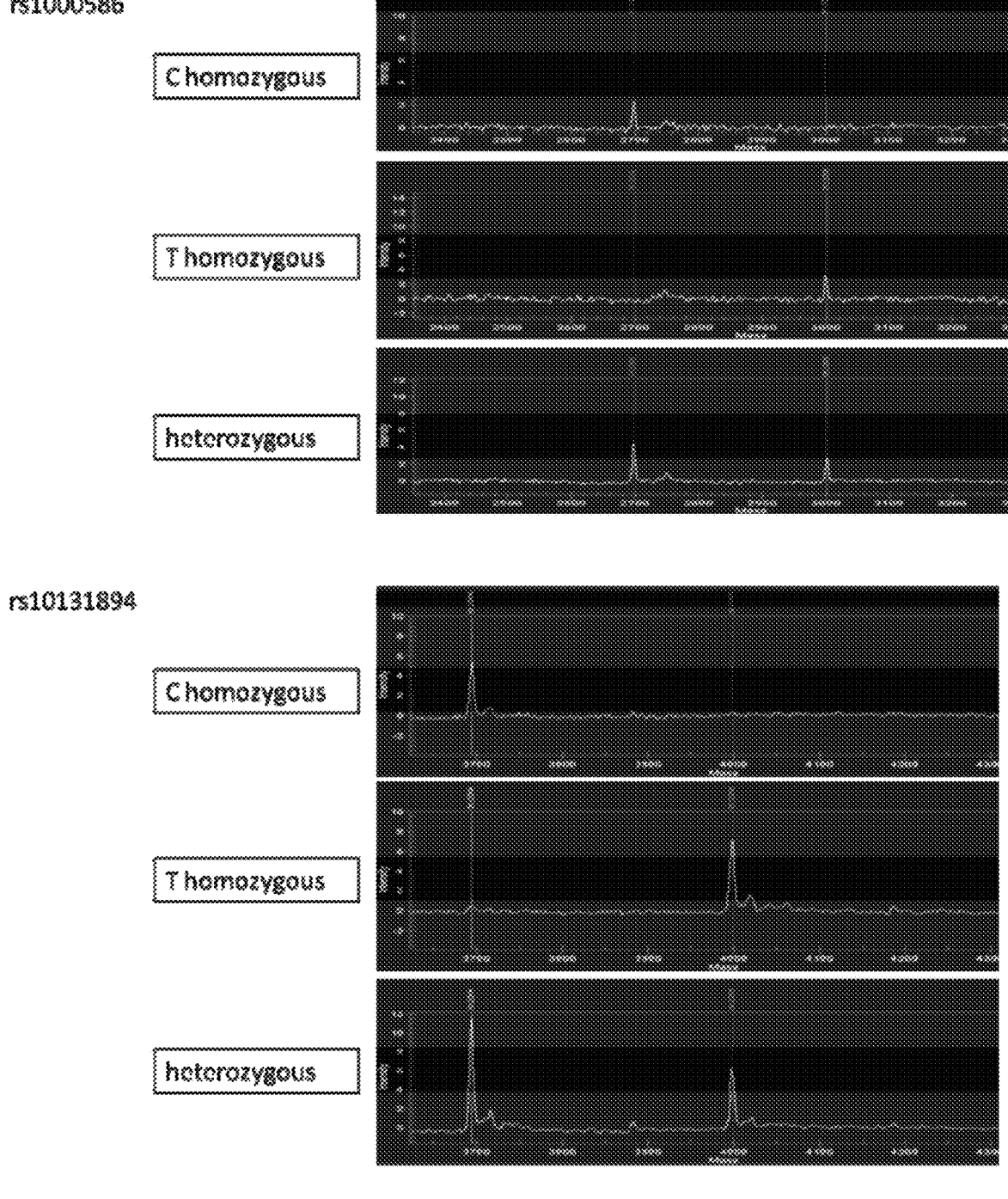
FIG. 8 shows MALDI-TOF MS spectra for genotyping of rs1000586 and rs10131894.

Extension primer sequences containing the mass tags and resulting masses of the cleaved products corresponding to specific alleles are listed in Table 7. Example spectra are shown in FIG. 8. For each of the two SNPs both homozygous as well as a heterozygous sample are displayed and show a clear distinction of the corresponding mass tags.

TABLE 7

| | | SEQ ID NO: | Mass Tag Sequence | SEQ ID NO: | Mass |
|---|---|---|---|---|---|
| Assay Name | Extension Primer Sequence | | | | |
| rs1000586_C | TTTCTCCCCACCTGACCCTGC | 329 | TTTCTCCCC | 333 | 2697.73 |
| rs1000586_T | TTTTCTCCCCACCTGACCCTGT | 330 | TTTTCTCCCC | 334 | 3001.93 |

Extension primers and mass tags released after cleavage

TABLE 7-continued

| Extension primers and mass tags released after cleavage | | | | | |
|---|---|---|---|---|---|
| Assay Name | Extension Primer Sequence | SEQ ID NO: | Mass Tag Sequence | SEQ ID NO: | Mass |
| rs10131894_C | TTATTCCCAGGUGCATGCATGCGCACA<u>C</u> | 331 | <u>TTATTCCCAGGU</u> | 335 | 3694.37 |
| rs10131894_G | TTATTTCCCAGGUGCATGCATGCGCACA<u>G</u> | 332 | <u>TTATTTCCCAGGU</u> | 336 | 3998.57 |

In Table 7, ribonucleotides are highlighted in bold, SNP specific nucleotides are underlined and mass tags are underlined. In FIG. 8, MALDI-TOF MS spectra are shown for genotyping of rs1000586 and rs10131894.

Example 7: Mass Tag Design

Mass Tags were designed to be at least 16 Daltons apart to avoid any overlap with potential salt adducts, and so a double charge of any mass signal would not interfere with a mass tag signal. The calculation of the mass tags must take into account the deoxyinosine and the nucleotide 3' to the deoxyinosine.

Nucleotide mass tags: MALDI-TOF flight behavior was examined for oligonucleotides which correspond to the mass tags used in a 70 plex (FIGS. 9 and 10) and 100 plex assay (FIGS. 11A and B).

All oligonucleotides corresponding to a 70 plex assay were called by the standard SEQUENOM Typer 3.4 software using the three parameters; area, peak height and signal-to-noise ratio at a comparable level (FIG. 9). Using oligonucleotides representing a 70 plex assay, the area value of each peak correlates to the sequence composition of that oligonucleotide. The higher percentage of guanidine and cytosine nucleotides results in larger area values; whereas the percentage of adenosine corresponds with lower area values (FIG. 10). Using oligonucleotides representing a 100 plex assay we examined the effects of oligonucleotide concentration (10, 5, 2.5 and 1 pmol final concentration per oligonucleotide) on signal-to-noise ratio (FIG. 11B). The lower oligonucleotide concentrations of 2.5 and 1 pmol gave consistently higher signal-to-noise ratio values than oligonucleotides concentrations of 10 and 5 pmol. This observation was confirmed by manual observation of the peaks seen in Typer 3.4. However, the four oligonucleotides concentrations gave comparable area values (data not shown).

Example 8: Extension Primer Design and dNTP/ddNTP Incorporation

Extension primers were designed using SEQUENOM's Assay Design software utilizing the following parameters SBE Mass Extend/goldPLEX extension, primer lengths between 20 and 35 bases (and corresponding mass window), and a minimum peak separation of 10 Daltons for analytes (the minimum possible) and 0 Daltons for mass extend primers.

Figure 12:
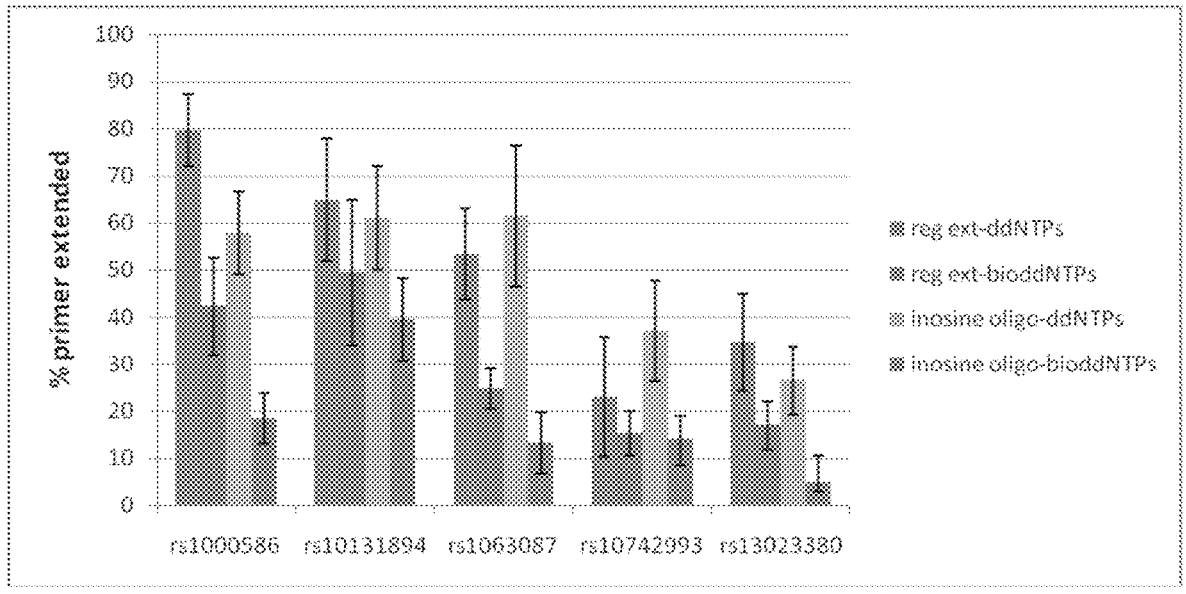
FIG. 12 shows extension rates for a 5 plex reaction. Comparing extension oligonucleotides with or without a deoxyinosine, and either standard ddNTPs or nucleotides containing a biotin moiety. Extension rates were calculated by dividing the area of extended product by the total area of the peak (extended product and unextended oligonucleotide) in Typer 3.4 (SEQUENOM). All experiments compare six DNAs.

Extension oligonucleotide and ddNTP role in extension reaction: To investigate the effects of extension oligonucleotide (with/without deoxyinosine nucleotide) and ddNTP composition (with/without biotin moiety) upon primer extension, we investigated extension rates of a 5 plex (FIG. 12). Assays generally show the best extension rates using unmodified extension oligonucleotides and ddNTPs. Extension oligonucleotides containing a deoxyinosine showed no significant reduction in extension rate. However, when using a ddNTP including a biotin moiety a reduction in extension rate was seen in all assays, when using either type of extension oligonucleotide.

Biotinylated dNTP/ddNTP extension: To compare the effects of extending by a single biotinylated ddNTP or a biotinylated dNTP and terminated by an unmodified ddNTP, we compared extension rates in a 7 plex and 5 plex. The 7 plex was extended by a biotinylated ddCTP or biotinylated dCTP and a ddATP, ddUTP, or ddGTP. The 5 plex was extended by a biotinylated ddUTP or biotinylated dUTP and a ddATP, ddCTP, or ddGTP. The experiment also compared two concentrations of biotinylated dNTP or ddNTP, either 210 or 420 pmol.

In both plexes, and in all individual assays extension rates when extended by a biotinylated dNTP and terminated by an unmodified ddNTP were significantly decreased when compared to extending by a single biotinylated ddNTPs (FIG. 13).

These results indicated that extension with a single biotinylated ddNTPs gives greater extension efficiency.

PCR Amplification

Prior to the extension reaction a PCR was carried out in a 5 µl reaction volume using the following reagents; 5 ng DNA, 1×PCR buffer, 500 µM each dNTP, 100 nM each PCR primer, 3 mM $MgCl_2$, and 0.15 U Taq (SEQUENOM).

Thermocycling was carried out using the following conditions: 7 minutes at 95° C.; followed by 45 cycles of 20 seconds at 95° C., 30 seconds at 56° C. and 1 minute at 72° C.; and concludes with 3 minutes at 72° C.

SAP Treatment

The PCR reaction was treated with SAP (shrimp alkaline phosphatase) to dephosphorylate unincorporated dNTPs. A 2 µl mixture containing 0.6 U SAP was added to the PCR product and then subjected to 40 minutes at 37° C. and 5 minutes at 85° C. in a Thermocycler.

Extension Reaction

Extension reaction reagents were combined in a 3 µl volume, which was added to the SAP treated PCR product. The total extension reaction contained the following reagents; 1× goldPLEX buffer, 0.2 µl of 250 µM stock each biotinylated ddNTP (50 pmol final), 0.8 µl of 2.5 µM solution each extension primer (2 pmol final) (IDT), and 0.05 µl goldPLEX enzyme (SEQUENOM).

Thermocycling was carried out using a 300 cycle program consisting of: 2 minutes at 94° C.; followed by 60 cycles of; 5 seconds at 94° C. followed by 5 cycles of 5 seconds at 52° C. and 5 seconds at 80° C.; and concludes with 3 minutes at 72° C.

Capture

For conditioning magnetic streptavidin beads were washed two times with 100 µl of 50 mM Tris-HCl, 1M NaCl, 0.5 mM EDTA, pH 7.5. The extension reaction was combined with 50 µg (5 µl) conditioned beads. Beads were incubated at room temperature for 1 hour with gentle agitation and then pelleted using a magnetic rack. The supernatant was removed. Subsequently the beads were washed 3 times with 100 μl of 50 mM Tris-HCl, 1 M NaCl, 0.5 mM EDTA, pH 7.5 and 3 times with 100 μl of water. For each wash step the beads were pelleted and the supernatant removed.

MALDI-TOF

Desalting was achieved by the addition of 6 mg CLEAN Resin (SEQUENOM). 15 nl of the cleavage reactions was dispensed robotically onto silicon chips preloaded with matrix (SpectroCHIP®, SEQUENOM). Mass spectra were acquired using a MassARRAY Compact Analyser (MALDI-TOF mass spectrometer).

Example 9: Enzyme, Buffer, Oligonucleotide and Biotin ddNTP Titration

Figure 14:
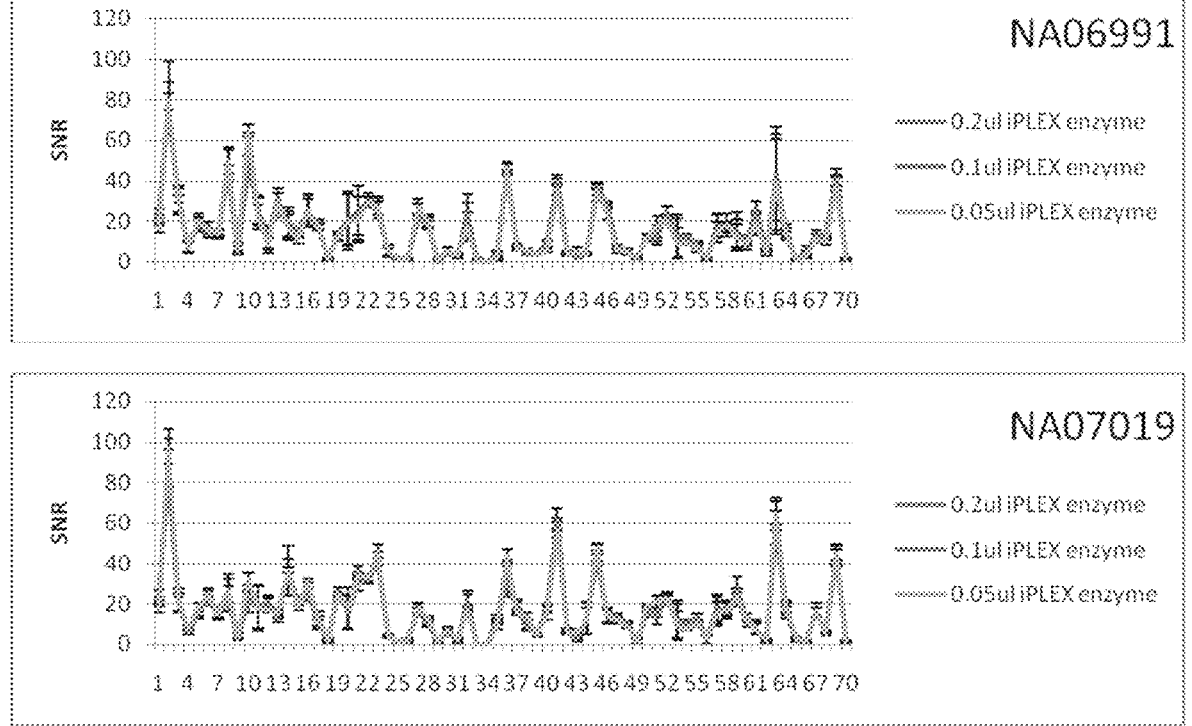
FIG. 14 shows a comparison of iPLEX Gold enzyme concentrations in an extension reaction using a 70 plex assay. All assays followed the same protocol except for the amount of iPLEX Gold enzyme used. All experiments include four replicates of the two CEPH DNAs NA06991 and NA07019. The results compare the signal-to-noise ratios of the extension products from Typer 3.4 (SEQUENOM).

Enzyme Titration:

The amount of post-PCR enzyme used in the extension reaction was examined. The standard PCR, extension, and immobilization/cleavage conditions (as outlined in the protocol in Example 8) were used except for the enzyme. The amount of enzyme used resulted in no difference in either manual calls or signal-to-noise ratio values for individual assays (FIG. 14).

Figure 15:
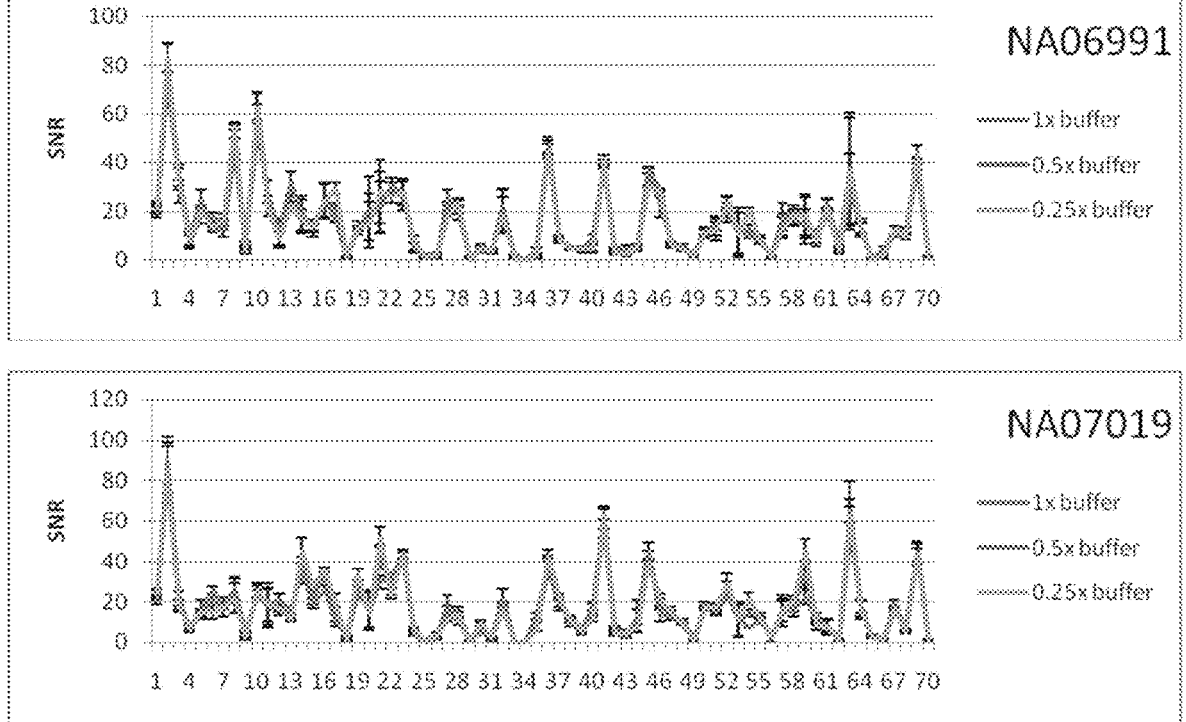
FIG. 15 shows a comparison of iPLEX Gold buffer concentration in extension reactions using a 70 plex assay. All assays followed the same protocol except for the amount of goldPLEX buffer used. All experiments include four replicates of the two CEPH DNAs NA06991 and NA07019. The results compare the signal-to-noise ratios of the extension products from Typer 3.4 (SEQUENOM).

Buffer Titration: The amount of goldPLEX buffer used in the extension reaction was examined. The standard PCR, extension, and immobilization/cleavage conditions (as outlined in the protocol in example 8) were used except for adjusting the amount of buffer. The amount of buffer used resulted in no difference in either manual calls or signal-to-noise ratio values for individual assays (FIG. 15).

Oligonucleotide Titration:

The amount of oligonucleotide used in the extension reaction was examined. The standard PCR, extension, and immobilization/cleavage conditions (as outlined in the protocol section) were used except for adjusting the amount of oligonucleotide.

Figure 16:
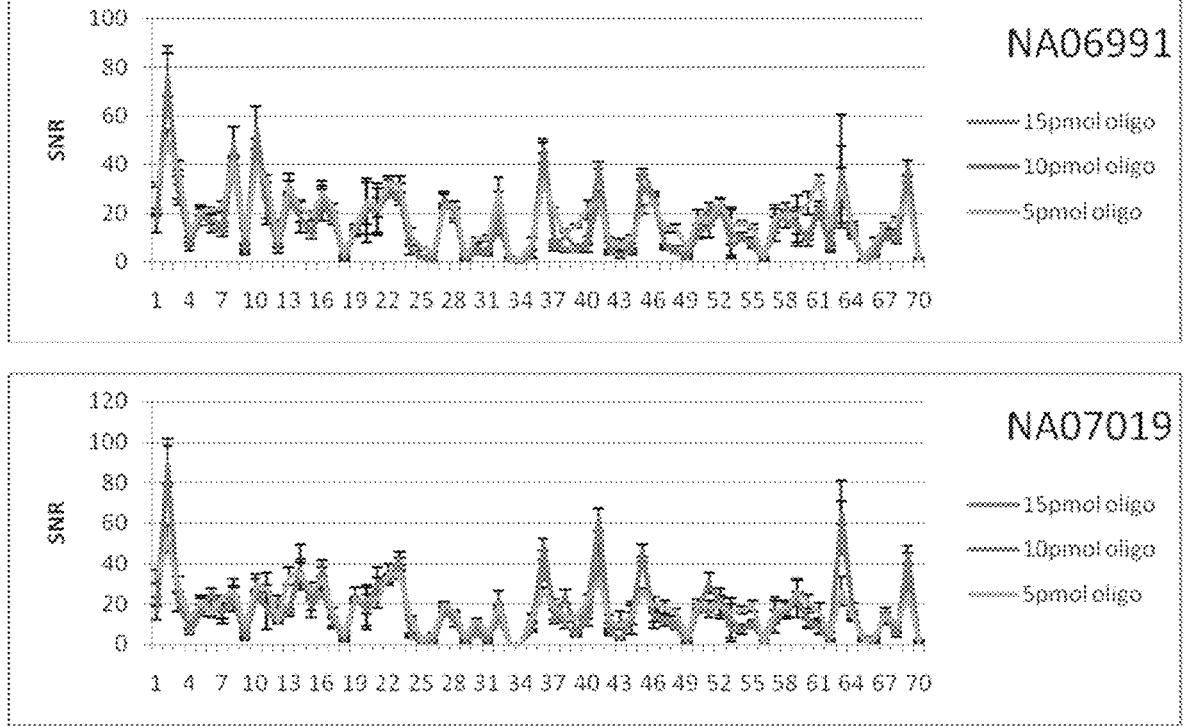

In the initial experiment (FIG. 16) final amounts of 15 pmol, 10 pmol and 5 pmol of each oligonucleotide were tested. The 10 and 15 pmol amounts gave similar results, but 5 pmol gave significantly more manual and software genotype calls. This can be seen by observing signal-to-noise ratio values (FIG. 9), where poorly performing assays showing an increased signal-to-noise ratio when using lower amounts of oligonucleotide.

Figure 17:
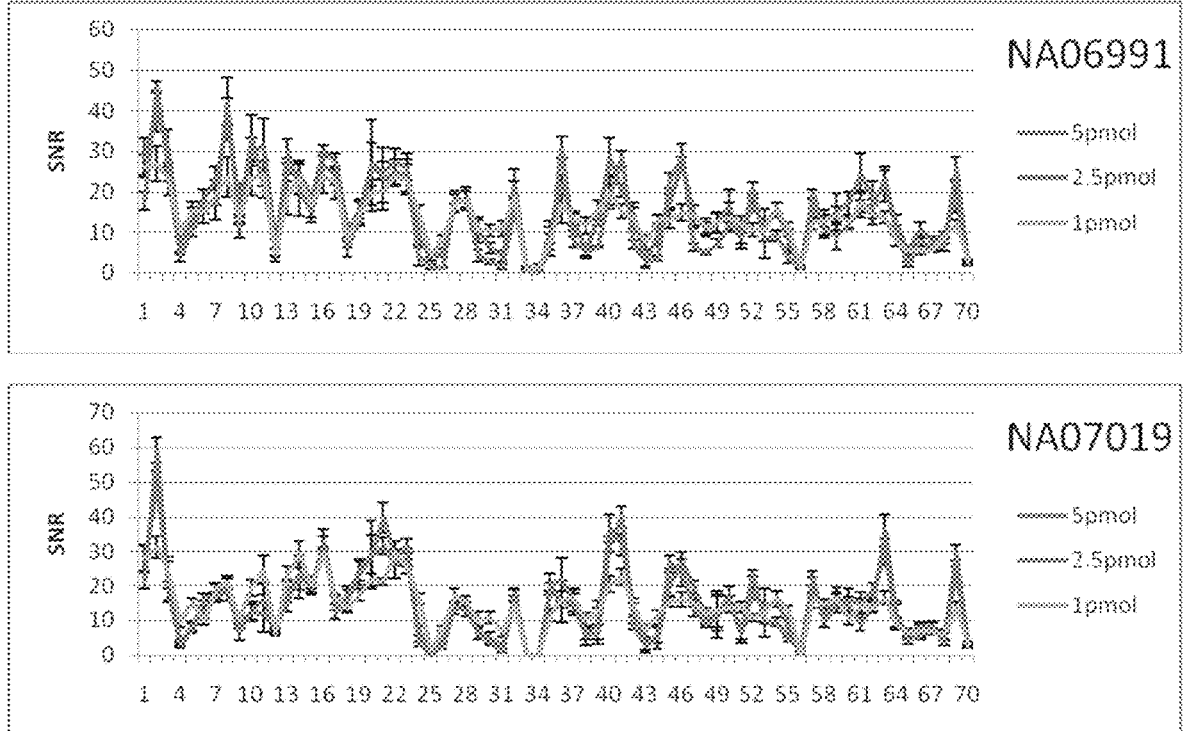

In follow-up experiments final amounts of 5 pmol, 2.5 pmol and 1 pmol of each oligonucleotide were tested (FIG. 17). The results for all three amounts gave similar results as assessed by signal-to-noise ratio and manual genotype calls. However, three individual assays, for which peaks were clearly seen when concentrations of 2.5 or 1 pmol were used, were difficult to call due to low intensity when a final concentration of 5 pmol was used. When using two 70 plex assays comparing final amounts of 2 pmol, 1 pmol and 0.5 pmol of each oligonucleotide the same amount of manual calls were seen for all concentrations. However, greater signal-to-noise ratios were seen when more oligonucleotide was used (FIGS. 18 and 19).

These results show the optimal amount of each oligonucleotide to be 2 pmol when using a 70 plex assay. However, similar results were seen with final amounts of each oligonucleotide ranging from 0.5 to 5 pmol.

Biotinylated ddNTP Concentration:

The amount of biotinylated ddNTP used in the extension reaction was examined. The standard PCR, extension, and immobilization/cleavage conditions (as outlined in the protocol in Example 8) were used except for adjusting the amount of biotinylated ddNTP.

In the initial experiment final amounts of 100, 200, 300 and 400 pmol of each biotinylated ddNTP in each extension reaction were tested. Manual calls and signal-to-noise ratio (FIG. 20), show similar results were seen with all test amounts of biotinylated ddNTP.

To further investigate the amount of biotinylated ddNTP needed in each extension reaction, an experiment compared 50 and 100 pmol of each biotinylated ddNTP in an alternative 70 plex assay. These assays again show no difference in manual calls or signal-to-noise ratio (FIG. 21). This indicates 50 pmol of each biotinylated ddNTP is sufficient to get an optimal extension reaction when using a 70 plex assay.

Example 10: Capture and Cleavage Optimization

Immobilization and Oligonucleotide Cleavage:

Binding capacity of magnetic streptavidin beads. Comparison of Solulink and Dynabeads MyOne C1 magnetic streptavidin beads to capture biotinylated oligonucleotide followed the capture protocol as described in Example 8. The experiment uses two oligonucleotides which correspond to extension products for the two possible alleles for an assay designed for SNP rs1000586. The oligonucleotides contain a deoxyinosine nucleotide and 3' biotinylated nucleotide. The oligonucleotides are bound to the magnetic streptavidin in the presence of either water or varying quantities of biotinylated dNTPs, and are cleaved by treatment with endonuclease V.

Dynabeads MyOne C1 magnetic streptavidin beads show no reduction in area in the presence of 10 or 100 pmol biotinylated ddNTP. However, a large decrease in signal is seen with the addition of 500 pmol of biotinylated ddNTP.

Solulink magnetic beads show no reduction in signal in the presence of up to and including 500 pmol of biotinylated dNTP. This indicates that unincorporated biotinylated ddNTP from an extension reaction would not cause a decrease in final signal if it does not total greater than 500 pmol.

Figure 22:
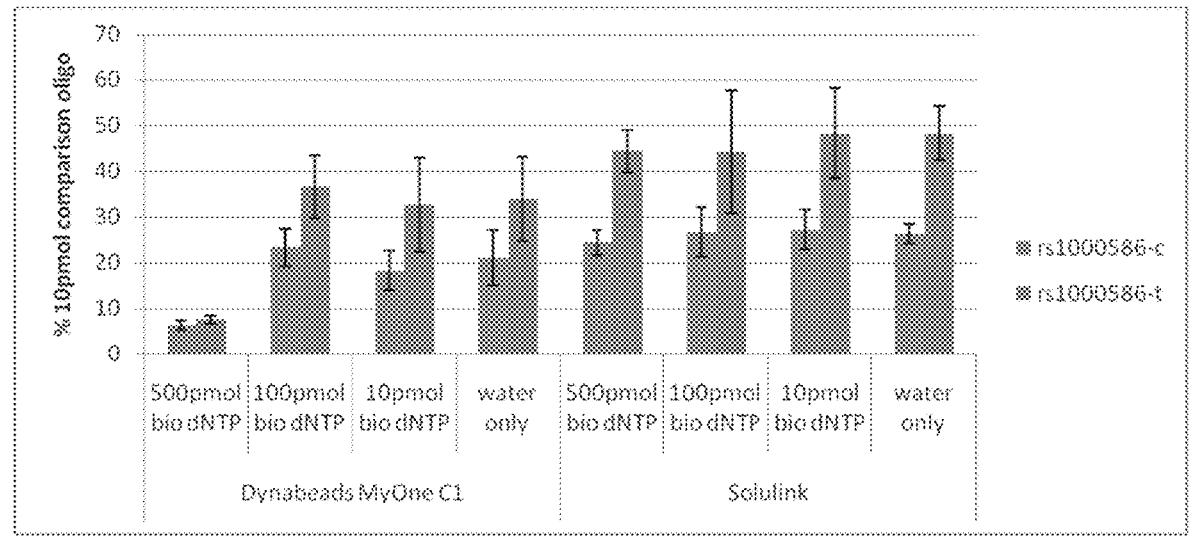
FIG. 22 shows a comparison of Solulink and Dynabeads MyOne C1 magnetic streptavidin beads for capturing the extend products. A total amount of 10 pmol of each oligonucleotide corresponding to the two possible alleles for assay rs1000586 were bound to the magnetic streptavidin beads, in the presence of either water or varying quantities of biotinylated dNTPs (total 10, 100 or 500 pmol). The mass tags were then cleaved from the bound oligonucleotide with 10 U of endonuclease V. The results compare the area of the mass tag peaks from Typer 3.4 (SEQUENOM) and are listed in comparison with 10 pmol of an oligonucleotide which has a similar mass.

These results in combination with experiments not outlined in this report indicate Solulink beads have a greater tolerance to biotinylated small molecules inhibiting the binding of biotinylated extension product. This is probably due to the greater binding capacity of the beads, which is reported to be 2500 vs. 500 pmol biotin oligonucleotides/mg (FIG. 22).

Cleavage

The mass tags were cleaved from the extension product by addition of a solution containing 12 U Endonuclease V (NEB) and 10 mM Magnesium Acetate (Sigma) and incubation at 37° C. for 4 hours in a Thermomixer R (Eppendorf) shaking at 1500 rpm. After incubation the magnetic beads were pelleted using a magnetic rack and the supernatant was removed.

Effect of Deoxyinosine Position on Cleavage Properties:

This experiment was designed to analyze the ability of endonuclease V to cleave an extension product containing a deoxyinosine nucleotide in different locations. Four oligonucleotides were designed to simulate an extension product (contained a 3' biotin and a deoxyinosine nucleotide), which only differed in the location of the deoxyinosine nucleotide. The deoxyinosine was placed 10, 15, 20 and 25 base pairs from the 3' nucleotide containing the biotin moiety.

Figure 23:
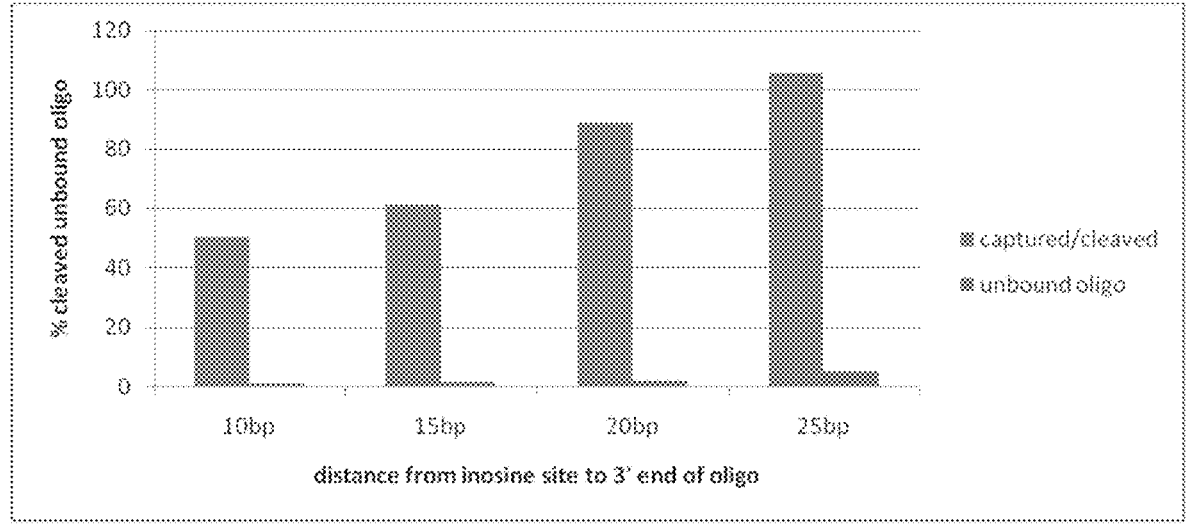
FIG. 23 shows analysis of the ability of endonuclease V to cleave an extension product containing a deoxyinosine nucleotide in different locations. The oligonucleotides were identical aside from the deoxyinosine being 10, 15, 20 or 25 bases from the 3' end of the oligonucleotide. After binding the oligonucleotide to the magnetic streptavidin beads, the supernatant was collected, cleaned by a nucleotide removal kit (Qiagen) and then cleaved by treatment with endonuclease V (termed unbound oligonucleotide). The beads were washed, and cleaved with endonuclease V, as outlined in protocol section (termed captured/cleaved). The results compare the area of the peaks from Typer 3.4 (SEQUENOM), and are listed as a percentage of oligonucleotide cleaved by endonuclease V without being bound to magnetic streptavidin beads.

The mass tag signal seen after cleavage of the supernatant from the binding step (unbound oligonucleotide) indicates a similar quantity of oligonucleotide was bound onto the magnetic streptavidin beads for all oligonucleotides. However, after cleaving the oligonucleotides bound to the magnetic streptavidin beads a clear pattern is seen. The larger the distance of deoxyinosine to the 3' end of the oligonucleotide the greater the signal and presumably the cleavage. These results led to design all extension oligonucleotides so the deoxyinosine is at least 20 nucleotides from the putative 3' end of the extension product (FIG. 23).

Bead and Endonuclease V titration: The quantity of Solulink magnetic streptavidin beads to efficiently capture biotinylated extension products, and endonuclease V to cleave captured product to release mass tags was evaluated in a series of experiments using 70 plex assays.

The initial experiment compared 10, 20 and 30 μl of Solulink magnetic streptavidin beads and 10, 20 and 30 units of endonuclease V. Signal-to-noise ratios show similar results with all combinations tested except when using 20 and 30 μl of magnetic beads in combination with 10 units of endonuclease V (FIG. 24). Identical results were seen when calling genotypes manually comparing 30 μl of beads and 30 U endonuclease V with 10 μl of beads and 10 U endonuclease V.

Figure 25:
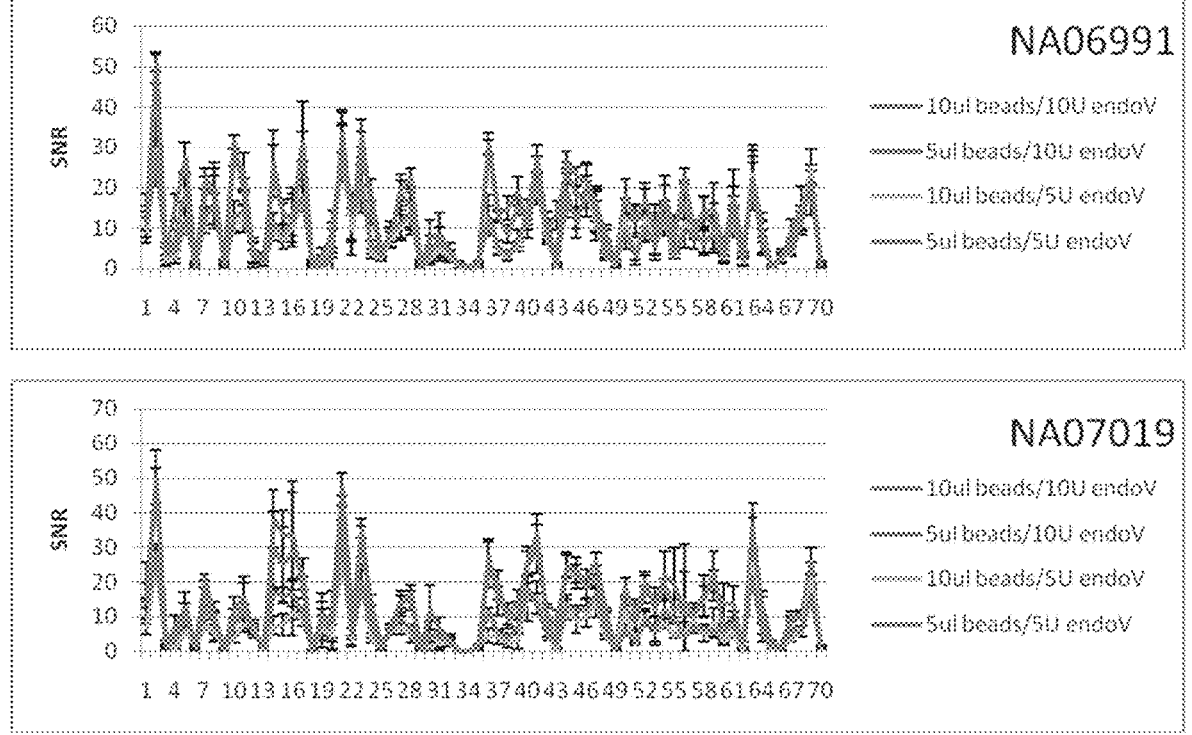
FIGS. 25 and 26 show a comparison of magnetic streptavidin beads and endonuclease V concentration using a 70 plex assay. All assays followed the same protocol except for the amount of magnetic streptavidin beads and endonuclease V. All experiments include four replicates of the two CEPH DNAs NA06991 and NA07019. The results compare the signal-to-noise ratio from Typer 3.4.

To follow up these results an experiment compared the following conditions; 10 μl beads/10 U endonuclease V; 5 μl beads/10 U endonuclease V, 10 μl beads/5 U endonuclease V, and 5 μl beads/5 U endonuclease V. When examining either manual genotype calls or signal-to-noise ratio similar results were seen when using either 10 or 5 μl of magnetic beads (FIG. 25). However, when using 5 U endonuclease V there was a significant reduction in both manual calls and signal-to-noise ratio when compared to 10 U endonuclease V.

Figure 26:
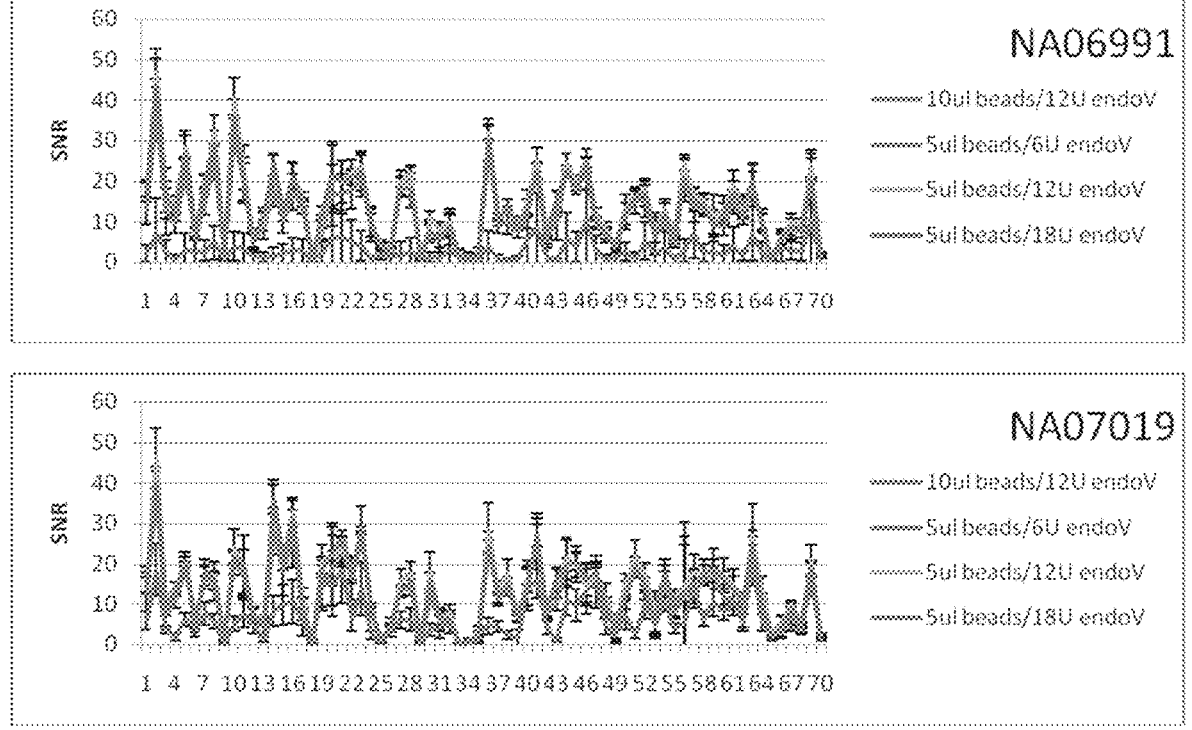

To confirm these results an additional experiment compared the following conditions; 10 μl beads/12 U endonuclease V; 5 μl beads/6 U endonuclease V, 5 μl beads/12 U endonuclease V, and 5 μl beads/18 U endonuclease V. When comparing both manual genotype calls and signal-to-noise ratios, similar results were seen when comparing 10 or 5 μl of Solulink magnetic beads (FIG. 26). When comparing different quantities of endonuclease V, similar results were seen with 12 and 18 U endonuclease V. However, when using 6 U of endonuclease V a reduction in signal was observed (FIG. 26).

Example 11: Alternative Oligonucleotide Cleavage Mechanism

Ribonucleotide:

Initial experiments used extension oligonucleotides which included a ribonucleotide. After extension and subsequent capture on magnetic streptavidin beads the mass tags are released by RNase A cleavage of the ribonucleotide. The method is outlined in the following section. The assays were developed for the SNPs rs1000586 and rs10131894 in combination. The 2 plex reaction worked well and the genotypes are clearly seen (FIG. 8). A challenge to overcome in the future is cleavage of the ribonucleotides-containing oligonucleotides due to freeze thawing.

Photocleavable:

To explore an alternative to cleavage of deoxyinosine with endonuclease V oligonucleotides containing a photocleavable linker were tested (IDT). The linker contains a 10-atom spacer arm which can be cleaved with exposure to UV light in the 300-350 nm spectral range.

Methylphosphonate:

As a further alternative to using cleavage of deoxyinosine with endonuclease V, oligonucleotides containing a methylphosphonate modification were examined. The oligonucleotides contain a modification of the phosphate backbone at a single position, where oxygen is substituted with a methyl group. This results in a neutrally charged backbone which can be cleaved by Sodium hydroxide (NaOH), or potassium hydroxide (KOH) and heat. A series of experiments showed that the oligonucleotides can be cleaved by addition of as little as 50 mM of NaOH or 200 mM KOH and heating at 70° C. for one hour.

dSpacer, Phosphorothioate/Phosphoramidite:

Three alternative cleavage mechanisms that have not been explored in detail are the replacement of a nucleotide with a 1', 2'-Dideoxyribose (dSpacer) and the backbone modifications creating either a phosphorothioate or phosphoramidite. A phosphorothioate modification replaces a bridging oxygen with a sulphur. This enables the backbone to be cleaved with treatment with either 30/50 mM aqueous sliver nitrate solution (with/without dithiothreitol) or 50 mM iodine in aqueous acetone. A phosphoramidite modification replaces a bridging oxygen with a amide group. The resulting P—N bond can be cleaved with treatment with 80% $CH_3COOH$ or during the MALDI-TOF procedure.

Figure 27A:
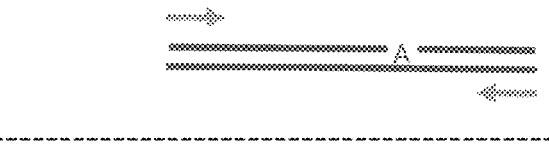
FIGS. 27A-27G show a schematic representation of a biotin competition method for releasing a biotinylated amplification product of interest from a streptavidin coated magnetic or paramagnetic bead.
Figure 27B:
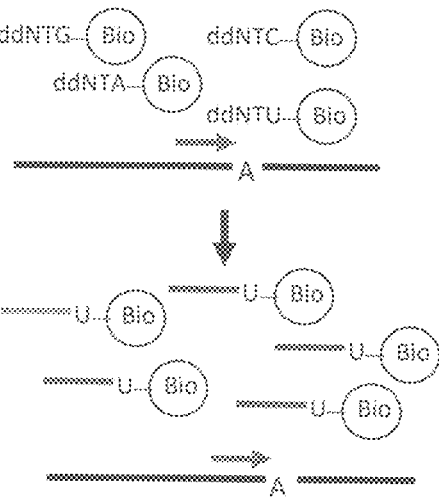
Figure 27C:
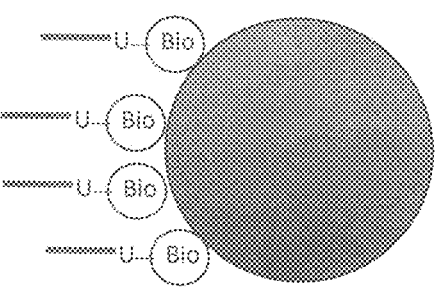
Figure 27D:
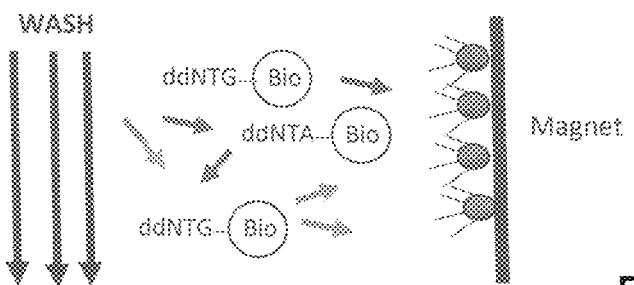

Example 12: Isolation of Biotinylated Extension Products Using a Biotin Competition Release Method A method for purifying biotinylated extension products and releasing the products from streptavidin coated magnetic beads using free biotin is described herein, and illustrated in FIGS. 27A-27G. In some embodiments, the method is utilized to purify and isolate and analyze single base extension reactions for polymorphism identification A genomic region of interest (e.g., a region having genetic variation) can be targeted using PCR based methods (see FIG. 27A). After PCR amplification of a region of interest, the reaction products were treated with shrimp alkaline phosphatase (SAP) to dephosphorylate unincorporated nucleotide triphosphates. The region of interest, including a polymorphism of interest, can be targeted by nucleotide probes using single base extension (SBE) reactions that correspond to the nucleotide residue of interest (e.g., polymorphism; see FIG. 27B). The SBE reactions utilize biotin labeled dideoxynucleotide triphosphate terminators. Biotinylated extension products were subsequently captured (see FIG. 27C), washed and purified away from (see FIG. 27D) unused reaction components utilizing streptavidin coated magnetic beads and magnetic separation.

Figure 27E:
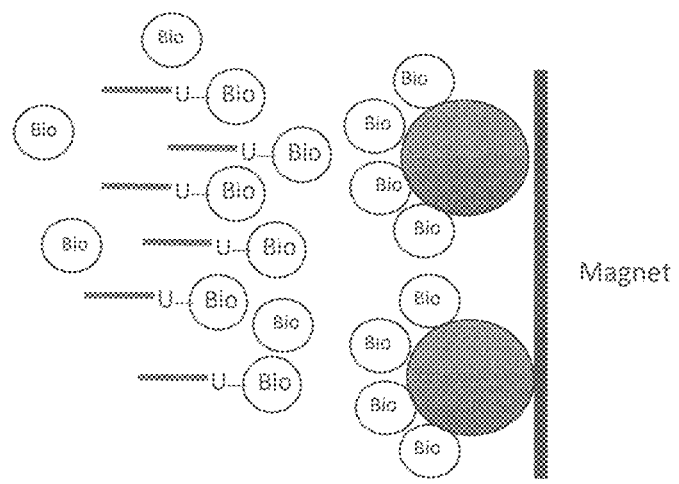
Figure 27F:
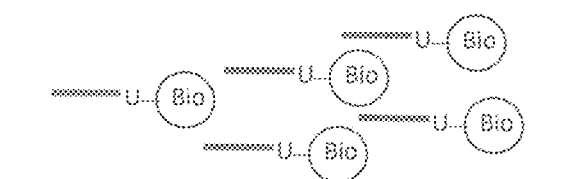
Figure 27G:
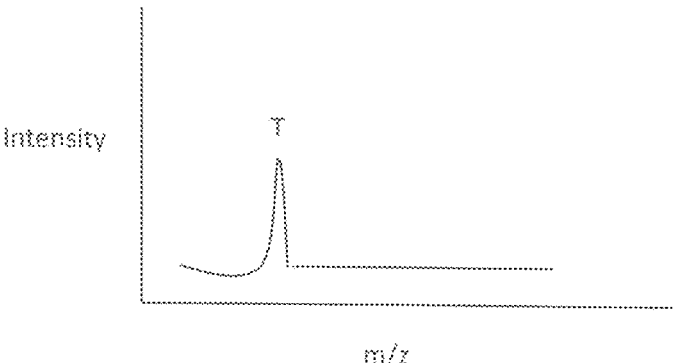

The purified extension products were subsequently eluted from the streptavidin coated magnetic beads by competition with free biotin under elevated temperature conditions (see FIG. 27E). The eluant containing the biotinylated extension products from the region of interest are dispensed (see FIG. 27F) onto a SpectroCHIP® (SEQUENOM) and analyzed using MALDI-TOF mass spectrometry (see FIG. 27G). Reaction components and conditions are described herein.

Methods

Reaction components used in PCR amplification reactions.

| Reagent | Final Concentration per Reaction |
|---|---|
| RNase-free ddH$_2$O | N/A |
| 10X Buffer | 1x |
| dNTPs (25 mM each) | 200 μM |
| MgCl$_2$ (25 mM) | 1.0 mM |
| HotStar Taq (5 U/μl) | N/A |
| Primer Mix (1 μl M) | 200 nM |
| Template | various |

Reaction components used in Shrimp Alkaline Phosphatase dephosphorylation reactions.

| Reagent | Final Concentration per Reaction |
|---|---|
| RNase-free ddH$_2$O | N/A |
| 10X SAP Buffer | 0.24X |
| SAP enzyme (1.7 U/ul) | 0.073 U |

Reaction components used in single base extension reactions.

| Reagent | Final Concentration per Reaction |
|---|---|
| H$_2$O | N/A |
| 10X Buffer | 0.222X |
| Primer mix (9 μM) | 1 μM |
| Biotinylated ddNTPs (250 μl μM) | 5.56 μM |
| Thermosequenase (32 U/μl) | 1.3 U |

Binding and wash solutions used isolate and purify biotinylated extension products.

| Solution | Composition |
|---|---|
| 2X Binding Buffer | 2M NaCl, 10 mM Tris pH 7.5, 1.0 mM EDTA |
| 10X WASH Buffer | 100 mM Tris-HCl pH 8.0 |
| 1X WASH Buffer | 10 mM Tris pH 8.0 |

Components and procedure for preparing streptavidin coated magnetic beads.

| Reagent | Volume per Reaction [μl] |
|---|---|
| Beads | 10 |

Place on magnet at least 3 min to concentrate beads; remove supernatant.

Add 2× Binding Buffer to the tube as follows:

| Reagent | Volume per Reaction [μl] |
|---|---|
| 2x Binding Buffer | 10 |

Mix gently, then place 2-3 min on magnet to capture beads; remove supernatant.

Add 2× Binding Buffer to the tube to repeat for a total of 2 washes as follows:

| Reagent | Volume per Reaction [μl] |
|---|---|
| 2x Binding Buffer | 10 |

Mix gently, then place 2-3 min on magnet to capture beads; remove supernatant.

Resuspend beads in 2× Binding Buffer as follows:

| Reagent | Volume per Reaction |
|---|---|
| | 25 |

Components and procedure for capturing biotinylated extension products using streptavidin coated magnetic beads.

Add an equal volume the 2× Binding Buffer with Beads to each well of PCR reaction:

25 μl Beads in 2× Binding Buffer

25 μl Extension product

Rotate plate to mix for 15-30 min at room temperature.

Place plate on magnetic separator, remove supernatant.

Components and procedure for purification and washing of biotinylated extension products using streptavidin coated magnetic beads.

Add 1×WASH Buffer as follows:

| Reagent | Volume per Reaction [μl] |
|---|---|
| 1x WASH Buffer | 50 |

Mix gently, then place 2-3 min on magnet to capture beads; remove supernatant.

Add 1×WASH Buffer to the tube to repeat for a total of 2 washes as follows:

| Reagent | Volume per Reaction [μl] |
|---|---|
| 1x WASH Buffer | 100 |

Mix gently, then place 2-3 min on magnet to capture beads; remove supernatant.

Add WATER as follows:

| Reagent | Volume per Reaction [μl] |
|---|---|
| WATER | 100 |

Mix gently, then place 2-3 min on magnet to capture beads; remove supernatant.

Add WATER to the tube to repeat for a total of 2 washes as follows:

| Reagent | Volume per Reaction [μl] |
| --- | --- |
| WATER | 100 |

Mix gently, then place 2-3 min on magnet to capture beads; remove supernatant.

Elution of captured biotinylated extension products from streptavidin coated magnetic beads for subsequent analysis.

The biotinylated extension products were eluted from the streptavidin coated magnetic beads using competition with free biotin at elevated temperatures. The reaction conditions are given in the table below.

Add 15 μl of BIOTIN (Resin treated, 25 ng/μl).

Heat to 90° C. for 5 min. then chill to 4° C.

Place on magnet for 2-3 min to capture beads.

After capturing the magnetic beads as described in the table, the eluant was removed from the beads and prepared for further analysis. In some embodiments, preparation for further analysis includes dispensing or spotting onto a solid support suitable for use in MALDI-TOF mass spectrometry. In certain embodiments, the solid support is a Spectro-CHIP® (SEQUENOM) solid support. The biotinylated extension products sometimes are analyzed by MALDI-TOF mass spectrometry, which uses differences in mass of the extension products to elucidate the genotype of the sample at the region of interest (e.g., at the site of the polymorphism). A representative spectrum tracing is shown in FIG. 28.

Figure 28:
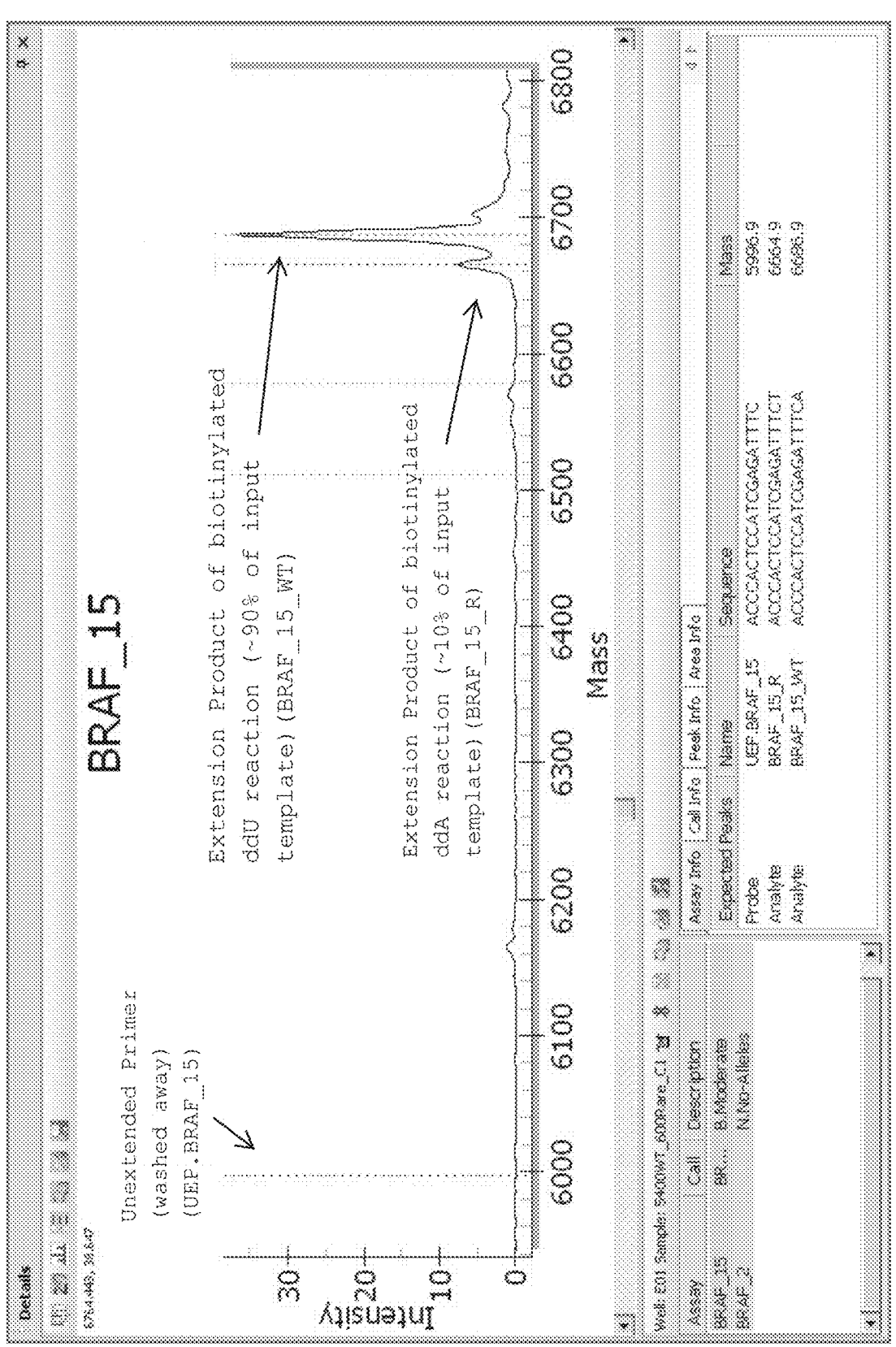
FIG. 28 is a representative mass spectrum of the mass difference of various allelic variants (e.g., polymorphism) as measured by MALDI-TOF MS analysis of single base extension products generated using biotinylated dideoxynucleotide terminators and released from the solid surface by biotin competition as described herein and illustrated in FIGS. 27A-27G. See Example 12 for experimental details and results.
Figures 29A, 29B, 29C, 29D:
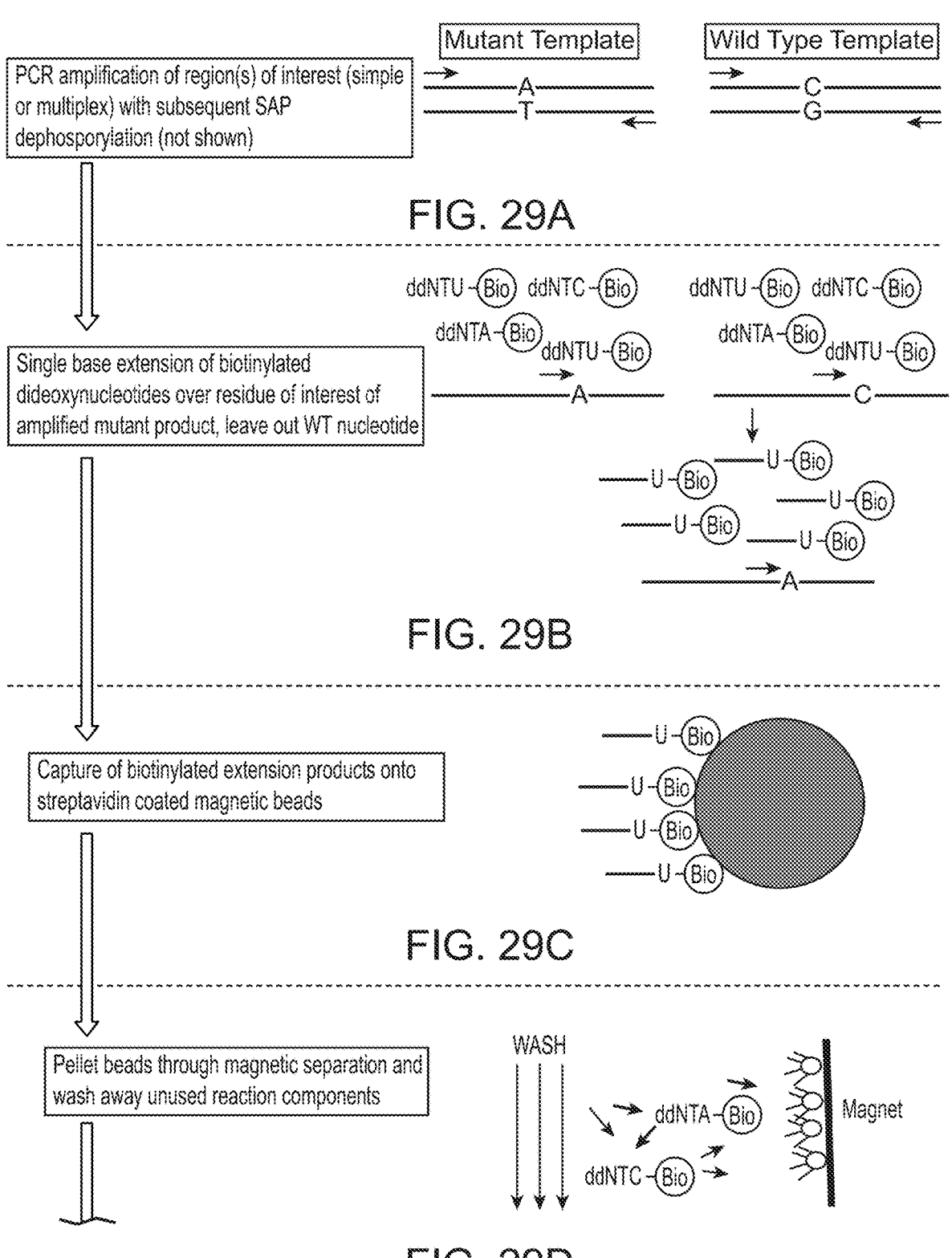
FIGS. 29A-29G illustrate a flow chart showing a mechanism of a biotin competition releasing step.
Figures 29E, 29F, 29G:
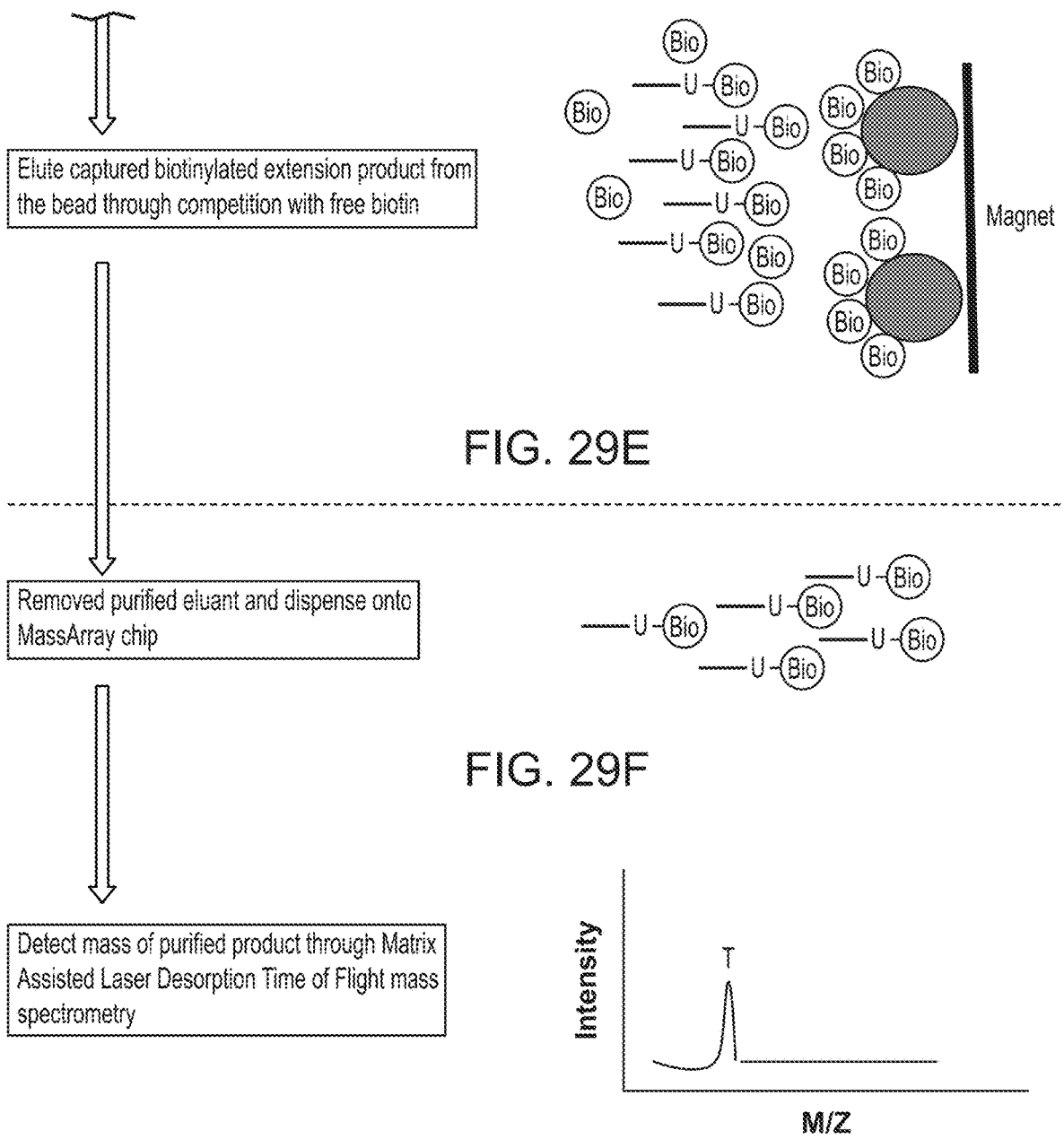

FIG. 28 illustrates the mass differences in single base reaction products analyzed by MALDI-TOF mass spectrometry. Unextended primer is shown on the spectrum tracing at a mass of approximately 5997 Daltons. Two extension reaction products also are shown in FIG. 28, a ddU reaction product representing about 10% of the input template and having a mass of approximately 6665 Daltons, and a ddA reaction product representing about 90% of the input template and having a mass of approximately 6687 Daltons. The additional dotted lines at mass 6510 and 6579 are the expected mass for alleles of the BRAF_2_WT and BRAF_2_R marker single base extension products.

Example 13: Extension and Releasing Extended Oligonucleotides from a Solid Phase A typical multiplex (i.e. iPLEX) was followed up to the extension step (e.g. Example 8). PCR amplification of the region of interest was performed followed by SAP dephophorylation of the unincorporated nucleotides. The single base extension utilized biotinylated dideoxynucleotides. This extension was performed by either including only the nucleotides corresponding to the minor species or all four nucleotides. Biotinylated oligonucleotides were captured using streptavidin beads from different manufacturers. For the releasing step, the inosine cleavage method was compared to using free-biotin to compete off bound biotinylated oligonucleotides. Other components of this reaction were similar to assays previously described (e.g. Example 8). Conditions used for the PCR amplification, SAP dephosphorylation and extension are shown in Table 8 below.

74

TABLE 8

| PCR Setup | | |
| --- | --- | --- |
| Reagent | Final Concentration per Reaction | Volume for Single Reaction (ul) |
| RNase-free ddH$_2$O | N/A | 0.16 |
| 10X Buffer | 1x | 0.50 |
| dNTPs (25 mM each) | 200 uM | 0.04 |
| MgCl$_2$ (25 mM) | 1.0 mM | 0.20 |
| HotStar Taq (5 U/ul) | N/A | 0.10 |
| Primer Mix (1 uM) | 200 nM | 1.00 |
| Competitor | Titration | 3.00 |
| TOTAL | | 5.00 |

| PCR Amplification Parameters | | |
| --- | --- | --- |
| 95 C. | 15 min | |
| 95 C. | 20 sec | 10 cycles |
| 56 C. | 20 sec | |
| 72 C. | 1 min | |
| 72 C. | 3 min | |
| 4 C. | ∞ | |

| SAP Setup | | |
| --- | --- | --- |
| Reagent | Final Concentration per Reaction | Volume for Single Reaction (ul) |
| RNase-free ddH$_2$O | N/A | 1.53 |
| 10X SAP Buffer | 0.24X | 0.17 |
| SAP enzyme (1.7 U/ul) | 0.073 U/ul | 0.30 |
| TOTAL | | 2.00 |

| SAP Incubation |
| --- |
| 37° C. for 20 minutes |
| 85° C. for 10 minutes |
| 4° C. forever |

| Extension Setup | | |
| --- | --- | --- |
| Reagent | Final Concentration per Reaction | Volume for Single Reaction (ml) |
| H$_2$O | N/A | 0.56 |
| 10X Buffer | 0.222X | 0.20 |
| Primer Mix (9 uM) | 1 uM | 1.00 |
| Biotinylated ddT&A (250 uM) | 5.56 uM | 0.20 |
| Thermosequenase (32 U/ul) | 1.3 U | 0.04 |
| TOTAL | | 2.00 |

| Extension Parameters | | |
| --- | --- | --- |
| 94° C. for 30 seconds | | |
| 94° C. for 5 seconds | | 40 cycles |
| 52° C. for 5 seconds | 5 cycles | |
| 80° C. for 5 seconds | | |
| 72° C. for 3 minutes | | |
| 4° C. forever | | |

After extension, the reaction was introduced to streptavidin coated magnetic beads. The extended products were allowed to capture for a short duration. Subsequent wash steps were conducted to remove reaction components except the captured extension products (Table 9). This procedure removed salts that produce interfering adducts in MALDI-TOF mass spectrometry, which allowed for the removal of the anion exchange resin procedure now employed with current iPLEX workflow. After washing, captured extension products were eluted from the beads by introducing a high molar free biotin solution at 25 ng/ul. After elution, the extension products remained in the eluent. The cleaned analyte was now ready for dispensing on the bioarray chip and was substantially free from unextended primer, salts, and other contaminants that can obscure a low abundant species on the MALDI-TOF spectra, thus allowing for a more sensitive detection. FIGS. 29A-29G depict a flow chart of this procedure.

TABLE 9

Bead Conditioning

Vortex MyOne Steptavidin C1 beads to completely resuspend beads.
Transfer beads to a tube as follows:

| Reagent | Vol per Reaction |
| --- | --- |
| Beads | 10 |

Place on magnet at least 3 min to concentrate beads; remove supernatant.
Add 2x Binding Buffer to the tube as follows:

| Reagent | Vol per Reaction |
| --- | --- |
| 2x Binding Buffer | 10 |

Mix gently, then place 2-3 min on magnet to capture beads.
Add 2x Binding Buffer to the tube to repeat for a total of 2 washes as follows:

| Reagent | Vol per Reaction |
| --- | --- |
| 2x Binding Buffer | 10 |

Mix gently, then place 2-3 min on magnet to capture beads; remove supernatant.

Capture

Resuspend beads in 2x Binding Buffer as follows:

| Reagent | Vol per Reaction |
| --- | --- |
| 2x Binding Buffer | 25 |

Add an equal volume the 2x Binding Buffer with Beads to each well of PCR reaction:
25 ul Beads in 2x Binding Buffer
25 ul PCR product
50 ul
Rotate plate to mix for 15-30 min at room temp.
Place plate on magnetic separator, remove supernatant.

Bead Wash

Add 1x WASH Buffer as follows:

| Reagent | Vol per Reaction |
| --- | --- |
| 1x WASH Buffer | 50 |

Mix gently, then place 2-3 min on magnet to capture beads; remove supernatant.
Add 1x WASH Buffer to the tube to repeat for a total of 2 washes as follows:

| Reagent | Vol per Reaction |
| --- | --- |
| 1x WASH Buffer | 100 |

Mix gently, then place 2-3 min on magnet to capture beads; remove supernatant.
Add WATER as follows:

| Reagent | Vol per Reaction |
| --- | --- |
| WATER | 100 |

Mix gently, then place 2-3 min on magnet to capture beads; remove supernatant.
Add WATER to the tube to repeat for a total of 2 washes as follows:

| Reagent | Vol per Reaction |
| --- | --- |
| WATER | 100 |

Mix gently, then place 2-3 min on magnet to capture beads; remove supernatant.

Elution

Add 15 of BIOTIN (Resin treated, 25 ng/ul).
Heat to 90 C. for 5 min. then chill to 4 C.

TABLE 9-continued

Place on magnet for 2-3 min to capture beads.
Remove supernatant to a clean 96-well plate and run on MALDI.

Inosine Cleavage

Figure 30A:
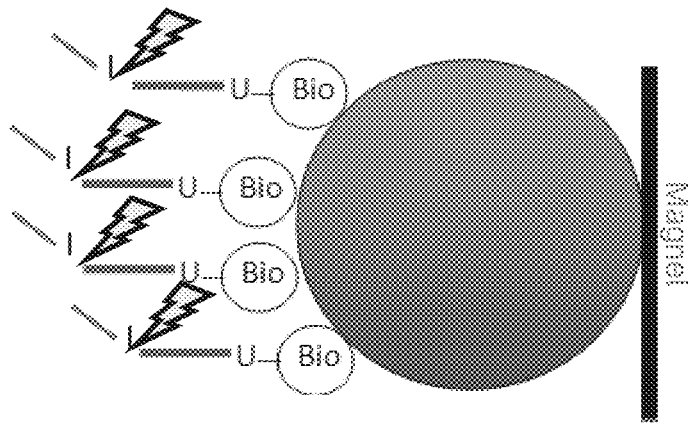
FIG. 30A illustrates a flow chart showing a mechanism of an inosine cleavage releasing step. Steps are the same as for a biotin capture method through the wash step with the exception that the extension oligonucleotides have a 5' mass tag separated by an inosine residue. The mass tags are cleaved from captured products through endonuclease V cleavage specific to inosine residues.
Figure 30B:
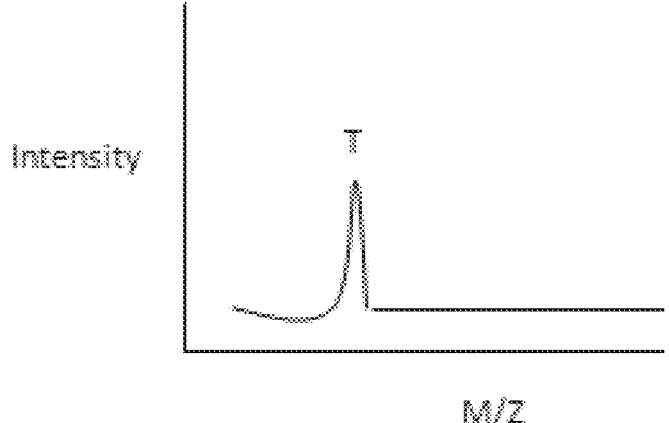
FIG. 30B illustrates a detection of cleaved mass tags on the MALDI. The mass represents a genetic variant.

As an alternate elution method, inosine cleavage of mass tags from the captured extension products was performed. This method deviated from the biotin competition approach for extension oligonucleotide design. This approach required a non-templated sequence on the 5' end of the extension primer to correspond to the extension product. In addition, this oligonucleotide was synthesized with an inosine residue that separates the complementary sequence of the target and the mass tag sequence identifier. Through this inosine residue, the mass tag was cleaved from the capture agent by endonuclease V activity. The cleavage portion of this process is illustrated in FIGS. 30A and 30B.

Streptavidin Bead Selection and Elution Evaluation (Biotin Vs Inosine Cleavage)

Five streptavidin bead products were selected for evaluation. The selection was based on surface characteristics and binding capacity of free biotin. These characteristics are listed in Table 10.

TABLE 10

Bead characteristics

| Bead | Surface | Binding capacity of free biotin (pmoles/mg beads) |
| --- | --- | --- |
| Dynal M270 | Hydrophilic | 650-1350 |
| Dynal M280 | Hydrophobic | 650-900 |
| Dynal C1 | Hydrophilic | >2,500 |
| Dynal T1 | Hydrophobic | >1,300 |
| Solulink | Hydrophilic | >1,300 |

The performance of the beads was evaluated using oligonucleotides synthesized with 3' biotin. Two oligonucleotides were designed with an identical "sequence specific" region; one had no 5' modification while the other contained a 5' mass tag with an inosine residue. To evaluate efficiency of capture and elution strategy, a comparative measure within each spectrum was employed. Additional oligonucleotides were designed so their respective size was within an acceptable mass range of the eluted products for comparison.

The testing procedure included capturing the 3' biotinylated oligonucleotides, performing a set of washes, and subsequent elution (biotin competition vs. inosine cleavage). This strategy alleviates variability that may have been introduced during the PCR and extension steps. Beads and elution strategies were evaluated by response to limiting the capturable oligonucleotide. This evaluation was performed by serially diluting the 3' biotinylated oligonucleotide from 2 uM to 0.031 uM. For each concentration tested, an equal amount of quantification oligonucleotide was added to the eluent to measure bead capture and elution efficiency.

Figure 31:
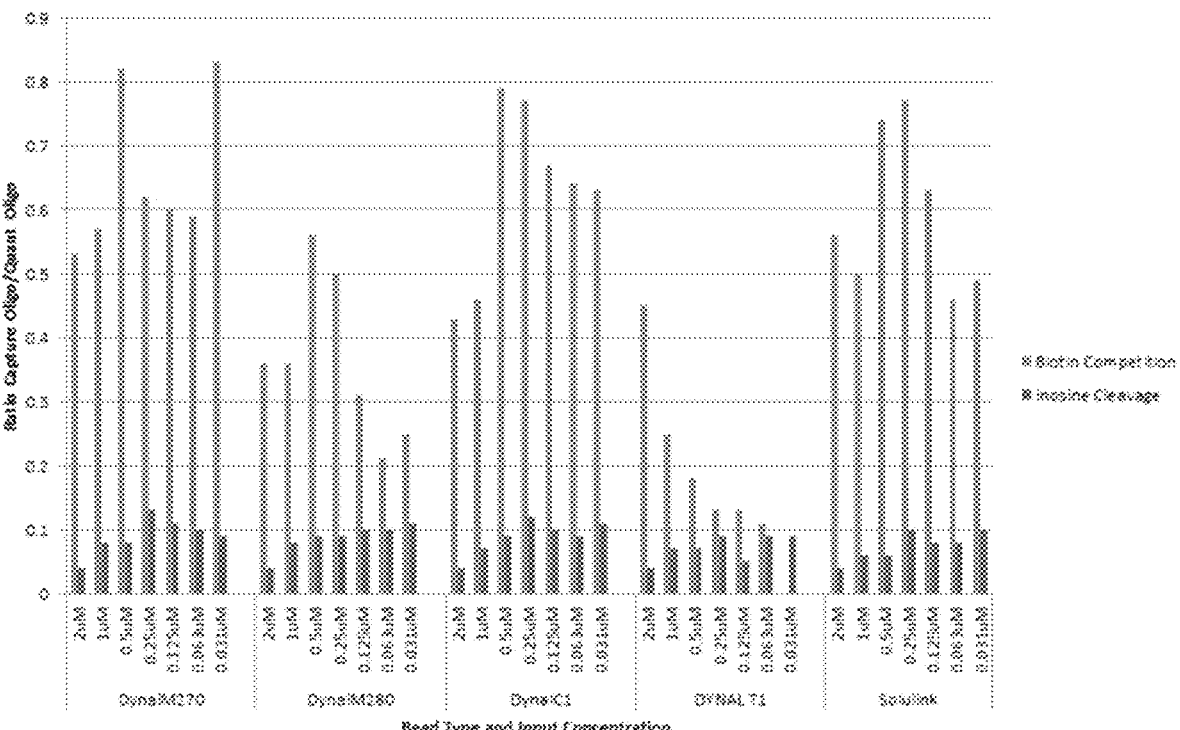
FIG. 31 shows comparative results of biotin competition vs. inosine cleavage using different concentrations of 3'-biotinylated oligonucleotide and different capture beads.
Figure 32:
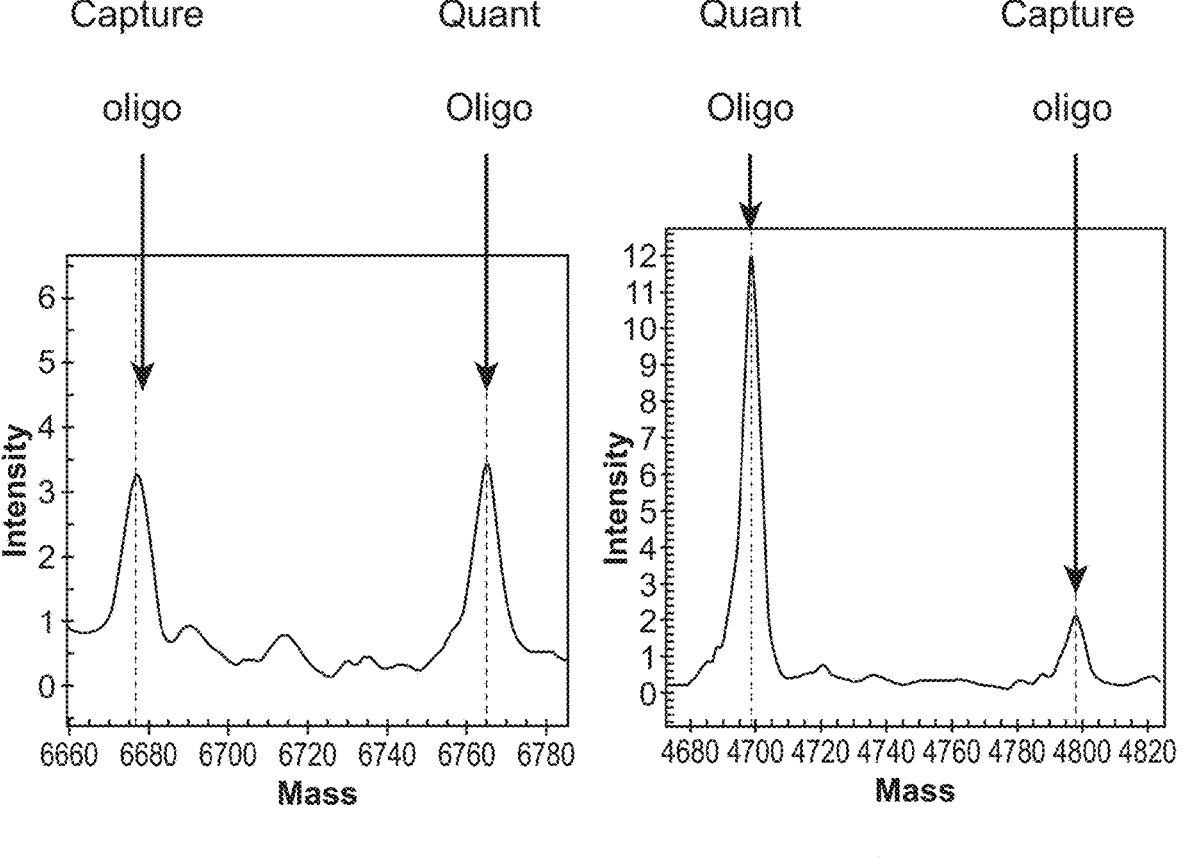
FIG. 32A and FIG. 32B show comparative results of biotin competition vs. inosine cleavage using Dynal Cl beads. The mass spectra peak representing detected capture oligonucleotide and detected quantification oligonucleotide are indicated by down arrows.

The ratio of capture oligonucleotide to quantification oligonucleotide heights was measured at each concentration for each bead evaluated. This initial experiment showed the biotin competition method to outperform the elution method. Both elution methods exhibited a captured product at the lowest starting input, but the biotin capture clearly showed more captured and eluted product, as displayed by the ratio. This outcome was evident regardless of bead used and the biotin competition was chosen as the elution strategy. The data also showed underperformance of DynalM280 and DynalT1. The data reflecting this experiment can be seen in FIG. 31 and FIGS. 32A and 32B.

Bead Evaluation

The next approach was to analyze capture beads for further development. This experimentation utilized all steps of the proposed ultra-sensitive detection workflow to evaluate bead performance from an extended product off a PCR template. In order to control input material, competitor oligonucleotides were used as template material. PCR, SAP, extension and capture were performed as outlined previously. The template complement, Biotin-ddUTP, was the sole nucleotide used in the extension reaction. Competitor oligonucleotide template concentration was serial diluted from approx. 60,000 molecules to approx. 30 molecules. Each dilution was replicated six times. For all reactions 1 ul of a 1 uM solution of extension oligonucleotides was used. The beads evaluated were Dynal M270, Dynal C1, and Solulink. To elucidate binding performance of each bead using the same strategy as employed in the previous study, 1 ul of a 1 uM quantification oligonucleotide solution was added to the eluent post biotin capture.

Figure 33:
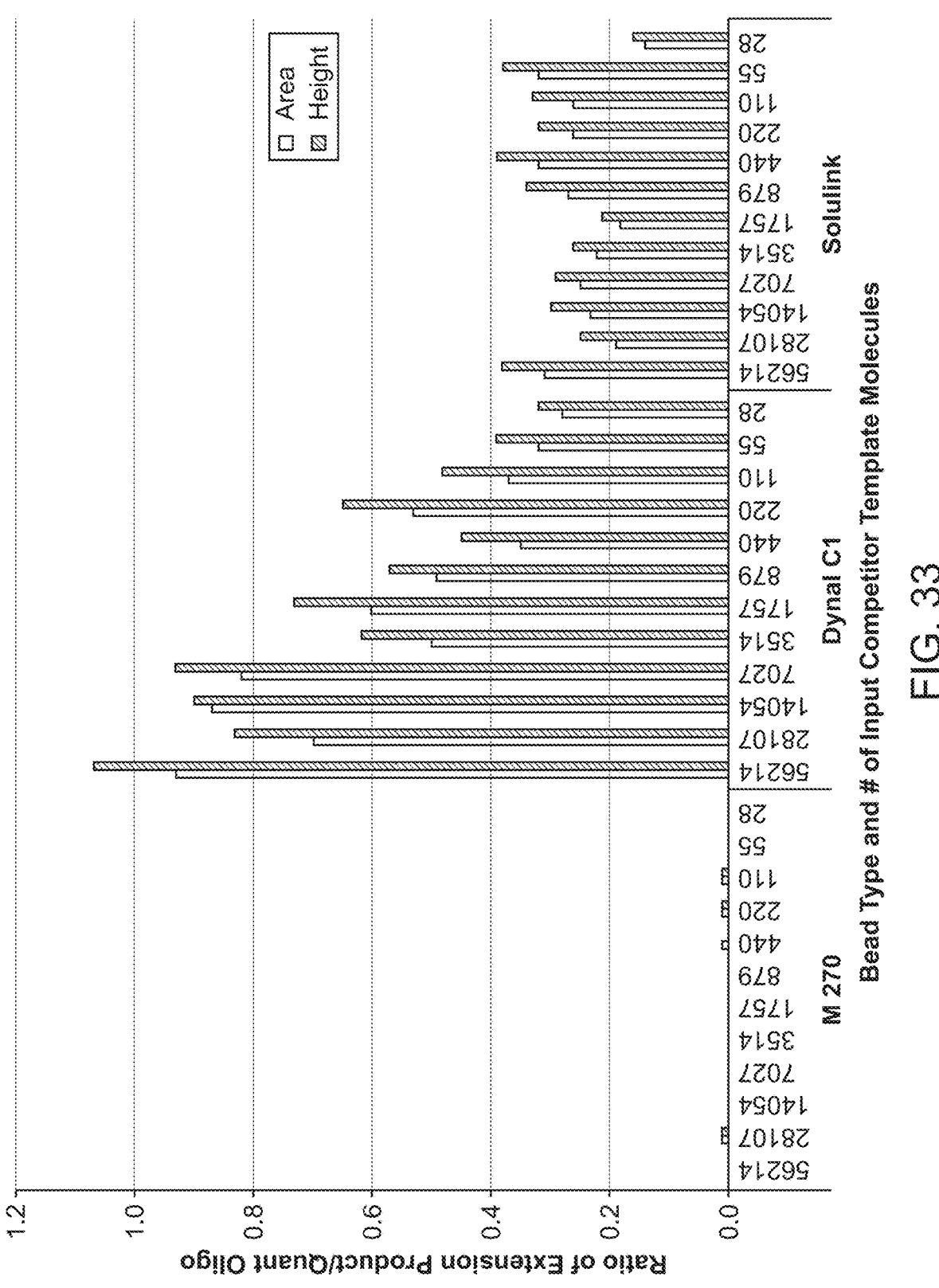
FIG. 33 shows an evaluation of different capture beads using a competitor template.
Figure 34A:
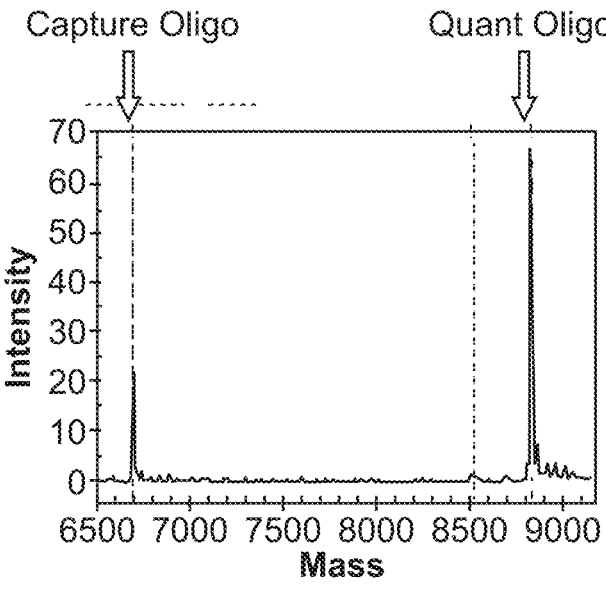
FIGS. 34A-34C show mass spectrometry results from an assay using a very low competitor template (about 30 molecules) for each bead type tested. The mass spectra peak representing the detected capture oligonucleotide and detected quantification oligonucleotide are indicated by down arrows.
Figure 34B:
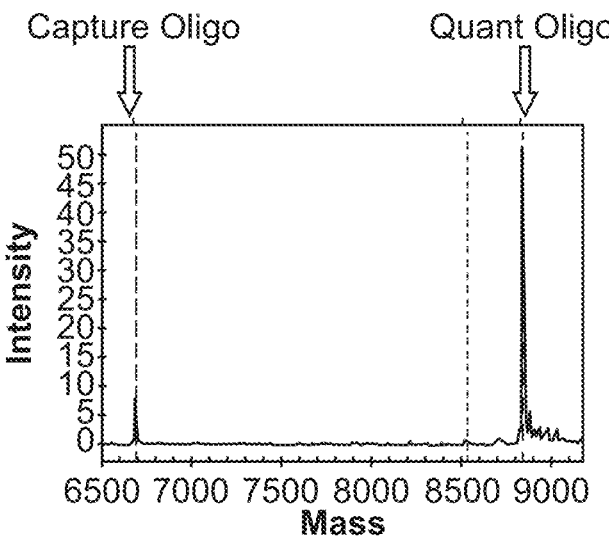
Figure 34C:
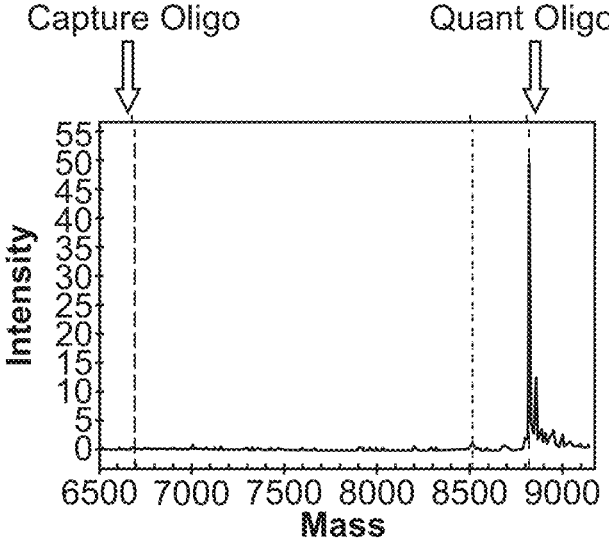

The results of this evaluation demonstrated Dynal C1 to outperform both Solulink and M270 at all template concentrations. M270 failed to capture any product. For Dynal C1, a gradual decline in the ratio of extension product to quantification oligonucleotide using either height or area as the measure was observed as it related to input amount. This same relationship was not observed with Solulink, suggesting a limit of capture. The data for this experiment can be seen in FIG. 33 and FIG. 34.

Genomic Variants (i.e. Genomic Mix Model)

With the essential components and procedures for the process established, development proceeded to actual samples. A model system was developed using samples and assays well characterized in a previous validation (Oncocarta validation). The genetic material used is commercially available from ATCC and is known to carry somatic mutations. Sample HTB-26D (genomic DNA of a cell line derived from breast adenomcarcinoma) carries a mutation in the serine/threonine-protein kinase B-Raf (BRAF) encoding region. Specifically, this sample has previously shown a somatic mutation in BRAF-2 (Wild type—G; Mutant—T). This sample was characterized as being 30% mutant. Sample HTB-38D (genomic DNA of cell line derived from colorectal adenocarcinoma) also carries a mutation in the BRAF region. This sample has previously shown a mutation in BRAF-15 (Wild type—T; Mutant—A). This sample was characterized as 15% mutant. HTB-26D is wild type for BRAF-15 and HTB-38D is wild type for BRAF-2.

One rationale for the selection of these assays and samples, beyond the ease of obtaining genetic material, was the specific genotypes involved. Biotin-ddCTP and biotin-ddTTP are only separated by 1 Da in mass. Although this mass difference is within the resolution of the MALDI-TOF instruments, a larger mass difference between products was evaluated. Subsequently, a different vendor was found to offer biotin-ddUTP with a 16 carbon linker (vs. the 11 carbon linker of the original set). Replacement of the 11 carbon linker with the 16 carbon linker in this assay alleviated any potential design issues.

Figure 35:
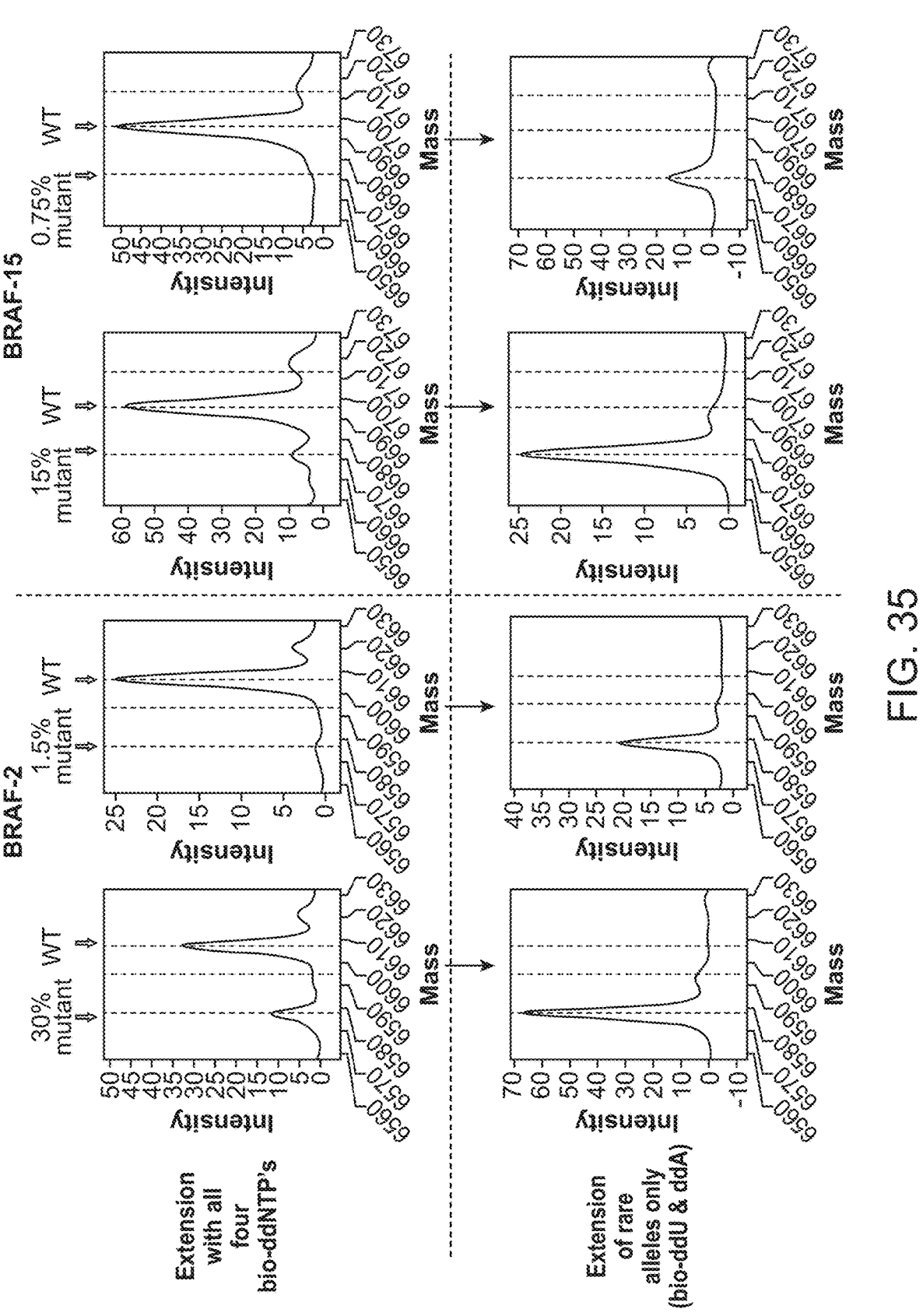
FIG. 35 shows the detection of BRAF-2 and BRAF-15 mutations using different extension compositions and demonstrates an increase in signal to noise ratio when ddNTPs corresponding to the wild type (e.g. more abundant variant) are excluded from the extension composition.

To evaluate sensitivity in this model system, the two samples were mixed to further dilute each corresponding somatic mutation. The two samples were mixed at different ratios, titrating the somatic mutation in BRAF-2 for sample 26D from 30% to 1.5% and titrating the BRAF-15 variant from 15% to 0.75% for sample 38D. Each titration point was run in duplicate and recombined after SAP. The mixed analyte was redistributed to two different reactions. One of the reactions was subject to all four biotin-ddNTP's while the other used just biotin-ddUTP (for BRAF-2) and biotin-ddATP (for BRAF-15). Capture and elution were performed with the Dynal-C1 beads and free-biotin competition. FIG. 35 shows the results for these four scenarios.

The BRAF-2 mutant showed a slight signal in the reaction run with all 4 biotin-ddNTP's (top left panel, FIG. 35). Ordinarily this sort of signal would not be considered significant above baseline noise. With just biotin-ddUTP (for BRAF-2 reaction, bottom left of FIG. 35) a very clear and distinct signal was observed for the mutant. This same observation held true for the 0.75% mutant in the BRAF-15 assay for sample 38D. A very clear and distinct signal was observed for the BRAF-15 mutant when just biotin-ddATP (bottom right of FIG. 35) was included in the extension composition. This data demonstrated a significant increase in the signal to noise ratio (SNR) by excluding the biotin-ddNTP's corresponding to the more abundant wild type sequence. In the case of BRAF-15, there was no observed signal for the mutant in the reaction when all 4 biotin-ddNTP's were included in the extension reaction (top right panel, FIG. 35).

Detection and Quantitation of a Low Abandance Variant

In some embodiments the amount of molecules of a target mutant variant (e.g. low abundant variant) present in an assay where the wild type (e.g. high abundance species) extension product is not generated is determined by the use of a synthetic template included in the extension reaction. The initial goal of this evaluation was to assess the ability to reliably detect the minor contribution (i.e. of a low abundance mutant) in a mixture at sensitive levels. The post-PCR enrichment strategy summarized here defines this ability is possible by effectively removing the wild type (e.g. high abundance species) extension product. It is possible to determine the amount (e.g. copy number, concentration, percentage) of target mutant molecules present (i.e. mutant extension products) in an assay (e.g. extension reaction), if the input quantity of template is known. The amount of target (e.g. copy number, concentration, percentage) mutant variant (i.e. mutant extension products) and/or percentage of target mutant variant in the sample is quantified by including a known amount of synthetic template in the extension reaction. The synthetic template can hybridize to an oligonucleotide species and contain a base substitution at the mutant position located just 3' of the oligonucleotide species to be extended. The base substitution is different than the wild type or target mutant variant (e.g. first variant, low abundant variant, SNP). The base substitution present in the synthetic template is not present in the sample prior to introduction of the synthetic template. A ddNTP that is complementary to the base substitution in the synthetic template is also introduced into the reaction. Oligonucleotide species that hybridize to the target mutant variant are co-amplified (e.g. co-extended) with oligonucleotide species that hybridize to the synthetic template. By performing multiple reactions, that include serial dilutions of a synthetic template, the amount and/or percentage of the target mutant variant can be ascertained. The amount and/or percentage of the target mutant variant is determined by the amount of synthetic template that yields equal extension product as the target mutant variant.

Figure 36:
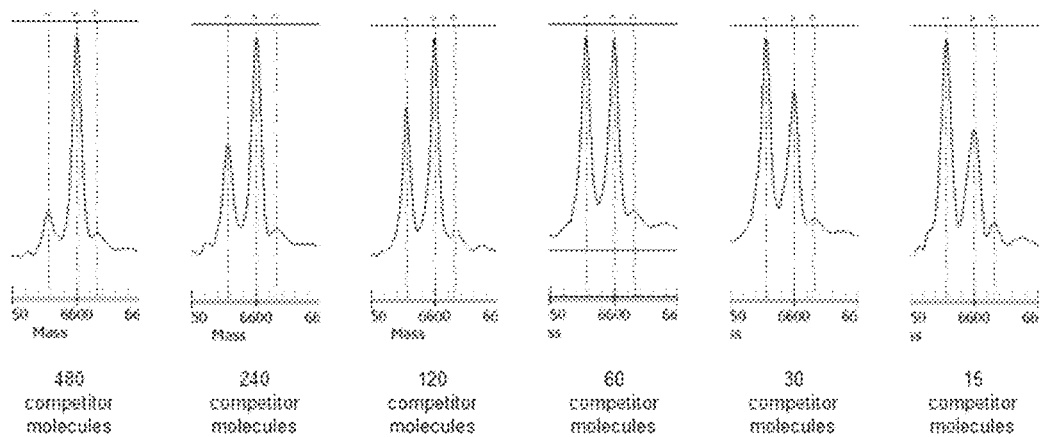
FIG. 36 shows results of a competition assay with a 1% rare allele.

Mutant quantification, as described, was carried out on a genomic mix model. With constant mutant percentages of 5, 1, 0.5 and 0.1, synthetic template titrations were applied targeting a theoretical number of molecules given a total input DNA of 20 ng. The result showed an accurate count of mutant molecules for the 5 and 1% samples. The process was not as accurate at lower levels, presumably due to PCR sampling bias with limited template. FIG. 36 shows the titration profile for the 1% mutant.

CONCLUSIONS

Elimination of the wild type extension product can increase sensitivity of the multiplex assay disclosed herein. In some embodiments, assays of the same plex have the same wild type genotype, or have the same mutant genotype. In some embodiments, synthetic templates or plasmid constructs with designed "mutations" against a genomic DNA of a healthy population (i.e. HAPMAP consortium samples) can be used. This strategy can alleviate design concerns and can have the distinct advantage of artificially creating different mutant percentages in different assays for the same plex (competitor only). In some embodiments, synthetic templates (e.g. plasmids or oligonucleotide templates) are used as controls. In some embodiments, synthetic templates (e.g. plasmids or oligonucleotide templates) are included in kits.

In some embodiments, designs are tailored toward the wild type (i.e more abundant) nucleotide. In this way all assays in one plex share the same nucleotide for wild type and the extension mix used leaves out this nucleotide. In some embodiments, designs can be tailored toward the mutant. In some embodiments, all assays in a plex have the same mutant base in common. In certain embodiments, the extension mix only contains the mutant base. In some embodiments, there is a risk of non-specific interaction with the overwhelming background wild type DNA. In some embodiments there should be at least one control plex representing each wild type base removed, or each mutant base left in depending on the design style chosen.
Workflow Improvements The processes as described are amenable to automation. Key steps to consider for automation can be bead conditioning, bead addition, bead washing, and aspiration of the eluted product.

Example 14: Detecting "Wild Type" and "Mutant" Genotypes Using Multiplex Assays and Kits Assay Design A hindrance to a more sensitive detection has been the presence of the wild type peak scaling the intensity to a point where low level mutants are no longer visible above baseline. Removing the wild type peak from detection has improved sensitivity and signal to noise ratio. Assays designed within a single plex have the same wild type peak in common with corresponding wild type base removed from the extension reaction, or designed to have the same mutant peak in common with only that specific base included in the extension reaction (Table 11). In terms of material cost, the strategy of choosing a plex directed toward the mutant allele with only one base used in the extension reaction is used for a model system.

Multiplex (i.e. Plex) designs are divided into three classes of assays. The three classes represent each of the other 3 nucleotides as the wild type. Four multiplex assays (i.e. plexes) are designed using this rationale with each plex targeting a different mutant base. This assay design strategy allows the exploration of all possible wild type/mutant combinations.

Figure 37:
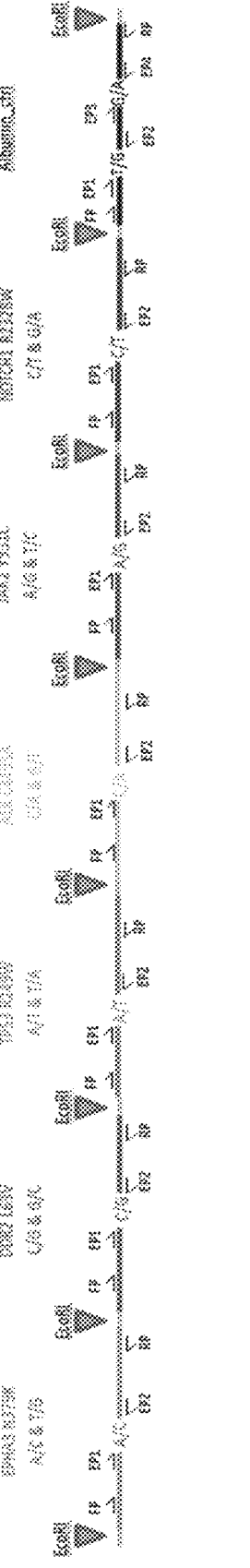
FIG. 37 illustrates a model plasmid that can be cleaved through EcoRI restriction digest to separate the regions and more adequately reflect a genomic context.

The design incorporates six regions from a Lung Panel. Each designed "mutant" is interrogated in the forward and reverse direction to facilitate the requirement of all possible wild type/mutant combinations. The design avoids overlap from extension oligonucleotide and PCR primer so as to avoid any potential exonuclease derived additional signals. The mutation designed into the model represents actual somatic mutations used in the Lung Panel. The design with multiplex is outlined in Table 12. The four multiplexes are designed so they can also be multiplexed together in one plex using acyclic extension mix. The design incorporates an EcoRI site separating the regions from each other (FIG. 37). Prior to using the model, the plasmid is cleaved through EcoRI restriction digest to separate the regions and more adequately reflect a genomic context.

TABLE 11

| | Extension nucleotide mix |
|---|---|
| Design with all assays sharing the same wild type nucleotide in a plex | |
| Plex with wild type-T | C, G, A |
| Plex with wild type-C | T, G, A |
| Plex with wild type-G | T, C, A |
| Plex with wild type-A | T, C, G |
| Design with all assays sharing the same mutant nucleotide in a plex | |
| Plex with mutant-T | T |
| Plex with mutant-C | C |
| Plex with mutant-G | G |
| Plex with mutant-A | A |

TABLE 12

| Multiplex | Region | Wild Type/Mutation | Extension Direction |
|---|---|---|---|
| Mutant C | DDR2_L63V | G/C | R |
| Multiplex | EPHA3_N379R | A/C | R |
| | JAK2_Y931C | T/C | R |
| | Alubmin_Ctrl_C | A/C | R |
| Mutant A | NOTCH1_R2328W | G/A | R |
| Multiplex | TP53_R249W | T/A | F |
| | ALK_C4453A | C/A | F |
| | Alubmin_Ctrl_A | G/A | F |
| Mutant T | ALK_C4493A | G/T | R |
| Multiplex | NOTCH1_R2328W | C/T | F |
| | TP53_R245W | A/T | R |
| | Alubmin_Ctrl_T | C/T | R |
| Mutant G | EPHA3_N379K | T/G | F |
| Multiplex | DDR2_L63V | C/G | F |
| | JAK2_Y931C | A/G | F |
| | Alubmin_Ctrl_G | T/G | F |

Controls

Elements of the process lead to controls for downstream analysis. Failure to capture a product can be due to limited template, failed PCR/extension, or failed capture and elution. To evaluate issues with these specific variables, a control assay is included in each plex designed. The control designed targets the human albumin gene. A control is represented in each reaction that is sufficiently templated with proper functioning PCR and extension. Four separate extension oligonucleotides are intended for this control. These extension oligonucleotides target a residue representing each of the four nucleotides and are used with the appropriate extension nucleotide mix.

Subsequent to the extension assay, a 5' biotinylated oligonucleotide with 3' inverted dTTP is spiked into all assays as a control for capture and elution. The absence of this signal coinciding with an absence of any analyte informs the user of a failed capture and/or elution. The molarity of this particular control should not overwhelm the reaction to avoid masking any low level mutant in detection.

Elution Optimization

Captured and washed products are eluted into 15 ul of high molar biotin solution. New hardware which pellets beads at the appropriate height for 15 ul elution is optimized for the process using Matrix PlateMate 2×2 and/or the Epimotion 5075. A titration experiment is used to evaluate the performance of the new plate. As a test of the process, this evaluation is done in triplicate for each dilution of capture control. The capture control is spiked into an iPLEX simulant solution. The test solution undergoes the typical post-extension process using the hardware.

Automation adjustments for the PlateMate are made prior to elution experimentation. The titration encompasses twelve steps of a serial dilution bringing input capture oligonucleotide from 2500 molecules to approximately 1 molecule. The method with new hardware is optimized for the ability to maintain a pellet during the washes without loss of beads. Ultimately, the performance is judged by the sensitivity as demonstrated by detection of capture oligonucleotide.

Quality Control

The four multiplexes are initially run with the typical iPLEX process using an acyclic extension mix on plasmid alone. This is performed as a quality measure of plasmid manufacturing. Restriction digest is also optimized and visualized in an agarose gel to ensure complete digestion into constituent fragments.

Capture Control Optimization

There is an initial experiment to determine what concentration of capture control is appropriate for subsequent experiments. This control is useful for those reactions where there is no mutant and therefore no extension peak. In this situation, it is necessary to determine if the absence of a peak is the result of the absence of sufficient template to generate an extension product or a failure of capture or elution. A titration of plasmid is performed in quadruplicate. For each replicate, a different concentration of capture oligonucleotide is used. The titration of plasmid mirrors the sensitivity experiment with eight dilutions from 50% mutant to 0.01% mutant and a no mutant reaction. The lowest concentration of capture control used is determined from the elution optimization experiment. This concentration is used as input for one replicate and doubling concentrations for the other three replicates. Performance of the capture control is evaluated by how mutant assay detection is effected by the presence of a capture control peak. The peak should not obscure low level mutant by being too prevalent in the spectra. However, the capture control peak must be clearly detected at low level mutant concentrations. The findings of this experiment are the basis for capture control concentration in subsequent sensitivity, specificity and concordance assays. The 3' inverted dT is not necessary for these reactions, as the oligonucleotide is not involved in the extension reaction. However, the control is designed this way as to allow incorporation of the control in the extension reaction itself.

Sensitivity and Specificity

Establishing a sensitivity threshold of the process involves titrating plasmid DNA relative to the human DNA. Sensitivity thresholds are determined when no mutant analyte is detectable or to a point were a single copy of the variant is used for the minority template. Various dilutions of the mixture are used. The number of template mutant molecules is 15000, 3750, 938, 235, 59, 15, 4 and 0. The respective number of wild type copies is 15000, 26250, 29062, 29765, 29941, 29985, 29996 and 30000. Combined, these eight mixtures represent a 50%, 12.5%, 3.13%, 0.78%, 0.2%, 0.05%, 0.01% and 0% mutant concentration, respectively. Total template is 90 ng/rxn, or 30,000 genomic copies. Every dilution of each plex is run with 48 replicates. An extra two plates running 48 non-templated reactions for each multiplex is run as a control to assess the extent of non-specific interactions. Additionally, a "golden standard" plate of 48 samples run in duplicate using the 50% mutant and 12.5% mutant establishes proper ratios are being employed. In total, the sensitivity and specificity trial requires nineteen 96 well plates. PCR and SAP is implemented according to current iPLEX protocol. Post-SAP reactions are subject to an extension reaction containing biotin-ddNTP's as the alternative terminating nucleotide substrate (except the "golden standard plate"). All other reaction components will remain the same. Table 13 shows the model system dilution setup in terms of molecules number and weight of each constituent DNA. Table 14 and Table 15 lists the entire process from PCR to extension in concentrations for each component on a per reaction basis.

Initial analysis considers at what point no signal is observed to establish a statistically significant sensitivity threshold. This analysis considers the overall data encompassing all multiplexes, and also takes into account variability that may occur when extending a specific base as well as what impact, if any, the wild type background genotype has on successful extension. This analysis evaluates how the sensitivity has effect on specificity.

TABLE 13

| Extension mix table | | | | | | |
|---|---|---|---|---|---|---|
| Weight (ng) | molecules | Weight (ng) | molecules | Total Weight (ng) | Total molecules | % Mutant |
| 45 | 15000 | 45 | 15000 | 90 | 30000 | 50 |
| 78.75 | 26250 | 11.25 | 3750 | 90 | 30000 | 12.5 |
| 87.19 | 29062 | 2.81 | 938 | 90 | 30000 | 3.13 |
| 89.3 | 29765 | 0.71 | 235 | 90 | 30000 | 0.78 |
| 89.82 | 29941 | 0.18 | 59 | 90 | 30000 | 0.2 |
| 89.96 | 29985 | 0.05 | 15 | 90 | 30000 | 0.05 |
| 89.99 | 29996 | 0.01 | 4 | 90 | 30000 | 0.01 |
| 90 | 30000 | 0 | 0 | 90 | 30000 | 0 |

Concordance

Concordance analysis considers the data collected from the sensitivity and specificity experiments. All replicates are gauged for agreement within each experiment as well as agreement across experiments. The "golden standard genotype" is established by running the model system itself in the model system quality control.

An additional measure of concordance is performed with samples provided by Horizon Diagnostics. Horizon Diagnostics provides genetically defined gDNA and FFPE cell reference standards. Evaluation considers no more than 23 samples that are FFPE prepared. Eight to fifteen mutations are selected from a list prepared by Horizon. To explore the power of the detection system, mutants selected are purchased with the corresponding wild type version, or mixed with in house healthy population samples. The samples provided by Horizon are in 50% mutant state and a dilution is required to evaluate sensitive detection in this context. The dilution series is the same as utilized in the sensitivity and specificity evaluation. In addition, a non-templated control is run to bring total sample number to 24. All samples are run in quadruplicate for a total of eight 96 well plate. This experimental design will include an iPLEX "golden standard" using the Horizon Diagnostic samples without dilution. This evaluation not only further assesses concordance to traditional iPLEX, but also gives information on performance of actual FFPE samples.

Control Variables

Pre-enrichment processing: All reactions are carried out according to iPLEX SOP up to the extension step. These processes are detailed in Table 14 and Table 15. All reagents used are controlled so that the same lot of reagents is used across the studies.

Bead Processing: Conditioning, wash, and elution steps have been established from other studies to produce a reliable system. After elution strategies have been decided upon from the Pre-Testing phase, a defined protocol is used for all ensuing experiments.

Sample DNA: DNA derived from three sources is used for all studies. The first is plasmid DNA containing the model system. Secondly is HapMap samples from Utah residents of European ancestry. Lastly is DNA provided by Horizon Diagnostics.

Instrumentation: Pre and Post-PCR instrumentation include either the PlateMate 2×2 and/or the Hamilton Micro Lab 4000. Nanodispensing is performed on the SEQUE-NOM Nanodispenser RS1000 with analyte detection using the MassARRAY Analyzer 4. All instrumentation serial numbers are cataloged.

TABLE 14

| | PCR Setup | |
| --- | --- | --- |
| Reagent | Final Concentration per Reaction | Volume for Single Reaction (ul) |
| RNase-free ddH$_2$O | N/A | 1.16 |
| 10X Buffer (w/20 mM MgCl$_2$) | 1x | 0.50 |
| dNTPs (25 mM each) | 200 uM | 0.04 |
| MgCl$_2$ (25 mM) | 1.0 mM | 0.20 |
| Fastart Taq (5 U/ul) | 0.1 U/rxn | 0.10 |
| Primer Mix (1 uM) | 200 nM | 1.00 |
| DNA (5 ng/ul) | 10 ng/rxn | 2.00 |
| TOTAL | | 5.00 |

| PCR Amplification Parameters | | |
| --- | --- | --- |
| 95 C. | 15 min | |
| 95 C. | 20 sec | 45 cycles |
| 56 C. | 20 sec | |
| 72 C. | 1 min | |
| 72 C. | 3 min | |
| 4 C. | ∞ | |

| | SAP Addition | |
| --- | --- | --- |
| Reagent | Final Concentration per Reaction | Volume for Single Reaction (ul) |
| RNase-free ddH$_2$O | N/A | 1.53 |
| 10X SAP Buffer | 0.24X | 0.17 |
| SAP enzyme (1.7 U/ul) | 0.073 U/ul | 0.30 |
| TOTAL | | 2.00 |

| SAP incubation | |
| --- | --- |
| 37° C. | 20 min |
| 85° C. | 5 min |
| 4° C. | ∞ |

TABLE 15

| | Extension Reaction | |
| --- | --- | --- |
| Reagent | Final Concentration per Reaction | Volume for Single Reaction (ml) |
| H$_2$O | N/A | 0.56 |
| 10X Buffer | 0.222X | 0.20 |
| Primer Mix (9 uM) | 1 uM | 1.00 |
| Biotinylated ddNTPs (250 uM) | 5.56 uM | 0.20 |
| Thermosequenase (32 U/ul) | 1.3 U/rxn | 0.04 |
| TOTAL | | 2.00 |

| Extension Parameters | | | |
| --- | --- | --- | --- |
| 94° C. | 30 sec | | |
| 94° C. | 5 sec | | 40 cycles |
| 52° C. | 5 sec | 5 cycles | |
| 80° C. | 5 sec | | |
| 72° C. | 3 min | | |
| 4° C. | ∞ | | |

Response Variables

The experiments employed in this test plan are evaluated for several parameters. Control variables have potential impact on several parameters. The ability of the process to deliver a reliable and desirable result is evaluated. Any bearing on response variable that can be reliably ascertained by control variables is accounted for.

Peak heights

Peak confidence scores

Expected genotypes

TABLE 16

| Bead Conditioning | |
| --- | --- |
| Vortex MyOne Steptavidin C1 beads to completely resuspend beads. Transfer beads to a tube as follows: | |
| Reagent | Vol per Reaction |
| Beads | 10 |
| Place on magnet at least 3 min to concentrate beads; remove supernatant. Add 2x Binding Buffer to the tube as follows: | |
| Reagent | Vol per Reaction |
| 2x Binding Buffer | 10 |
| Mix gently, then place 2-3 min on magnet to capture beads. Add 2x Binding Buffer to the tube to repeat for a total of 2 washes as follows: | |
| Reagent | Vol per Reaction |
| 2x Binding Buffer | 10 |
| Mix gently, then place 2-3 min on magnet to capture beads; remove supernatant. | |
| Capture | |
| Resuspend beads in 2x Binding Buffer as follows: | |
| Reagent | Vol per Reaction |
| 2x Binding Buffer | 25 |
| Add an equal volume the 2x Binding Buffer with Beads to each well of PCR reaction: 25 ul Beads in 2x Binding Buffer 25 ul PCR product 50 ul Rotate plate to mix for 15-30 min at room temp. Place plate on magnetic separator, remove supernatant. | |

TABLE 16-continued

Bead Wash

| Add 1x WASH Buffer as follows:<br>Reagent | Vol per Reaction |
|---|---|
| 1x WASH Buffer | 50 |

Mix gently, then place 2-3 min on magnet to capture beads; remove supernatant.

| Add 1x WASH Buffer to the tube to repeat for a total of 2 washes as follows:<br>Reagent | Vol per Reaction |
|---|---|
| 1x WASH Buffer | 100 |

Mix gently, then place 2-3 min on magnet to capture beads; remove supernatant.

| Add WATER as follows:<br>Reagent | Vol per Reaction |
|---|---|
| WATER | 100 |

Mix gently, then place 2-3 min on magnet to capture beads; remove supernatant.

| Add WATER to the tube to repeat for a total of 2 washes as follows:<br>Reagent | Vol per Reaction |
|---|---|
| WATER | 100 |

Mix gently, then place 2-3 min on magnet to capture beads; remove supernatant.

Elution

Add 15 of BIOTIN (Resin treated, 25 ng/ul).
Heat to 90 C. for 5 min. then chill to 4 C.
Place on magnet for 2-3 min to capture beads.
Remove supernatant to a clean 96-well plate and run on MALDI.

Bead Process

Beads are conditioned in in 2× binding buffer and a final volume of 25 ul conditioned beads are added to the 9 ul extension reaction. Water is added to bring the total volume to 50 ul. Bead capture is executed in a 96 well plate to accommodate the volume. Capture of extension products is performed on the hematology rotator at room temperature for 30 minutes. After capture, the beads are washed of reaction components in a 1× Tris buffer solution. This wash is repeated for a total of two washes. The beads are then washed with water. The water wash is also repeated for a total of two more washes. Each wash step utilizes 100 ul total volume. A 96 well plate magnet is used to pellet beads. The wash steps can be done manually or through the use of automation. Washed beads are re-suspended in 15 ul of concentrated free biotin solution (25 ng/ul; resin treated). Free biotin is allowed to out compete the biotinylated extension products at 90° C. for 5 min. Of the 15 ul re-suspension, 10 ul is aspirated while beads are pelleted under magnet. This 10 ul clean eluent is dispensed into a 384 well plate for dispensing. Bead conditioning and washing parameters are shown in Table 16.

Dispensing parameters require some alterations to typical dispensing protocols given volume height and analyte characteristics. Aspiration offset is set to 8 mm and dispense speed is changed to approximately 150 mm/sec or other higher dispense speed to account for viscosity difference in this analyte from typical iPLEX biochemistry.

Example 15: Non-Limiting Examples of Embodiments

Provided hereafter are non-limiting examples of certain embodiments of the technology.

A1. A method for determining the presence or absence of a plurality of target nucleic acids in a composition, which comprises:
- (a) preparing amplicons of the target nucleic acids by amplifying the target nucleic acids, or portions thereof, under amplification conditions;
- (b) contacting the amplicons in solution with a set of oligonucleotides under hybridization conditions, where each oligonucleotide in the set includes a hybridization sequence capable of specifically hybridizing to one amplicon under the hybridization conditions when the amplicon is present in the solution;
- (c) generating extended oligonucleotides that include a capture agent by extending oligonucleotides hybridized to the amplicons by one or more nucleotides, wherein one of the one of more nucleotides is a terminating nucleotide and one or more of the nucleotides added to the oligonucleotides includes the capture agent;
- (d) contacting the extended oligonucleotides with a solid phase under conditions in which the capture agent interacts with the solid phase;
- (e) releasing the extended oligonucleotides that have interacted with the solid phase by competition with a competitor; and
- (f) detecting the extended oligonucleotides released in (e) by mass spectrometry; whereby the presence or absence of each target nucleic acid is determined by the presence or absence of the corresponding extended oligonucleotide.

A1.1. The method of embodiment A1, wherein (i) the mass of one oligonucleotide species detectably differs from the masses of the other oligonucleotide species in the set; and (ii) each oligonucleotide species specifically corresponds to a specific amplicon and thereby specifically corresponds to a specific target nucleic acid.

A1.2. A method for determining the presence or absence of a plurality of target nucleic acids in a composition, which comprises:
- (a) preparing amplicons of the target nucleic acids by amplifying the target nucleic acids, or portions thereof, under amplification conditions;
- (b) contacting the amplicons in solution with a set of oligonucleotides under hybridization conditions, wherein:
- (i) each oligonucleotide in the set comprises a hybridization sequence capable of specifically hybridizing to one amplicon under the hybridization conditions when the amplicon is present in the solution,
- (ii) each oligonucleotide in the set comprises a mass distinguishable tag located 5' of the hybridization sequence,
- (iii) the mass of the mass distinguishable tag of one oligonucleotide detectably differs from the masses of mass distinguishable tags of the other oligonucleotides in the set; and
- (iv) each mass distinguishable tag specifically corresponds to a specific amplicon and thereby specifically corresponds to a specific target nucleic acid;
- (c) generating extended oligonucleotides that comprise a capture agent by extending oligonucleotides hybridized to the amplicons by one or more nucleotides, wherein one of the one of more nucleotides is a terminating nucleotide and one or more of the nucleotides added to the oligonucleotides comprises the capture agent;

(d) contacting the extended oligonucleotides with a solid phase under conditions in which the capture agent interacts with the solid phase;

(e) releasing the mass distinguishable tags in association with the extended oligonucleotides that have interacted with the solid phase from the solid phase by competition with a competitor; and (f) detecting the mass distinguishable tags released in (e) by mass spectrometry; whereby the presence or absence of each target nucleic acid is determined by the presence or absence of the corresponding mass distinguishable tag.

A2. The method of any one of embodiments A1 to A1.2, wherein competition with a competitor comprises contacting the solid phase with a competitor.

A3. The method of any one of embodiments A1 to A2, wherein the competitor consists of free capture agent, or a competing fragment or multimer thereof.

A3.1. The method of embodiment A3, wherein the competitor consists of free capture agent.

A4. The method of any one of embodiments A1 to A3.1, wherein the nucleotide that comprises the capture agent is a capture agent conjugated to a nucleotide triphosphate.

A5. The method of embodiment A4, wherein the nucleotide triphosphate is a dideoxynucleotide triphosphate.

A6. The method of any one of embodiments A1 to A5, wherein the capture agent comprises a member of a binding pair.

A7. The method of any one of embodiments A1 to A6, wherein the capture agent comprises biotin.

A8. The method of embodiment A7, wherein the solid phase comprises avidin or streptavidin.

A9. The method of any one of embodiments A1 to A6, wherein the capture agent comprises avidin or streptavidin.

A10. The method of embodiment A9, wherein the solid phase comprises biotin.

A11. The method of any one of embodiments A1 to A10, wherein releasing the mass distinguishable tags by competition with free capture agent is carried out under elevated temperature conditions.

A12. The method of embodiment A11, wherein the elevated temperature conditions comprise treatment for about 5 minutes at about 90 degrees Celsius.

A13. The method of any one of embodiments A1 to A12, wherein (c) is carried out in one container and the method further comprises transferring the released mass distinguishable tags to another container between (e) and (f).

A14. The method of any one of embodiments A1 to A13, wherein the solution containing amplicons produced in (a) is treated with an agent that removes terminal phosphates from any nucleotides not incorporated into the amplicons.

A15. The method of any one of embodiments A1 to A14, wherein the terminal phosphate is removed by contacting the solution with a phosphatase.

A16. The method of embodiment A15, wherein the phosphatase is alkaline phosphatase.

A17. The method of embodiment A16, wherein the alkaline phosphatase is shrimp alkaline phosphatase.

A18. The method of any one of embodiments A1 to A17, wherein the terminal nucleotides in the extended oligonucleotides comprise the capture agent.

A19. The method of any one of embodiments A1 to A18, wherein one or more non-terminal nucleotides in the extended oligonucleotides comprise the capture agent.

A20. The method of any one of embodiments A1 to A19, wherein the hybridization sequence is about 5 to about 200 nucleotides in length.

A21. The method of any one of embodiments A1 to A20, wherein the solid phase is selected from a flat surface, a bead, a silicon chip, or combinations of the foregoing.

A22. The method of any one of embodiments A1 to A21, wherein the solid phase is paramagnetic.

A23. The method of any one of embodiments A1 to A22, wherein the mass spectrometry is matrix-assisted laser desorption ionization (MALDI) mass spectrometry.

A24. The method of any one of embodiments A1 to A23, wherein the mass spectrometry is electrospray (ES) mass spectrometry.

A25. The method of any one of embodiments A1 to A24, wherein the presence or absence of about 1 to about 50 or more target nucleic acids is detected.

A26. The method of any one of embodiments A1 to A25, wherein the mass distinguishable tag consists of nucleotides.

A27. The method of any one of embodiments A1 to A26, wherein the mass distinguishable tag is a nucleotide compomer.

A28. The method of embodiment A27, wherein the nucleotide compomer is about 5 nucleotides to about 150 nucleotides in length.

A29. The method of any one of embodiments A1 to A28, wherein the target nucleic acids are genomic DNA.

A30. The method of embodiment A29, wherein the genomic DNA is human genomic DNA.

A31. The method of any one of embodiments A1 to A30, wherein the detecting in (f) comprises a signal to noise ratio greater than the signal to noise ratio for a method in which releasing does not comprise competition with a competitor.

B1. A method for detecting the presence, absence or amount of a plurality of genetic variants in a composition, comprising:

(a) preparing a plurality of amplicons derived from a plurality of target nucleic acid species, or portions thereof, wherein each target nucleic acid species comprises a first variant and a second variant;

(b) hybridizing the amplicons to oligonucleotide species, wherein each oligonucleotide species hybridizes to an amplicon derived from a target nucleic acid species, thereby generating hybridized oligonucleotide species; and (c) contacting the hybridized oligonucleotide species with an extension composition comprising one or more terminating nucleotides under extension conditions; wherein:

(i) at least one of the one or more terminating nucleotides comprises a capture agent, and (ii) the hybridized oligonucleotide species that hybridize to the first variant are extended by a terminating nucleotide and the hybridized oligonucleotide species that hybridize to the second variant are not extended by a terminating nucleotide, thereby generating extended oligonucleotide species;

(d) capturing the extended oligonucleotide species to a solid phase that captures the capture agent;

(e) releasing the extended oligonucleotide species bound to the solid phase in (d) from the solid phase; and (f) detecting the mass of each extended oligonucleotide species released from the solid phase in (e) by mass spectrometry; whereby the presence, absence or amount of the genetic variants is detected.

B2. The method of embodiment 1, wherein each oligonucleotide species comprises a mass distinguishable tag located 5' of the hybridization sequence B3. The method of embodiment 1 or 2, wherein the first variant is a lower abundance variation and the second variant is a higher abundance variation.

B4. The method of any one of embodiments 1 to 3, wherein the genetic variants are single nucleotide polymorphism (SNP) variants, the first variant is a lower abundance allele and the second variant is a higher abundance allele.

B5. The method of any one of embodiments 1 to 4, wherein the one or more terminating nucleotides consist of one terminating nucleotide.

B6. The method of any one of embodiments 1 to 4, wherein the one or more terminating nucleotides consist of two terminating nucleotides.

B7. The method of any one of embodiments 1 to 4, wherein the one or more terminating nucleotides consist of three terminating nucleotides.

B8. The method of any one of embodiments 1 to 4, wherein the one or more terminating nucleotides independently are selected from ddATP, ddGTP, ddCTP, ddTTP and ddUTP.

B9. The method of any one of embodiments 1 to 4 wherein the extension composition comprises a non-terminating nucleotide.

B10. The method of embodiment 9, wherein the extension composition comprises one or more extension nucleotides, which extension nucleotides comprise no capture agent.

B11. The method of any one of embodiments 1 to 10, wherein releasing the extended oligonucleotide species comprises contacting the solid phase with a releasing agent.

B12. The method of embodiment 11 wherein the capture agent comprises biotin or a biotin analogue, the solid phase comprises streptavidin and the releasing agent comprises free biotin or a biotin analogue.

B13. The method of embodiments 11 or 12 wherein the releasing agent has a higher affinity for the solid phase than the capture agent.

B14. The method of any one of embodiments 11 to 13 wherein releasing the extended oligonucleotide species in (e) comprises heating from about 30° C. to about 100° C.

B15. The method of embodiment 14, comprising heating from about 60° C. to about 100° C.

B16. The method of embodiment 14, comprising heating from about 89° C. to about 100° C.

B17. The method of embodiment 14, comprising heating to about 90° C.

B18. The method of any one of embodiments 1 to 17, wherein the plurality of target nucleic acid species is 20 or more target nucleic acid species.

B19. The method of any one of embodiments 1 to 18, wherein the plurality of target nucleic acid species is 200 or more target nucleic acid species.

B20. The method of any one of embodiments 1 to 19, wherein the plurality of target nucleic acid species is 200 to 300 target nucleic acid species.

B21. The method of any one of embodiments 1 to 20, wherein the extension conditions in (c) comprise cycling 20 to 300 times.

B22. The method of any one of embodiments 1 to 19 wherein the extension conditions in (c) comprise cycling 200 to 300 times.

B23. The method of any one of embodiments 1 to 22 wherein the extension reaction comprises a competitor oligonucleotide.

B24. The method of any one of embodiments 1 to 23 comprising washing the solid phase after the extended oligonucleotide species is captured.

B25. The embodiment of B24 wherein the washing removes salts that produce interfering adducts in mass spectrometry analysis.

B26. The embodiment of B25 wherein extended oligonucleotides are not contacted with an ion exchange resin.

B27. The method of any one of embodiments B1 to B26, wherein the detecting in (f) is with a signal to noise ratio greater than a signal to noise ratio for detecting after releasing without competition with a competitor.

B28. The method of any one of embodiments B1 to B27, wherein a signal to noise ratio for extending only a mutant allele is greater than a signal to noise ratio for extending a wild type and a mutant allele.

B29. The method of any one of embodiments B1 to B28, wherein the sensitivity of detecting a mutant allele in (f) is greater for extending only a mutant allele than for extending a wild type and a mutant allele.

B30. The method of any one of embodiments B1 to B29, wherein the extended oligonucleotide species of the second variant is not detected.

B31. The method of any one of embodiments B12 to B30, wherein the free biotin or biotin analogue is added at a concentration from about 10 to about 100 ug/ml.

B32. The embodiment of B31, wherein the free biotin or biotin analogue is added at a concentration of about 25 ug/ml.

B33. The method of any one of embodiments B1 to B32 wherein the composition comprises a synthetic template and the amount and/or percentage of a first variant in the composition is determined wherein the synthetic template comprises a variant different than in the first variant and second variant and hybridizes to the same oligonucleotides species.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

---

What is claimed is:

1. A method for detecting the presence, absence or amount of a plurality of genetic variants in a composition, comprising:

(a) preparing a plurality of amplicons derived from a plurality of target nucleic acid species, or portions thereof, wherein each target nucleic acid species comprises a first variant and a second variant and wherein the first variant is a lower abundance variant and the second variant is a higher abundance variant;

(b) hybridizing the amplicons to oligonucleotide species, wherein each oligonucleotide species has a mass that detectably differs from the masses of the other oligo-nucleotide species and each oligonucleotide species specifically hybridizes to an amplicon derived from a target nucleic acid species, thereby generating hybridized oligonucleotide species;

(c) contacting the hybridized oligonucleotide species with an extension composition comprising one or more terminating nucleotides under extension conditions; wherein:

(i) at least one of the one or more terminating nucleotide comprises a capture agent, and (ii) the hybridized oligonucleotide species that hybridize to the first variant are extended by a terminating nucleotide and the hybridized oligonucleotide species that hybridize to the second variant are not extended by a terminating nucleotide, thereby generating extended oligonucleotide species;

(d) capturing the extended oligonucleotide species to a solid phase that captures the capture agent;

(e) releasing the extended oligonucleotide species bound to the solid phase in (d) from the solid phase; and (f) detecting the mass of each extended oligonucleotide species released from the solid phase in (e) by mass spectrometry; whereby the presence, absence or amount of the genetic variants is detected.

2. The method of claim 1, wherein the terminating nucleotides consist of one terminating nucleotide, two terminating nucleotides or three terminating nucleotides.

3. The method of claim 1, wherein the terminating nucleotides independently are selected from ddATP, ddGTP, ddCTP, ddTTP and ddUTP.

4. The method of claim 1, wherein the plurality of target nucleic acid species is about 2 to about 500 target nucleic acid species.

5. The method of claim 4, wherein the plurality of target nucleic acid species is about 5, 10, 25, 50, 75, 100, 150 or 200 target nucleic acid species.

6. The method of claim 1, wherein the capture agent comprises biotin or a biotin analogue.

7. The method of claim 6, wherein the solid phase comprises avidin or a modified form of avidin or streptavidin or a modified form of streptavidin.

8. The method of claim 7, wherein releasing the extended oligonucleotide species is by a releasing agent comprising free biotin or a biotin analogue.

9. A method for detecting the presence, absence or amount of a plurality of genetic variants in a composition, comprising:

(a) preparing a plurality of amplicons derived from a plurality of target nucleic acid species, or portions thereof, wherein each target nucleic acid species comprises a first variant and a second variant and wherein the first variant is a lower abundance variant and the second variant is a higher abundance variant;

(b) hybridizing the amplicons to oligonucleotide species, wherein each oligonucleotide species comprises a mass distinguishable tag located 5' of the hybridization sequence, the mass of the mass distinguishable tag of each oligonucleotide species detectably differs from the masses of mass distinguishable tags of the other oligonucleotide species, and each mass distinguishable tag specifically corresponds to an amplicon derived from a target nucleic acid species, thereby generating hybridized oligonucleotide species;

(c) contacting the hybridized oligonucleotide species with an extension composition comprising one or more terminating nucleotides under extension conditions; wherein:

(i) at least one of the one or more terminating nucleotide comprises a capture agent, and (ii) the hybridized oligonucleotide species that hybridize to the first variant are extended by a terminating nucleotide and the hybridized oligonucleotide species that hybridize to the second variant are not extended by a terminating nucleotide, thereby generating extended oligonucleotide species;

(d) capturing the extended oligonucleotide species to a solid phase that captures the capture agent;

(e) releasing the extended oligonucleotide species bound to the solid phase in (d) from the solid phase; and (f) detecting the mass distinguishable tags associated with or cleaved from the extended oligonucleotide species captured to the solid phase in (d), or detecting the mass distinguishable tags associated with or cleaved from the extended oligonucleotide species released from the solid phase in (e), by mass spectrometry; whereby the presence, absence or amount of the genetic variants is detected.

10. The method of claim 9, wherein the mass distinguishable tag is cleaved from the extended oligonucleotide species.

11. The method of claim 9, wherein the mass distinguishable tag is a nucleotide compomer.

12. The method of claim 11, wherein the nucleotide compomer is about 1 to 30, 5 to 35, 10 to 30, 15 to 30, 20 to 35, 25 to 35, 30 to 40, 35 to 45, 40 to 50, or 25 to 50 nucleotides in length.

13. The method of claim 9, wherein the terminating nucleotides independently are selected from ddATP, ddGTP, ddCTP, ddTTP and ddUTP.

14. The method of claim 9, wherein the plurality of target nucleic acid species is about 2 to about 500 target nucleic acid species.

15. The method of claim 14, wherein the plurality of target nucleic acid species is about 5, 10, 25, 50, 75, 100, 150 or 200 target nucleic acid species.

\* \* \* \* \*